United States Patent
Vincent et al.

(10) Patent No.: US 11,680,108 B2
(45) Date of Patent: Jun. 20, 2023

(54) ANTI-ERBB3 ANTIBODIES

(71) Applicant: AVEO Pharmaceuticals, Inc., Cambridge, MA (US)

(72) Inventors: Sylvie Vincent, Somerville, MA (US); William M. Winston, Jr., Marlborough, MA (US); Fang Wang, Belmont, MA (US); Solly Weiler, Newton, MA (US); Kristan Meetze, Lexington, MA (US); Lyne Breault, Roslindale, MA (US); Steve Bottega, Cambridge, MA (US); Ting Chen, Acton, MA (US); Michael DePrima, Somerville, MA (US); Christina Fleet, Melrose, MA (US); Steven Tyler, Boston, MA (US); Jin-Kyeung Woo, Newton, MA (US); Jeno Gyuris, Lincoln, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 444 days.

(21) Appl. No.: 16/667,056

(22) Filed: Oct. 29, 2019

(65) Prior Publication Data
US 2020/0299406 A1 Sep. 24, 2020

Related U.S. Application Data

(60) Continuation of application No. 15/448,164, filed on Mar. 2, 2017, now Pat. No. 10,494,441, which is a division of application No. 14/987,374, filed on Jan. 4, 2016, now Pat. No. 9,598,498, which is a division of application No. 13/919,582, filed on Jun. 17, 2013, now Pat. No. 9,228,021, which is a division of application No. 13/082,852, filed on Apr. 8, 2011, now Pat. No. 8,481,687.

(60) Provisional application No. 61/322,712, filed on Apr. 9, 2010.

(51) Int. Cl.
*A61K 39/00* (2006.01)
*C07K 16/32* (2006.01)
*C07K 16/30* (2006.01)
*A61K 39/395* (2006.01)

(52) U.S. Cl.
CPC .............. *C07K 16/32* (2013.01); *C07K 16/30* (2013.01); *A61K 39/39558* (2013.01); *A61K 2039/505* (2013.01); *C07K 2317/24* (2013.01); *C07K 2317/51* (2013.01); *C07K 2317/515* (2013.01); *C07K 2317/565* (2013.01); *C07K 2317/73* (2013.01); *C07K 2317/76* (2013.01); *C07K 2317/92* (2013.01)

(58) Field of Classification Search
CPC .............................................. A61K 2039/505
See application file for complete search history.

(56) References Cited

U.S. PATENT DOCUMENTS

| | | |
|---|---|---|
| 5,183,884 A | 2/1993 | Kraus et al. |
| 5,480,968 A | 1/1996 | Kraus et al. |
| 5,820,859 A | 10/1998 | Kraus et al. |
| 5,916,755 A | 6/1999 | Kraus et al. |
| 5,968,511 A | 10/1999 | Akita et al. |
| 6,639,060 B1 | 10/2003 | Kraus et al. |
| 7,285,649 B2 | 10/2007 | Akita et al. |
| 7,705,130 B2 | 4/2010 | Rothe et al. |
| 7,846,440 B2 | 12/2010 | Schoeberl et al. |
| 8,481,687 B2 | 7/2013 | Vincent et al. |
| 9,228,021 B2 | 1/2016 | Vincent et al. |
| 9,598,498 B2 | 3/2017 | Vincent et al. |
| 10,494,441 B2 | 12/2019 | Vincent et al. |
| 2004/0197332 A1 | 10/2004 | Ullrich et al. |
| 2007/0009972 A1 | 1/2007 | Chao et al. |
| 2007/0122407 A1 | 5/2007 | Akita et al. |
| 2008/0124345 A1 | 5/2008 | Rothe et al. |
| 2009/0291085 A1 | 11/2009 | Schoeberl et al. |
| 2010/0266584 A1 | 10/2010 | Schoeberl et al. |
| 2010/0310557 A1 | 12/2010 | Keyt et al. |
| 2011/0171222 A1 | 7/2011 | Bossenmaier et al. |

FOREIGN PATENT DOCUMENTS

| | | |
|---|---|---|
| WO | WO-2007/077028 A2 | 7/2007 |
| WO | WO-2008/100624 A2 | 8/2008 |
| WO | WO-2010/127181 A1 | 11/2010 |
| WO | WO-2011/022727 A2 | 2/2011 |
| WO | WO-2011/044311 A2 | 4/2011 |

OTHER PUBLICATIONS

Chen et al. (1996) "An Immunological Approach Reveals Biological Differences between the Two NDF/Heregulin Receptors, ErbB-3 and ErbB-4" J. Biol. Chem. 271: 7620-7629.
International Search Report and Written Opinion, International Patent Application No. PCT/US2011/031829, dated Dec. 19, 2011 (17 pages).
Sithanandam et al. (2008) "The ERBB3 receptor in cancer and cancer gene therapyERBB3 in cancer" Cancer Gene Therapy 15:413-448.
Schoeberl et al. (2010) "An ErbB3 Antibody, MM-121, Is Active in Cancers with Ligand-Dependent Activation" Cancer Res. 70(6):2485-2494.
Schoeberl et al. (2009) "Therapeutically Targeting ErbB3: A Key Node in Ligand-Induced Activation of the ErbB Receptor-PI3K Axis" Science Signaling 2:1-14 (from www.SCIENCESIGNALING.org).
Sheng et al. (2010) "An activated ErbB3/NRG1 autocrine loop supports in vivo proliferation in ovarian cancer cells" Cancer Cell. 17(3):298-310.

(Continued)

*Primary Examiner* — Stephen L Rawlings
(74) *Attorney, Agent, or Firm* — Dechert LLP; Chad E. Davis; Andrew T Wilkins

(57) ABSTRACT

Monoclonal antibodies that bind and inhibit activation of epidermal growth factor receptor related member ErbB3/HER3 are disclosed. The antibodies can be used to treat cell proliferative diseases and disorders, including certain forms of cancer, associated with activation of ErbB3/HER3.

16 Claims, 26 Drawing Sheets

Specification includes a Sequence Listing.

(56) References Cited

OTHER PUBLICATIONS

Anti-ErbB3 Antibodies, U.S. Appl. No. 13/082,852, filed Apr. 8, 2011, U.S. Pat. No. 8,481,687, Jul. 9, 2013.
Anti-ErbB3 Antibodies, U.S. Appl. No. 13/919,582, filed Jun. 17, 2013, U.S. Pat. No. 9,228,021, Jan. 5, 2016.
Anti-ErbB3 Antibodies, U.S. Appl. No. 14/987,374, filed Jan. 4, 2016, U.S. Pat. No. 9,598,498, Mar. 21, 2017.
Anti-ErbB3 Antibodies, U.S. Appl. No. 15/448,164, filed Mar. 2, 2017, U.S. Pat. No. 10,494,441, Dec. 3, 2019.

FIG. 2

Complete Heavy Chain Variable Region Amino Acid Alignments

| Antibody | | | CDR1 | | CDR2 | |
|---|---|---|---|---|---|---|
| 04D01 | (1) | QVQLQQPGAELVRPGTSVKLSCKASGYTFTSH--WLH | WVKQRPGQGLEWIG | VLDPSDFYSNYNQNFKGKA | |
| 09D03 | (1) | QVTLKESGPGILRPSQTLSLTCSFSGFSLSTFGLSVG | WIRQPSGKGLEWLA | HIWWDDDK--YYNPALKSRL | |
| 11G01 | (1) | QVQLQQSDAELVKPGASVKISCKVSGYTFTDH--ITH | WMKQRPEQGLEWIG | YIYPRDGYIKYNEKFKGKA | |
| 12A07 | (1) | QVQLLQPGAELVRPGTSVKLSCKTSGYTFSSY--WMH | WVKQRPGQGLEWIG | MIDPSDVYTNYNPKFKGKA | |
| 18H02 | (1) | QIQLVQSGPELKKPGEAVKISCKSSGYTFTY---GMS | WVKQAPGRALKWMG | WINTYSGVPTYADDFKGRF | |
| 22A02 | (1) | QVQLQQPGAELVRPGTSVKLSCKASGYTFTNY--WMH | WVKQRPGQGLEWIG | MIDPSDSYTNYNPKFKGKA | |
| 24C05 | (1) | EVQLVESGGGLVKPGGSLKLSCAASGFTFSDY---AMS | WVRQTPEKRLEWVA | TISDGGTYTYYPDNVKGRF | |

| | | | CDR3 | | | |
|---|---|---|---|---|---|---|
| 04D01 | (69) | TLTVDTSSSTAYMQLSSLTSEDSAVYYCAR | GLL-SGDYAMDY | WGQGTSVTVSS | (SEQ ID NO: 2) |
| 09D03 | (70) | TISKDTSKNQVFLKIANVDTADTATYYCAR | IG-ADALPFDY | WGQGTTLTVSS | (SEQ ID NO: 12) |
| 11G01 | (69) | TLTADKSSSTAYMQVNSLTSEDSAVYFCAR | G------YYYAMDY | WGQGTSVTVSS | (SEQ ID NO: 22) |
| 12A07 | (69) | TLTVDTSSSTAYMQLSSLTSEDSAVYYCAR | G--------NYSGDY | WGQGTTLTVSS | (SEQ ID NO: 31) |
| 18H02 | (69) | AFSLESSASTAYLQINNLKNEDTATYFCAR | GRDGYQVAWFAY | WGQGTLVTVSA | (SEQ ID NO: 38) |
| 22A02 | (69) | TLTVDTSSSTAYMQLSSLTSEDSAVYYCAR | G--------NYSGDY | WGQGTTLTVSS | (SEQ ID NO: 48) |
| 24C05 | (69) | TISRDNAKNNLYLQMSHLKSEDTAMYYCAR | EWG--DYDGFDY | WGQGTTLTVSS | (SEQ ID NO: 54) |

FIG. 3

Heavy Chain CDR Amino Acid Alignments

| Antibody | CDR1 | | CDR2 | | CDR3 | |
|---|---|---|---|---|---|---|
| 04D01 | SH--WLH | (SEQ ID NO: 5) | VLDPSDFYSNYNQNFKG | (SEQ ID NO: 6) | GLL-SGDYAMDY | (SEQ ID NO: 7) |
| 09D03 | TFGLSVG | (SEQ ID NO: 15) | HIWDDD--KYYNPALKS | (SEQ ID NO: 16) | IG---ADALPFDY | (SEQ ID NO: 17) |
| 11G01 | DH--IIH | (SEQ ID NO: 25) | YIYPRDGYIKYNEKFKG | (SEQ ID NO: 26) | G------YYYAMDY | (SEQ ID NO: 27) |
| 12A07 | SY--WMH | (SEQ ID NO: 34) | MIDPSDVYTNYNPKFKG | (SEQ ID NO: 35) | -------NYSGDY | (SEQ ID NO: 36) |
| 18H02 | TY--GMS | (SEQ ID NO: 41) | WINTYSGVPTYADDFKG | (SEQ ID NO: 42) | GRDGYQVAWFAY | (SEQ ID NO: 43) |
| 22A02 | NY--WMH | (SEQ ID NO: 51) | MIDPSDSYTNYNPKFKG | (SEQ ID NO: 52) | -------NYSGDY | (SEQ ID NO: 36) |
| 24C05 | DY--AMS | (SEQ ID NO: 57) | TISDGGTYTYYPDNVKG | (SEQ ID NO: 58) | EWG--DYDGFDY | (SEQ ID NO: 59) |

FIG. 4

Complete Light (Kappa) Chain Variable Region Amino Acid Alignments

| Antibody | | CDR1 | CDR2 |
|---|---|---|---|
| 04D01 | (1) | DVLMTQIPLSLPVSLGDQASISC RSSQSIVHSNGNTYLE WYLQKPGQSPKLLIY KVSNRFS GVPDRFSGS |
| 09D03 | (1) | DIVLTQTAPSVPVTPGESVSISC RSSKSLLHSNGNTYLY WFLQRPGQSPQLLIY RMSNLAS GVPDRFSGS |
| 11G01 | (1) | DVLMTQTPLSLPVSLGDQASISC RSSQSIVHSIGNTYLE WYLQKPGQSPKLLIY KVSNRFS GVPERFSGS |
| 12A07 | (1) | DVLMTQIPLSLPVSLGDQASISC RSSQSIVHSNGNTYLE WYLQKPGQSPKLLIY KVSNRFS GVPDRFSGS |
| 18H02 | (1) | ETTVTQSPASLSMAIGDKVTIRC ITSTDIDDD----MN WFQQKPGEPPKLLIS EGNTLRP GVPSRFSGS |
| 22A02 | (1) | DVLMTQTPLSLPVSLGDQASISC RSSQSIVHSNGNTYLE WYLQKPGQSPKLLIY KVSNRFS GVPDRFSGS |
| 24C05 | (1) | DIQMTQSPSSLSASLGERVSLTC RASQEISG-------YLS WLQQKPDGTIKRLIY AASTLDS GVPKRFSGS |

| | | CDR3 | |
|---|---|---|---|
| 04D01 | (71) | GSGTDFTLKISRVEAEDLGVYYC FQGSYVPWT FGGGTKLEIK | (SEQ ID NO: 4) |
| 09D03 | (71) | GSGTAFTLRISRVEAEDVGVYYC MQHLEYPFT FGSGTKLEIK | (SEQ ID NO: 14) |
| 11G01 | (71) | GSGTDFTLKISRVEAEDLGVYYC FQGSHVPFT FGSGTKLEIK | (SEQ ID NO: 24) |
| 12A07 | (71) | GSGTDFTLKISRVEAEDLGVYYC FQGSYVPWT FGGGTKLEIK | (SEQ ID NO: 33) |
| 18H02 | (66) | GYGTDFIFTIENMLSEDVADYYC LQSDNLPYT FGGGTKLEIK | (SEQ ID NO: 40) |
| 22A02 | (71) | GSGTDFTLKISRVEAEDLGVYYC FQGSYVPWT FGGGTKLEIK | (SEQ ID NO: 50) |
| 24C05 | (66) | RSGSDYSLTIGSLESEDLADYYC LQYDSYPYT FGGGTKLEIK | (SEQ ID NO: 56) |

FIG. 5

Light (Kappa) Chain CDR Amino Acid Alignments

| Antibody | CDR1 | CDR2 | CDR3 |
|---|---|---|---|
| 04D01 | RSSQSIVHSNGNTYLE (SEQ ID NO: 8) | KVSNRFS (SEQ ID NO: 9) | FQGSYVPWT (SEQ ID NO: 10) |
| 09D03 | RSSKSLLHSNGNTYLY (SEQ ID NO: 18) | RMSNLAS (SEQ ID NO: 19) | MQHLEYPFT (SEQ ID NO: 20) |
| 11G01 | RSSQSIVHSIGNTYLE (SEQ ID NO: 28) | KVSNRFS (SEQ ID NO: 9) | FQGSHVPFT (SEQ ID NO: 29) |
| 12A07 | RSSQSIVHSNGNTYLE (SEQ ID NO: 8) | KVSNRFS (SEQ ID NO: 9) | FQGSYVPWT (SEQ ID NO: 10) |
| 18H02 | ITSTDIDDD------MN (SEQ ID NO: 44) | EGNTLRP (SEQ ID NO: 45) | LQSDNLPYT (SEQ ID NO: 46) |
| 22A02 | RSSQSIVHSNGNTYLE (SEQ ID NO: 8) | KVSNRFS (SEQ ID NO: 9) | FQGSYVPWT (SEQ ID NO: 10) |
| 24C05 | RASQEISG------YLS (SEQ ID NO: 60) | AASTLDS (SEQ ID NO: 61) | LQYDSYPYT (SEQ ID NO: 62) |

FIG. 15

Complete Humanized Heavy Chain Variable Region Amino Acid Alignments

```
Heavy Chain                          CDR1                                      CDR2
           24C05 (1)   EVQLVESGGGLVKPGGSLKLSCAASGFTFSDYAMSWVRQTPEKRLEWVATISDGGTYTYYPDNVKGRFTI
   Sh24C05 Hv3-7  (1)  EVQLVESGGGLVQPGGSLRLSCAASGFTFSDYAMSWVRQAPGKGLEWVSTISDGGTYTYYPDSVKGRFTI
   Sh24C05 Hv3-11 (1)  QVQLVESGGGLVKPGGSLRLSCAASGFTFSDYAMSWIRQAPGKGLEWVSTISDGGTYTYYPDSVKGRFTI
Sh24C05 Hv3-11 N62S (1) QVQLVESGGGLVKPGGSLRLSCAASGFTFSDYAMSWIRQAPGKGLEWVSTISDGGTYTYYPDNVKGRFTI
   Sh24C05 Hv3-21 (1)  EVQLLESGGGLVQPGGSLRLSCAASGFTFSDYAMSWVRQAPGKGLEWVSTISDGGTYTYYPDNVKGRFTI
   Sh24C05 Hv3-23 (1)  EVQLVESGGGLVQPGGSLRLSCAASGFTFSDYAMSWVRQAPGKGLEWVATISDGGTYTYYPDNVKGRFTI
   Sh24C05 Hv3-30 (1)  QVQLVESGGGVVQPGRSLRLSCAASGFTFSDYAMSWVRQAPGKGLEWVSTISDGGTYTYYPDNVKGRFTI
     Hu24C05 HvA  (1)  EVQLVESGGGLVKPGGSLRLSCAASGFTFSDYAMSWVRQAPGKGLEWVATISDGGTYTYYPDNVKGRFTI CDR3
           24C05 (71)  SRDNAKNNLYLQMSHLKSEDTAMYYCAREWGDYDGFDYWGQGTTLTVSS (SEQ ID NO: 54)
   Sh24C05 Hv3-7  (71) SRDNAKNSLYLQMNSLRAEDTAVYYCAREWGDYDGFDYWGQGTLVTVSS (SEQ ID NO: 150)
   Sh24C05 Hv3-11 (71) SRDNAKNSLYLQMNSLRAEDTAVYYCAREWGDYDGFDYWGQGTLVTVSS (SEQ ID NO: 152)
Sh24C05 Hv3-11 N62S (71) SRDNAKNSLYLQMNSLRAEDTAVYYCAREWGDYDGFDYWGQGTLVTVSS (SEQ ID NO: 154)
   Sh24C05 Hv3-21 (71) SRDNAKNSLYLQMNSLRAEDTAVYYCAREWGDYDGFDYWGQGTLVTVSS (SEQ ID NO: 156)
   Sh24C05 Hv3-23 (71) SRDNSKNTLYLQMNSLRAEDTAVYYCAREWGDYDGFDYWGQGTLVTVSS (SEQ ID NO: 158)
   Sh24C05 Hv3-30 (71) SRDNSKNTLYLQMSSLRAEDTAVYYCAREWGDYDGFDYWGQGTLVTVSS (SEQ ID NO: 160)
     Hu24C05 HvA  (71) SRDNAKNSLYLQMNSLRAEDTAVYYCAREWGDYDGFDYWGQGTLVTVSS (SEQ ID NO: 162)
```

FIG. 16

Complete Humanized Light (Kappa) Chain Variable Region Amino Acid Alignments

```
Light Chain                         CDR1                                    CDR2
24C05          (1)  DIQMTQSPSSLSASLGERVSLTC RASQEISGYLS WLQQKPDGTIKRLIY AASTLDS GVPKRFSGGSRSGSD
Sh24C05 Kv1-9  (1)  DIQLTQSPSFLSASVGDRVTITC RASQEISGYLS WYQQKPGKAPKLLIY AASTLDS GVPSRFSGSGSGTE
Sh24C05 Kv1-16 (1)  DIQMTQSPSSLSASVGDRVTITC RASQEISGYLS WFQQKPGKAPKSLIY AASTLDS GVPSRFSGSGSGTD
Sh24C05 Kv1-17 (1)  DIQMTQSPSSLSASVGDRVTITC RASQEISGYLS WYQQKPGKAPKRLIY AASTLDS GVPSRFSGSGSGTE
Sh24C05 Kv1-33 (1)  DIQMTQSPSSLSASVGDRVTITC RASQEISGYLS WYQQKPGKAPKLLIY AASTLDS GVPSRFSGSGSGTD
Sh24C05 Kv1-39 (1)  DIQMTQSPSSLSASVGDRVTITC RASQEISGYLS WYQQKPGKAPKLLIY AASTLDS GVPSRFSGSGSGTD
Hu24C05 KvA    (1)  DIQMTQSPSSLSASVGDRVTITC RASQEISGYLS WLQQKPGGAIKRLIY AASTLDS GVPSRFSGSGSGSD CDR3
24C05          (71) YSLTIGSLESEDLADYYC LQYDSYPYT FGGGTKLEIK   (SEQ ID NO: 56)
Sh24C05 Kv1-9  (71) FTLTISSLQPEDFATYYC LQYDSYPYT FGQGTKLEIK   (SEQ ID NO: 164)
Sh24C05 Kv1-16 (71) FTLTISSLQPEDFATYYC LQYDSYPYT FGQGTKLEIK   (SEQ ID NO: 166)
Sh24C05 Kv1-17 (71) FTLTISSLQPEDIATYYC LQYDSYPYT FGQGTKLEIK   (SEQ ID NO: 168)
Sh24C05 Kv1-33 (71) FTFTISSLQPEDFATYYC LQYDSYPYT FGQGTKLEIK   (SEQ ID NO: 170)
Sh24C05 Kv1-39 (71) FTLTISSLQPEDFATYYC LQYDSYPYT FGQGTKLEIK   (SEQ ID NO: 172)
Hu24C05 KvA    (71) YTLTISSLQPEDFATYYC LQYDSYPYT FGQGTKLEIK   (SEQ ID NO: 174)
```

ANTI-ERBB3 ANTIBODIES

CROSS-REFERENCE TO RELATED APPLICATIONS

This application is a continuation of U.S. patent application Ser. No. 15/448,164, filed Mar. 2, 2017, now U.S. Pat. No. 10,494,441, which is a divisional of U.S. patent application Ser. No. 14/987,374, filed Jan. 4, 2016, now U.S. Pat. No. 9,598,498, which is a divisional of U.S. patent application Ser. No. 13/919,582, filed Jun. 17, 2013, now U.S. Pat. No. 9,228,021, which is a divisional of U.S. patent application Ser. No. 13/082,852 filed Apr. 8, 2011, now U.S. Pat. No. 8,481,687, which claims priority to and the benefit of U.S. Provisional Patent Application No. 61/322,712, filed Apr. 9, 2010; the entire contents of each of which is incorporated herein by reference.

FIELD OF THE INVENTION

The field of the invention is molecular biology, immunology and oncology. More particularly, the field is humanized antibodies that bind human ErbB3/HER3.

BACKGROUND

HER3/c-ErbB3 (referred to herein as ErbB3) is a member of the epidermal growth factor receptor (EGFR) family. ErbB3 binds neuregulin/heregulin (NRG/HRG). Receptors in the EGFR family are single transmembrane receptors with an intracellular tyrosine kinase domain. While the other EGFR family members, i.e., EGFR/HER1/ErbB1, HER2/ErbB2, and HER4/ErbB4, each have tyrosine kinase activity, ErbB3 has little or no tyrosine kinase activity, and thus is "kinase-dead."

The extracellular domain (ECD) of the EGFR family contains four domains. Domains 1 and 3 (also known as domains L1 and L2) are responsible for ligand binding. Cysteine-rich domains 2 and 4 (also known as domains C1 and C2) are involved in dimerization with receptor partners. Upon ligand binding, the ECD undergoes conformational changes. The interaction of domains 2 and 4, which maintains the tethered (inactive) conformation of the receptor, is relieved, and an extended (active) conformation is adopted. The extended conformation favors dimerization with other receptor partners. HER2/ErbB2 is the only exception to this general rule, i.e., Her2-ECD is constitutively in the extended conformation. No ligand for HER2 has been identified thus far.

Because ErbB3 lacks an intrinsic kinase activity, it must dimerize with another active tyrosine kinase receptor to be activated by tyrosine phosphorylation. Dimerization can occur between two different receptors (heterodimerization), e.g., ErbB3 and EGFR/HER1/ErbB1, HER2/ErbB2, or HER4/ErbB4. Recently, ErbB3 was also shown to dimerize with MET. Upon association with another tyrosine kinase receptor, ErbB3 is activated by phosphorylation of at least nine tyrosine residues in the ErbB3 intracellular domain, and then rapidly associates with adaptors or downstream signaling molecules. Six of the ErbB3 phosphorylated tyrosine residues associate directly with the p85 subunit of Phosphatidylinositol 3-Kinase (PIK3), which results in activation of the cellular survival pathway controlled by the PI3K/Akt axis. Constitutive activation of ErbB3 by unregulated dimerization and/or unregulated phosphorylation of ErbB3 can lead to certain cancers.

Overexpression of ErbB3 is associated with poor prognosis in various carcinomas (e.g., breast, ovarian, prostate, colorectal, pancreatic, gastric, and head and neck cancers). Overexpression of ErbB3 also correlates with local to distal metastasis in lung, gastric, and colorectal cancers, and bone invasion in prostate cancer (Sithanandam et al., 2008, CANCER GENE THERAPY 15:413). Overexpression of ErbB3 has been linked to resistance to several cancer treatments, including treatment with EGFR tyrosine kinase inhibitors in non-small cell lung cancer (NSCLC) and head and neck cancers, treatment with Her2 inhibitor in breast cancers, and treatment with radiotherapy in pancreatic cancers. Moreover, overexpression of NRG, a ligand for ErbB3, was also linked to resistance to EGFR tyrosine kinase inhibitor treatment. Chen et al. describe the use of anti-ErbB3 monoclonal antibodies that inhibit NRG function and show growth inhibitory activity against breast and ovarian cancer cells (Chen et al., 1996, J. BIOL. CHEM. 271: 7620).

There is a need for improved anti-ErbB3 antibodies that can be used as therapeutic agents.

SUMMARY

The invention is based on the discovery of a family of antibodies that specifically bind human ErbB3. The antibodies contain ErbB3 binding sites based on CDRs that specifically bind human ErbB3. When used as therapeutic agents, the antibodies are engineered, e.g., humanized, to reduce or eliminate an immune response when administered to a human patient.

The antibodies disclosed herein prevent or inhibit the activation of human ErbB3. In some embodiments, the antibodies prevent ErbB3 from binding to a ligand, e.g., NRG/HRG, thereby neutralizing the biological activity of ErbB3. In other embodiments, the anti-ErbB3 antibodies inhibit ErbB3 dimerization, thereby neutralizing the biological activity of ErbB3. The antibodies disclosed herein can be used to inhibit the proliferation of tumor cells in vitro or in vivo. When administered to a human cancer patient (or an animal model such as a mouse model), the antibodies inhibit or reduce tumor growth in the human patient (or animal model).

These and other aspects and advantages of the invention are illustrated by the following figures, detailed description and claims. As used herein, "including" means without limitation, and examples cited are non-limiting.

DESCRIPTION OF THE DRAWINGS

The invention can be more completely understood with reference to the following drawings.

FIG. 2 is a schematic diagram showing the amino acid sequence of the complete immunoglobulin heavy chain variable region of the antibodies denoted as 04D01, 09D03, 11G01, 12A07, 18H02, 22A02, and 24C05. The amino acid sequences for each antibody are aligned against one another, and Complementary Determining Sequences (CDR) (Kabat definition), $CDR_1$, $CDR_2$, and $CDR_3$, are identified in boxes. The unboxed sequences represent framework (FR) sequences.

FIG. 3 is a schematic diagram showing the $CDR_1$, $CDR_2$, and $CDR_3$ sequences (Kabat definition) for each of the immunoglobulin heavy chain variable region sequences in FIG. 2.

FIG. 4 is a schematic diagram showing the amino acid sequence of the complete immunoglobulin light chain variable region of antibodies 04D01, 09D03, 11G01, 12A07, 18H02, 22A02, and 24C05. The amino acid sequences for each antibody are aligned against one another, and CDR$_1$, CDR$_2$, and CDR$_3$ sequences (Kabat definition) are identified in boxes. The unboxed sequences represent framework (FR) sequences.

FIG. 5 is a schematic diagram showing the CDR$_1$, CDR$_2$, and CDR$_3$ sequences (Kabat definition) for each of the immunoglobulin light chain variable region sequences in FIG. 4.

FIG. 15 is a schematic diagram showing the amino acid sequences of the complete heavy chain variable region of 24C05 and the complete humanized heavy chain variable regions denoted as Sh24C05 Hv3-7, Sh24C05 Hv3-11, Sh24C05 Hv3-11 N62S, Sh24C05 Hv3-21, Sh24C05 Hv3-23, Sh24C05 Hv3-30, and Hu24C05 HvA. The amino acid sequences for each heavy chain variable regions are aligned against one another, and Complementary Determining Sequences (CDR) (Kabat definition), CDR$_1$, CDR$_2$, and CDR$_3$, are identified in boxes. The unboxed sequences represent framework (FR) sequences.

FIG. 16 is a schematic diagram showing the amino acid sequences of the complete light chain variable region of 24C05 and the complete humanized light chain variable regions denoted as Sh24C05 Kv1-9, Sh24C05 Kv1-16, Sh24C05 Kv1-17, Sh24C05 Kv1-33, Sh24C05 Kv1-39, and Hu24C05 KvA. The amino acid sequences for each light chain variable regions are aligned against one another, and CDR$_1$, CDR$_2$, and CDR$_3$ sequences (Kabat definition) are identified in boxes. The unboxed sequences represent framework (FR) sequences.

DETAILED DESCRIPTION

Figure 1:
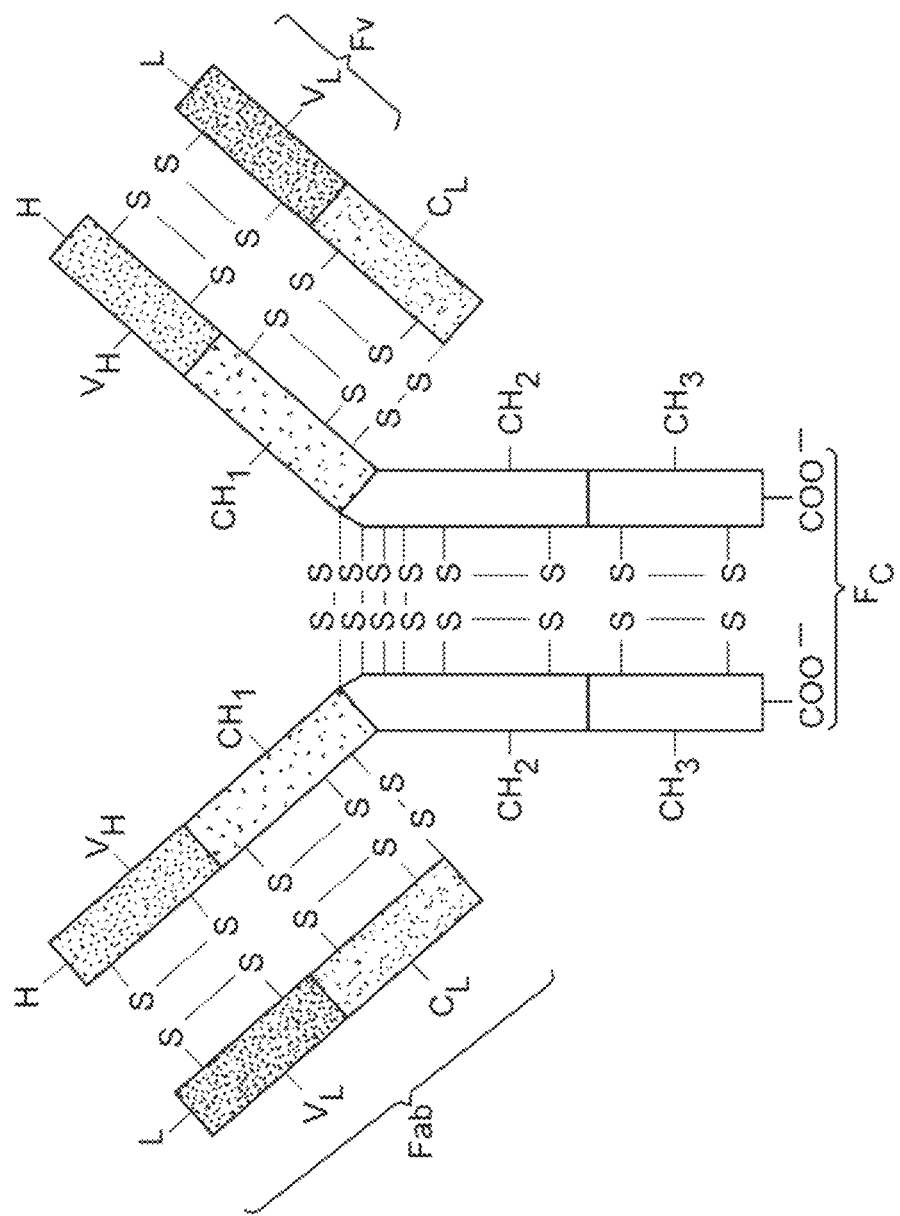
FIG. 1 (prior art) is a schematic representation of a typical antibody.

The ErbB3 antibodies disclosed herein are based on the antigen binding sites of certain monoclonal antibodies selected for their ability to neutralize the biological activity of human ErbB3 polypeptides. The antibodies contain immunoglobulin variable region CDR sequences that define a binding site for ErbB3. In some embodiments, the antibodies prevent ErbB3 from binding to a ligand, e.g., NRG/HRG, thereby neutralizing the biological activity of ErbB3. In other embodiments, the anti-ErbB3 antibodies inhibit ErbB3 dimerization, thereby neutralizing the biological activity of ErbB3. In still other embodiments, the anti-ErbB3 antibodies inhibit phosphorylation of ErbB3 and downstream signaling.

Because of the neutralizing activity of these antibodies, they are useful for inhibiting the growth and/or proliferation of certain cancer cells and tumors. The antibodies can be engineered to minimize or eliminate an immune response when administered to a human patient. In some embodiments, the antibodies are fused or conjugated to other moieties, such as detectable labels or effector molecules such as small molecule toxins.

I. Antibodies that Bind ErbB3

In some embodiments, the antibody comprises: (a) an immunoglobulin heavy chain variable region comprising the structure $CDR_{H1}$-$CDR_{H2}$-$CDR_{H3}$ and (b) immunoglobulin light chain variable region, wherein the heavy chain variable region and the light chain variable region together define a single binding site for binding human ErbB3. A $CDR_{H1}$ comprises an amino acid sequence selected from the group consisting of SEQ ID NO: 5 (04D01), SEQ ID NO:15 (09D03), SEQ ID NO: 25 (11G01), SEQ ID NO: 34 (12A07), SEQ ID NO: 41 (18H02), SEQ ID NO: 51 (22A02), SEQ ID NO: 57 (24C05), and SEQ ID NO: 75 (24C05); a $CDR_{H2}$ comprises an amino acid sequence selected from the group consisting of SEQ ID NO: 6 (04D01), SEQ ID NO:16 (09D03), SEQ ID NO: 26 (11G01), SEQ ID NO: 35 (12A07), SEQ ID NO: 42 (18H02), SEQ ID NO: 52 (22A02), SEQ ID NO: 58 (24C05), and SEQ ID NO: 148 (Sh24C05 Hv3-11 N62S); and a $CDR_{H3}$ comprises an amino acid sequence selected from the group consisting of SEQ ID NO: 7 (04D01), SEQ ID NO: 17 (09D03), SEQ ID NO: 27 (11G01), SEQ ID NO: 36 (12A07, 22A02), SEQ ID NO: 43 (18H02), and SEQ ID NO: 59 (24C05). Throughout the specification a particular SEQ ID NO. is followed in parentheses by the antibody that was the origin of that sequence. For example, "SEQ ID NO: 5 (04D01)" means that SEQ ID NO: 5 comes from antibody 04D01.

In some embodiments, the antibody comprises an immunoglobulin heavy chain variable region comprising a $CDR_{H1}$ comprising the amino acid sequence of SEQ ID NO: 5 (04D01), a $CDR_{H2}$ comprising the amino acid sequence of SEQ ID NO: 6 (04D01), and a $CDR_{H3}$ comprising the amino acid sequence of SEQ ID NO: 7 (04D01).

In some embodiments, the antibody comprises an immunoglobulin heavy chain variable region comprising a $CDR_{H1}$ comprising the amino acid sequence of SEQ ID NO: 15 (09D03), a $CDR_{H2}$ comprising the amino acid sequence of SEQ ID NO: 16 (09D03), and a $CDR_{H3}$ comprising the amino acid sequence of SEQ ID NO: 17 (09D03).

In some embodiments, the antibody comprises an immunoglobulin heavy chain variable region comprising a $CDR_{H1}$ comprising the amino acid sequence of SEQ ID NO: 25 (11G01), a $CDR_{H2}$ comprising the amino acid sequence of SEQ ID NO: 26 (11G01), and a $CDR_{H3}$ comprising the amino acid sequence of SEQ ID NO: 27 (11G01).

In some embodiments, the antibody comprises an immunoglobulin heavy chain variable region comprising a $CDR_{H1}$ comprising the amino acid sequence of SEQ ID NO: 34 (12A07), a $CDR_{H2}$ comprising the amino acid sequence of SEQ ID NO: 35 (12A07), and a $CDR_{H3}$ comprising the amino acid sequence of SEQ ID NO: 36 (12A07, 22A02).

In some embodiments, the antibody comprises an immunoglobulin heavy chain variable region comprising a $CDR_{H1}$ comprising the amino acid sequence of SEQ ID NO: 41 (18H02), a $CDR_{H2}$ comprising the amino acid sequence of SEQ ID NO: 42 (18H02), and a $CDR_{H3}$ comprising the amino acid sequence of SEQ ID NO: 43 (18H02).

In some embodiments, the antibody comprises an immunoglobulin heavy chain variable region comprising a $CDR_{H1}$ comprising the amino acid sequence of SEQ ID NO: 51 (22A02), a $CDR_{H3}$ comprising the amino acid sequence of SEQ ID NO: 52 (22A02), and a $CDR_{H3}$ comprising the amino acid sequence of SEQ ID NO: 36 (12A07, 22A02).

In some embodiments, the antibody comprises an immunoglobulin heavy chain variable region comprising a $CDR_{H1}$ comprising the amino acid sequence of SEQ ID NO: 57 (24C05) or SEQ ID NO: 75 (24C05), a $CDR_{H2}$ comprising the amino acid sequence of SEQ ID NO: 58 (24C05), and a $CDR_{H3}$ comprising the amino acid sequence of SEQ ID NO: 59 (24C05).

In certain embodiments, the antibody comprises an immunoglobulin heavy chain variable region comprising a $CDR_{H1}$ comprising the amino acid sequence of SEQ ID NO: 57 (24C05), a $CDR_{H2}$ comprising the amino acid sequence of SEQ ID NO: 58 (24C05), and a $CDR_{H3}$ comprising the amino acid sequence of SEQ ID NO: 59 (24C05).

In other embodiments, the antibody comprises an immunoglobulin heavy chain variable region comprising a $CDR_{H1}$ comprising the amino acid sequence of SEQ ID NO: 75 (24C05), a $CDR_{H2}$ comprising the amino acid sequence of SEQ ID NO: 58 (24C05), and a CDR$_{H3}$ comprising the amino acid sequence of SEQ ID NO: 59 (24C05).

In certain embodiments, the antibody comprises an immunoglobulin heavy chain variable region a CDR$_{H1}$ comprising the amino acid sequence of SEQ ID NO: 57 (24C05) or SEQ ID NO: 75 (24C05), a CDR$_{H2}$ comprising the amino acid sequence of SEQ ID NO: 148 (Sh24C05 Hv3-11 N62S), and a CDR$_{H3}$ comprising the amino acid sequence of SEQ ID NO: 59 (24C05).

Preferably, the CDR$_{H1}$, CDR$_{H2}$, and CDR$_{H3}$ sequences are interposed between human or humanized immunoglobulin FRs. The antibody can be an intact antibody or an antigen-binding antibody fragment.

In some embodiments, the antibody comprises (a) an immunoglobulin light chain variable region comprising the structure CDR$_{L1}$-CDR$_{L2}$-CDR$_{L3}$, and (b) an immunoglobulin heavy chain variable region, wherein the IgG light chain variable region and the IgG heavy chain variable region together define a single binding site for binding human ErbB3. A CDR$_{L1}$ comprises an amino acid sequence selected from the group consisting of SEQ ID NO: 8 (04D01, 12A07, 22A02), SEQ ID NO: 18 (09D03), SEQ ID NO: 28 (11G01), SEQ ID NO: 44 (18H02), and SEQ ID NO: 60 (24C05); a CDR$_{L2}$ comprises an amino acid sequence selected from the group consisting of SEQ ID NO: 9 (04D01, 11G01, 12A07, 22A02), SEQ ID NO: 19 (09D03), SEQ ID NO: 45 (18H02), and SEQ ID NO: 61 (24C05); and a CDR$_{L3}$ comprises an amino acid sequence selected from the group consisting of SEQ ID NO: 10 (04D01, 12A07, 22A02), SEQ ID NO: 20 (09D03), SEQ ID NO: 29 (11G01), SEQ ID NO: 46 (18H02), and SEQ ID NO: 62 (24C05).

In some embodiments, the antibody comprises an immunoglobulin light chain variable region comprising: a CDR$_{L1}$ comprising the amino acid sequence of SEQ ID NO: 8 (04D01, 12A07, 22A02); a CDR$_{L2}$ comprising the amino acid sequence of SEQ ID NO: 9 (04D01, 11G01, 12A07, 22A02); and a CDR$_{L3}$ comprising the amino acid sequence of SEQ ID NO: 10 (04D01, 12A07, 22A02).

In some embodiments, the antibody comprises an immunoglobulin light chain variable region comprising: a CDR$_{L1}$ comprising the amino acid sequence of SEQ ID NO: 18 (09D03); a CDR$_{L2}$ comprising the amino acid sequence of SEQ ID NO: 19 (09D03); and a CDR$_{L3}$ comprising the amino acid sequence of SEQ ID NO: 20 (09D03).

In some embodiments, the antibody comprises an immunoglobulin light chain variable region comprising: a CDR$_{L1}$ comprising the amino acid sequence of SEQ ID NO: 28 (11G01); a CDR$_{L2}$ comprising the amino acid sequence of SEQ ID NO: 9 (04D01, 11G01, 12A07, 22A02); and a CDR$_{L3}$ comprising the amino acid sequence of SEQ ID NO: 29 (11G01).

In some embodiments, the antibody comprises an immunoglobulin light chain variable region comprising: a CDR$_{L1}$ comprising the amino acid sequence of SEQ ID NO: 44 (18H02); a CDR$_{L2}$ comprising the amino acid sequence of SEQ ID NO: 45 (18H02); and a CDR$_{L3}$ comprising the amino acid sequence of SEQ ID NO: 46 (18H02).

In one embodiment, the antibody comprises an immunoglobulin light chain variable region comprising: a CDR$_{L1}$ comprising the amino acid sequence of SEQ ID NO: 60 (24C05); a CDR$_{L2}$ comprising the amino acid sequence of SEQ ID NO: 61 (24C05); and a CDR$_{L3}$ comprising the amino acid sequence of SEQ ID NO: 62 (24C05).

Preferably, the CDR$_{L1}$, CDR$_{L2}$, and CDR$_{L3}$ sequences are interposed between human or humanized immunoglobulin FRs. The antibody can be an intact antibody or an antigen-binding antibody fragment.

In some embodiments, the antibody comprises: (a) an IgG heavy chain variable region comprising the structure CDR$_{H1}$-CDR$_{H2}$-CDR$_{H3}$ and (b) an IgG light chain variable region comprising the structure CDR$_{L1}$-CDR$_{L2}$-CDR$_{L3}$, wherein the heavy chain variable region and the light chain variable region together define a single binding site for binding human ErbB3. The CDR$_{H1}$ is an amino acid sequence selected from the group consisting of SEQ ID NO: 5 (04D01), SEQ ID NO:15 (09D03), SEQ ID NO: 25 (11G01), SEQ ID NO: 34 (12A07), SEQ ID NO: 41 (18H02), SEQ ID NO: 51 (22A02), SEQ ID NO: 57 (24C05), and SEQ ID NO: 75 (24C05); the CDR$_{H2}$ is an amino acid sequence selected from the group consisting of SEQ ID NO: 6 (04D01), SEQ ID NO:16 (09D03), SEQ ID NO: 26 (11G01), SEQ ID NO: 35 (12A07), SEQ ID NO: 42 (18H02), SEQ ID NO: 52 (22A02), SEQ ID NO: 58 (24C05), and SEQ ID NO: 148 (Sh24C05 Hv3-11 N62S); and the CDR$_{H3}$ is an amino acid sequence selected from the group consisting of SEQ ID NO: 7 (04D01), SEQ ID NO: 17 (09D03), SEQ ID NO: 27 (11G01), SEQ ID NO: 36 (12A07, 22A02), SEQ ID NO: 43 (18H02), and SEQ ID NO: 59 (24C05). The CDR$_{L1}$ is an amino acid sequence selected from the group consisting of SEQ ID NO: 8 (04D01, 12A07, 22A02), SEQ ID NO: 18 (09D03), SEQ ID NO: 28 (11G01), SEQ ID NO: 44 (18H02), and SEQ ID NO: 60 (24C05); the CDR$_{L2}$ is an amino acid sequence selected from the group consisting of SEQ ID NO: 9 (04D01, 11G01, 12A07, 22A02), SEQ ID NO: 19 (09D03), SEQ ID NO: 45 (18H02), and SEQ ID NO: 61 (24C05); and the CDR$_{L3}$ is an amino acid sequence selected from the group consisting of SEQ ID NO: 10 (04D01, 12A07, 22A02), SEQ ID NO: 20 (09D03), SEQ ID NO: 29 (11G01), SEQ ID NO: 46 (18H02), and SEQ ID NO: 62 (24C05).

In another embodiment, the antibody comprises an immunoglobulin heavy chain variable region selected from the group consisting of SEQ ID NO: 2 (04D01), SEQ ID NO: 12 (09D03), SEQ ID NO: 22 (11G01), SEQ ID NO: 31 (12A07), SEQ ID NO: 38 (18H02), SEQ ID NO: 48 (22A02), SEQ ID NO: 54 (24C05), and SEQ ID NO: 154 (Sh24C05 Hv3-11 N62S), and an immunoglobulin light chain variable region selected from the group consisting of SEQ ID NO: 4 (04D01), SEQ ID NO: 14 (09D03), SEQ ID NO: 24 (11G01), SEQ ID NO: 33 (12A07), SEQ ID NO: 40 (18H02), SEQ ID NO: 50 (22A02), SEQ ID NO: 56 (24C05), SEQ ID NO: 166 (Sh24C05 Kv1-16), and SEQ ID NO: 168 (Sh24C05 Kv1-17).

In another embodiment, the antibody comprises an immunoglobulin heavy chain variable region comprising the amino acid sequence of SEQ ID NO: 2 (04D01), and an immunoglobulin light chain variable region comprising the amino acid sequence of SEQ ID NO: 4 (04D01).

In another embodiment, the antibody comprises an immunoglobulin heavy chain variable region comprising the amino acid sequence of SEQ ID NO: 12 (09D03), and an immunoglobulin light chain variable region comprising the amino acid sequence of SEQ ID NO: 14 (09D03).

In another embodiment, the antibody comprises an immunoglobulin heavy chain variable region comprising the amino acid sequence of SEQ ID NO: 22 (11G01), and an immunoglobulin light chain variable region comprising the amino acid sequence of SEQ ID NO: 24 (11G01).

In another embodiment, the antibody comprises an immunoglobulin heavy chain variable region comprising the amino acid sequence of SEQ ID NO: 31 (12A07), and an immunoglobulin light chain variable region comprising the amino acid sequence of SEQ ID NO: 33 (12A07).

In another embodiment, the antibody comprises an immunoglobulin heavy chain variable region comprising the amino acid sequence of SEQ ID NO: 38 (18H02), and an immunoglobulin light chain variable region comprising the amino acid sequence of SEQ ID NO: 40 (18H02).

In another embodiment, the antibody comprises an immunoglobulin heavy chain variable region comprising the amino acid sequence of SEQ ID NO: 48 (22A02), and an immunoglobulin light chain variable region comprising the amino acid sequence of SEQ ID NO: 50 (22A02).

In another embodiment, the antibody comprises an immunoglobulin heavy chain variable region comprising the amino acid sequence of SEQ ID NO: 54 (24C05), and an immunoglobulin light chain variable region comprising the amino acid sequence of SEQ ID NO: 56 (24C05).

In another embodiment, the antibody comprises an immunoglobulin heavy chain variable region comprising the amino acid sequence of SEQ ID NO: 154 (Sh24C05 Hv3-11 N62S), and an immunoglobulin light chain variable region comprising the amino acid sequence of SEQ ID NO: 166 (Sh24C05 Kv1-16).

In another embodiment, the antibody comprises an immunoglobulin heavy chain variable region comprising the amino acid sequence of SEQ ID NO: 154 (Sh24C05 Hv3-11 N62S), and an immunoglobulin light chain variable region comprising the amino acid sequence of SEQ ID NO: 168 (Sh24C05 Kv1-17).

In other embodiments, the antibody comprises (i) an immunoglobulin heavy chain selected from the group consisting of SEQ ID NO: 109 (04D01), SEQ ID NO: 113 (09D03), SEQ ID NO: 117 (11G01), SEQ ID NO: 121 (12A07), SEQ ID NO: 125 (18H02), SEQ ID NO: 129 (22A07), SEQ ID NO: 133 (24C05), SEQ ID NO: 190 (Sh24C05 Hv3-11 N62S IgG1), and SEQ ID NO: 192 (Sh24C05 Hv3-11 N62S IgG2), and (ii) an immunoglobulin light chain selected from the group consisting of SEQ ID NO: 111 (04D01), SEQ ID NO: 115 (09D03), SEQ ID NO: 119 (11G01), SEQ ID NO: 123 (12A07), SEQ ID NO: 127 (18H02), SEQ ID NO: 131 (22A07), SEQ ID NO: 135 (24C05), SEQ ID NO: 204 (Sh24C05 Kv1-16 kappa), and SEQ ID NO: 206 (Sh24C05 Kv1-17 kappa).

In another embodiment, the antibody comprises an immunoglobulin heavy chain comprising the amino acid sequence of SEQ ID NO: 109 (04D01), and an immunoglobulin light chain comprising the amino acid sequence of SEQ ID NO: 111 (04D01).

In another embodiment, the antibody comprises an immunoglobulin heavy chain comprising the amino acid sequence of SEQ ID NO: 113 (09D03), and an immunoglobulin light chain comprising the amino acid sequence of SEQ ID NO: 115 (09D03).

In another embodiment, the antibody comprises an immunoglobulin heavy chain comprising the amino acid sequence of SEQ ID NO: 117 (11G01), and an immunoglobulin light chain comprising the amino acid sequence of SEQ ID NO: 119 (11G01).

In another embodiment, the antibody comprises an immunoglobulin heavy chain comprising the amino acid sequence of SEQ ID NO: 121 (12A07), and an immunoglobulin light chain comprising the amino acid sequence of SEQ ID NO: 123 (12A07).

In another embodiment, the antibody comprises an immunoglobulin heavy chain comprising the amino acid sequence of SEQ ID NO: 125 (18H02), and an immunoglobulin light chain comprising the amino acid sequence of SEQ ID NO: 127 (18H02).

In another embodiment, the antibody comprises an immunoglobulin heavy chain comprising the amino acid sequence of SEQ ID NO: 129 (22A02), and an immunoglobulin light chain comprising the amino acid sequence of SEQ ID NO: 131 (22A02).

In another embodiment, the antibody comprises an immunoglobulin heavy chain comprising the amino acid sequence of SEQ ID NO: 133 (24C05), and an immunoglobulin light chain comprising the amino acid sequence of SEQ ID NO: 135 (24C05).

In another embodiment, the antibody comprises an immunoglobulin heavy chain comprising the amino acid sequence of SEQ ID NO: 190 (Sh24C05 Hv3-11 N62S IgG1), and an immunoglobulin light chain comprising the amino acid sequence of SEQ ID NO: 204 (Sh24C05 Kv1-16 kappa).

In another embodiment, the antibody comprises an immunoglobulin heavy chain comprising the amino acid sequence of SEQ ID NO: 192 (Sh24C05 Hv3-11 N62S IgG2), and an immunoglobulin light chain comprising the amino acid sequence of SEQ ID NO: 204 (Sh24C05 Kv1-16 kappa).

In another embodiment, the antibody comprises an immunoglobulin heavy chain comprising the amino acid sequence of SEQ ID NO: 190 (Sh24C05 Hv3-11 N62S IgG1), and an immunoglobulin light chain comprising the amino acid sequence of SEQ ID NO: 206 (Sh24C05 Kv1-17 kappa).

In another embodiment, the antibody comprises an immunoglobulin heavy chain comprising the amino acid sequence of SEQ ID NO: 192 (Sh24C05 Hv3-11 N62S IgG2), and an immunoglobulin light chain comprising the amino acid sequence of SEQ ID NO: 206 (Sh24C05 Kv1-17 kappa).

As used herein, unless otherwise indicated, the term "antibody" means an intact antibody (e.g., an intact monoclonal antibody) or antigen-binding fragment of an antibody (e.g., an antigen-binding fragment of a monoclonal antibody), including an intact antibody or antigen-binding fragment that has been modified, engineered, or chemically conjugated. Examples of antibodies that have been modified or engineered include chimeric antibodies, humanized antibodies, and multispecific antibodies (e.g., bispecific antibodies). Examples of antigen-binding fragments include Fab, Fab', (Fab')$_2$, Fv, single chain antibodies (e.g., scFv), minibodies, and diabodies. An example of a chemically conjugated antibody is an antibody conjugated to a toxin moiety.

FIG. 1 shows a schematic representation of an intact monoclonal antibody that contains four polypeptide chains. Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($CH_1$, $CH_2$ and $CH_3$ in FIG. 1). The variable regions determine the specificity of the antibody.

Each variable region contains three hypervariable regions known as complementarity determining regions (CDRs) flanked by four relatively conserved regions known as framework regions (FRs). The three CDRs, referred to as $CDR_1$, $CDR_2$, and $CDR_3$, contribute to the antibody binding specificity.

In certain embodiments, an isolated antibody that binds human ErbB3 comprises an immunoglobulin heavy chain variable region comprising an amino acid sequence that is at least 70%, 75%, 80%, 85%, 90%, 95%, 98%, or 99% identical to the entire variable region or the framework region sequence of SEQ ID NO: 2 (04D01), SEQ ID NO: 12 (09D03), SEQ ID NO: 22 (11G01), SEQ ID NO: 31 (12A07), SEQ ID NO: 38 (18H02), SEQ ID NO: 48 (22A02), SEQ ID NO: 54 (24C05), and SEQ ID NO: 154 (Sh24C05 Hv3-11 N62S).

In certain embodiments, an isolated antibody that binds human ErbB3 comprises an immunoglobulin light chain variable region comprising an amino acid sequence that is at least 70%, 75%, 80%, 85%, 90%, 95%, 98%, or 99% identical to the entire variable region or the framework region sequence of SEQ ID NO: 4 (04D01), SEQ ID NO: 14 (09D03), SEQ ID NO: 24 (11G01), SEQ ID NO: 33 (12A07), SEQ ID NO: 40 (18H02), SEQ ID NO: 50 (22A02), SEQ ID NO: 56 (24C05), SEQ ID NO: 166 (Sh24C05 Kv1-16), and SEQ ID NO: 168 (Sh24C05 Kv1-17).

In each of the foregoing embodiments, it is contemplated herein that immunoglobulin heavy chain variable region sequences and/or light chain variable region sequences that together bind human ErbB3 may contain amino acid alterations (e.g., at least 1, 2, 3, 4, 5, or 10 amino acid substitutions, deletions, or additions) in the framework regions of the heavy and/or light chain variable regions.

In some embodiments, an isolated antibody binds hErbB3 with a $K_D$ of 350 pM, 300 pM, 250 pM, 200 pM, 150 pM, 100 pM, 75 pM, 50 pM, 20 pM, 10 pM or lower. Unless otherwise specified, $K_D$ values are determined by surface plasmon resonance methods. The surface plasmon resonance methods can be performed using the conditions described, for example, in Examples 3 and 12, where the measurements were performed at 25° C. and 37° C., respectively.

In some embodiments, the antibodies inhibit hErbB3 binding to NRG1-β1. For example, the antibodies can have an $IC_{50}$ (concentration at 50% of maximum inhibition) of about 5 nM, 2 nM or lower, when assayed using the protocols described in Examples 4 and 13.

II. Production of Antibodies

Methods for producing antibodies disclosed herein are known in the art. For example, DNA molecules encoding light chain variable regions and heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding the antibodies disclosed herein can be incorporated (ligated) into expression vectors, which can be introduced into host cells through conventional transfection or transformation techniques. Exemplary host cells are E. coli cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If a DNA construct encoding an antibody disclosed herein is to be expressed in eukaryotic host cells, e.g., CHO cells, it is first inserted into an expression vector containing a suitable eukaryotic promoter, a secretion signal, IgG enhancers, and various introns. This expression vector optionally contains sequences encoding all or part of a constant region, enabling an entire, or a part of, a heavy and/or light chain to be expressed. In some embodiments, a single expression vector contains both heavy and light chain variable regions to be expressed.

The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A method of producing a polypeptide comprising an immunoglobulin heavy chain variable region or a polypeptide comprising an immunoglobulin light chain variable region may comprise growing a host cell transfected with an expression vector under conditions that permits expression of the polypeptide comprising the immunoglobulin heavy chain variable region or the polypeptide comprising the immunoglobulin light chain variable region. The polypeptide comprising a heavy chain variable region or the polypeptide comprising the light chain variable region then may be purified using techniques well known in the art, e.g., affinity tags such as glutathione-S-transferase (GST) and histidine tags.

A method of producing a monoclonal antibody that binds human ErbB3, or an antigen-binding fragment of the antibody, may comprise growing a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial chains), under conditions that permit expression of both chains. The intact antibody (or antigen-binding fragment) can be harvested and purified using techniques well known in the art, e.g., Protein A, Protein G, affinity tags such as glutathione-S-transferase (GST) and histidine tags. It is within ordinary skill in the art to express the heavy chain and the light chain from a single expression vector or from two separate expression vectors.

III. Modifications to the Antibodies

Methods for reducing or eliminating the antigenicity of antibodies and antibody fragments are known in the art. When the antibodies are to be administered to a human, the antibodies preferably are "humanized" to reduce or eliminate antigenicity in humans. Preferably, a humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, PROC. NAT. ACAD. SCI. 81:6851-6855, Neuberger et al., 1984, NATURE 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-ErbB3 antibody are grafted onto human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. IMMUNOL 169:1119-1125.

Other methods to reduce immunogenicity include "reshaping," "hyperchimerization," and "veneering/resurfacing." See, e.g., Vaswami et al., 1998, ANNALS OF ALLERGY, ASTHMA, & IMMUNOL. 81:105; Roguska et al., 1996, PROT. ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. Nos. 5,766,886; 5,770,196; 5,821,123; and 5,869,619.

Any suitable approach, including any of the above approaches, can be used to reduce or eliminate human immunogenicity of an antibody disclosed herein.

Methods of making multispecific antibodies are known in the art. Multi-specific antibodies include bispecific antibodies. Bispecific antibodies are antibodies that have binding specificities for at least two different epitopes. Exemplary bispecific antibodies bind to two different epitopes of the antigen of interest. Bispecific antibodies can be prepared as full length antibodies or antibody fragments (e.g., F(ab')$_2$ bispecific antibodies and diabodies) as described, for example, in Milstein et al., NATURE 305:537-539 (1983), WO 93/08829, Traunecker et al., EMBO J., 10:3655-3659 (1991), WO 94/04690, Suresh et al., METHODS IN ENZYMOLOGY, 121:210 (1986), WO96/27011, Brennan et al., SCIENCE, 229: 81 (1985), Shalaby et al., J. EXP. MED., 175: 217-225 (1992), Kostelny et al., J. IMMUNOL., 148(5):1547-1553 (1992), Hollinger et al., PNAS, 90:6444-6448, Gruber et al., J. IMMUNOL., 152:5368 (1994), Wu et al., NAT. BIOTECHNOL., 25(11): 1290-1297, U.S. Patent Publication No. 2007/0071675, and Bostrom et al., SCIENCE 323:1640-1644 (2009).

In some embodiments, the antibody is conjugated to an effector agent such as a small molecule toxin or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

IV. Use of the Antibodies

The antibodies disclosed herein can be used to treat various forms of cancer, e.g., breast, ovarian, prostate, cervical, colorectal, lung (e.g., non-small cell lung cancer), pancreatic, gastric, skin, kidney, head and neck, and schwannoma cancers. The cancer cells are exposed to a therapeutically effective amount of the antibody so as to inhibit or reduce proliferation of the cancer cell. In some embodiments, the antibodies inhibit cancer cell proliferation by at least 40%, 50%, 60%, 70%, 80%, 90%, 95%, 98%, 99%, or 100%.

In some embodiments, the antibody inhibits or reduces proliferation of a tumor cell by inhibiting binding of human ErbB3 to an ErbB3 ligand, e.g., Neuregulin/Heregulin especially NRGβ1/NRG1-β1/NRGβ1/HRGβ1 and NRGα1/NRG1-α1/NRGα1/HRGα1. The antibody can be used in a method to inhibit tumor growth in a human patient. The method comprises administering to the patient a therapeutically effective amount of the antibody.

Cancers associated with ErbB3 overexpression and/or activation include breast cancer, ovarian cancer, prostate cancer, cervical cancer, lung cancer (e.g., non-small cell lung cancer), some forms of brain cancer (e.g., schwannoma), melanomas, skin, kidney, and gastrointestinal cancers (e.g., colorectal, pancreatic, gastric, head and neck).

As used herein, "treat, "treating" and "treatment" mean the treatment of a disease in a mammal, e.g., in a human.

This includes: (a) inhibiting the disease, i.e., arresting its development; and (b) relieving the disease, i.e., causing regression of the disease state; and (c) curing the disease.

Generally, a therapeutically effective amount of active component is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount and the disease being treated. Exemplary dosing frequencies are once per day, once per week and once every two weeks. A preferred route of administration is parenteral, e.g., intravenous infusion. Formulation of monoclonal antibody-based drugs is within ordinary skill in the art. In some embodiments, the monoclonal antibody is lyophilized and reconstituted in buffered saline at the time of administration.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods well known in the pharmaceutical art. For example, see *Remington's Pharmaceutical Sciences*, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

EXAMPLES

The following Examples are merely illustrative and are not intended to limit the scope or content of the invention in any way.

Example 1—Production of Anti-hErbB3 Monoclonal Antibodies

Immunizations, fusions, and primary screens were conducted at Maine Biotechnology Services Inc. following the Repetitive Immunization Multiple Sites (RIMMS) protocol. Three AJ mice and three Balb/c mice were immunized with recombinant human ErbB3/Fc (R&D Systems, Cat. No. 348-RB). Two sets of immunization were performed with either cleaved rhErbB3 (Immunization A) or with cleaved rhErbB3 cross-linked to its ligand, recombinant human NRG1-β1/HRG1-β1-EGF domain (R&D Systems, Cat. No. 396-HB) (Immunization B). Two AJ mice per immunization with sera displaying high anti-ErbB3 activity by Enzyme Linked Immunosorbent Assay (ELISA) were chosen for subsequent fusion. Spleens and lymph nodes from the appropriate mice were harvested. B-cells then were harvested and fused with a myeloma line. Fusion products were serially diluted onto forty 96-well plates to near clonality. A total of 5280 supernatants from the resulting fusions were screened for binding to recombinant rhErbB3/Fc, using ELISA. The same supernatants were also screened for their binding to human ErbB3 overexpressed in CHO cells (by Mesoscale electrochemiluminescence assay). Three hundred supernatants identified as containing antibodies against ErbB3 were further characterized by in vitro biochemical and cell-based assays as discussed below. A panel of hybridomas was selected, and the hybridomas were subcloned and expanded. Hybridoma cell lines were transferred to BioXCell (formerly Bio-Express) for antibody expression and purification by affinity chromatography on Protein G resin under standard conditions.

Anti-hErbB3 monoclonal antibody 04D01 was generated from Immunization A described above. Anti-hErbB3 monoclonal antibodies 09D03, 11G01, 12A07, 18H02, 22A02 and 24C05 were generated from Immunization B described above.

Example 2—Sequence Analysis of Anti-hErbB3 Monoclonal Antibodies

The light-chain isotype and heavy chain isotype of each monoclonal antibody in Example 1 was determined using the ISOSTRIP® Mouse Monoclonal Antibody Isotyping Kit according the manufacturer's instructions (Roche Applied Science). All antibodies were determined to be Kappa light chain and IgG1 or IgG2b IgG heavy chain.

The heavy and light chain variable regions of the mouse monoclonal antibodies were sequenced using 5' RACE (Rapid Amplification of cDNA Ends). Total RNA was extracted from each monoclonal hybridoma cell line using the RNEASY® Miniprep kit according to the vendor's instructions (Qiagen). Full-length first strand cDNA containing 5' ends was generated using either the GENERACER™ Kit (Invitrogen) or SMARTER™ RACE cDNA Amplification Kit (Clontech) according to the manufacturer's instructions using random primers for 5' RACE.

The variable regions of the Kappa and Heavy (IgG1 or IgG2b) IgG chains were amplified by PCR, using KOD Hot Start Polymerase (Novagen) or Advantage 2 Polymerase Mix (Clontech) according to the manufacturer's instructions. For amplification of 5' cDNA ends in conjunction with the GENERACER™ Kit, the GENERACER™ 5' Primer, 5' cgactggagcacgaggacactga 3' (SEQ ID NO: 136) (Invitrogen) was used as a 5' primer. For amplification of 5' cDNA ends in conjunction with the SMARTER™ RACE cDNA Amplification Kit, the Universal Primer Mix A primer (Clontech), a mix of 5'CTAATACGACTCACTATAGGGCAAGCAGTGGTATCAACGCAGAGT 3' (SEQ ID NO: 137) and 5' CTAATACGACTCACTATAGGGC 3' (SEQ ID NO: 138), was used as a 5' primer. Heavy chain variable regions were amplified using the above 5' primers and a 3' IgG1 Constant Region specific primer, either 5' TATGCAAGGCTTACAACCACA 3' (SEQ ID NO: 139) or 5' GCCAGTGGATAGACAGATGGGGGTGTCG 3' (SEQ ID NO: 140). IgG2b sequences were amplified with either 5' AGGACAGGGGTTGATTGTTGA 3' (SEQ ID NO: 141), 5' GGCCAGTGGATAGACTGATGGGGGTGTTGT 3' (SEQ ID NO: 142), or 5' GGAGGAACCAGTTGTATCTCCACACCCA 3' (SEQ ID NO: 143). Kappa chain variable regions were amplified with the above 5' primers and a 3' Kappa Constant Region specific primer, either 5' CTCATTCCTGTTGAAGCTCTTGACAAT 3' (SEQ ID NO: 144) or 5' CGACTGAGGCACCTCCAGATGTT 3' (SEQ ID NO: 145).

Individual PCR products were isolated by agarose gel electrophoresis and purified using the QIAQUICK® Gel Purification kit according to the manufacturer's instructions (Qiagen). The PCR products were subsequently cloned into the PCR®4BLUNT plasmid using the ZERO BLUNT® TOPO® PCR Cloning Kit according to the manufacturer's instructions (Invitrogen) and transformed into DH5-α bacteria (Invitrogen) through standard molecular biology techniques. Plasmid DNA isolated from transformed bacterial clones was sequenced using M13 Forward (5' GTAAAACGACGGCCAGT 3') (SEQ ID NO: 146) and M13 Reverse primers (5' CAGGAAACAGCTATGACC 3') (SEQ ID NO: 147) by Beckman Genomics, using standard dideoxy DNA sequencing methods to identify the sequence of the variable region sequences. The sequences were analyzed using Vector NTI software (Invitrogen) and the IMGT/V-Quest software to identify and confirm variable region sequences.

The nucleic acid sequences encoding and the protein sequences defining variable regions of the murine monoclonal antibodies are summarized below (amino terminal signal peptide sequences are not shown). CDR sequences (Kabat definition) are shown in bold/underlined in the amino acid sequences.

Nucleic Acid Sequence Encoding the Heavy Chain Variable Region of the 04D01 Antibody (SEQ ID NO: 1)

```
  1 caggtccaac tgcagcagcc tggggctgaa ctggtgaggc ctgggacttc agtgaagttg
 61 tcctgcaagg cttctggcta caccttcacc agccactggt tgcactgggt gaagcagagg
121 cctggacaag gccttgagtg gatcggagtg cttgatcctt ctgatttta tagtaactac
181 aatcaaaact tcaagggcaa ggccacattg actgtagaca catcctccag cacagcctac
241 atgcagctca gcagcctgac atctgaggac tctgcggtct attactgtgc acgaggccta
301 ctatccgggg actatgctat ggactactgg ggtcaaggaa cctcagtcac cgtctcctca
```

Protein Sequence Defining the Heavy Chain Variable Region of the 04D01 Antibody (SEQ ID NO: 2)

```
  1 qvqlqqpgae lvrpgtsvkl sckasgytft shwlhwvkqr pgqglewigv ldpsdfysny
 61 nqnfkgkatl tvdtssstay mqlssltsed savyycargl lsgdyamdyw gqgtsvtvss
```

Nucleic Acid Sequence Encoding the Kappa Chain Variable Region of the 04D01 Antibody (SEQ ID NO: 3)

```
  1 gatgttttga tgacccaaat tccactctcc ctgcctgtca gtcttggaga tcaagcctcc
 61 atctcttgca gatctagtca gagcattgta catagtaatg gaaacaccta tttagaatgg
121 tacctgcaga accaggcca gtctccaaag tcctgatct acaaagtttc taaccgattt
181 tctggggtcc cagacaggtt cagtggcagt ggatcaggga cagatttcac actcaagatc
241 agcagagtgg aggctgagga tctgggagtt tattactgct ttcaaggttc atatgttccg
301 tggacgttcg gtggaggcac caagctggaa atcaaa
```

Protein Sequence Defining the Kappa Chain Variable Region of the 04D01 Antibody (SEQ ID NO: 4)

```
  1 dvlmtgipls lpvslgdgas iscrssqsiv hsngntylew ylqkpggspk sliykvsnrf
 61 sgvpdrfsgs gsgtdftlki srveaedlgv yycfqgsyvp wtfgggtkle ik
```

Nucleic Acid Sequence Encoding the Heavy Chain Variable Region of the 09D03 Antibody (SEQ ID NO: 11)

```
  1 caggttactc taaaagagtc tggccctggg atattgcggc cctcccagac cctcagtctg
 61 acttgttctt tctctgggtt ttcactgagc acttttggtt tgagtgtagg ctggattcgt
121 cagccttcag ggaagggtct ggagtggctg gcacacattt ggtgggatga tgataagtac
181 tataacccag cccttaagag tcggctcaca atctccaagg atacctccaa aaaccaggta
241 ttcctcaaga tcgccaatgt ggacactgca gatactgcca catactactg tgctcgaata
301 ggggcggacg cccttccttt tgactactgg ggccaaggca ccactctcac agtctcctca
```

Protein Sequence Defining the Heavy Chain Variable Region of the 09D03 Antibody (SEQ ID NO: 12)

```
  1 qvtlkesgpg ilrpsqtlsl tcsfsgfsls tfglsvgwir qpsgkglewl ahiwwdddky
 61 ynpalksrlt iskdtsknqv flkianvdta dtatyycari gadalpfdyw gqgttltvss
```

Nucleic Acid Sequence Encoding the Kappa Chain Variable Region of the 09D03 Antibody (SEQ ID NO: 13)

```
  1 gatattgtgt tgactcagac tgcaccctct gtacctgtca ctcctggaga gtcagtatcc
 61 atctcctgca ggtctagtaa gagtctcctg catagtaatg caacacttta cttgtattgg
121 ttcctgcaga ggccaggcca gtctcctcag ctcctgatat atcggatgtc aaccttgcc
181 tcaggagtcc cagacaggtt cagtggcagt gggtcaggaa ctgctttcac actgagaatc
241 gtagagtgg aggctgagga tgtgggtgtt tattactgta tgcaacatct agaatatcct
301 ttcacgttcg gctcggggac aaagttggaa ataaaa
```

Protein Sequence Defining the Kappa Chain Variable Region of the 09D03 Antibody (SEQ ID NO: 14)

```
  1 divltqtaps vpvtpgesys iscrssksll hsngntylyw flqrpgqspq lliyrmsnla
 61 sgvpdrfsgs gsgtaftlri srveaedvgv yycmqhleyp ftfgsgtkle ik
```

Nucleic Acid Sequence Encoding the Heavy Chain Variable Region of the 11G01 Antibody (SEQ ID NO: 21)

```
  1 caggttcagc tgcaacagtc tgacgctgag ttggtgaaac ctggagcttc agtgaagata
 61 tcctgcaagg tttctggcta caccttcact gaccatatta ttcactggat gaagcagagg
121 cctgaacagg gcctggaatg gattggatat atttatccta gagatggtta tattaagtac
181 aatgagaagt tcaagggcaa ggccacattg actgcagaca atcctccag cacagcctac
```

```
241 atgcaggtca acagcctgac atctgaggac tctgcagtct atttctgtgc aagggttac 301 tattatgcta tggactactg gggtcaagga acctcagtca ccgtctcctc a
```

Protein Sequence Defining the Heavy Chain Variable Region of the 11G01 Antibody (SEQ ID NO: 22)

```
 1 qvqlqqsdae lvkpgasvki sckvsgytft dhiihwmkqr peqglewigy iyprdgyiky 61 nekfkgkatl tadkssstay mqvnsltsed savyfcagy yyamdywgqg tsvtvss
```

Nucleic Acid Sequence Encoding the Kappa Chain Variable Region of the 11G01 Antibody (SEQ ID NO: 23)

```
  1 gatgttttga tgcccaaac tccactctcc ctgcctgtca gtcttggaga tcaagcctcc 61 atctcttgca gatctagtca gagcattgta catagtattg aaacaccta tttagaatgg 121 tacctgcaga accaggcca gtctccaaag ctcctgatct acaaagtttc caaccgattt 181 tctggggtcc cagagaggtt cagtggcagt ggatcaggga cagatttcac actcaagatc 241 agcagagtgg aggctgagga tctgggagtt tattactgct ttcaaggttc acatgttcca 301 ttcacgttcg gctcgggac aaagttggaa ataaaa
```

Protein Sequence Defining the Kappa Chain Variable Region of the 11G01 Antibody (SEQ ID NO: 24)

```
 1 dvlmtqtpls lpvslgdqas iscrssqsiv hsigntylew ylqkpgqspk lliykvsnrf 61 sgvperfsgs gsgtdftlki srveaedlgv yycfqgshvp ftfgsgtkle ik
```

Nucleic Acid Sequence Encoding the Heavy Chain Variable Region of the 12A07 Antibody (SEQ ID NO: 30)

```
  1 caggtccaac tgctgcagcc tggggctgag ctggtgaggc ctggacttc agtgaagttg 61 tcctgcaaga cttctggcta caccttctcc agctactgga tgcactgggt aaagcagagg 121 cctggacaag gccttgagtg gatcggaatg attgatcctt ctgatgttta tactaactac 181 aatccaaagt tcaagggcaa ggccacattg actgttgaca catcctccag cacagcctac 241 atgcagctca gcagcctgac atctgaggac tctgcggtct attactgtgc aagaaactac 301 tctggggact actggggcca aggcaccact ctcacagtct cctca
```

Protein Sequence Defining the Heavy Chain Variable Region of the 12A07 Antibody (SEQ ID NO: 31)

```
 1 qvqllqpgae lvrpgtsvkl scktsgytfs
   sywmhwvkqr pgqglewigm idpsdvytny 61 npkfkgkatl tvdtssstay mqlssltsed savyycarny
   sgdywgqgtt ltvss
```

Nucleic Acid Sequence Encoding the Kappa Chain Variable Region of the 12A07 Antibody (SEQ ID NO: 32)

```
  1 gatgttttga tgacccaaat tccactctcc ctgcctgtca gtcttggaga tcaagcctcc 61 atctcttgta gatctagtca gagcattgtc catagtaatg aaacaccta tttagaatgg 121 tacctgcaga accaggcca gtctccaaag ctcctgatct acaaagtttc caaccgattt 181 tctggggtcc cagacaggtt cagtggcagt ggatcaggga cagatttcac actcaagatc
```

-continued

```
241 agcagagtgg aggctgagga tctgggagtt tattactgct ttcaaggttc atatgttccg 301 tggacgttcg gtggaggcac aagctggaa atcaaa
```

Protein Sequence Defining the Kappa Chain Variable Region of the 12A07 Antibody (SEQ ID NO: 33)

```
  1 dvlmtqipls lpvslgdqas iscrssqsiv hsngntylew ylqkpgqspk lliykvsnrf

61 sgvpdrfsgs gsgtdftlki srveaedlgv yycfqgsyvp wtfgggtkle ik
```

Nucleic Acid Sequence Encoding the Heavy Chain Variable Region of the 18H02 Antibody (SEQ ID NO: 37)

```
  1 cagatccagt tggtacagtc tggacctgaa ctgaagaagc ctggagaggc agtcaagatc 61 tcctgcaagt cttctgggta taccttcaca acctatggaa tgagctgggt gaaacaggct 121 ccaggaaggg ctttaaagtg gatgggctgg ataaacacct actctggagt gccaacatat 181 gctgatgact caagggacg gtttgccttc tctttggaat cctctgccag cactgcctat 241 ttgcagatca acaacctcaa aaatgaggac acggctacat atttctgtgc aagagggagg 301 gatggttacc aagtggcctg gtttgcttac tggggccaag ggacgctggt cactgtctct 361 gca
```

Protein Sequence Defining the Heavy Chain Variable Region of the 18H02 Antibody (SEQ ID NO: 38)

```
  1 qiqlvqsgpe lkkpgeavki sckssgytft tygmswvkqa pgralkwmgw intysgvpty

61 addfkgrfaf slessastay lqinnlkned tatyfcargr dgyqvawfay wgqgtlvtvs 121 a
```

Nucleic Acid Sequence Encoding the Kappa Chain Variable Region of the 18H02 Antibody (SEQ ID NO: 39)

```
  1 gaaacaactg tgacccagtc tccagcatcc ctgtccatgg ctataggaga taaagtcacc 61 atcagatgca taaccagcac tgatattgat gatgatatga actggttcca gcagaagcca 121 ggggaacctc ctaagctcct tatttcagaa ggcaatactc ttcgtcctgg agtcccatcc 181 cgattctccg gcagtggcta tggtacagat tttatttta caattgaaaa catgctctct 241 gaagatgttg cagattacta ctgtttgcaa agtgataact gccgtacac gttcggaggg 301 gggaccaagc tggaaataaa a
```

Protein Sequence Defining the Kappa Chain Variable Region of the 18H02 Antibody (SEQ ID NO: 40)

```
  1 ettvtqspas lsmaigdkvt ircitstdid ddmnwfqqkp geppkllise gntlrpgvps 61 rfsgsgygtd fiftienmls edvadyyclq sdnlpytfgg gtkleik
```

Nucleic Acid Sequence Encoding the Heavy Chain Variable Region of the 22A02 Antibody (SEQ ID NO: 47)

```
  1 caggtccaac tgcagcagcc tggggctgag ctggtgaggc ctggacttc agtgaagttg 61 tcctgcaagg cttctggcta caccttcacc aactactgga tgcactgggt aaagcagagg
```

-continued
```
121 cctggacaag gccttgagtg gatcggaatg attgatcctt ctgatagtta tactaactac 181 aatccaaagt tcaagggtaa ggccacattg actgtagaca catcctccag cacagcctac 241 atgcagctca gcagcctgac atctgaggac tctgcggtct attactgtgc aagaaactac 301 tctggggact actggggcca aggcaccact ctcacagtct cctca
```

Protein Sequence Defining the Heavy Chain Variable Region of the 22A02 Antibody (SEQ ID NO: 48)

```
  1 qvqlqqpgae lvrpgtsvkl sckasgytft nywmhwvkqr pgqglewigm idpsdsytny 61 npkfkgkatl tvdtssstay mqlssltsed savyycarny sgdywgqgtt ltvss
```

Nucleic Acid Sequence Encoding the Kappa Chain Variable Region of the 22A02 Antibody (SEQ ID NO: 49)

```
  1 gatgttttga tgacccaaac tccactctcc ctgcctgtca gtcttggaga tcaagcctcc 61 atctcttgca gatctagtca gagcattgta catagtaatg gaaacaccta tttagaatgg 121 tacctgcaga aaccaggcca gtctccaaag ctcctgatct acaaagtttc caaccgattt 181 tctggggtcc cagacaggtt cagtggcagt ggatcaggga cagatttcac actcaagatc 241 agcagagtgg aggctgagga tctgggagtt tattattgct ttcaaggttc atatgttccg 301 tggacgttcg gtggaggcac caagctggaa atcaaa
```

Protein Sequence Defining the Kappa Chain Variable Region of the 22A02 Antibody (SEQ ID NO: 50)

```
  1 dvlmtgtpls lpvslgdqas iscrssqsiv hsngntylew ylqkpgqspk lliykvsnrf 61 sgvpdrfsgs gsgtdftlki srveaedlgv yycfqgsyvp wtfgggtkle ik
```

Nucleic Acid Sequence Encoding the Heavy Chain Variable Region of the 24C05 Antibody (SEQ ID NO: 53)

```
  1 gaggtgcagc tggtggaatc tgggggaggc ttagtgaagc ctggagggtc cctgaaactc 61 tcctgtgcag cctctggatt cactttcagt gactatgcca tgtcttgggt tcgccagact 121 ccggaaaaga ggctggagtg gtcgcaacc attagtgatg gtggtactta cacctactat 181 ccagacaatg taaagggccg attcaccatc tccagagaca atgccaagaa caacctgtac 241 ctgcaaatga gccatctgaa gtctgaggac acagccatgt attactgtgc aagagaatgg 301 ggtgattacg acggatttga ctactggggc caaggcacca ctctcacagt ctcctcg
```

Protein Sequence Defining the Heavy Chain Variable Region of the 24C05 Antibody (SEQ ID NO: 54)

```
  1 evqlvesggg lvkpggslkl scaasgftfs dyamswvrqt pekrlewvat isdggtytyy 61 pdnvkgrfti srdnaknnly lqmshlksed tamyycarew gdydgfdywg qgttltvss
```

Nucleic Acid Sequence Encoding the Kappa Chain Variable Region of the 24C05 Antibody (SEQ ID NO: 55)

```
  1 gacatccaga tgacccagtc tccatcctcc ttatctgcct ctctgggaga aagagtcagt 61 ctcacttgtc gggcaagtca ggaaattagt ggttacttaa gctggcttca gcagaaacca 121 gatggaacta ttaaacgcct gatctacgcc gcatccactt tagattctgg tgtcccaaaa
```

-continued

```
181 aggttcagtg gcagtaggtc tgggtcagat tattctctca ccatcggcag ccttgagtct 241 gaagatcttg cagactatta ctgtctacaa tatgatagtt atccgtacac gttcggaggg 301 gggaccaagc tggaaataaa a
```

Protein Sequence Defining the Kappa Chain Variable Region of the 24C05 Antibody (SEQ ID NO: 56)

```
 1 diqmtqspss lsaslgervs ltcrasqeis gylswlqqkp dgtikrliya astldsgvpk 61 rfsgsrsgsd ysltigsles edladyyclq ydsypytfgg gtkleik
```

The amino acid sequences defining the immunoglobulin heavy chain variable regions for the antibodies produced in Example 1 are aligned in FIG. 2. Amino terminal signal peptide sequences (for proper expression/secretion) are not shown. CDR$_1$, CDR$_2$, and CDR$_3$ (Kabat definition) are identified by boxes. FIG. 3 shows an alignment of the separate CDR$_1$, CDR$_2$, and CDR$_3$ sequences for each antibody.

The amino acid sequences defining the immunoglobulin light chain variable regions for the antibodies in Example 1 are aligned in FIG. 4. Amino terminal signal peptide sequences (for proper expression/secretion) are not shown. CDR$_1$, CDR$_2$ and CDR$_3$ are identified by boxes. FIG. 5 shows an alignment of the separate CDR$_1$, CDR$_2$, and CDR$_3$ sequences for each antibody.

Table 1 is a concordance chart showing the SEQ ID NO. of each sequence discussed in this Example.

TABLE 1

| SEQ. ID NO. | Nucleic Acid or Protein |
|---|---|
| 1 | 04D01 Heavy Chain Variable Region-nucleic acid |
| 2 | 04D01 Heavy Chain Variable Region-protein |
| 3 | 04D01 Light (kappa) Chain Variable Region-nucleic acid |
| 4 | 04D01 Light (kappa) Chain Variable Region-protein |
| 5 | 04D01 Heavy Chain CDR$_1$ |
| 6 | 04D01 Heavy Chain CDR$_2$ |
| 7 | 04D01 Heavy Chain CDR$_3$ |
| 8 | 04D01 Light (kappa) Chain CDR$_1$ |
| 9 | 04D01 Light (kappa) Chain CDR$_2$ |
| 10 | 04D01 Light (kappa) Chain CDR$_3$ |
| 11 | 09D03 Heavy Chain Variable Region-nucleic acid |
| 12 | 09D03 Heavy Chain Variable Region-protein |
| 13 | 09D03 Light (kappa) Chain Variable Region-nucleic acid |
| 14 | 09D03 Light (kappa) Chain Variable Region-protein |
| 15 | 09D03 Heavy Chain CDR$_1$ |
| 16 | 09D03 Heavy Chain CDR$_2$ |
| 17 | 09D03 Heavy Chain CDR$_3$ |
| 18 | 09D03 Light (kappa) Chain CDR$_1$ |
| 19 | 09D03 Light (kappa) Chain CDR$_2$ |
| 20 | 09D03 Light (kappa) Chain CDR$_3$ |
| 21 | 11G01 Heavy Chain Variable Region-nucleic acid |
| 22 | 11G01 Heavy Chain Variable Region-protein |
| 23 | 11G01 Light (kappa) Chain Variable Region-nucleic acid |
| 24 | 11G01 Light (kappa) Chain Variable Region-protein |
| 25 | 11G01 Heavy Chain CDR$_1$ |
| 26 | 11G01 Heavy Chain CDR$_2$ |
| 27 | 11G01 Heavy Chain CDR$_3$ |
| 28 | 11G01 Light (kappa) Chain CDR$_1$ |
| 9 | 11G01 Light (kappa) Chain CDR$_2$ |
| 29 | 11G01 Light (kappa) Chain CDR$_3$ |
| 30 | 12A07 Heavy Chain Variable Region-nucleic acid |
| 31 | 12A07 Heavy Chain Variable Region-protein |
| 32 | 12A07 Light (kappa) Chain Variable Region-nucleic acid |
| 33 | 12A07 Light (kappa) Chain Variable Region-protein |
| 34 | 12A07 Heavy Chain CDR$_1$ |
| 35 | 12A07 Heavy Chain CDR$_2$ |

TABLE 1-continued

| SEQ. ID NO. | Nucleic Acid or Protein |
|---|---|
| 36 | 12A07 Heavy Chain CDR$_3$ |
| 8 | 12A07 Light (kappa) Chain CDR$_1$ |
| 9 | 12A07 Light (kappa) Chain CDR$_2$ |
| 10 | 12A07 Light (kappa) Chain CDR$_3$ |
| 37 | 18H02 Heavy Chain Variable Region-nucleic acid |
| 38 | 18H02 Heavy Chain Variable Region-protein |
| 39 | 18H02 Light (kappa) Chain Variable Region-nucleic acid |
| 40 | 18H02 Light (kappa) Chain Variable Region-protein |
| 41 | 18H02 Heavy Chain CDR$_1$ |
| 42 | 18H02 Heavy Chain CDR$_2$ |
| 43 | 18H02 Heavy Chain CDR$_3$ |
| 44 | 18H02 Light (kappa) Chain CDR$_1$ |
| 45 | 18H02 Light (kappa) Chain CDR$_2$ |
| 46 | 18H02 Light (kappa) Chain CDR$_3$ |
| 47 | 22A02 Heavy Chain Variable Region-nucleic acid |
| 48 | 22A02 Heavy Chain Variable Region-protein |
| 49 | 22A02 Light (kappa) Chain Variable Region-nucleic acid |
| 50 | 22A02 Light (kappa) Chain Variable Region-protein |
| 51 | 22A02 Heavy Chain CDR$_1$ |
| 52 | 22A02 Heavy Chain CDR$_2$ |
| 36 | 22A02 Heavy Chain CDR$_3$ |
| 8 | 22A02 Light (kappa) Chain CDR$_1$ |
| 9 | 22A02 Light (kappa) Chain CDR$_2$ |
| 10 | 22A02 Light (kappa) Chain CDR$_3$ |
| 53 | 24C05 Heavy Chain Variable Region-nucleic acid |
| 54 | 24C05 Heavy Chain Variable Region-protein |
| 55 | 24C05 Light (kappa) Chain Variable Region-nucleic acid |
| 56 | 24C05 Light (kappa) Chain Variable Region-protein |
| 57 | 24C05 Heavy Chain CDR$_1$ |
| 58 | 24C05 Heavy Chain CDR$_2$ |
| 59 | 24C05 Heavy Chain CDR$_3$ |
| 60 | 24C05 Light (kappa) Chain CDR$_1$ |
| 61 | 24C05 Light (kappa) Chain CDR$_2$ |
| 62 | 24C05 Light (kappa) Chain CDR$_3$ |

Mouse monoclonal antibody heavy chain CDR sequences (Kabat, Chothia, and IMGT definitions) are shown in Table 2.

TABLE 2

| | CDR1 | CDR2 | CDR3 |
|---|---|---|---|
| | Kabat | | |
| 04D01 | SHWLH (SEQ ID NO: 5) | VLDPSDFYSNYNQN FKG (SEQ ID NO: 6) | GLLSGDYAMDY (SEQ ID NO: 7) |
| 09D03 | TFGLSVG (SEQ ID NO: 15) | HIWWDDDKYYNPA LKS (SEQ ID NO: 16) | IGADALPFDY (SEQ ID NO: 17) |
| 11G01 | DHIIH (SEQ ID NO: 25) | YIYPRDGYIKYNEK FKG (SEQ ID NO: 26) | GYYYAMDY (SEQ ID NO: 27) |

TABLE 2-continued

|  | CDR1 | CDR2 | CDR3 |
|---|---|---|---|
| 12A07 | SYWMH (SEQ ID NO: 34) | MIDPSDVYTNYNPK FKG (SEQ ID NO: 35) | NYSGDY (SEQ ID NO: 36) |
| 18H02 | TYGMS (SEQ ID NO: 41) | WINTYSGVPTYADD FKG (SEQ ID NO: 42) | GRDGYQVAWFAY (SEQ ID NO: 43) |
| 22A02 | NYWMH (SEQ ID NO: 51) | MIDPSDSYTNYNPK FKG (SEQ ID NO: 52) | NYSGDY (SEQ ID NO: 36) |
| 24C05 | DYAMS (SEQ ID NO: 57) | TISDGGTYTYYPDN VKG (SEQ ID NO: 58) | EWGDYDGFDY (SEQ ID NO: 59) |
| Chothia |  |  |  |
| 04D01 | GYTFTSH (SEQ ID NO: 63) | DPSDFY (SEQ ID NO: 64) | GLLSGDYAMDY (SEQ ID NO: 7) |
| 09D03 | GFSLSTFGL (SEQ ID NO: 65) | WWDDD (SEQ ID NO: 66) | IGADALPFDY (SEQ ID NO: 17) |
| 11G01 | GYTFTDH (SEQ ID NO: 67) | YPRDGY (SEQ ID NO: 68) | GYYYAMDY (SEQ ID NO: 27) |
| 12A07 | GYTFSSY (SEQ ID NO: 69) | DPSDVY (SEQ ID NO: 70) | NYSGDY (SEQ ID NO: 36) |
| 18H02 | GYTFTTY (SEQ ID NO: 71) | NTYSGV (SEQ ID NO: 72) | GRDGYQVAWFAY (SEQ ID NO: 43) |
| 22A02 | GYTFTNY (SEQ ID NO: 73) | DPSDSY (SEQ ID NO: 74) | NYSGDY (SEQ ID NO: 36) |
| 24C05 | GFTFSDY (SEQ ID NO: 75) | SDGGTY (SEQ ID NO: 76) | EWGDYDGFDY (SEQ ID NO: 59) |
| IMGT |  |  |  |
| 04D01 | GYTFTSHW (SEQ ID NO: 77) | LDPSDFYS (SEQ ID NO: 78) | ARGLLSGDYAM DY (SEQ ID NO: 79) |
| 09D03 | GFSLSTFGLS (SEQ ID NO: 80) | IWWDDDK (SEQ ID NO: 81) | ARIGADALPFDY (SEQ ID NO: 82) |
| 11G01 | GYTFTDHI (SEQ ID NO: 83) | IYPRDGYI (SEQ ID NO: 84) | ARGYYYAMDY (SEQ ID NO: 85) |
| 12A07 | GYTFSSYW (SEQ ID NO: 86) | IDPSDVYT (SEQ ID NO: 87) | ARNYSGDY (SEQ ID NO: 88) |
| 18H02 | GYTFTTYG (SEQ ID NO: 89) | INTYSGVP (SEQ ID NO: 90) | ARGRDGYQVAWF AY (SEQ ID NO: 91) |
| 22A02 | GYTFTNYW (SEQ ID NO: 92) | IDPSDSYT (SEQ ID NO: 93) | ARNYSGDY (SEQ ID NO: 88) |
| 24C05 | GFTFSDYA (SEQ ID NO: 94) | ISDGGTYT (SEQ ID NO: 95) | AREWGDYDGFDY (SEQ ID NO: 96) |

Mouse monoclonal antibody Kappa light chain CDR sequences (Kabat, Chothia, and IMGT definitions) are shown in Table 3.

TABLE 3

|  | CDR1 | CDR2 | CDR3 |
|---|---|---|---|
| Kabat/Chothia |  |  |  |
| 04D01 | RSSQSIVHSNGNTYLE (SEQ ID NO: 8) | KVSNRFS (SEQ ID NO: 9) | FQGSYVPWT (SEQ ID NO: 10) |
| 09D03 | RSSKSLLHSNGNTYLY (SEQ ID NO: 18) | RMSNLAS (SEQ ID NO: 19) | MQHLEYPFT (SEQ ID NO: 20) |
| 11G01 | RSSQSIVHSIGNTYLE (SEQ ID NO: 28) | KVSNRFS (SEQ ID NO: 9) | FQGSHVPFT (SEQ ID NO: 29) |
| 12A07 | RSSQSIVHSNGNTYLE (SEQ ID NO: 8) | KVSNRFS (SEQ ID NO: 9) | FQGSYVPWT (SEQ ID NO: 10) |
| 18H02 | ITSTDIDDDMN (SEQ ID NO: 44) | EGNTLRP (SEQ ID NO: 45) | LQSDNLPYT (SEQ ID NO: 46) |
| 22A02 | RSSQSIVHSNGNTYLE (SEQ ID NO: 8) | KVSNRFS (SEQ ID NO: 9) | FQGSYVPWT (SEQ ID NO: 10) |
| 24C05 | RASQEISGYLS (SEQ ID NO: 60) | AASTLDS (SEQ ID NO: 61) | LQYDSYPYT (SEQ ID NO: 62) |
| IMGT |  |  |  |
| 04D01 | QSIVHSNGNTY (SEQ ID NO: 97) | KVS | FQGSYVPWT (SEQ ID NO: 10) |
| 09D03 | KSLLHSNGNTY (SEQ ID NO: 98) | RMS | MQHLEYPFT (SEQ ID NO: 20) |
| 11G01 | QSIVHSIGNTY (SEQ ID NO: 99) | KVS | FQGSHVPFT (SEQ ID NO: 29) |
| 12A07 | QSIVHSNGNTY (SEQ ID NO: 97) | KVS | FQGSYVPWT (SEQ ID NO: 10) |
| 18H02 | TDIDDD (SEQ ID NO: 100) | EGN | LQSDNLPYT (SEQ ID NO: 46) |
| 22A02 | QSIVHSNGNTY (SEQ ID NO: 97) | KVS | FQGSYVPWT (SEQ ID NO: 10) |
| 24C05 | QEISGY (SEQ ID NO: 101) | AAS | LQYDSYPYT (SEQ ID NO: 62) |

In Tables 2 and 3, the longest CDR sequences for the immunoglobulin heavy chain and light chain are shown in bold.

To create the complete heavy or kappa chain antibody sequences, each variable sequence above is combined with its respective constant region. For example, a complete heavy chain comprises a heavy variable sequence followed by the murine IgG1 or IgG2b heavy chain constant sequence and a complete kappa chain comprises a kappa variable sequence followed by the murine kappa light chain constant sequence.

Nucleic Acid Sequence Encoding the Murine IgG1 Heavy Chain Constant Region (SEQ ID NO: 102)

```
  1  gccaaaacga caccccatc tgtctatcca ctggcccctg gatctgctgc ccaaactaac
 61  tccatggtga ccctgggatg cctggtcaag ggctatttcc ctgagccagt gacagtgacc
121  tggaactctg gatccctgtc cagcggtgtg cacaccttcc cagctgtcct gcagtctgac
181  ctctacactc tgagcagctc agtgactgtc ccctccagca cctggcccag ccagaccgtc
241  acctgcaacg ttgcccaccc ggccagcagc accaaggtgg acaagaaaat tgtgcccagg
301  gattgtggtt gtaagccttg catatgtaca gtcccagaag tatcatctgt cttcatcttc
361  cccccaaagc ccaaggatgt gctcaccatt actctgactc ctaaggtcac gtgtgttgtg
421  gtagacatca gcaaggatga tcccgaggtc cagttcagct ggtttgtaga tgatgtggag
481  gtgcacacag ctcagacgca accccgggag gagcagttca acagcacttt ccgctcagtc
541  agtgaacttc ccatcatgca ccaggactgg ctcaatggca aggagttcaa atgcagggtc
601  aacagtgcag ctttccctgc ccccatcgag aaaaccatct ccaaaaccaa aggcagaccg
661  aaggctccac aggtgtacac cattccacct cccaaggagc agatggccaa ggataaagtc
721  agtctgacct gcatgataac agacttcttc cctgaagaca ttactgtgga gtggcagtgg
781  aatgggcagc cagcggagaa ctacaagaac actcagccca tcatggacac agatggctct
841  tacttcgtct acagcaagct caatgtgcag aagagcaact gggaggcagg aaatactttc
901  acctgctctg tgttacatga gggcctgcac aaccaccata ctgagaagag cctctcccac
961  tctcctggta aa
```

Protein Sequence Defining the Murine IgG1 Heavy Chain Constant Region (SEQ ID NO: 103)

```
  1  akttppsvyp lapgsaaqtn smvtlgclvk gyfpepvtvt wnsgslssgv htfpavlqsd
 61  lytlsssvtv psstwpsqtv tcnvahpass tkvdkkivpr dcgckpcict vpevssvfif
121  ppkpkdvlti tltpkvtcvv vdiskddpev qfswfvddve vhtaqtqpre eqfnstfrsv
181  selpimhqdw lngkefkcrv nsaafpapie ktisktkgrp kapqvytipp pkeqmakdkv
241  sltcmitdff peditvewqw ngqpaenykn tqpimdtdgs yfvysklnvq ksnweagntf
301  tcsvlheglh nhhtekslsh spgk
```

Nucleic Acid Sequence Encoding the Murine IgG2b Heavy Chain Constant Region (SEQ ID NO: 104)

```
  1  gccaaaacaa caccccatc agtctatcca ctggcccctg ggtgtggaga tacaactggt
 61  tcctctgtga ctctgggatg cctggtcaag ggctacttcc ctgagtcagt gactgtgact
121  tggaactctg gatccctgtc cagcagtgtg cacaccttcc cagctctcct gcagtctgga
181  ctctacacta tgagcagctc agtgactgtc ccctccagca cctggccaag tcagaccgtc
241  acctgcagcg ttgctcaccc agccagcagc accacggtgg acaaaaaact tgagcccagc
301  gggcccattt caacaatcaa ccctgtcct ccatgcaagg agtgtcacaa atgcccagct
361  cctaacctcg agggtggacc atccgtcttc atcttccctc caaatatcaa ggatgtactc
421  atgatctccc tgacacccaa ggtcacgtgt gtggtggtgg atgtgagcga ggatgaccca
481  gacgtccaga tcagctggtt tgtgaacaac gtggaagtac acacagctca gacacaaacc
541  catagagagg attacaacag tactatccgg gtggtcagca ccctccccat ccagcaccag
601  gactggatga gtggcaagga gttcaaatgc aaggtcaaca acaaagacct cccatcaccc
```

-continued

```
661 atcgagagaa ccatctcaaa aattaaaggg ctagtcagag ctccacaagt atacatcttg 721 ccgccaccag cagagcagtt gtccaggaaa gatgtcagtc tcacttgcct ggtcgtgggc 781 ttcaaccctg gagacatcag tgtggagtgg accagcaatg ggcatacaga ggagaactac 841 aaggacaccg caccagtcct agactctgac ggttcttact tcatatatag caagctcaat 901 atgaaaacaa gcaagtggga gaaaacagat tccttctcat gcaacgtgag acacgagggt 961 ctgaaaaatt actacctgaa gaagaccatc tcccggtctc cgggtaaa
```

Protein Sequence Defining the Murine IgG2b Heavy Chain Constant Region (SEQ ID NO: 105)

```
  1 akttppsvyp lapgcgdttg ssvtlgclvk gyfpesvtvt wnsgslsssv htfpallqsg 61 lytmsssvtv psstwpsqtv tcsvahpass ttvdkkleps gpistinpcp pckechkcpa 121 pnleggpsvf ifppnikdvl misltpkvtc vvvdvseddp dvqiswfvnn vevhtaqtqt 181 hredynstir vvstlpiqhq dwmsgkefkc kvnnkdlpsp iertiskikg lvrapqvyil 241 pppaeqlsrk dvsltclvvg fnpgdisvew tsnghteeny kdtapvldsd gsyfiyskln 301 mktskwektd sfscnvrheg lknyylkkti srspgk
```

Nucleic Acid Sequence Encoding the Murine Kappa Light Chain Constant Region (SEQ ID NO: 106)

```
  1 cgggctgatg ctgcaccaac tgtatccatc ttcccaccat ccagtgagca gttaacatct 61 ggaggtgcct cagtcgtgtg cttcttgaac aacttctacc ccagagacat caatgtcaag 121 tggaagattg atggcagtga acgacaaaat ggtgtcctga acagttggac tgatcaggac 181 agcaaagaca gcacctacag catgagcagc accctcacat tgaccaagga cgagtatgaa 241 cgacataaca gctatacctg tgaggccact cacaagacat caacttcacc cattgtcaag 301 agcttcaaca ggaatgagtg t
```

Protein Sequence Defining the Murine Kappa Light Chain Constant Region (SEQ ID NO: 107)

```
  1 radaaptvsi fppsseqlts ggasvvcfln nfyprdinvk wkidgserqn gvlnswtdqd 61 skdstysmss tltltkdeye rhnsytceat hktstspivk sfnrnec
```

The following sequences represent the actual or contemplated full length heavy and light chain sequences (i.e., containing both the variable and constant regions sequences) for each antibody described in this Example. Signal sequences for proper secretion of the antibodies are also included at the 5' end of the DNA sequences or the amino terminal end of the protein sequences. The variable region sequences can be ligated to other constant region sequences, to produce active full length IgG heavy and light chains.

Nucleic Acid Sequence Encoding the Full Length Heavy Chain Sequence (Heavy Chain Variable Region and IgG1 Constant Region) of 04D01 (SEQ ID NO: 108)

```
  1 atgggatgga gctgtatcat tgtcctcttg gtatcaacag ctacaggtgt ccactcccag 61 gtccaactgc agcagcctgg ggctgaactg gtgaggcctg ggacttcagt gaagttgtcc 121 tgcaaggctt ctggctacac cttcaccagc cactggttgc actgggtgaa gcagaggcct 181 ggacaaggcc ttgagtggat cggagtgctt gatccttctg atttttatag taactacaat 241 caaaacttca gggcaaggc cacattgact gtagacacat cctccagcac agcctacatg 301 cagctcagca gcctgacatc tgaggactct gcggtctatt actgtgcacg aggcctacta 361 tccggggact atgctatgga ctactggggt caaggaacct cagtcaccgt ctcctcagcc
```

-continued

```
 421 aaaacgacac ccccatctgt ctatccactg gcccctggat ctgctgccca aactaactcc 481 atggtgaccc tgggatgcct ggtcaagggc tatttccctg agccagtgac agtgacctgg 541 aactctggat ccctgtccag cggtgtgcac accttcccag ctgtcctgca gtctgacctc 601 tacactctga gcagctcagt gactgtcccc tccagcacct ggcccagcca gaccgtcacc 661 tgcaacgttg cccacccggc cagcagcacc aaggtggaca gaaaattgt gcccagggat 721 tgtggttgta agccttgcat atgtacagtc ccagaagtat catctgtctt catcttcccc 781 ccaaagccca aggatgtgct caccattact ctgactccta aggtcacgtg tgttgtggta 841 gacatcagca aggatgatcc cgaggtccag ttcagctggt ttgtagatga tgtggaggtg 901 cacacagctc agacgcaacc ccgggaggag cagttcaaca gcactttccg ctcagtcagt 961 gaacttccca tcatgcacca ggactggctc aatggcaagg agttcaaatg cagggtcaac 1021 agtgcagctt tccctgcccc catcgagaaa accatctcca aaccaaagg cagaccgaag 1081 gctccacagg tgtacaccat tccacctccc aaggagcaga tggccaagga taaagtcagt 1141 ctgacctgca tgataacaga cttcttccct gaagacatta ctgtggagtg gcagtggaat 1201 gggcagccag cggagaacta caagaacact cagcccatca tggacacaga tggctcttac 1261 ttcgtctaca gcaagctcaa tgtgcagaag agcaactggg aggcaggaaa tactttcacc 1321 tgctctgtgt tacatgaggg cctgcacaac caccatactg agaagagcct ctcccactct 1381 cctggtaaa
```

Protein Sequence Defining the Full Length Heavy Chain Sequence (Heavy Chain Variable Region and IgG1 Constant Region) of 04D01 (SEQ ID NO: 109)

```
  1 mgwsciivll vstatgvhsq vqlqqpgael vrpgtsvkls ckasgytfts hwlhwvkqrp 61 gqglewigvl dpsdfysnyn qnfkgkatlt vdtssstaym qlssltseds avyycargll 121 sgdyamdywg qgtsvtvssa kttppsvypl apgsaaqtns mvtlgclvkg yfpepvtvtw 181 nsgslssgvh tfpavlqsdl ytlsssvtvp sstwpsqtvt cnvahpasst kvdkkivprd 241 cgckpcictv pevssvfifp pkpkdvltit ltpkvtcvvv diskddpevq fswfvddvev 301 htaqtqpree qfnstfrsvs elpimhqdwl ngkefkcrvn saafpapiek tisktkgrpk 361 apqvytippp keqmakdkvs ltcmitdffp editvewqwn gqpaenyknt qpimdtdgsy 421 fvysklnvqk snweagntft csvlheglhn hhtekslshs pgk
```

Nucleic Acid Sequence Encoding the Full Length Light Chain Sequence (Kappa Chain Variable Region and Constant Region) of 04D01 (SEQ ID NO: 110)

```
  1 atgaagttgc ctgttaggct gttggtgctg atgttctgga ttcctgcttc cagcagtgat 61 gttttgatga cccaaattcc actctccctg cctgtcagtc ttggagatca agcctccatc 121 tcttgcagat ctagtcagag cattgtacat agtaatggaa acacctattt agaatggtac 181 ctgcagaaac caggccagtc tccaaagtcc ctgatctaca agtttctaa ccgattttct 241 ggggtcccag acaggttcag tggcagtgga tcagggacag atttcacact caagatcagc 301 agagtggagg ctgaggatct gggagtttat tactgctttc aaggttcata tgttccgtgg 361 acgttcggtg gaggcaccaa gctggaaatc aaacgggctg atgctgcacc aactgtatcc
```

-continued

```
 421 atcttcccac catccagtga gcagttaaca tctggaggtg cctcagtcgt gtgcttcttg
 481 aacaacttct accccagaga catcaatgtc aagtggaaga ttgatggcag tgaacgacaa
 541 aatggtgtcc tgaacagttg gactgatcag gacagcaaag acagcaccta cagcatgagc
 601 agcaccctca cattgaccaa ggacgagtat gaacgacata cagctatac ctgtgaggcc
 661 actcacaaga catcaacttc acccattgtc aagagcttca caggaatga gtgt
```

Protein Sequence Defining the Full Length Light Chain Sequence (Kappa Chain Variable Region and Constant Region) of 04D01 (SEQ ID NO: 111)

```
   1 mklpvrllvl mfwipasssd vlmtqiplsl pvslgdqasi scrssqsivh sngntylewy
  61 lqkpgqspks liykvsnrfs gvpdrfsgsg sgtdftlkis rveaedlgvy ycfqgsyvpw
 121 tfgggtklei kradaaptvs ifppsseqlt sggasvvcfl nnfyprdinv kwkidgserq
 181 ngvlnswtdq dskdstysms stltltkdey erhnsytcea thktstspiv ksfnrnec
```

Nucleic Acid Sequence Encoding the Full Length Heavy Chain Sequence (Heavy Chain Variable Region and IgG2b Constant Region) of 09D03 (SEQ ID NO: 112)

```
    1 atgggcaggc ttacttcttc attcctgtta ctgattgtcc ctgcatatgt cctgtcccag
   61 gttactctaa aagagtctgg ccctgggata ttgcggccct cccagaccct cagtctgact
  121 tgttctttct ctgggttttc actgagcact tttggtttga gtgtaggctg gattcgtcag
  181 ccttcaggga agggtctgga gtggctggca cacatttggt gggatgatga taagtactat
  241 aacccagccc ttaagagtcg gctcacaatc tccaaggata cctccaaaaa ccaggtattc
  301 ctcaagatcg ccaatgtgga cactgcagat actgccacat actactgtgc tcgaataggg
  361 gcggacgccc ttcctttga ctactgggc caaggcacca ctctcacagt ctcctcagcc
  421 aaaacaacac ccccatcagt ctatccactg gcccctgggt gtggagatac aactggttcc
  481 tccgtgacct ctgggtgcct ggtcaagggg tacttccctg agccagtgac tgtgacttgg
  541 aactctggat ccctgtccag cagtgtgcac accttcccag ctctcctgca gtctggactc
  601 tacactatga gcagctcagt gactgtcccc tccagcacct ggccaagtca gaccgtcacc
  661 tgcagcgttg ctcacccagc cagcagcacc acggtggaca aaaaacttga gcccagcggg
  721 cccatttcaa caatcaaccc ctgtcctcca tgcaaggagt gtcacaaatg cccagctcct
  781 aacctcgagg gtggaccatc cgtcttcatc ttccctccaa atatcaagga tgtactcatg
  841 atctccctga cacccaaggt cacgtgtgtg gtggtggatg tgagcgagga tgacccagac
  901 gtccagatca gctggtttgt gaacaacgtg gaagtacaca cagctcagac acaaacccat
  961 agagaggatt acaacagtac tatccgggtg gtcagcaccc tccccatcca gcaccaggac
 1021 tggatgagtg gcaaggagtt caaatgcaag gtgaacaaca agacctccc atcacccatc
 1081 gagagaacca tctcaaaaat taagggcta gtcagagctc acaagtata cactttgccg
 1141 ccaccagcag agcagttgtc caggaaagat gtcagtctca cttgcctggt cgtgggcttc
 1201 aaccctggag acatcagtgt ggagtggacc agcaatgggc atacagagga gaactacaag
 1261 gacaccgcac cagttcttga ctctgacggt tcttacttca tatatagcaa gctcaatatg
 1321 aaaacaagca gtgggagaa aacagattcc ttctcatgca cgtgagaca cgagggtctg
 1381 aaaaattact acctgaagaa gaccatctcc cggtctccgg taaa
```

Protein Sequence Defining the Full Length Heavy Chain Sequence (Heavy Chain Variable Region and IgG2b Constant Region) of 09D03 (SEQ ID NO: 113)

```
  1  mgrltssfll livpayvlsq vtlkesgpgi lrpsqtlslt csfsgfslst fglsvgwirq
 61  psgkglewla hiwwdddkyy npalksrlti skdtsknqvf lkianvdtad tatyycarig
121  adalpfdywg qgttltvssa kttppsvypl apgcgdttgs svtsgclvkg yfpepvtvtw
181  nsgslsssvh tfpallgsgl ytmsssvtvp sstwpsqtvt csvahpasst tvdkklepsg
241  pistinpcpp ckechkcpap nleggpsvfi fppnikdvlm isltpkvtcv vvdvseddpd
301  vqiswfvnnv evhtaqtqth redynstirv vstlpiqhqd wmsgkefkck vnnkdlpspi
361  ertiskikgl vrapqvytlp ppaeqlsrkd vsltclvvgf npgdisvewt snghteenyk
421  dtapvldsdg syfiysklnm ktskwektds fscnvrhegl knyylkktis rspgk
```

Nucleic Acid Sequence Encoding the Full Length Light Chain Sequence (Kappa Chain Variable Region and Constant Region) of 09D03 (SEQ ID NO: 114)

```
  1  atgaggtgcc tagctgagtt cctggggctg cttgtgctct ggatccctgg agccattggg
 61  gatattgtgt tgactcagac tgcaccctct gtacctgtca ctcctggaga gtcagtatcc
121  atctcctgca ggtctagtaa gagtctcctg catagtaatg caacactta cttgtattgg
181  ttcctgcaga ggccaggcca gtctcctcag ctcctgatat atcggatgtc aaccttgcc
241  tcaggagtcc cagacaggtt cagtggcagt gggtcaggaa ctgctttcac actgagaatc
301  agtagagtgg aggctgagga tgtgggtgtt tattactgta tgcaacatct agaatatcct
361  ttcacgttcg gctcgggac aaagttggaa ataaaacggg ctgatgctgc accaactgta
421  tccatcttcc caccatccag tgagcagtta acatctggag gtgcctcagt cgtgtgcttc
481  ttgaacaact ctaccccag agacatcaat gtcaagtgga gattgatgg cagtgaacga
541  caaaatggtg tcctgaacag ttggactgat caggacagca agacagcac ctacagcatg
601  agcagcaccc tcacattgac caaggacgag tatgaacgac ataacagcta cctgtgag
661  gccactcaca agacatcaac ttcacccatt gtcaagagct caacaggaa tgagtgt
```

Protein Sequence Defining the Full Length Light Chain Sequence (Kappa Chain Variable Region and Constant Region) of 09D03 (SEQ ID NO: 115)

```
  1  mrclaeflgl lvlwipgaig divltqtaps vpvtpgesvs iscrssksll hsngntylyw
 61  flqrpggspq lliyrmsnla sgvpdrfsgs gsgtaftlri srveaedvgv yycmqhleyp
121  ftfgsgtkle ikradaaptv sifppsseql tsggasvvcf lnnfyprdin vkwkidgser
181  qngvlnswtd qdskdstysm sstltltkde yerhnsytce athktstspi vksfnrnec
```

Nucleic Acid Sequence Encoding the Full Length Heavy Chain Sequence (Heavy Chain Variable Region and IgG1 Constant Region) of 11G01 (SEQ ID NO: 116)

```
  1  atggaatgga gctgggtctc tctcttcttc ctgtcagtaa ctacaggtgt ccactcccag
 61  gttcagctgc aacagtctga cgctgagttg gtgaaacctg agcttcagt gaagatatcc
121  tgcaaggttt ctggctacac cttcactgac atattattc actggatgaa gcagaggcct
181  gaacagggcc tggaatggat tggatatatt tatcctagag atggttatat taagtacaat
241  gagaagttca agggcaaggc cacattgact gcagacaaat cctccagcac agcctacatg
```

```
301 caggtcaaca gcctgacatc tgaggactct gcagtctatt tctgtgcaag gggttactat
361 tatgctatgg actactgggg tcaaggaacc tcagtcaccg tctcctcagc caaaacgaca
421 cccccatctg tctatccact ggcccctgga tctgctgccc aaactaactc catggtgacc
481 ctgggatgcc tggtcaaggg ctatttccct gagccagtga cagtgacctg aactctgga
541 tccctgtcca gcggtgtgca caccttccca gctgtcctgc agtctgacct ctacactctg
601 agcagctcag tgactgtccc ctccagcacc tggcccagcc agaccgtcac ctgcaacgtt
661 gcccacccgg ccagcagcac caaggtggac aagaaaattg tgcccaggga ttgtggttgt
721 aagccttgca tatgtacagt cccagaagta tcatctgtct tcatcttccc cccaaagccc
781 aaggatgtgc tcaccattac tctgactcct aaggtcacgt gtgttgtggt agacatcagc
841 aaggatgatc ccgaggtcca gttcagctgg tttgtagatg atgtggaggt gcacacagct
901 cagacgcaac cccgggagga gcagttcaac agcactttcc gctcagtcag tgaacttccc
961 atcatgcacc aggactggct caatggcaag gagttcaaat gcagggtcaa cagtgcagct
1021 ttccctgccc ccatcgagaa aaccatctcc aaaaccaaag gcagaccgaa ggctccacag
1081 gtgtacacca ttccacctcc caaggagcag atggccaagg ataaagtcag tctgacctgc
1141 atgataacag acttcttccc tgaagacatt actgtggagt ggcagtggaa tgggcagcca
1201 gcggagaact acaagaacac tcagcccatc atggacacag atggctctta cttcgtctac
1261 agcaagctca atgtgcagaa gagcaactgg gaggcaggaa atactttcac ctgctctgtg
1321 ttacatgagg gcctgcacaa ccaccatact gagaagagcc tctcccactc tcctggtaaa
```

Protein Sequence Defining the Full Length Heavy Chain Sequence (Heavy Chain Variable Region and IgG1 Constant Region) of 11G01 (SEQ ID NO: 117)

```
  1 mewswvslff lsvttgvhsq vqlqqsdael vkpgasvkis ckvsgytftd hiihwmkqrp
 61 eqglewigyi yprdgyikyn ekfkgkatlt adkssstaym qvnsltseds avyfcargyy
121 yamdywgqgt svtvssaktt ppsvyplapg saaqtnsmvt lgclvkgyfp epvtvtwnsg
181 slssgvhtfp avlqsdlytl sssvtvpsst wpsqtvtcnv ahpasstkvd kkivprdcgc
241 kpcictvpev ssvfifppkp kdvltitltp ktcvvvdis kddpevqfsw fvddvevhta
301 qtqpreeqfn stfrsvselp imhqdwlngk efkcrvnsaa fpapiektis ktkgrpkapq
361 vytipppkeq makdkvsltc mitdffpedi tvewqwngqp aenykntqpi mdtdgsyfvy
421 sklnvqksnw eagntftcsv lheglhnhht ekslshspgk
```

Nucleic Acid Sequence Encoding the Full Length Light Chain Sequence (Kappa Chain Variable Region and Constant Region) of 11G01 (SEQ ID NO: 118)

```
  1 atgaagttgc ctgttaggct gttggtgctg atgttctgga ttcctgcttc cagaagtgat
 61 gttttgatga cccaaactcc actctccctg cctgtcagtc ttggagatca agcctccatc
121 tcttgcagat ctagtcagag cattgtacat agtattggaa acacctattt agaatggtac
181 ctgcagaaac caggccagtc tccaaagctc ctgatctaca agtttccaa ccgattttct
241 ggggtcccag agaggttcag tggcagtgga tcagggacag atttcacact caagatcagc
301 agagtggagg ctgaggatct gggagtttat tactgctttc aaggttcaca tgttccattc
361 acgttcggct cggggacaaa gttggaaata aaacgggctg atgctgcacc aactgtatcc
421 atcttcccac catccagtga gcagttaaca tctggaggtg cctcagtcgt gtgcttcttg
```

-continued

```
481 aacaacttct accccaaaga catcaatgtc aagtggaaga ttgatggcag tgaacgacaa
541 aatggcgtcc tgaacagttg gactgatcag gacagcaaag acagcaccta cagcatgagc
601 agcaccctca cgttgaccaa ggacgagtat gaacgacata acagctatac ctgtgaggcc
661 actcacaaga tcaacttc acccattgtc aagagcttca acaggaatga gtgt
```

Protein Sequence Defining the Full Length Light Chain Sequence (Kappa Chain Variable Region and Constant Region) of 11G01 (SEQ ID NO: 119)

```
  1 mklpvrllvl mfwipasrsd vlmtqtplsl pvslgdqasi scrssqsivh signtylewy
 61 lqkpgqspkl liykvsnrfs gvperfsgsg sgtdftlkis rveaedlgvy ycfqgshvpf
121 tfgsgtklei kradaaptvs ifppsseqlt sggasvvcfl nnfypkdinv kwkidgserq
181 ngvlnswtdq dskdstysms stltltkdey erhnsytcea thktstspiv ksfnrnec
```

Nucleic Acid Sequence Encoding the Full Length Heavy Chain Sequence (Heavy Chain Variable Region and IgG1 Constant Region) of 12A07 (SEQ ID NO: 120)

```
   1 atgggatgga gctgtatcat tgtcctcttg gtatcaacag ctacatgtgt ccactcccag
  61 gtccaactgc tgcagcctgg ggctgagctg gtgaggcctg ggacttcagt gaagttgtcc
 121 tgcaagactt ctggctacac cttctccagc tactggatgc actgggtaaa gcagaggcct
 181 ggacaaggcc ttgagtggat cggaatgatt gatccttctg atgtttatac taactacaat
 241 ccaaagttca gggcaaggc cacattgact gttgacacat cctccagcac agcctacatg
 301 cagctcagca gcctgacatc tgaggactct gcggtctatt actgtgcaag aaactactct
 361 ggggactact ggggccaagg caccactctc acagtctcct cagccaaaac gacacccccca
 421 tctgtctatc cactggcccc tggatctgct gcccaaacta actccatggt gaccctggga
 481 tgcctggtca agggctattt ccctgagcca gtgacagtga cctggaactc tggatccctg
 541 tccagcggtg tgcacacctt cccagctgtc ctgcagtctg acctctacac tctgagcagc
 601 tcagtgactg tcccctccag cacctggccc agccagaccg tcacctgcaa cgttgcccac
 661 ccggccagca gcaccaaggt ggacaagaaa attgtgccca gggattgtgg ttgtaagcct
 721 tgcatatgta cagtcccaga agtatcatct gtcttcatct tccccccaaa gcccaaggat
 781 gtgctcacca ttactctgac tcctaaggtc acgtgtgttg tggtagacat cagcaaggat
 841 gatcccgagg tccagttcag ctggtttgta gatgatgtgg aggtgcacac agctcagacg
 901 caacccgggg aggagcagtt caacagcact ttccgctcag tcagtgaact tcccatcatg
 961 caccaggact ggctcaatgg caaggagttc aaatgcaggg tcaacagtgc agctttccct
1021 gcccccatcg agaaaaccat ctccaaaacc aaaggcagac cgaaggctcc acaggtgtac
1081 accattccac ctcccaagga gcagatggcc aaggataaag tcagtctgac ctgcatgata
1141 acagacttct ccctgaaga cattactgtg gagtggcagt ggaatgggca gccagcggag
1201 aactacaaga acactcagcc catcatggac acagatggc cttacttcgt ctacagcaag
1261 ctcaatgtgc agaagagcaa ctgggaggca ggaaatactt tcacctgctc tgtgttacat
1321 gagggcctgc acaaccacca tactgagaag agcctctccc actctcctgg taaa
```

Protein Sequence Defining the Full Length Heavy Chain Sequence (Heavy Chain Variable Region and IgG1 Constant Region) of 12A07 (SEQ ID NO: 121)

```
  1  mgwsciivll vstatcvhsq vqllqpgael vrpgtsvkls cktsgytfss ywmhwvkqrp
 61  gqglewigmi dpsdvytnyn pkfkgkatlt vdtssstaym qlssltseds avyycarnys
121  gdywgqgttl tvssakttpp svyplapgsa aqtnsmvtlg clvkgyfpep vtvtwnsgsl
181  ssgvhtfpav lqsdlytlss svtvpsstwp sqtvtcnvah passtkvdkk ivprdcgckp
241  cictvpevss vfifppkpkd vltitltpkv tcvvvdiskd dpevqfswfv ddvevhtaqt
301  qpreeqfnst frsvselpim hqdwlngkef kcrvnsaafp apiektiskt kgrpkapqvy
361  tipppkeqma kdkvsltcmi tdffpeditv ewqwngqpae nykntqpimd tdgsyfvysk
421  lnvqksnwea gntftcsvlh eglhnhhtek slshspgk
```

Nucleic Acid Sequence Encoding the Full Length Light Chain Sequence (Kappa Chain Variable Region and Constant Region) of 12A07 (SEQ ID NO: 122)

```
  1  atgaagttgc ctgttaggct gttggtgctg atgttctgga ttcctgcttc cagcagtgat
 61  gttttgatga cccaaattcc actctccctg cctgtcagtc ttggagatca agcctccatc
121  tcttgtagat ctagtcagag cattgtccat agtaatggaa acacctattt agaatggtac
181  ctgcagaaac caggccagtc tccaaagctc ctgatctaca agtttccaa ccgattttct
241  ggggtcccag acaggttcag tggcagtgga tcagggacag atttcacact caagatcagc
301  agagtggagg ctgaggatct gggagtttat tactgctttc aaggttcata tgttccgtgg
361  acgttcggtg gaggcaccaa gctggaaatc aaacgggctg atgctgcacc aactgtatcc
421  atcttcccac catccagtga gcagttaaca tctggaggtg cctcagtcgt gtgcttcttg
481  aacaacttct accccagaga catcaatgtc aagtggaaga ttgatggcag tgaacgacaa
541  aatggtgtcc tgaacagttg gactgatcag gacagcaaag acagcaccta cagcatgagc
601  agcaccctca cattgaccaa ggacgagtat gaacgacata cagctatac ctgtgaggcc
661  actcacaaga catcaacttc acccattgtc aagagcttca caggaatga gtgt
```

Protein Sequence Defining the Full Length Light Chain Sequence (Kappa Chain Variable Region and Constant Region) of 12A07 (SEQ ID NO: 123)

```
  1  mklpvrllvl mfwipasssd vlmtqiplsl pvslgdqasi scrssqsivh sngntylewy
 61  lqkpgqspkl liykvsnrfs gvpdrfsgsg sgtdftlkis rveaedlgvy ycfqgsyvpw
121  tfggtklei kradaaptvs ifppsseqlt sggasvvcfl nnfyprdinv kwkidgserq
181  ngvlnswtdq dskdstysms stltltkdey erhnsytcea thktstspiv ksfnrnec
```

Nucleic Acid Sequence Encoding the Full Length Heavy Chain Sequence (Heavy Chain Variable Region and IgG1 Constant Region) of 18H02 (SEQ ID NO: 124)

```
  1  atgggttggc tgtggaactt gctattcctg atggcagctg cccaaagtgc ccaagcacag
 61  atccagttgg tacagtctgg acctgaactg aagaagcctg gagaggcagt caagatctcc
121  tgcaagtctt ctgggtatac cttcacaacc tatggaatga ctgggtgaa acaggctcca
181  ggaagggctt taaagtggat gggctggata aacacctact ctggagtgcc aacatatgct
241  gatgacttca agggacggtt tgccttctct ttggaatcct ctgccagcac tgcctatttg
```

-continued

```
 301 cagatcaaca acctcaaaaa tgaggacacg gctacatatt tctgtgcaag agggagggat
 361 ggttaccaag tggcctggtt tgcttactgg ggccaaggga cgctggtcac tgtctctgca
 421 gccaaaacga caccccatc tgtctatcca ctggcccctg gatctgctgc ccaaactaac
 481 tccatggtga ccctgggatg cctggtcaag ggctatttcc ctgagccagt gacagtgacc
 541 tggaactctg gatccctgtc cagcggtgtg cacaccttcc cagctgtcct gcagtctgac
 601 ctctacactc tgagcagctc agtgactgtc ccctccagca cctggcccag ccagaccgtc
 661 acctgcaacg ttgcccaccc ggccagcagc accaaggtgg acaagaaaat tgtgcccagg
 721 gattgtggtt gtaagccttg catatgtaca gtcccagaag tatcatctgt cttcatcttc
 781 cccccaaagc caaggatgt gctcaccatt actctgactc taaggtcac gtgtgttgtg
 841 gtagacatca gcaaggatga tcccgaggtc cagttcagct ggtttgtaga tgatgtggag
 901 gtgcacacag ctcagacgca accccgggag gagcagttca acagcacttt ccgctcagtc
 961 agtgaacttc ccatcatgca ccaggactgg ctcaatggca aggagttcaa atgcagggtc
1021 aacagtgcag ctttccctgc ccccatcgag aaaaccatct ccaaaccaa aggcagaccg
1081 aaggctccac aggtgtacac cattccacct cccaaggagc agatggccaa ggataaagtc
1141 agtctgacct gcatgataac agacttcttc cctgaagaca ttactgtgga gtggcagtgg
1201 aatgggcagc cagcggagaa ctacaagaac actcagccca tcatggacac agatggctct
1261 tacttcgtct acagcaagct caatgtgcag aagagcaact gggaggcagg aaatactttc
1321 acctgctctg tgttacatga gggcctgcac aaccaccata ctgagaagag cctctcccac
1381 tctcctggta aatga
```

Protein Sequence Defining the Full Length Heavy Chain Sequence (Heavy Chain Variable Region and IgG1 Constant Region) of 18H02 (SEQ ID NO: 125)

```
  1 mgwlwnllfl maaaqsaqaq iqlvqsgpel kkpgeavkis ckssgytftt ygmswvkqap
 61 gralkwmgwi ntysgvptya ddfkgrfafs lessastayl qinnlknedt atyfcargrd
121 gyqvawfayw gqgtivtvsa akttppsvyp lapgsaaqtn smvtlgclvk gyfpepvtvt
181 wnsgslssgv htfpavlqsd lytlsssvtv psstwpsqtv tcnvahpass tkvdkkivpr
241 dcgckpcict vpevssvfif ppkpkdvlti tltpkvtcvv vdiskddpev qfswfvddve
301 vhtaqtqpre eqfnstfrsv selpimhqdw lngkefkcrv nsaafpapie ktisktkgrp
361 kapqvytipp pkeqmakdkv sltcmitdff peditvewqw ngqpaenykn tqpimdtdgs
421 yfvysklnvq ksnweagntf tcsvlheglh nhhtekslsh spgk
```

Nucleic Acid Sequence Encoding the Full Length Light Chain Sequence (Kappa Chain Variable Region and Constant Region) of 18H02 (SEQ ID NO: 126)

```
  1 atgttctcac tagctcttct cctcagtctt cttctcctct gtgtctctga ttctagggca
 61 gaaacaactg tgacccagtc tccagcatcc ctgtccatgg ctataggaga taaagtcacc
121 atcagatgca taaccagcac tgatattgat gatgatatga actggttcca gcagaagcca
181 ggggaacctc ctaagctcct tatttcagaa ggcaatactt tcgtcctgg agtcccatcc
241 cgattctccg gcagtggcta tggtacagat tttattttta caattgaaaa catgctctct
301 gaagatgttg cagattacta ctgtttgcaa agtgataact gccgtacac gttcggaggg
361 gggaccaagc tggaaataaa acgggctgat gctgcaccaa ctgtatccat cttcccacca
```

-continued

```
421 tccagtgagc agttaacatc tggaggtgcc tcagtcgtgt gcttcttgaa caacttctac 481 cccagagaca tcaatgtcaa gtggaagatt gatggcagtg aacgacaaaa tggtgtcctg 541 aacagttgga ctgatcagga cagcaaagac agcacctaca gcatgagcag caccctcaca 601 ttgaccaagg acgagtatga acgacataac agctatacct gtgaggccac tcacaagaca 661 tcaacttcac ccattgtcaa gagcttcaac aggaatgagt gttag
```

Protein Sequence Defining the Full Length Light Chain Sequence (Kappa Chain Variable Region and Constant Region) of 18H02 (SEQ ID NO: 127)

```
  1 mfslalllsl lllcvsdsra ettvtqspas lsmaigdkvt ircitstdid ddmnwfqqkp 61 geppkllise gntlrpgvps rfsgsgygtd fiftienmls edvadyyclq sdnlpytfgg 121 gtkleikrad aaptvsifpp sseqltsgga svvcflnnfy prdinvkwki dgserqngvl 181 nswtdqdskd stysmsstlt ltkdeyerhn sytceathkt stspivksfn rnec
```

Nucleic Acid Sequence Encoding the Full Length Heavy Chain Sequence (Heavy Chain Variable Region and IgG1 Constant Region) of 22A02 (SEQ ID NO: 128)

```
   1 atgggatgga gctgtatcat tgtcctcttg gtatcaacag ctacaggtgt ccactcccag 61 gtccaactgc agcagcctgg ggctgagctg gtgaggcctg gacttcagt gaagttgtcc 121 tgcaaggctt ctggctacac cttcaccaac tactggatgc actgggtaaa gcagaggcct 181 ggacaaggcc ttgagtggat cggaatgatt gatccttctg atagttatac taactacaat 241 ccaaagttca agggtaaggc cacattgact gtagacacat cctccagcac agcctacatg 301 cagctcagca gcctgacatc tgaggactct gcggtctatt actgtgcaag aaactactct 361 ggggactact ggggccaagg caccactctc acagtctcct cagccaaaac gacacccca 421 tctgtctatc cactggcccc tggatctgct gcccaaacta actccatggt gaccctggga 481 tgcctggtca agggctattt ccctgagcca gtgacagtga cctggaactc tggatccctg 541 tccagcggtg tgcacacctt cccagctgtc ctgcagtctg acctctacac tctgagcagc 601 tcagtgactg tcccctccag cacctggccc agccagaccg tcacctgcaa cgttgcccac 661 ccggccagca gcaccaaggt ggacaagaaa attgtgccca gggattgtgg ttgtaagcct 721 tgcatatgta cagtcccaga agtatcatct gtcttcatct tccccccaaa gcccaaggat 781 gtgctcacca ttactctgac tcctaaggtc acgtgtgttg tggtagacat cagcaaggat 841 gatcccgagg tccagttcag ctggtttgta gatgatgtgg aggtgcacac agctcagacg 901 caaccccggg aggagcagtt caacagcact ttccgctcag tcagtgaact cccatcatg 961 caccaggact ggctcaatgg caaggagttc aaatgcaggg tcaacagtgc agctttccct 1021 gcccccatcg agaaaaccat ctccaaaacc aaaggcagac cgaaggctcc acaggtgtac 1081 accattccac ctcccaagga gcagatggcc aaggataaag tcagtctgac ctgcatgata 1141 acagacttct tccctgaaga cattactgtg gagtggcagt ggaatgggca gccagcggag 1201 aactacaaga acactcagcc catcatggac acagatggct cttacttcgt ctacagcaag 1261 ctcaatgtgc agaagagcaa ctgggaggca ggaaatactt tcacctgctc tgtgttacat 1321 gagggcctgc acaaccacca tactgagaag agcctctccc actctcctgg taaa
```

Protein Sequence Defining the Full Length Heavy Chain Sequence (Heavy Chain Variable Region and IgG1 Constant Region) of 22A02 (SEQ ID NO: 129)

```
  1 mgwsciivll vstatgvhsq vqlqqpgael vrpgtsvkls ckasgytftn ywmhwvkqrp
 61 gqglewigmi dpsdsytnyn pkfkgkatlt vdtssstaym qlssltseds avyycarnys
121 gdywgqgttl tvssakttpp svyplapgsa aqtnsmvtlg clvkgyfpep vtvtwnsgsl
181 ssgvhtfpav lqsdlytlss svtvpsstwp sqtvtcnvah passtkvdkk ivprdcgckp
241 cictvpevss vfifppkpkd vltitltpkv tcvvvdiskd dpevqfswfv ddvevhtaqt
301 qpreeqfnst frsvselpim hqdwlngkef kcrvnsaafp apiektiskt kgrpkapqvy
361 tipppkeqma kdkvsltcmi tdffpeditv ewqwngqpae nykntqpimd tdgsyfvysk
421 lnvqksnwea gntftcsvlh eglhnhhtek slshspgk
```

Nucleic Acid Sequence Encoding the Full Length Light Chain Sequence (Kappa Chain Variable Region and Constant Region) of 22A02 (SEQ ID NO: 130)

```
  1 atgaagttgc ctgttaggct gttggtgctg atgttctgga ttcctgcttc cagcagtgat
 61 gttttgatga cccaaactcc actctccctg cctgtcagtc ttggagatca agcctccatc
121 tcttgcagat ctagtcagag cattgtacat agtaatggaa acacctattt agaatggtac
181 ctgcagaaac caggccagtc tccaaagctc ctgatctaca agtttccaa ccgattttct
241 ggggtcccag acaggttcag tggcagtgga tcaggacag atttcacact caagatcagc
301 agagtggagg ctgaggatct gggagtttat tattgctttc aaggttcata tgttccgtgg
361 acgttcggtg gaggcaccaa gctggaaatc aaacgggctg atgctgcacc aactgtatcc
421 atcttcccac catccagtga gcagttaaca tctggaggtg cctcagtcgt gtgcttcttg
481 aacaacttct accccagaga catcaatgtc aagtggaaga ttgatggcag tgaacgacaa
541 aatggtgtcc tgaacagttg gactgatcag gacagcaaag acagcaccta cagcatgagc
601 agcaccctca cattgaccaa ggacgagtat gaacgacata cagctatac ctgtgaggcc
661 actcacaaga catcaacttc acccattgtc aagagcttca acaggaatga gtgt
```

Protein Sequence Defining the Full Length Light Chain Sequence (Kappa Chain Variable Region and Constant Region) of 22A02 (SEQ ID NO: 131)

```
  1 mklpvrllvl mfwipasssd vlmtqtplsl pvslgdqasi scrssqsivh sngntylewy
 61 lqkpgqspkl liykvsnrfs gvpdrfsgsg sgtdftlkis rveaedlgvy ycfqgsyvpw
121 tfggtklei kradaaptvs ifppsseqlt sggasvvcfl nnfyprdinv kwkidgserq
181 ngvlnswtdq dskdstysms stltltkdey erhnsytcea thktstspiv ksfnrnec
```

Nucleic Acid Sequence Encoding the Full Length Heavy Chain Sequence (Heavy Chain Variable Region and IgG1 Constant Region) of 24C05 (SEQ ID NO: 132)

```
  1 atgaacttcg ggctcagctt gatgttcctt gtccttgtct taaaaggtgt ccagtgtgag
 61 gtgcagctgg tggaatctgg gggaggctta gtgaagcctg agggtccct gaaactctcc
121 tgtgcagcct ctggattcac tttcagtgac tatgccatgt cttgggttcg ccagactccg
181 gaaaagaggc tggagtgggt cgcaaccatt agtgatggtg gtacttacac ctactatcca
241 gacaatgtaa agggccgatt caccatctcc agagacaatg ccaagaacaa cctgtacctg
```

-continued

```
 301 caaatgagcc atctgaagtc tgaggacaca gccatgtatt actgtgcaag agaatggggt
 361 gattacgacg gatttgacta ctggggccaa ggcaccactc tcacagtctc ctcggccaaa
 421 acgacacccc catctgtcta tccactggcc cctggatctg ctgcccaaac taactccatg
 481 gtgaccctgg gatgcctggt caagggctat ttccctgagc cagtgacagt gacctggaac
 541 tctggatccc tgtccagcgg tgtgcacacc ttccagctg tcctgcagtc tgacctctac
 601 actctgagca gctcagtgac tgtccctcc agcacctggc ccagccagac cgtcacctgc
 661 aacgttgccc acccggccag cagcaccaag gtggacaaga aaattgtgcc cagggattgt
 721 ggttgtaagc cttgcatatg tacagtccca gaagtatcat ctgtcttcat cttcccccca
 781 aagcccaagg atgtgctcac cattactctg actcctaagg tcacgtgtgt tgtggtagac
 841 atcagcaagg atgatcccga ggtccagttc agctggtttg tagatgatgt ggaggtgcac
 901 acagctcaga cgcaaccccg ggaggagcag ttcaacagca ctttccgctc agtcagtgaa
 961 cttcccatca tgcaccagga ctggctcaat ggcaaggagt tcaaatgcag ggtcaacagt
1021 gcagctttcc ctgcccccat cgagaaaacc atctccaaaa ccaaaggcag accgaaggct
1081 ccacaggtgt acaccattcc acctcccaag gagcagatgg ccaaggataa agtcagtctg
1141 acctgcatga taacagactt cttccctgaa gacattactg tggagtggca gtggaatggg
1201 cagccagcgg agaactacaa gaacactcag cccatcatgg acacagatgg ctcttacttc
1261 gtctacagca agctcaatgt gcagaagagc aactgggagg caggaaatac tttcacctgc
1321 tctgtgttac atgagggcct gcacaaccac catactgaga agagcctctc ccactctcct
1381 ggtaaa
```

Protein Sequence Defining the Full Length Heavy Chain Sequence (Heavy Chain Variable Region and IgG1 Constant Region) of 24C05 (SEQ ID NO: 133)

```
  1 mnfglslmfl vlvlkgvqce vqlvesgggl vkpggslkls caasgftfsd yamswvrqtp
 61 ekrlewvati sdggtytyyp dnvkgrftis rdnaknnlyl qmshlksedt amyycarewg
121 dydgfdywgq gttltvssak ttppsvypla pgsaaqtnsm vtlgclvkgy fpepvtvtwn
181 sgslssgvht fpavlqsdly tlsssvtvps stwpsqtvtc nvahpasstk vdkkivprdc
241 gckpcictvp evssvfifpp kpkdvltitl tpkvtcvvvd iskddpevqf swfvddvevh
301 taqtqpreeq fnstfrsvse lpimhqdwln gkefkcrvns aafpapiekt isktkgrpka
361 pqvytipppk eqmakdkvsl tcmitdffpe ditvewqwng qpaenykntq pimdtdgsyf
421 vysklnvqks nweagntftc svlheglhnh htekslshsp gk
```

Nucleic Acid Sequence Encoding the Full Length Light Chain Sequence (Kappa Chain Variable Region and Constant Region) of 24C05 (SEQ ID NO: 134)

```
  1 atggacatga gggttcctgc tcacgttttt ggcttcttgt tgctctggtt ccaggtacc
 61 agatgtgaca tccagatgac ccagtctcca tcctcctat ctgcctctct gggagaaaga
121 gtcagtctca cttgtcgggc aagtcaggaa attagtggtt acttaagctg gcttcagcag
181 aaaccagatg gaactattaa acgcctgatc tacgccgcat ccactttaga ttctggtgtc
241 ccaaaaaggt tcagtggcag taggtctggg tcagattatt ctctcaccat cggcagcctt
301 gagtctgaag atcttgcaga ctattactgt ctacaatatg atagttatcc gtacacgttc
361 ggagggggga ccaagctgga aataaaacgg gctgatgctg caccaactgt atccatcttc
```

-continued

```
421 ccaccatcca gtgagcagtt aacatctgga ggtgcctcag tcgtgtgctt cttgaacaac 481 ttctacccca gagacatcaa tgtcaagtgg aagattgatg gcagtgaacg acaaaatggt 541 gtcctgaaca gttggactga tcaggacagc aaagacagca cctacagcat gagcagcacc 601 ctcacattga ccaaggacga gtatgaacga cataacagct atacctgtga ggccactcac 661 aagacatcaa cttcacccat tgtcaagagc ttcaacagga atgagtgt
```

Protein Sequence Defining the Full Length Light Chain Sequence (Kappa Chain Variable Region and Constant Region) of 24C05 (SEQ ID NO: 135)

```
  1 mdmrvpahvf gflllwfpgt rcdiqmtqsp sslsaslger vsltcrasqe isgylswlqq 61 kpdgtikrli yaastldsgv pkrfsgsrsg sdysltigsl esedladyyc lqydsypytf 121 gggtkleikr adaaptvsif ppsseqltsg gasvvcflnn fyprdinvkw kidgserqng 181 vlnswtdqds kdstysmsst ltltkdeyer hnsytceath ktstspivks fnrnec
```

For convenience, Table 4 provides a concordance chart showing the correspondence between the full length sequences of the antibodies discussed in this Example with those presented in the Sequence Listing.

TABLE 4

| SEQ ID NO. | Nucleic Acid or Protein |
|---|---|
| 108 | 04D01 Heavy Variable + IgG1 Constant-nucleic acid |
| 109 | 04D01 Heavy Variable + IgG1 Constant-protein |
| 110 | 04D01 Kappa Variable + Constant-nucleic acid |
| 111 | 04D01 Kappa Variable + Constant-protein |
| 112 | 09D03 Heavy Variable + IgG2b Constant-nucleic acid |
| 113 | 09D03 Heavy Variable + IgG2b Constant-protein |
| 114 | 09D03 Kappa Variable + Constant-nucleic acid |
| 115 | 09D03 Kappa Variable + Constant-protein |
| 116 | 11G01 Heavy Variable + IgG1 Constant-nucleic acid |
| 117 | 11G01 Heavy Variable + IgG1 Constant-protein |
| 118 | 11G01 Kappa Variable + Constant-nucleic acid |
| 119 | 11G01 Kappa Variable + Constant-protein |
| 120 | 12A07 Heavy Variable + IgG1 Constant-nucleic acid |
| 121 | 12A07 Heavy Variable + IgG1 Constant-protein |
| 122 | 12A07 Kappa Variable + Constant-nucleic acid |
| 123 | 12A07 Kappa Variable + Constant-protein |
| 124 | 18H02 Heavy Variable + IgG1 Constant-nucleic acid |
| 125 | 18H02 Heavy Variable + IgG1 Constant-protein |
| 126 | 18H02 Kappa Variable + Constant-nucleic acid |
| 127 | 18H02 Kappa Variable + Constant-protein |
| 128 | 22A02 Heavy Variable + IgG1 Constant-nucleic acid |
| 129 | 22A02 Heavy Variable + IgG1 Constant-protein |
| 130 | 22A02 Kappa Variable + Constant-nucleic acid |
| 131 | 22A02 Kappa Variable + Constant-protein |
| 132 | 24C05 Heavy Variable + IgG1 Constant-nucleic acid |
| 133 | 24C05 Heavy Variable + IgG1 Constant-protein |
| 134 | 24C05 Kappa Variable + Constant-nucleic acid |
| 135 | 24C05 Kappa Variable + Constant-protein |

Example 3—Binding Affinities

The binding affinities and kinetics of the binding of monoclonal antibodies 04D01, 09D03, 11G01, 12A07, 18H02, 22A02 and 24C05 to recombinant human ErbB3/Fc fusion protein (rhErbB3-Fc) were measured by surface plasmon resonance using a BIACORE® T100 (Biacore) instrument.

Rabbit anti-mouse IgGs (Biacore, Cat. No. BR-1008-38) were immobilized on carboxymethylated dextran CM4 sensor chips (Biacore, Cat. No. BR-1005-34) by amine coupling (Biacore, Cat. No. BR-1000-50) using a standard coupling protocol according to vendor's instructions. The analyses were performed at 25° C., using PBS (Invitrogen, Cat. No. 14040-133) containing 0.05% surfactant P20 (Biacore, Cat. No. BR-1000-54) as running buffer.

The antibodies were captured in individual flow cells at a flow rate of 10 µl/minute. Injection time was varied for each antibody to yield an $R_{max}$ between 30 and 60 RU. Buffer or rhErbB3-Fc diluted in running buffer was injected sequentially over a reference surface (no antibody captured) and the active surface (antibody to be tested) for 300 seconds at 60 µl/minute. The dissociation phase was monitored for up to 3600 seconds. The surface was then regenerated with two 60-seconds injection of 10 mM Glycine-HCl, pH 1.7 (made from Glycine pH 1.5 (Biacore, Cat. No. BR-1003-54) and pH 2.0 (Biacore, Cat. No. BR-1003-55)) at a flow rate of 60 µl/minute. The rhErbB3-Fc concentration range tested was 0.125 nM to 20 nM.

Kinetic parameters were determined using the kinetic function of the BIAevaluation software (Biacore) with double reference subtraction. Kinetic parameters for each antibody, $k_a$ (association rate constant), $k_d$ (dissociation rate constant) and $K_D$ (equilibrium dissociation constant) were determined. Kinetic values of the monoclonal antibodies on rhErbB3-Fc at 25° C. are summarized in Table 5.

TABLE 5

| Antibody | $k_a$ (1/Ms) | Standard Deviation | $k_d$ (1/s) | Standard Deviation | $K_D$ (M) | Standard Deviation | n |
|---|---|---|---|---|---|---|---|
| 04D01 | 3.8E+05 | 3.0E+04 | 9.3E−05 | 1.9E−05 | 2.5E−10 | 5.6E−11 | 5 |
| 09D03 | 2.7E+05 | 3.2E+04 | 2.0E−05 | 1.2E−05 | 8.0E−11 | 5.5E−11 | 3 |
| 11G01 | 2.7E+05 | 9.2E+04 | 2.2E−05 | 9.6E−06 | 9.1E−11 | 5.5E−11 | 4 |
| 12A07 | 6.2E+05 | 8.1E+04 | 1.9E−04 | 1 0E−04 | 3 0E−10 | 1 4E−10 | 3 |
| 18H02 | 2.8E+05 | 3.1E+04 | 2.5E−05 | 8.8E−06 | 9.1E−11 | 3.7E−11 | 4 |

TABLE 5-continued

| Antibody | $k_a$ (1/Ms) | Standard Deviation | $k_d$ (1/s) | Standard Deviation | $K_D$ (M) | Standard Deviation | n |
|---|---|---|---|---|---|---|---|
| 22A02 | 7.0E+05 | 8.1E+04 | 2.2E−04 | 1.4E−04 | 3.2E−10 | 2.4E−10 | 3 |
| 24C05 | 1.5E+06 | 2.0E+05 | 9.2E−06 | 3.0E−06 | 6.5E−12 | 2.8E−12 | 4 |

The data in Table 5 demonstrate that the antibodies bind rhErbB3 with a $K_D$ of about 350 pM or less, 250 pM or less, 200 pM or less, 150 pM or less, 100 pM or less, 50 pM or less, or 10 pM or less.

Example 4—Neutralization Activity

In this example, the antibodies produced in Example 1 were tested for ability to inhibit rhErbB3 binding to NRG1-β1 and NRG1-α1. The antibodies were tested by electrochemiluminescence (ECL) assay for inhibition of hErbB3 binding to NRG1-β1. MA2400 96-well standard binding plates (Meso Scale Discovery, Cat. No. L15XA-6) were coated with 50 μl of 0.5 μg/mL rhErbB3/Fc (R&D systems, Cat. No. 348-RB) in PBS (Invitrogen, Cat. No. 14040-133) for overnight at 4° C. with no agitation. The plates then were washed 3 times with PBS+0.1% TWEEN®20 (Sigma P5927) and blocked with 200 μl of PBS containing 5% BSA (Sera Care Life Sciences, Cat. No. AP-4510-80) for 1.5 hour at room temperature. After washing the plates 3 times with PBS, 25 μl of the antibody dilutions were added to the plates for another hour at room temperature with agitation. Ligand NRG1-β1 (R&D Systems, Cat. No. 377-HB, 26 kDa) was added to the wells at the final concentration of 0.25 μg/ml. The plates were washed three times with PBS and incubated with 25 μl of 1 μg/mL biotinylated antibody against human NRG1-β1(R&D systems, Cat. No BAF377) preincubated for one hour with SULTO-TAG Streptavidin (Meso Scale Discovery, Cat. No R32AD-5) for one hour at room temperature with agitation. The plates then were washed 3 times with PBS, and 150 μl of 1× read buffer (Meso Scale Discovery, Cat. No. R92TC-1) was added to each well before the plates were analyzed on a SECTOR® Imager 2400 (Meso Scale Discovery) instrument.

Figure 6A:
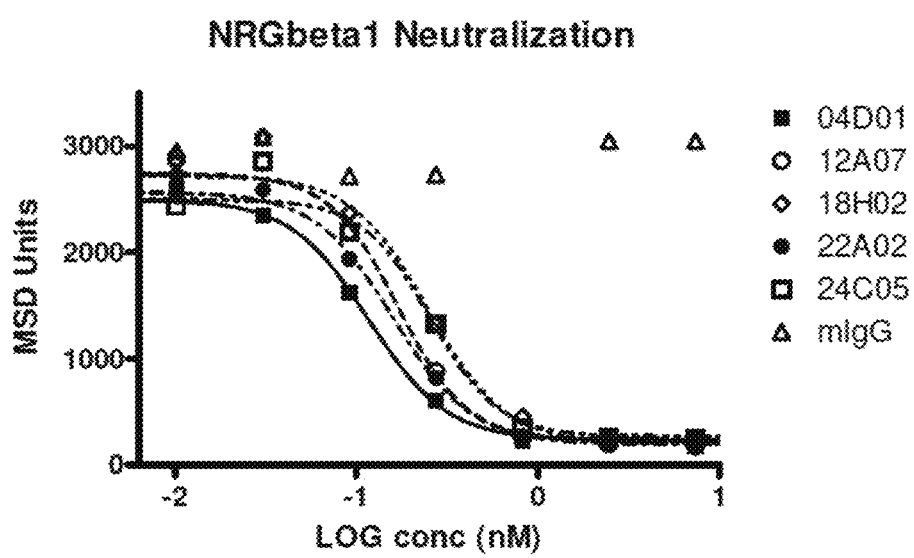
FIGS. 6A and 6B are graphs summarizing results from an experiment to measure the neutralization activity of negative control (murine IgG (Δ)) and anti-ErbB3 monoclonal antibodies 04D01 (■), 12A07 (○), 18H02 (◇), 22A02 (●) and 24C05 (□) to inhibit NRG1-β1 binding to hErbB3 (FIG. 6A) and to measure the enhanced binding of NRG1-β1 to rhErbB3 by the anti-ErbB3 mAb 09D03 (▲) and 11G01 (*) (FIG. 6B).
Figure 6B:
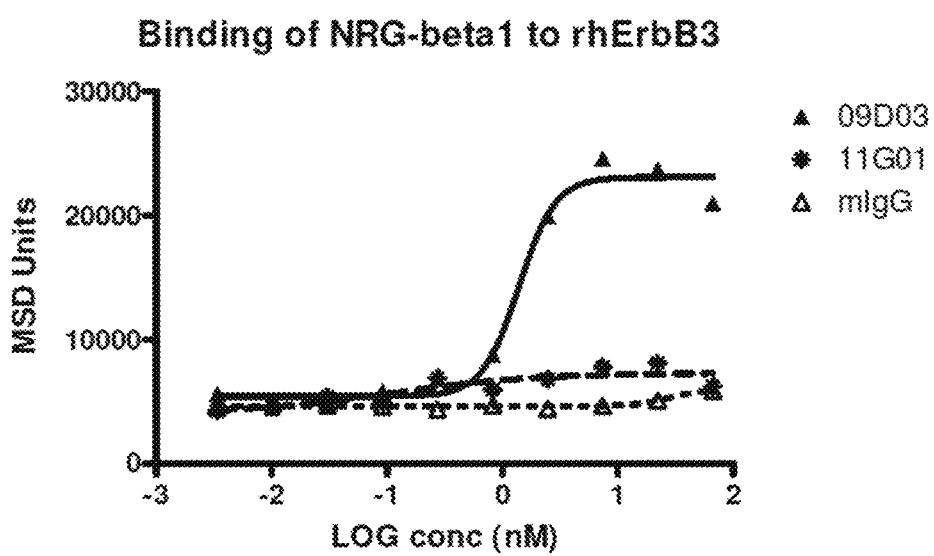

The interaction of NRG1-β1 with ErbB3 was inhibited by antibodies 04D01, 12A07, 18H02, 22A02 and 24C05 (FIG. 6A). The interaction of NRG1-β1 with rhErbB3 was enhanced by antibody 09D03, but not as well as by antibody 11G01 (FIG. 6B).

The murine anti-human ErbB3 antibody $IC_{50}$ values for neutralization of NRG1-β1 binding to rhErbB3 for the antibodies (i.e., 04D01, 12A07, 18H02, 22A02 and 24C05) were calculated and are summarized in Table 6.

TABLE 6

| | $IC_{50}$ (nM) | | |
|---|---|---|---|
| Antibody | Average | Standard Deviation | n |
| 04D01 | 0.2232 | 0.0711 | 4 |
| 12A07 | 0.2351 | 0.0530 | 4 |
| 18H02 | 0.3460 | 0.0873 | 4 |
| 22A02 | 0.2418 | 0.0755 | 4 |
| 24C05 | 0.3367 | 0.0764 | 4 |

The results show that antibodies 04D01, 12A07, 18H02, 22A02, and 24C05 efficiently neutralized NRG1-β1 binding to rhErbB3. Antibodies 09D03 and 11G01 enhanced hNRG1-β1 binding to hErbB3.

The antibodies were tested by ECL assay for inhibition of hErbB3 binding to the second ErbB3 ligand, NRG1-α1. To assay inhibition of binding of NRG1-α1 to rhErbB3, the same method used for NRG1-β1 was used, except for the following changes: concentrations of plated rhErbB3/Fc (R&D 4518-RB) and of ligand NRG1-α1 (Thermo Scientific, RP-317-P1AX) were 1 μg/ml and 1.5 μg/ml, respectively.

Figure 7:
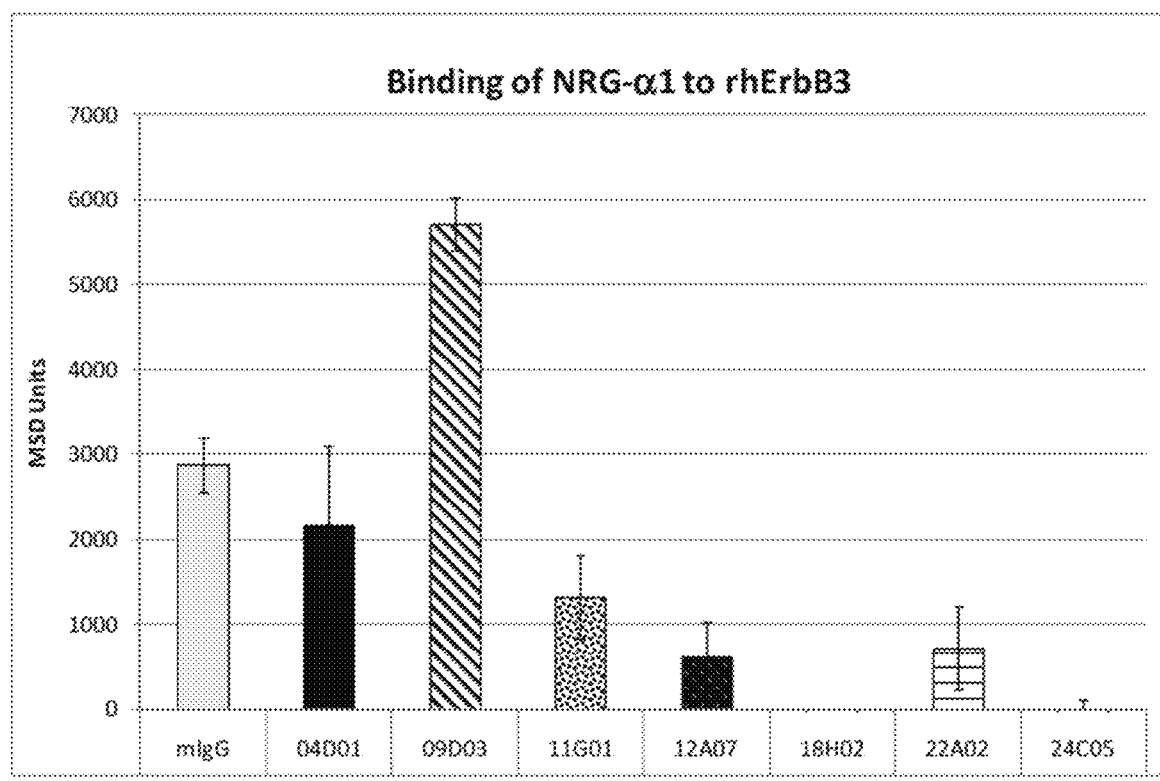
FIG. 7 is a graph summarizing results from an experiment to measure the neutralization activity of negative control (murine IgG) and anti-ErbB3 monoclonal antibodies 04D01, 09D03, 11G01, 12A07, 18H02, 22A02 and 24C05 to inhibit NRG1-α1 binding to rhErbB3.

The interaction of NRG1-α1 with rhErbB3 was inhibited by 11G01, 12A07, 18H02, 22A02, and 24C05 IgG1, and was enhanced by antibody 09D03 (FIG. 7).

Example 5—Binding to ErbB3 Domain II

Figure 8:
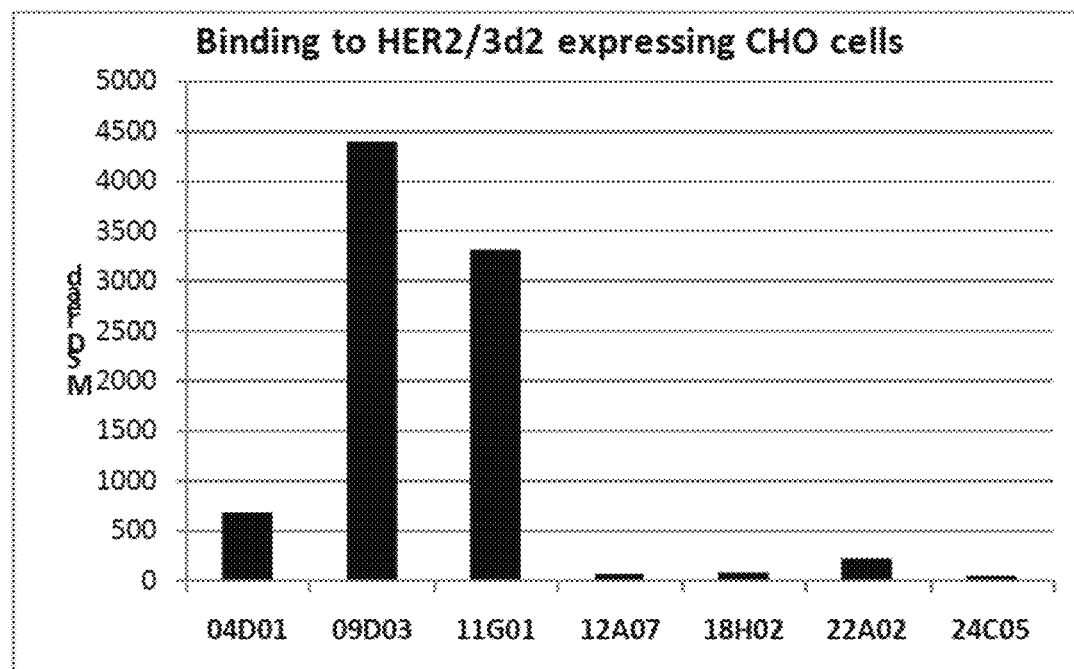
FIG. 8 is a graph summarizing results from an experiment to measure the cell surface recognition of the anti-ErbB3 antibodies of the chimeric protein Her2/3d2 expressed at the surface of CHO cells.

In this example, the antibodies produced in Example 1 were tested for binding to the dimerization domain (domain 2) of hErbB3-ECD. Domain 2 of hErbB3 (118 amino acids, position 210-327) was cloned in place of domain 2 of Her2 (119 amino acids, position AA220-338) into the full-length Her2 receptor. The hybrid construct Her2/3d2 was cloned into pLenti6.3 and packaged by transient transfection of 293T cells into a Lentivirus using the VIRAPOWER™ Lentiviral Support Kit (Invitrogen, Cat. No. K497000). CHO cells were infected with the lentivirus expressing the Her2/3d2 hybrid protein. The binding of the anti-ErbB3 hybridoma supernatants to Her2/3d2 were tested on these engineered CHO cells by ECL with sulfo-tagged anti-mouse antibodies. Data on the binding of the hybridoma supernatants to the chimeric protein Her2/3d2 expressed on the cell surface of CHO cells are summarized in FIG. 8. These results show that antibodies 09D03 and 11G01 bound to the ErbB3 domain II, AA210-327.

Example 6—Anti-Proliferative Activity

This example describes a characterization of the antibodies produced in Example 1 for their ability to inhibit NRG1-β1 dependent proliferation of cells. Antibodies were tested in the BaF/3 cell system engineered to express both human Her2 and ErbB3 and in the human MCF7 breast cancer cells which naturally express both Her2 and ErbB3 and grow in response to NRG1-β1 stimulation.

BaF/3 cells were infected by two lentiviruses engineered to express human Her2 or human ErbB3. Infected cells were selected with blasticidin (15 μg/ml; Invitrogen, Cat. No. R21001) and individual colonies were isolated and tested for expression of both receptors. Her2/ErbB3 expressing clones were maintained in culture under blasticidin selection with [80% RPMI Medium 1640 (GIBCO, Cat. No. 11875-093), 10% fetal bovine serum (GIBCO, Cat. No. 10438-026) and 10% WEHI cell conditioned media {90% ISCOVE's Modified Dulbecco's Medium (GIBCO, Cat. No. 12440053), 10% fetal bovine serum (GIBCO, Cat. No. 10438-026)+2 mM L-glutamine (GIBCO, Cat. No. 25030-081)+0.0025 mM mercaptoethanol (Invitrogen, Cat. No. 21985-023)}]. To screen for antagonistic ErbB3 antibodies, cells were rinsed with PBS, and grown in the absence of blasticidin and WEHI conditioned media. Assays were conducted in a 96-well plate (5,000 cells/well) in the presence of NRG1-β1 (100 ng/ml) and various concentrations of antibodies (0.018-5000 ng/ml in 100 μl final volume). MTT (3-(4,5-Dimethylthiazol-2-yl)-2,5-diphenyltetrazolium bromide) assays were conducted 3-4 days post NRG1-β1 stimulation.

Figure 9:
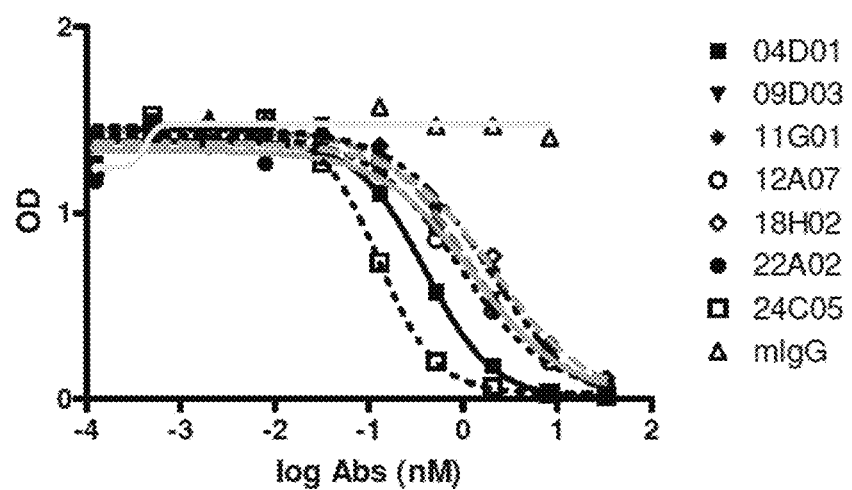
FIG. 9 is a graph summarizing results from an experiment to measure the anti-proliferation activity of negative control IgG (murine IgG (Δ)) and anti-ErbB3 monoclonal antibodies 04D01 (■), 09D03 (▼), 11G01 (♦), 12A07 (○), 18H02 (◇), 22A02 (●) and 24C05 (□) in BaF/3 cells expressing Her2 and ErbB3 in presence of NRG1-β1.

An example of the dose-dependent inhibition of NRG1-β1 dependent cell proliferation of Her2/ErbB3-BaF/3 by murine anti-human ErbB3 antibodies is shown in FIG. 9. Inhibition data of NRG1-β1 dependent Her2/ErbB3-BaF/3 cell line proliferation with monoclonal antibodies (i.e., 04D01, 09D03, 11G01, 12A07, 18H02, 22A02 and 24C05) are summarized in Table 7.

TABLE 7

Her2/ErbB3-BaF/3, NRG1-β1 dep. Proliferation

| Antibody | $IC_{50}$ (nM)-Average | Standard deviation | n |
|---|---|---|---|
| 04D01 | 0.373 | 0.061 | 3 |
| 09D03 | 1.395 | 0.268 | 3 |
| 11G01 | 1.934 | 0.116 | 3 |
| 12A07 | 0.854 | 0.059 | 3 |
| 18H02 | 1.930 | 0.276 | 3 |
| 22A02 | 1.291 | 0.151 | 3 |
| 24C05 | 0.145 | 0.031 | 3 |

The results in Table 7 show that antibodies 04D01, 09D03, 11G01, 12A07, 18H02, 22A02 and 24C05 strongly inhibited NRG1-β1-induced proliferation of BaF/3 cells expressing Her2/ErbB3.

MCF7 cells (ATCC, Cat. No. HTB-22) were maintained as recommended by ATCC. Cells were plated at 5,000 cells/well in a 96-well plate. Cells were starved overnight in the absence of serum. The following day, NRG1-β1 (40 ng/ml) and various concentrations of antibodies (12.8 pg/ml-20 μg/ml in 100 μl final volume) were added to the cells. MTT (3-(4,5-Dimethylthiazol-2-yl)-2,5-diphenyltetrazolium bromide) assays were conducted three days post NRG1-β1 stimulation.

Figure 10:
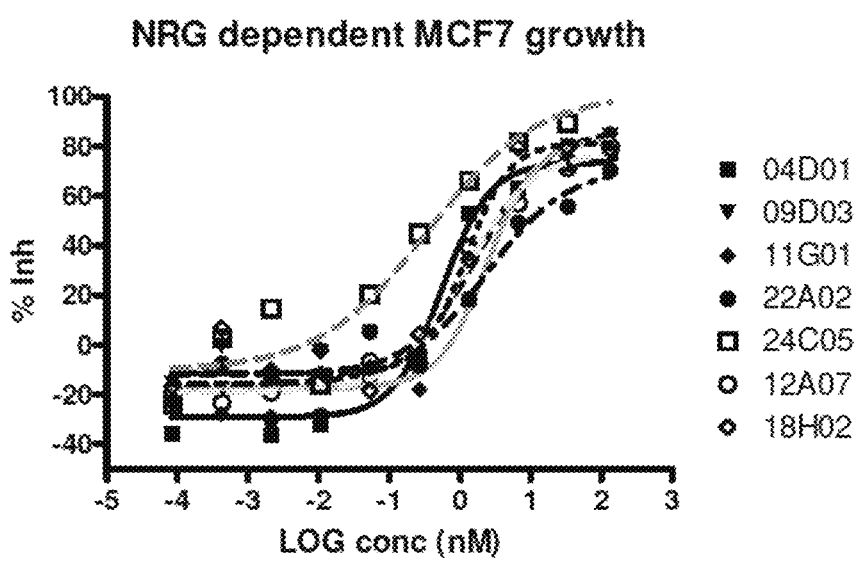
FIG. 10 is a graph summarizing results from an experiment to measure the anti-proliferation activity of anti-ErbB3 monoclonal antibodies 04D01 (■), 09D03(▼), 11G01 (♦), 12A07 (○), 18H02 (◇), 22A02 (●) and 24C05 (□) in MCF7 cells in the presence of NRG1-β1.

An example of the dose-dependent inhibition of NRG1-β1 dependent proliferation of MCF7 cells by murine anti-human ErbB3 antibodies is shown in FIG. 10. Inhibition data of NRG1-β1 dependent MCF7 cell proliferation with antibodies 04D01, 09D03, 11G01, 12A07, 18H02, 22A02 and 24C05 are summarized in Table 8.

TABLE 8

MCF7 cells, NRG1-β1 dependent Proliferation

| Antibody | $IC_{50}$ (nM)-Average | Standard deviation | n |
|---|---|---|---|
| 04D01 | 0.47 | 0.23 | 3 |
| 09D03 | 2.28 | 0.60 | 3 |
| 11G01 | 1.98 | 1.34 | 3 |
| 12A07 | 0.74 | 0.48 | 3 |
| 18H02 | 1.00 | 0.20 | 3 |
| 22A02 | 1.62 | 0.60 | 3 |
| 24C05 | 0.39 | 0.04 | 3 |

The results in Table 8 demonstrate that antibodies 04D01, 09D03, 11G01, 12A07, 18H02, 22A02, and 24C05 strongly inhibited NRG1-β1-induced proliferation of MCF7 cells.

The antibodies produced in Example 1 were also tested for their ability to inhibit proliferation of ErbB3 expressing human cancer cells. Breast cancer cells SKBR-3 overexpress Her2 and are sensitive to Her2-specific inhibitory antibodies.

SKBR-3 cells (ATCC, Cat. No. HTB-30) were maintained as recommended by ATCC. Cells were plated at 5,000 cells/well in a 96-well plate in the presence of 5 μg/ml of antibodies but without exogenous NRG1-β1. MTT (3-(4,5-Dimethylthiazol-2-yl)-2,5-diphenyltetrazolium bromide) assays were conducted after three days in culture.

Figure 11:
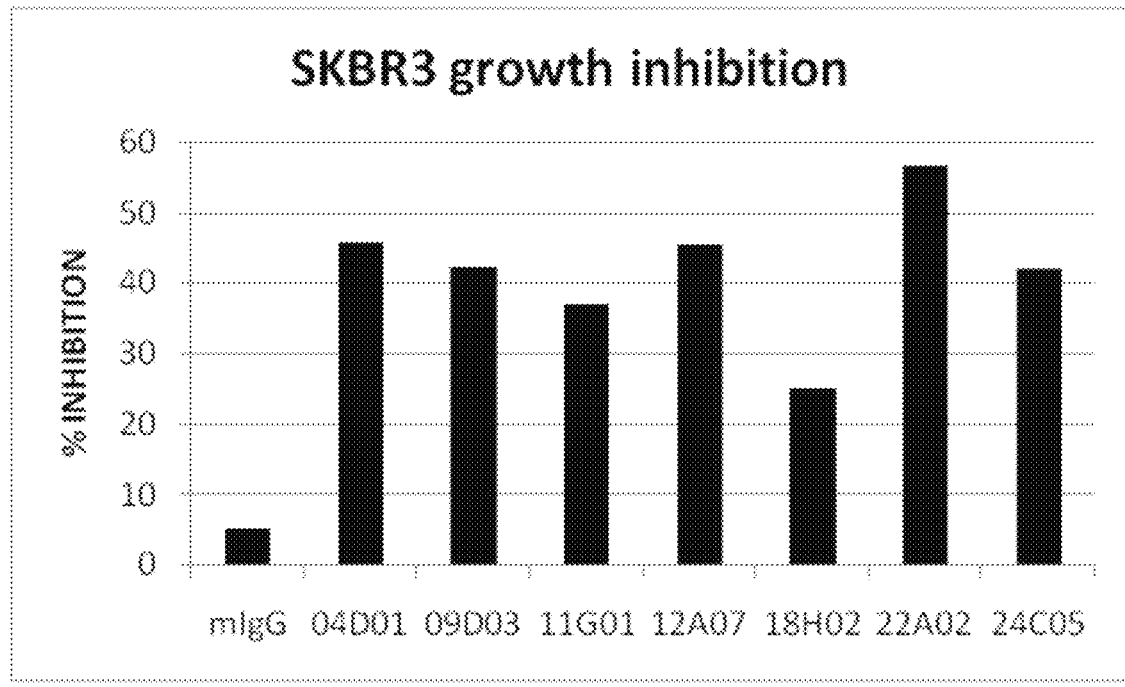
FIG. 11 is a graph summarizing results from an experiment to measure the anti-proliferation activity of negative control (murine IgG) and anti-ErbB3 monoclonal antibodies 04D01, 09D03, 11G01, 12A07, 18H02, 22A02 and 24C05 in SKBR-3 cells treated with 5 μg/ml of antibodies in the presence of serum.

An example of inhibition of cell proliferation of SKBR-3 cells by murine anti-human ErbB3 antibodies is shown in FIG. 11. The results in FIG. 11 show that antibodies 04D01, 09D03, 11G01, 12A07, 18H02, 22A02 and 24C05 inhibited proliferation of SKBR-3 cells.

Example 7—Inhibition of Downstream Signaling

This example describes a characterization of the antibodies produced in Example 1 for their ability to inhibit NRG1-β1 dependent phosphorylation of ErbB3 and the downstream kinase Akt, as the readout for PI3K activation. These antibodies were also tested for their ability to inhibit steady state phosphorylation of ErbB3 and Akt in exponentially growing cells.

Breast cancer cells SKBR-3 and MCF7 and prostate cancer cells DU145 were maintained as recommended by ATCC. Cells were starved overnight in 0% FBS, treated for one hour with 5 μg/ml of antibody followed by NRG1-β1 stimulation. Lysates were either analyzed by ELISA with the Phospho-ErbB3 kit from R&D Systems (Cat. No DYC1769) or with the Phospho-Akt ELISA kit from Cell Signaling (Cat. No 7143).

Figure 12:
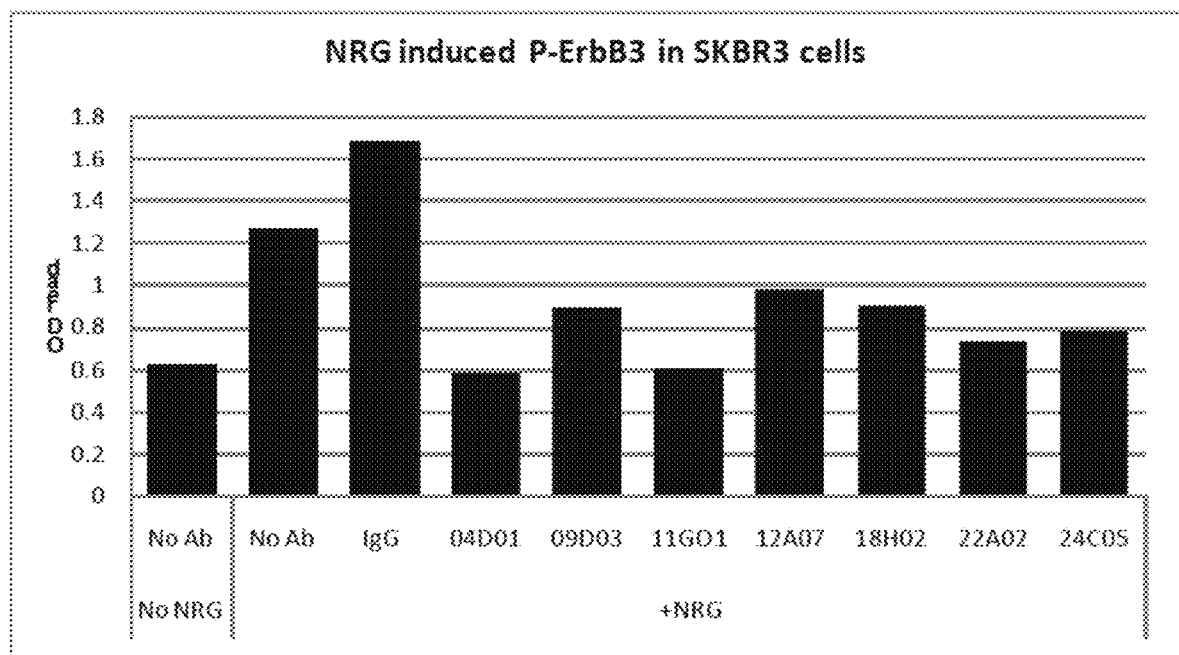
FIG. 12 is graph summarizing results from an experiment to measure the inhibitory activity of negative control IgG and anti-ErbB3 monoclonal antibodies 04D01, 09D03, 11G01, 12A07, 18H02, 22A02 and 24C05 on the phosphorylation of ErbB3 induced by NRG in SKBR-3 cells. No antibody/no ligand and no antibody controls are also shown.

An example of the inhibition of the NRG1-β1 induced phosphorylation of ErbB3 in SKBR-3 cells by murine anti-human ErbB3 antibodies is shown in FIG. 12. The results in FIG. 12 demonstrated that antibodies 04D01, 09D03, 11G01, 12A07, 18H02, 22A02 and 24C05 inhibited at least 50% of the phosphorylation of ErbB3 induced by NRG1-β1 in SKBR-3 cells.

Figure 13A:
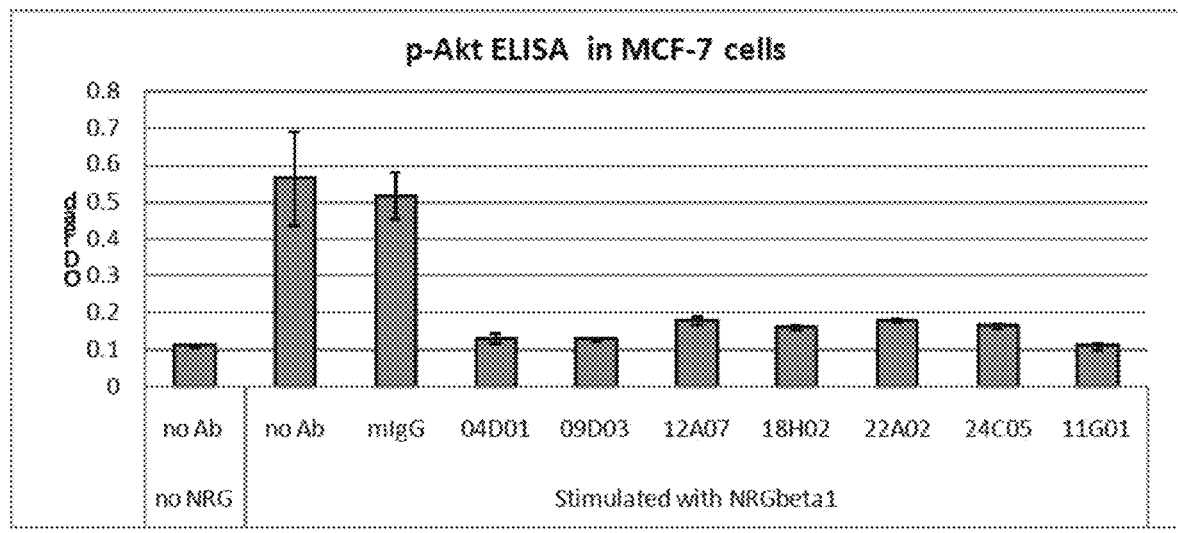
FIGS. 13A and 13B are graphs representing results from an experiment to measure the inhibitory activity of anti-ErbB3 monoclonal antibodies 04D01, 09D03, 11G01, 12A07, 18H02, 22A02 and 24C05 on the phosphorylation of Akt in response to NRG1-β1 in MCF7 cells (FIG. 13A) and in DU145 cells (FIG. 13B) as determined by ELISA. No antibody/no ligand and no antibody controls are also shown.
Figure 13B:
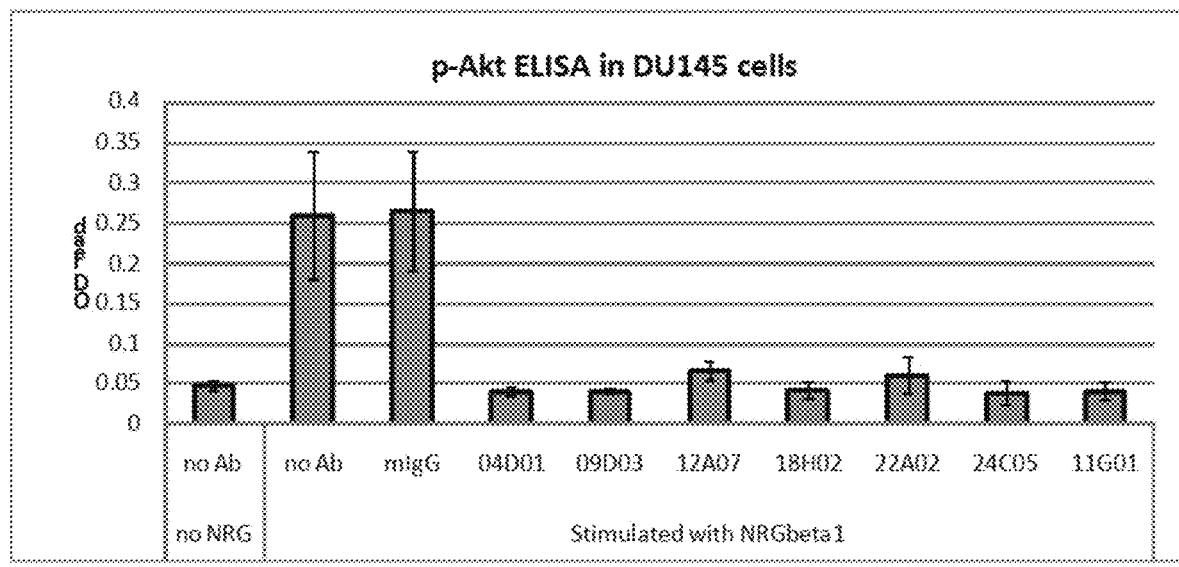

An example of the inhibition of the NRG1-β1 induced phosphorylation of Akt in MCF7 and DU145 cells by murine anti-human ErbB3 antibodies is shown in FIG. 13A and FIG. 13B, respectively. The results in FIGS. 13A and 13B demonstrated that antibodies 04D01, 09D03, 11G01, 12A07, 18H02, 22A02 and 24C05 inhibited at least 80% of the phosphorylation of Akt in response to the NRG1-β1 in both MCF7 and DU145 cells.

The capacity of the anti-ErbB3 antibodies to inhibit the steady state phosphorylation status of ErbB3 and Akt in a breast cancer cell line SKBR-3 and a pancreatic cancer cell line BxPC3 were tested by treating these exponentially growing cells for one hour in presence of antibodies at 5 μg/ml.

Western blot analysis of these experiments demonstrated that antibodies 04D01, 09D03, 11G01, 12A07, 18H02, 22A02 and 24C05 inhibited the steady state level of phosphorylation of Akt and ErbB3 in both SKBR-3 and BxPC3 cells.

Example 8—Inhibition of NRG1-β1-Induced EGFR Phosphorylation

In this example, the antibodies produced in Example 1 were tested for their ability to inhibit NRG1-β1 dependent phosphorylation of EGFR in the ovarian cancer cell line NCI/ADR-RES. NCI/ADR-RES cells (DTP/DCTD NCI tumor repository) were starved overnight in 0% FBS, pre-treated with antibody (5 μg/ml) for one hour followed by NRG1-β1 (20 ng/ml) stimulation for 15 minutes. The phosphorylation of EGFR on tyrosine 1068 was analyzed by Western blot. The results of this experiment demonstrated that antibodies 04D01, 09D03, 11G01, 12A07, 18H02, 22A02 and 24C05 inhibited the phosphorylation of EGFR in response to the NRG1-β1 in NCI/ADR-RES cells.

Example 9—Inhibition of EGF-induced ErbB3 Phosphorylation

In this example, the antibodies produced in Example 1 were tested for their ability to inhibit EGF dependent phosphorylation of ErbB3 in the EGFR overexpressing, epidermoid cancer cell line A431. A431 cells (ATCC, Cat. No CRL-1555) were starved overnight in 0% FBS, pretreated with antibody (5 µg/ml) for one hour followed by EGF (R&D Systems, Cat. No. 236-EG) (50 ng/ml) stimulation for 15 minutes. The phosphorylation of ErbB3 was analyzed by Western blot. The results of this experiment demonstrated that antibodies 04D01, 09D03, 12A07, 18H02, 22A02 and 24C05 inhibited to various extents the phosphorylation of ErbB3 in response to the EGF in A431 cells.

Example 10—Inhibition of NRG1-β1-Induced Her2/ErbB3 Heterodimer Formation

This example describes a characterization of the antibodies produced in Example 1 for their ability to inhibit the formation of the Her2/ErbB3 dimer in response to NRG1-β1 in SKBR-3 cells. Breast cancer cells SKBR-3 were starved overnight in 0% FBS, treated for one hour with 5 µg/ml of antibody followed by NRG1-β1 stimulation (30 ng/ml, 30 min). Lysates were immunoprecipitated with anti-Her2 antibody (R&D Systems, Cat. No. BAF1129) and analyzed by Western blot with polyclonal anti-ErbB3 antibody (Santa Cruz, Cat. No. SC285).

The results of this experiment demonstrated that antibodies 04D01, 09D03, 11G01, 12A07, 18H02, 22A02 and 24C05 inhibited NRG1-β1-induced Her2/ErbB3 dimer formation in SKBR-3 cells.

Example 11—Inhibition of BxPC3 Tumor Xenograft Growth

The ability of murine monoclonal antibodies produced in Example 1 to inhibit tumor growth was tested in a pancreatic BxPC3 xenograft model. Human pancreatic BxPC3 cells were grown in culture in 37° C. in an atmosphere containing 5% CO2, using RMPI medium containing 10% fetal bovine serum. BxPC3 cells were inoculated subcutaneously into the flank of 8-week old female CB.17 SCID mice (Taconic Labs) with $10 \times 10^6$ cells per mouse in 50% MATRIGEL® (BD Biosciences, Cat No. 356237). Tumor measurements were taken twice weekly using vernier calipers. Tumor volume was calculated using the formula: width×width× length/2. When tumors reached approximately 200 mm³, the mice were randomized into 9 groups of 10 mice each. One group received PBS and another received human IgG control (huIgG). Each of the other eight groups received one of the antibody, 04D01, 09D03, 18H02, 11G01, 24C05, 22A02, or 12A07. All antibodies were dosed at 20 mg/kg body weight, twice per week, by intra-peritoneal injection for 6 weeks. Tumor volumes and mouse body weights were recorded twice per week. Tumor growth inhibition was analyzed using ANOVA and is expressed as percent inhibition compared to the PBS control.

Figure 14:
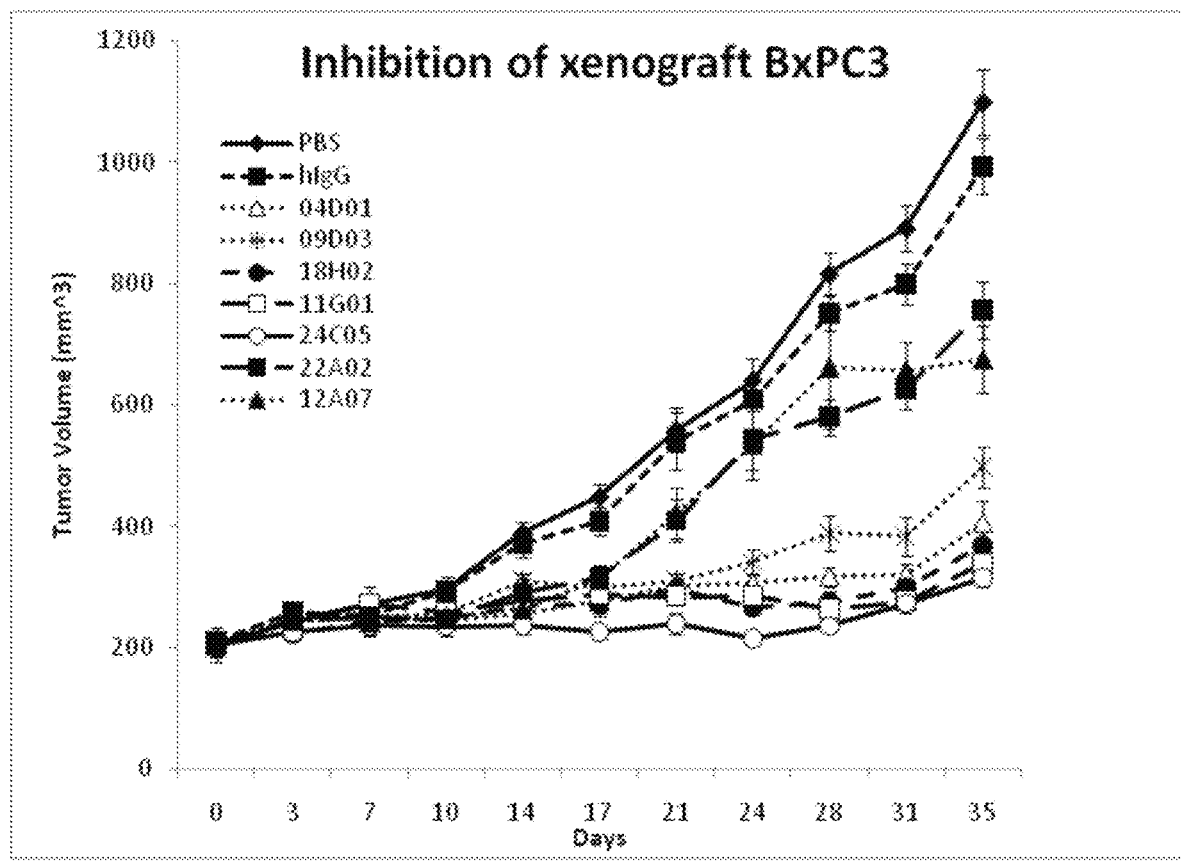
FIG. 14 is a graph summarizing results from an experiment to measure the tumor inhibitory activity of the anti-ErbB3 antibodies 04D01 (Δ), 09D03 (*), 11G01 (□), 12A07 (▲), 18H02 (●), 22A02 (■), 24C05 (○) and a human IgG control (- -■- -) dosed at 20 mg/kg in a BxPC3 pancreatic tumor xenograft model in CB17 SCID mice (vehicle control, PBS (♦)).

The results in FIG. 14 show that antibody 24C05 inhibited tumor growth by 76% in this model (p<0.001). Antibodies 04D01, 18H02 and 11G01 also inhibited tumor growth in this model at 64%, 71%, and 72%, respectively (p<0.001). Antibodies 12A07 and 22A02 demonstrated the least activity, i.e., near 40% tumor growth inhibition, while antibody 09D03 gave 60% tumor growth inhibition in this model.

Example 12—Humanization of Anti-ErbB3 Antibodies

A. Construction of Humanized and Chimeric Anti-ErbB3 Antibodies

This Example describes the humanization of the murine antibody designated 24C05, and the characterization of the resulting humanized antibodies. The humanized anti-ErbB3 antibodies were designed using the SUPERHUMANIZATION™ method (Arana Therapeutics Ltd. and Hwang, W. Y. et al. (2005) METHODS 36:35-42) or the CDR grafting method with back mutations (some human framework residues were changed to murine residues) (See e.g., U.S. Pat. Nos. 5,530,101; 5,693,761; 5,693,762; 5,585,089; 6,180,370; 7,022,500). With the exception of heavy chain CDR1, the Kabat CDR definitions were used for CDR grafting onto human frameworks. A combination of Kabat and Chothia definitions were used for grafting heavy CDR1. The designed amino acid sequences were converted to codon-optimized DNA sequences and synthesized by DNA2.0, Inc. to include (in the following order): 5' HindIII restriction site, Kozak consensus sequence, amino terminal signal sequence, humanized variable region, human IgG1 or Kappa constant region, stop codon, and a 3' EcoRI restriction site. Additionally, one humanized heavy chain, Sh24C05 Hv3-11 Heavy IgG1, was mutated using overlap extension PCR to enhance humanization, resulting in the Sh24C05 Hv3-11 N62S heavy chain IgG1. A human IgG2 version of the Sh24C05 Hv3-11 N62S heavy chain was also constructed.

The anti-ErbB3 antibody chains humanized according to the SUPERHUMANIZATION™ method, as described herein, are designated with the prefix "Sh" before the antibody chain name. The anti-ErbB3 antibody chains humanized by the CDR grafting method with back mutations, as described herein, are designated with the prefix "Hu" before the antibody chain name.

Chimeric (murine variable region and human constant region) 24C05 heavy (human IgG1) and light (human Kappa) chains were also constructed. The murine variable regions were fused to the human constant region using overlap extension PCR, including (in the following order): 5' HindIII restriction site, Kozak consensus sequence, amino terminal signal sequence, mouse variable region, human IgG1 or Kappa constant region, stop codon, and 3' EcoRI restriction site.

The humanized and chimeric heavy chains were subcloned into pEE6.4 (Lonza Biologics) via HindIII and EcoRI sites using In-Fusion™ PCR cloning (Clontech). The humanized and chimeric Kappa light chains were subcloned into pEE14.4 (Lonza Biologics) via HindIII and EcoRI sites using In-Fusion™ PCR cloning.

Humanized antibody chains or chimeric antibody chains were transiently transfected into 293T cells to produce antibody. Antibody was either purified or used in cell culture media supernatant for subsequent in vitro analysis. Binding of the chimeric and humanized antibodies to human ErbB3 was measured as described below. The results are summarized in Table 15.

Additionally, some humanized antibody heavy and light chain combinations were stably expressed in CHOK1SV cells using the GS XCEED™ System (Lonza Biologics) in order to produce large quantities of purified humanized antibody. A single expression vector was constructed by combining pEE6.4 and pEE14.4 based vectors. First, pEE6.4 containing full length humanized heavy chain cDNA was digested with NotI and SalI to isolate the hCMV-MIE promoter+full length humanized heavy chain cDNA+SV40 polyA fragment. This fragment was inserted into the pEE14.4 vector already containing full length humanized light chain cDNA via NotI/SalI sites, thus creating an expression vector that simultaneously expresses heavy and light chains. The combined heavy and light chain vector was linearized and transfected into CHOK1SV cells. Stable clones were selected in the presence of methionine sulfoximine.

Each of the possible combinations of the humanized immunoglobulin heavy chain and immunoglobulin light chain variable regions are set forth below in Table 9.

TABLE 9

| Light Chain Variable Region | Heavy Chain Variable Region |
|---|---|
| Hu24C05 KvA (SEQ ID NO: 174) | Hu24C05 HvA (SEQ ID NO: 162) |
| Hu24C05 KvA (SEQ ID NO: 174) | Sh24C05 Hv3-21 (SEQ ID NO: 156) |
| Hu24C05 KvA (SEQ ID NO: 174) | Sh24C05 Hv3-23 (SEQ ID NO: 158) |
| Hu24C05 KvA (SEQ ID NO: 174) | Sh24C05 Hv3-30 (SEQ ID NO: 160) |
| Hu24C05 KvA (SEQ ID NO: 174) | Sh24C05 Hv3-7 (SEQ ID NO: 150) |
| Hu24C05 KvA (SEQ ID NO: 174) | Sh24C05 Hv3-11 (SEQ ID NO: 152) |
| Hu24C05 KvA (SEQ ID NO: 174) | Sh24C05 Hv3-11 N62S (SEQ ID NO: 154) |
| Sh24C05 Kv1-16 (SEQ ID NO: 166) | Hu24C05 HvA (SEQ ID NO: 162) |
| Sh24C05 Kv1-16 (SEQ ID NO: 166) | Sh24C05 Hv3-21 (SEQ ID NO: 156) |
| Sh24C05 Kv1-16 (SEQ ID NO: 166) | Sh24C05 Hv3-23 (SEQ ID NO: 158) |
| Sh24C05 Kv1-16 (SEQ ID NO: 166) | Sh24C05 Hv3-30 (SEQ ID NO: 160) |
| Sh24C05 Kv1-16 (SEQ ID NO: 166) | Sh24C05 Hv3-7 (SEQ ID NO: 150) |
| Sh24C05 Kv1-16 (SEQ ID NO: 166) | Sh24C05 Hv3-11 (SEQ ID NO: 152) |
| Sh24C05 Kv1-16 (SEQ ID NO: 166) | Sh24C05 Hv3-11 N62S (SEQ ID NO: 154) |
| Sh24C05 Kv1-17 (SEQ ID NO: 168) | Hu24C05 HvA (SEQ ID NO: 162) |
| Sh24C05 Kv1-17 (SEQ ID NO: 168) | Sh24C05 Hv3-21 (SEQ ID NO: 156) |
| Sh24C05 Kv1-17 (SEQ ID NO: 168) | Sh24C05 Hv3-23 (SEQ ID NO: 158) |
| Sh24C05 Kv1-17 (SEQ ID NO: 168) | Sh24C05 Hv3-30 (SEQ ID NO: 160) |
| Sh24C05 Kv1-17 (SEQ ID NO: 168) | Sh24C05 Hv3-7 (SEQ ID NO: 150) |
| Sh24C05 Kv1-17 (SEQ ID NO: 168) | Sh24C05 Hv3-11 (SEQ ID NO: 152) |
| Sh24C05 Kv1-17 (SEQ ID NO: 168) | Sh24C05 Hv3-11 N62S (SEQ ID NO: 154) |
| Sh24C05 Kv1-33 (SEQ ID NO: 170) | Hu24C05 HvA (SEQ ID NO: 162) |
| Sh24C05 Kv1-33 (SEQ ID NO: 170) | Sh24C05 Hv3-21 (SEQ ID NO: 156) |
| Sh24C05 Kv1-33 (SEQ ID NO: 170) | Sh24C05 Hv3-23 (SEQ ID NO: 158) |
| Sh24C05 Kv1-33 (SEQ ID NO: 170) | Sh24C05 Hv3-30 (SEQ ID NO: 160) |
| Sh24C05 Kv1-33 (SEQ ID NO: 170) | Sh24C05 Hv3-7 (SEQ ID NO: 150) |
| Sh24C05 Kv1-33 (SEQ ID NO: 170) | Sh24C05 Hv3-11 (SEQ ID NO: 152) |
| Sh24C05 Kv1-33 (SEQ ID NO: 170) | Sh24C05 Hv3-11 N62S (SEQ ID NO: 154) |
| Sh24C05 Kv1-9 (SEQ ID NO: 164) | Hu24C05 HvA (SEQ ID NO: 162) |
| Sh24C05 Kv1-9 (SEQ ID NO: 164) | Sh24C05 Hv3-21 (SEQ ID NO: 156) |
| Sh24C05 Kv1-9 (SEQ ID NO: 164) | Sh24C05 Hv3-23 (SEQ ID NO: 158) |
| Sh24C05 Kv1-9 (SEQ ID NO: 164) | Sh24C05 Hv3-30 (SEQ ID NO: 160) |
| Sh24C05 Kv1-9 (SEQ ID NO: 164) | Sh24C05 Hv3-7 (SEQ ID NO: 150) |
| Sh24C05 Kv1-9 (SEQ ID NO: 164) | Sh24C05 Hv3-11 (SEQ ID NO: 152) |
| Sh24C05 Kv1-9 (SEQ ID NO: 164) | Sh24C05 Hv3-11 N62S (SEQ ID NO: 154) |
| Sh24C05 Kv1-39 (SEQ ID NO: 172) | Hu24C05 HvA (SEQ ID NO: 162) |
| Sh24C05 Kv1-39 (SEQ ID NO: 172) | Sh24C05 Hv3-21 (SEQ ID NO: 156) |
| Sh24C05 Kv1-39 (SEQ ID NO: 172) | Sh24C05 Hv3-23 (SEQ ID NO: 158) |
| Sh24C05 Kv1-39 (SEQ ID NO: 172) | Sh24C05 Hv3-30 (SEQ ID NO: 160) |
| Sh24C05 Kv1-39 (SEQ ID NO: 172) | Sh24C05 Hv3-7 (SEQ ID NO: 150) |
| Sh24C05 Kv1-39 (SEQ ID NO: 172) | Sh24C05 Hv3-11 (SEQ ID NO: 152) |
| Sh24C05 Kv1-39 (SEQ ID NO: 172) | Sh24C05 Hv3-11 N62S (SEQ ID NO: 154) |

The nucleic acid sequences encoding and the protein sequences defining variable regions of the humanized 24C05 antibodies are summarized below (amino terminal signal peptide sequences are not shown). CDR sequences (Kabat definition) are shown in bold and are underlined in the amino acid sequences.

Nucleic Acid Sequence Encoding the Sh24C05 Hv3-7
Heavy Chain Variable Region (SEQ ID NO: 149)

```
  1 gaggttcagc tggtggaatc tggcggtggg cttgtacaac caggaggctc cctcagactg 61 agttgtgccg cttcagggtt cacattctcc gactatgcga tgtcatgggt gcgccaagca 121 cccgggaaag gactggagtg ggttgccact atcagcgatg gcggaacgta tacctattac 181 cctgacaatg tgaagggtcg gttcaccatt tccagggata acgcaaagaa cagtctctac 241 ctgcagatga acagcctgag ggctgaggac accgccgtct actactgcgc ccgagaatgg 301 ggagattatg atgggtttga ctattggggc cagggcactt tggtgacagt cagttct
```

Protein Sequence Defining the Sh24C05 Hv3-7 Heavy
Chain Variable Region (SEQ ID NO: 150)

```
  1 evqlvesggg lvqpggslrl scaasgftfs dyamswvrqa pgkglewvat isdggtytyy 61 pdnvkgrfti srdnaknsly lqmnslraed tavyycarew gdydgfdywg qgtlvtvss
```

Nucleic Acid Sequence Encoding the Sh24C05 Hv3-11
Heavy Chain Variable Region (SEQ ID NO: 151)

```
  1 caagttcagc tggtggaatc tggcggtggg cttgtaaagc caggaggctc cctcagactg 61 agttgtgccg cttcagggtt cacattctcc gactatgcga tgtcatggat caggcaagca 121 cccgggaaag gactggagtg ggttagcact atcagcgatg gcggaacgta tacctattac 181 cctgacaatg tgaagggtcg gttcaccatt tccagggata acgcaaagaa cagtctctac 241 cttcagatga acagcctgag ggctgaggac accgccgtct actactgcgc ccgagaatgg 301 ggagattatg atgggtttga ctattggggc cagggcactt tggtgacagt cagttct
```

Protein Sequence Defining the Sh24C05 Hv3-11 Heavy
Chain Variable Region (SEQ ID NO: 152)

```
  1 qvqlvesggg lvkpggslrl scaasgftfs dyamswirqa pgkglewvst isdggtytyy 61 pdnvkgrfti srdnaknsly lqmnslraed tavyycarew gdydgfdywg qgtlvtvss
```

Nucleic Acid Sequence Encoding the Sh24C05 Hv3-11
N62S Heavy Chain Variable Region (SEQ ID NO: 153)

```
  1 caagttcagc tggtggaatc tggcggtggg cttgtaaagc caggaggctc cctcagactg 61 agttgtgccg cttcagggtt cacattctcc gactatgcga tgtcatggat caggcaagca 121 cccgggaaag gactggagtg ggttagcact atcagcgatg gcggaacgta tacctattac 181 cctgactccg tgaagggtcg gttcaccatt tccagggata acgcaaagaa cagtctctac 241 cttcagatga acagcctgag ggctgaggac accgccgtct actactgcgc ccgagaatgg 301 ggagattatg atgggtttga ctattggggc cagggcactt tggtgacagt cagttct
```

Protein Sequence Defining the Sh24C05 Hv3-11 N62S
Heavy Chain Variable Region (SEQ ID NO: 154)

```
  1 qvqlvesggg lvkpggslrl scaasgftfs dyamswirqa pgkglewvst isdggtytyy 61 pdsvkgrfti srdnaknsly lqmnslraed tavyycarew gdydgfdywg qgtlvtvss
```

Nucleic Acid Sequence Encoding the Sh24C05 Hv3-21
Heavy Chain Variable Region (SEQ ID NO: 155)

```
  1 gaggttcagc tggtggaatc tggcggtggg cttgtaaagc caggaggctc cctcagactg
 61 agttgtgccg cttcagggtt cacattctcc gactatgcga tgtcatgggt gcgccaagca
121 cccgggaaag gactggagtg ggttagcact atcagcgatg gcggaacgta tacctattac
181 cctgacaatg tgaagggtcg gttcaccatt tccagggata acgcaaagaa cagtctctat
241 ttgcagatga acagcctgag ggctgaggac accgccgtct actactgcgc ccgagaatgg
301 ggagattatg atgggtttga ctattggggc cagggcactt tggtgacagt cagttct
```

Protein Sequence Defining the Sh24C05 Hv3-21 Heavy
Chain Variable Region (SEQ ID NO: 156)

```
  1 evqlvesggg lvkpggslrl scaasgftfs dyamswvrqa pgkglewvst isdggtytyy
 61 pdnvkgrfti srdnaknsly lqmnslraed tavyycarew gdydgfdywg qgtlvtvss
```

Nucleic Acid Sequence Encoding the Sh24C05 Hv3-23
Heavy Chain Variable Region (SEQ ID NO: 157)

```
  1 gaggttcagc ttctggaatc tggcggtggg cttgtacagc caggaggctc cctcagactg
 61 agttgtgccg cttcagggtt cacattctcc gactatgcga tgtcatgggt gcgccaagca
121 cccgggaaag gactggagtg ggtttcaact atcagcgatg gcggaacgta tacctattac
181 cctgacaatg tgaagggtcg gttcaccatt tccagggata acagcaagaa cacactctat
241 ctccagatga acagcctgag ggctgaggac accgccgtct actactgcgc ccgagaatgg
301 ggagattatg atgggtttga ctattggggc cagggcactt tggtgacagt cagttct
```

Protein Sequence Defining the Sh24C05 Hv3-23 Heavy
Chain Variable Region (SEQ ID NO: 158)

```
  1 evqllesggg lvqpggslrl scaasgftfs dyamswvrqa pgkglewvst isdggtytyy
 61 pdnvkgrfti srdnskntly lqmnslraed tavyycarew gdydgfdywg qgtlvtvss
```

Nucleic Acid Sequence Encoding the Sh24C05 Hv3-30
Heavy Chain Variable Region (SEQ ID NO: 159)

```
  1 caggttcagc tggtggaatc tggcggtggg gtagtacaac caggacggtc cctcagactg
 61 agttgtgccg cttcagggtt cacattctcc gactatgcga tgtcatgggt gcgccaagca
121 cccgggaaag gactggagtg ggttgccact atcagcgatg gcggaacgta tacctattac
181 cctgacaatg tgaagggtcg gttcaccatt tccagggata actcaaagaa caccctctat
241 ctccaaatga gtagcctgag ggctgaggac accgccgtct actactgcgc ccgagaatgg
301 ggagattatg atgggtttga ctattggggc cagggcactt tggtgacagt cagttct
```

Protein Sequence Defining the Sh24C05 Hv3-30 Heavy
Chain Variable Region (SEQ ID NO: 160)

```
  1 qvqlvesggg vvqpgrslrl scaasgftfs dyamswvrqa pgkglewvat isdggtytyy
 61 pdnvkgrfti srdnskntly lqmsslraed tavyycarew gdydgfdywg qgtlvtvss
```

Nucleic Acid Sequence Encoding the Hu24C05 HvA
Heavy Chain Variable Region (SEQ ID NO: 161)

```
  1 gaggttcagc tggtggaatc tggcggtggg cttgtaaagc caggaggctc cctcagactg
 61 agttgtgccg cttcagggtt cacattctcc gactatgcga tgtcatgggt gcgccaagca
121 cccgggaaag gactggagtg ggttgccact atcagcgatg gcggaacgta tacctattac
181 cctgacaatg tgaagggtcg gttcaccatt tccagggata cgcaaagaa cagtctctac
241 cttcagatga acagcctgag ggctgaggac accgccgtct actactgcgc ccgagaatgg
301 ggagattatg atgggtttga ctattgggc cagggcactt tggtgacagt cagttct
```

Protein Sequence Defining the Hu24C05 HvA Heavy
Chain Variable Region (SEQ ID NO: 162)

```
  1 evqlvesggg lvkpggslrl scaasgftfs dyamswvrqa pgkglewvat isdggtytyy
 61 pdnvkgrfti srdnaknsly lqmnslraed tavyycarew gdydgfdywg qgtlvtvss
```

Nucleic Acid Sequence Encoding the Sh24C05 Kv1-9
Kappa Chain Variable Region (SEQ ID NO: 163)

```
  1 gatattcagt tgacccaatc acctagcttc ctctcagctt ccgtgggcga cagagttacc
 61 ataacctgtc gggcaagcca ggagatttct gggtacctgt cctggtacca acagaagccc
121 ggaaaagccc ctaagctgtt gatctatgct gcgtcaacct ggatagcgg tgtcccgagt
181 cgattctccg gttctggctc cggaacagag ttcactctga caatttctag ccttcagcca
241 gaagatttcg ccacgtacta ttgcctccag tacgacagct atccctatac atttgggcag
301 ggcactaaac tggagatcaa a
```

Protein Sequence Defining the Sh24C05 Kv1-9 Kappa
Chain Variable Region (SEQ ID NO: 164)

```
  1 diqltqspsf lsasvgdrvt itcrasqeis gylswyqqkp gkapklliya astldsgvps
 61 rfsgsgsgte ftltisslqp edfatyyclq ydsypytfgq gtkleik
```

Nucleic Acid Sequence Encoding the Sh24C05 Kv1-16
Kappa Chain Variable Region (SEQ ID NO: 165)

```
  1 gatattcaga tgacccaatc acctagcagt ctctcagctt ccgtgggcga cagagttacc
 61 ataacctgtc gggcaagcca ggagatttct gggtacctgt cctggtttca acagaagccc
121 ggaaaggccc cgaagagctt gatctatgct gcgtcaacct ggatagcgg tgtcccgagt
181 cgattctccg gttctggctc cggaaccgac tttactctga caatttctag ccttcagcca
241 gaagatttcg ccacgtacta ttgcctccag tacgacagct atccctatac atttgggcag
301 ggcactaaac tggagatcaa a
```

Protein Sequence Defining the Sh24C05 Kv1-16 Kappa
Chain Variable Region (SEQ ID NO: 166)

```
  1 diqmtqspss lsasvgdrvt itcrasqeis gylswfqqkp gkapksliya astldsgvps
 61 rfsgsgsgtd ftltisslqp edfatyyclq ydsypytfgq gtkleik
```

Nucleic Acid Sequence Encoding the Sh24C05 Kv1-17 Kappa Chain Variable Region (SEQ ID NO: 167)

```
  1 gatattcaga tgacccaatc acctagcagt ctctcagctt ccgtgggcga cagagttacc
 61 ataacctgtc gggcaagcca ggagatttct gggtacctgt cctggtatca acagaagccc
121 ggaaaagccc caaagaggtt gatctatgct gcgtcaacct tggatagcgg tgtcccgagt
181 cgattctccg gttctggctc cggaaccgag ttcactctga caatttctag ccttcagcca
241 gaagatttcg ccacgtacta ttgcctccag tacgacagct atccctatac atttgggcag
301 ggcactaaac tggagatcaa a
```

Protein Sequence Defining the Sh24C05 Kv1-17 Kappa Chain Variable Region (SEQ ID NO: 168)

```
 1 diqmtqspss lsasvgdrvt itcrasqeis gylswyqqkp gkapkrliya astldsgvps
61 rfsgsgsgte ftltisslqp edfatyyclq ydsypytfgq gtkleik
```

Nucleic Acid Sequence Encoding the Sh24C05 Kv1-33 Kappa Chain Variable Region (SEQ ID NO: 169)

```
  1 gatattcaga tgacccaatc acctagcagt ctctcagctt ccgtgggcga cagagttacc
 61 ataacctgtc gggcaagcca ggagatttct gggtacctgt cctggtacca acagaagccc
121 ggaaaggccc ccaagctgtt gatctatgct gcgtcaacct tggatagcgg tgtcccgagt
181 cgattctccg gttctggctc cggaacagac tttactttta caatttctag ccttcagcca
241 gaggacatcg ccacgtacta ttgcctccag tacgacagct atccctatac atttgggcag
301 ggcactaaac tggagatcaa a
```

Protein Sequence Defining the Sh24C05 Kv1-33 Kappa Chain Variable Region (SEQ ID NO: 170)

```
 1 diqmtqspss lsasvgdrvt itcrasqeis gylswyqqkp gkapklliya astldsgvps
61 rfsgsgsgtd ftftisslqp ediatyyclq ydsypytfgq gtkleik
```

Nucleic Acid Sequence Encoding the Sh24C05 Kv1-39 Kappa Chain Variable Region (SEQ ID NO: 171)

```
  1 gatattcaga tgacccaatc acctagcagt ctctcagctt ccgtgggcga cagagttacc
 61 ataacctgtc gggcaagcca ggagatttct gggtacctgt cctggtatca acagaagccc
121 ggaaaagccc ctaagctgtt gatctatgct gcgtcaacct tggatagcgg tgtcccgagt
181 cgattctccg gttctggctc cggaactgac ttcactctga caatttctag ccttcagcca
241 gaagatttcg ccacgtacta ttgcctccag tacgacagct atccctatac atttgggcag
301 ggcactaaac tggagatcaa a
```

Protein Sequence Defining the Sh24C05 Kv1-39 Kappa Chain Variable Region (SEQ ID NO: 172)

```
 1 diqmtqspss lsasvgdrvt itcrasqeis gylswyqqkp gkapklliya astldsgvps
61 rfsgsgsgtd ftltisslqp edfatyyclq ydsypytfgq gtkleik
```

Nucleic Acid Sequence Encoding the Hu24C05 KvA Kappa Chain Variable Region (SEQ ID NO: 173)

```
  1 gatattcaga tgacccaatc acctagcagt ctctcagctt ccgtgggcga cagagttacc
 61 ataacctgtc gggcaagcca ggagatttct gggtacctgt cctggctgca acagaagccc
121 ggaggcgcca tcaagaggtt gatctatgct gcgtcaacct tggatagcgg tgtcccgagt
181 cgattctccg gttctggctc cggaagtgac tacactctga caatttctag ccttcagcca
241 gaagatttcg ccacgtacta ttgcctccag tacgacagct atccctatac atttgggcag
301 ggcactaaac tggagatcaa a
```

Protein Sequence Defining the Hu24C05 KvA Kappa Chain Variable Region (SEQ ID NO: 174)

```
 1 diqmtqspss lsasvgdrvt itcrasqeis gylswlqqkp ggaikrliya astldsgvps
61 rfsgsgsgsd ytltisslqp edfatyyclq ydsypytfgq gtkleik
```

The amino acid sequences defining the immunoglobulin heavy chain variable regions for the antibodies produced in Example 12 are aligned in FIG. 15. Amino terminal signal peptide sequences (for proper expression/secretion) are not shown. CDR$_1$, CDR$_2$, and CDR$_3$ (Kabat definition) are identified by boxes.

The amino acid sequences defining the immunoglobulin light chain variable regions for the antibodies in Example 12 are aligned in FIG. 16. Amino terminal signal peptide sequences (for proper expression/secretion) are not shown. CDR$_1$, CDR$_2$ and CDR$_3$ are identified by boxes.

Table 10 is a concordance chart showing the SEQ ID NO. of each sequence discussed in this Example.

TABLE 10

| SEQ. ID NO. | Nucleic Acid or Protein |
|---|---|
| 149 | Sh24C05 Hv3-7 Heavy Chain Variable Region-nucleic acid |
| 150 | Sh24C05 Hv3-7 Heavy Chain Variable Region-protein |
| 57 | Sh24C05 Hv3-7 Heavy Chain CDR$_1$ |
| 58 | Sh24C05 Hv3-7 Heavy Chain CDR$_2$ |
| 59 | Sh24C05 Hv3-7 Heavy Chain CDR$_3$ |
| 151 | Sh24C05 Hv3-11 Heavy Chain Variable Region-nucleic acid |
| 152 | Sh24C05 Hv3-11 Heavy Chain Variable Region-protein |
| 57 | Sh24C05 Hv3-11 Heavy Chain CDR$_1$ |
| 58 | Sh24C05 Hv3-11 Heavy Chain CDR$_2$ |
| 59 | Sh24C05 Hv3-11 Heavy Chain CDR$_3$ |
| 153 | Sh24C05 Hv3-11 N62S Heavy Chain Variable Region-nucleic acid |
| 154 | Sh24C05 Hv3-11 N62S Heavy Chain Variable Region-protein |
| 57 | Sh24C05 Hv3-11 N62S Heavy Chain CDR$_1$ |
| 148 | Sh24C05 Hv3-11 N62S Heavy Chain CDR$_2$ |
| 59 | Sh24C05 Hv3-11 N62S Heavy Chain CDR$_3$ |
| 155 | Sh24C05 Hv3-21 Heavy Chain Variable Region-nucleic acid |
| 156 | Sh24C05 Hv3-21 Heavy Chain Variable Region-protein |
| 57 | Sh24C05 Hv3-21 Heavy Chain CDR$_1$ |
| 58 | Sh24C05 Hv3-21 Heavy Chain CDR$_2$ |
| 59 | Sh24C05 Hv3-21 Heavy Chain CDR$_3$ |
| 157 | Sh24C05 Hv3-23 Heavy Chain Variable Region-nucleic acid |
| 158 | Sh24C05 Hv3-23 Heavy Chain Variable Region-protein |
| 57 | Sh24C05 Hv3-23 Heavy Chain CDR$_1$ |
| 58 | Sh24C05 Hv3-23 Heavy Chain CDR$_2$ |
| 59 | Sh24C05 Hv3-23 Heavy Chain CDR$_3$ |
| 159 | Sh24C05 Hv3-30 Heavy Chain Variable Region-nucleic acid |
| 160 | Sh24C05 Hv3-30 Heavy Chain Variable Region-protein |
| 57 | Sh24C05 Hv3-30 Heavy Chain CDR$_1$ |
| 58 | Sh24C05 Hv3-30 Heavy Chain CDR$_2$ |
| 59 | Sh24C05 Hv3-30 Heavy Chain CDR$_3$ |
| 161 | Hu24C05 HvA Heavy Chain Variable Region-nucleic acid |
| 162 | Hu24C05 HvA Heavy Chain Variable Region-protein |
| 57 | Hu24C05 HvA Heavy Chain CDR$_1$ |
| 58 | Hu24C05 HvA Heavy Chain CDR$_2$ |
| 59 | Hu24C05 HvA Heavy Chain CDR$_3$ |
| 163 | Sh24C05 Kv1-9 Light (kappa) Chain Variable Region-nucleic acid |
| 164 | Sh24C05 Kv1-9 Light (kappa) Chain Variable Region-protein |
| 60 | Sh24C05 Kv1-9 Light (kappa) Chain CDR$_1$ |
| 61 | Sh24C05 Kv1-9 Light (kappa) Chain CDR$_2$ |
| 62 | Sh24C05 Kv1-9 Light (kappa) Chain CDR$_3$ |
| 165 | Sh24C05 Kv1-16 Light (kappa) Chain Variable Region-nucleic acid |
| 166 | Sh24C05 Kv1-16 Light (kappa) Chain Variable Region-protein |
| 60 | Sh24C05 Kv1-16 Light (kappa) Chain CDR$_1$ |
| 61 | Sh24C05 Kv1-16 Light (kappa) Chain CDR$_2$ |
| 62 | Sh24C05 Kv1-16 Light (kappa) Chain CDR$_3$ |
| 167 | Sh24C05 Kv1-17 Light (kappa) Chain Variable Region-nucleic acid |
| 168 | Sh24C05 Kv1-17 Light (kappa) Chain Variable Region-protein |
| 60 | Sh24C05 Kv1-17 Light (kappa) Chain CDR$_1$ |
| 61 | Sh24C05 Kv1-17 Light (kappa) Chain CDR$_2$ |
| 62 | Sh24C05 Kv1-17 Light (kappa) Chain CDR$_3$ |
| 169 | Sh24C05 Kv1-33 Light (kappa) Chain Variable Region-nucleic acid |
| 170 | Sh24C05 Kv1-33 Light (kappa) Chain Variable Region-protein |
| 60 | Sh24C05 Kv1-33 Light (kappa) Chain CDR$_1$ |
| 61 | Sh24C05 Kv1-33 Light (kappa) Chain CDR$_2$ |
| 62 | Sh24C05 Kv1-33 Light (kappa) Chain CDR$_3$ |
| 171 | Sh24C05 Kv1-39 Light (kappa) Chain Variable Region-nucleic acid |
| 172 | Sh24C05 Kv1-39 Light (kappa) Chain Variable Region-protein |
| 60 | Sh24C05 Kv1-39 Light (kappa) Chain CDR$_1$ |
| 61 | Sh24C05 Kv1-39 Light (kappa) Chain CDR$_2$ |
| 62 | Sh24C05 Kv1-39 Light (kappa) Chain CDR$_3$ |
| 173 | Hu24C05 KvA Light (kappa) Chain Variable Region-nucleic acid |
| 174 | Hu24C05 KvA Light (kappa) Chain Variable Region-protein |

TABLE 10-continued

| SEQ. ID NO. | Nucleic Acid or Protein | |
|---|---|---|
| 60 | Hu24C05 KvA Light (kappa) Chain CDR₁ | |
| 61 | Hu24C05 KvA Light (kappa) Chain CDR₂ | 5 |
| 62 | Hu24C05 KvA Light (kappa) Chain CDR₃ | |

Humanized monoclonal antibody heavy chain CDR sequences (Kabat, Chothia, and IMGT definitions) are shown in Table 11.

TABLE 11

| | CDR1 | CDR2 | CDR3 |
|---|---|---|---|
| *Kabat* | | | |
| 24C05 | DYAMS (SEQ ID NO: 57) | TISDGGTYTYYPDNVKG (SEQ ID NO: 58) | EWGDYDGFDY (SEQ ID NO: 59) |
| Sh24C05 Hv3-7 | DYAMS (SEQ ID NO: 57) | TISDGGTYTYYPDNVKG (SEQ ID NO: 58) | EWGDYDGFDY (SEQ ID NO: 59) |
| Sh24C05 Hv3-11 | DYAMS (SEQ ID NO: 57) | TISDGGTYTYYPDNVKG (SEQ ID NO: 58) | EWGDYDGFDY (SEQ ID NO: 59) |
| Sh24C05 Hv3-11 N62S | DYAMS (SEQ ID NO: 57) | TISDGGTYTYYPDSVKG (SEQ ID NO: 148) | EWGDYDGFDY (SEQ ID NO: 59) |
| Sh24C05 Hv3-21 | DYAMS (SEQ ID NO: 57) | TISDGGTYTYYPDNVKG (SEQ ID NO: 58) | EWGDYDGFDY (SEQ ID NO: 59) |
| Sh24C05 Hv3-23 | DYAMS (SEQ ID NO: 57) | TISDGGTYTYYPDNVKG (SEQ ID NO: 58) | EWGDYDGFDY (SEQ ID NO: 59) |
| Sh24C05 Hv3-30 | DYAMS (SEQ ID NO: 57) | TISDGGTYTYYPDNVKG (SEQ ID NO: 58) | EWGDYDGFDY (SEQ ID NO: 59) |
| Hu24C05 HvA | DYAMS (SEQ ID NO: 57) | TISDGGTYTYYPDNVKG (SEQ ID NO: 58) | EWGDYDGFDY (SEQ ID NO: 59) |
| *Chothia* | | | |
| 24C05 | GFTFSDY (SEQ ID NO: 75) | SDGGTY (SEQ ID NO: 76) | EWGDYDGFDY (SEQ ID NO: 59) |
| Sh24C05 Hv3-7 | GFTFSDY (SEQ ID NO: 75) | SDGGTY (SEQ ID NO: 76) | EWGDYDGFDY (SEQ ID NO: 59) |
| Sh24C05 Hv3-11 | GFTFSDY (SEQ ID NO: 75) | SDGGTY (SEQ ID NO: 76) | EWGDYDGFDY (SEQ ID NO: 59) |
| Sh24C05 Hv3-11 N62S | GFTFSDY (SEQ ID NO: 75) | SDGGTY (SEQ ID NO: 76) | EWGDYDGFDY (SEQ ID NO: 59) |
| Sh24C05 Hv3-21 | GFTFSDY (SEQ ID NO: 75) | SDGGTY (SEQ ID NO: 76) | EWGDYDGFDY (SEQ ID NO: 59) |
| Sh24C05 Hv3-23 | GFTFSDY (SEQ ID NO: 75) | SDGGTY (SEQ ID NO: 76) | EWGDYDGFDY (SEQ ID NO: 59) |
| Sh24C05 Hv3-30 | GFTFSDY (SEQ ID NO: 75) | SDGGTY (SEQ ID NO: 76) | EWGDYDGFDY (SEQ ID NO: 59) |
| Hu24C05 HvA | GFTFSDY (SEQ ID NO: 75) | SDGGTY (SEQ ID NO: 76) | EWGDYDGFDY (SEQ ID NO: 59) |
| *IMGT* | | | |
| 24C05 | GFTFSDYA (SEQ ID NO: 94) | ISDGGTYT (SEQ ID NO: 95) | AREWGDYDGFDY (SEQ ID NO: 96) |
| Sh24C05 Hv3-7 | GFTFSDYA (SEQ ID NO: 94) | ISDGGTYT (SEQ ID NO: 95) | AREWGDYDGFDY (SEQ ID NO: 96) |
| Sh24C05 Hv3-11 | GFTFSDYA (SEQ ID NO: 94) | ISDGGTYT (SEQ ID NO: 95) | AREWGDYDGFDY (SEQ ID NO: 96) |
| Sh24C05 Hv3-11 N62S | GFTFSDYA (SEQ ID NO: 94) | ISDGGTYT (SEQ ID NO: 95) | AREWGDYDGFDY (SEQ ID NO: 96) |
| Sh24C05 Hv3-21 | GFTFSDYA (SEQ ID NO: 94) | ISDGGTYT (SEQ ID NO: 95) | AREWGDYDGFDY (SEQ ID NO: 96) |
| Sh24C05 Hv3-23 | GFTFSDYA (SEQ ID NO: 94) | ISDGGTYT (SEQ ID NO: 95) | AREWGDYDGFDY (SEQ ID NO: 96) |
| Sh24C05 Hv3-30 | GFTFSDYA (SEQ ID NO: 94) | ISDGGTYT (SEQ ID NO: 95) | AREWGDYDGFDY (SEQ ID NO: 96) |
| Hu24C05 HvA | GFTFSDYA (SEQ ID NO: 94) | ISDGGTYT (SEQ ID NO: 95) | AREWGDYDGFDY (SEQ ID NO: 96) |

Humanized monoclonal antibody Kappa light chain CDR sequences (Kabat, Chothia, and IMGT definitions) are shown in Table 12.

TABLE 12

|  | CDR1 | CDR2 | CDR3 |
|---|---|---|---|
| Kabat/Chothia | | | |
| 24C05 | RASQEISGYLS (SEQ ID NO: 60) | AASTLDS (SEQ ID NO: 61) | LQYDSYPYT (SEQ ID NO: 62) |
| Sh24C05 Kv1-9 | RASQEISGYLS (SEQ ID NO: 60) | AASTLDS (SEQ ID NO: 61) | LQYDSYPYT (SEQ ID NO: 62) |
| Sh24C05 Kv1-16 | RASQEISGYLS (SEQ ID NO: 60) | AASTLDS (SEQ ID NO: 61) | LQYDSYPYT (SEQ ID NO: 62) |
| Sh24C05 Kv1-17 | RASQEISGYLS (SEQ ID NO: 60) | AASTLDS (SEQ ID NO: 61) | LQYDSYPYT (SEQ ID NO: 62) |
| Sh24C05 Kv1-33 | RASQEISGYLS (SEQ ID NO: 60) | AASTLDS (SEQ ID NO: 61) | LQYDSYPYT (SEQ ID NO: 62) |
| Sh24C05 Kv1-39 | RASQEISGYLS (SEQ ID NO: 60) | AASTLDS (SEQ ID NO: 61) | LQYDSYPYT (SEQ ID NO: 62) |
| Flu24C05 KvA | RASQEISGYLS (SEQ ID NO: 60) | AASTLDS (SEQ ID NO: 61) | LQYDSYPYT (SEQ ID NO: 62) |
| IMGT | | | |
| 24C05 | QEISGY (SEQ ID NO: 101) | AAS | LQYDSYPYT (SEQ ID NO: 62) |
| Sh24C05 Kv1-9 | QEISGY (SEQ ID NO: 101) | AAS | LQYDSYPYT (SEQ ID NO: 62) |
| Sh24C05 Kv1-16 | QEISGY (SEQ ID NO: 101) | AAS | LQYDSYPYT (SEQ ID NO: 62) |
| Sh24C05 Kv1-17 | QEISGY (SEQ ID NO: 101) | AAS | LQYDSYPYT (SEQ ID NO: 62) |
| Sh24C05 Kv1-33 | QEISGY (SEQ ID NO: 101) | AAS | LQYDSYPYT (SEQ ID NO: 62) |
| Sh24C05 Kv1-39 | QEISGY (SEQ ID NO: 101) | AAS | LQYDSYPYT (SEQ ID NO: 62) |
| Hu24C05 KvA | QEISGY (SEQ ID NO: 101) | AAS | LQYDSYPYT (SEQ ID NO: 62) |

In Tables 11 and 12, the longest CDR sequences for the immunoglobulin heavy chain and light chain are shown in bold.

To create the complete chimeric and humanized heavy or kappa chain antibody sequences, each variable sequence above is combined with its respective human constant region. For example, a complete heavy chain comprises a heavy variable sequence followed by a human IgG1 heavy chain constant sequence or a human IgG2 heavy chain constant sequence. A complete kappa chain comprises a kappa variable sequence followed by the human kappa light chain constant sequence.

Nucleic Acid Sequence Encoding the Human IgG1 Heavy Chain Constant Region (SEQ ID NO: 175)

```
  1 gcctcaacaa aaggaccaag tgtgttccca ctcgcccta gcagcaagag tacatccggg
 61 ggcactgcag cactcggctg cctcgtcaag gattattttc cagagccagt aaccgtgagc
121 tggaacagtg gagcactcac ttctggtgtc catacttttc ctgctgtcct gcaaagctct
181 ggcctgtact cactcagctc cgtcgtgacc gtgccatctt catctctggg cactcagacc
241 tacatctgta atgtaaacca caagcctagc aatactaagg tcgataagcg ggtggaaccc
301 aagagctgcg acaagactca cacttgtccc ccatgccctg ccctgaact tctgggcggt
361 cccagcgtct ttttgttccc accaaagcct aaagatactc tgatgataag tagaacaccc
421 gaggtgacat gtgttgttgt agacgtttcc cacgaggacc cagaggttaa gttcaactgg
481 tacgttgatg gagtcgaagt acataatgct aagaccaagc ctagagagga gcagtataat
541 agtacatacc gtgtagtcag tgttctcaca gtgctgcacc aagactggct caacggcaaa
601 gaatacaaat gcaaagtgtc caacaaagca ctcccagccc tatcgagaa gactattagt
661 aaggcaaagg ggcagcctcg tgaaccacag gtgtacactc tgccacccag tagagaggaa
721 atgacaaaga accaagtctc attgacctgc ctggtgaaag gcttctaccc cagcgacatc
781 gccgttgagt gggagagtaa cggtcagcct gagaacaatt acaagacaac ccccccagtg
```

-continued

```
841 ctggatagtg acgggtcttt ctttctgtac agtaagctga ctgtggacaa gtcccgctgg 901 cagcagggta acgtcttcag ctgttccgtg atgcacgagg cattgcacaa ccactacacc 961 cagaagtcac tgagcctgag cccagggaag
```

Protein Sequence Defining the Human IgG1 Heavy Chain
Constant Region (SEQ ID NO: 176)

```
  1 astkgpsvfp lapsskstsg gtaalgclvk dyfpepvtvs wnsgaltsgv htfpavlqss 61 glyslssvvt vpssslgtqt yicnvnhkps ntkvdkrvep kscdkthtcp pcpapellgg 121 psvflfppkp kdtlmisrtp evtcvvvdvs hedpevkfnw yvdgvevhna ktkpreeqyn 181 styrvvsvlt vlhqdwlngk eykckvsnka lpapiektis kakgqprepq vytlppsree 241 mtknqvsltc lvkgfypsdi avewesngqp ennykttppv ldsdgsffly skltvdksrw 301 qqgnvfscsv mhealhnhyt qkslslspgk
```

Nucleic Acid Sequence Encoding the Human IgG2 Heavy
Chain Constant Region (SEQ ID NO: 177)

```
  1 gcctccacca agggcccatc ggtcttcccc ctggcgccct gctccaggag cacctccgag 61 agcacagcgg ccctgggctg cctggtcaag gactacttcc ccgaaccggt gacggtgtcg 121 tggaactcag gcgctctgac cagcggcgtg cacaccttcc cagctgtcct acagtcctca 181 ggactctact ccctcagcag cgtggtgacc gtgccctcca gcaacttcgg cacccagacc 241 tacacctgca acgtagatca caagcccagc aacaccaagg tggacaagac agttgagcgc 301 aaatgttgtg tcgagtgccc accgtgccca gcaccacctg tggcaggacc gtcagtcttc 361 ctcttccccc caaaacccaa ggacaccctc atgatctccc ggacccctga ggtcacgtgc 421 gtggtggtgg acgtgagcca cgaagacccc gaggtccagt tcaactggta cgtggacggc 481 gtggaggtgc ataatgccaa gacaaagcca cgggaggagc agttcaacag cacgttccgt 541 gtggtcagcg tcctcaccgt tgtgcaccag gactggctga acggcaagga gtacaagtgc 601 aaggtctcca acaaaggcct cccagccccc atcgagaaaa ccatctccaa aaccaaaggg 661 cagccccgag aaccacaggt gtacaccctg cccccatccc gggaggagat gaccaagaac 721 caggtcagcc tgacctgcct ggtcaaaggc ttctacccca gcgacatcgc cgtggagtgg 781 gagagcaatg ggcagccgga gaacaactac aagaccacac ctcccatgct ggactccgac 841 ggctccttct tcctctacag caagctcacc gtggacaaga gcaggtggca gcaggggaac 901 gtcttctcat gctccgtgat gcatgaggct ctgcacaacc actacacgca gaagagcctc 961 tccctgtctc cgggtaaa
```

Protein Sequence Defining the Human IgG2 Heavy Chain
Constant Region (SEQ ID NO: 178)

```
  1 astkgpsvfp lapcsrstse staalgclvk dyfpepvtvs wnsgaltsgv htfpavlqss 61 glyslssvvt vpssnfgtqt ytcnvdhkps ntkvdktver kccvecppcp appvagpsvf 121 lfppkpkdtl misrtpevtc vvvdvshedp evqfnwyvdg vevhnaktkp reeqfnstfr 181 vvsvltvvhq dwlngkeykc kvsnkglpap iektisktkg qprepqvytl ppsreemtkn 241 qvsltclvkg fypsdiavew esngqpenny kttppmldsd gsfflysklt vdksrwqqgn 301 vfscsvmhea lhnhytqksl slspgk
```

Nucleic Acid Sequence Encoding the Human Kappa Light Chain Constant Region (SEQ ID NO: 179)

```
  1 cgcacagttg ctgcccccag cgtgttcatt ttcccaccta gcgatgagca gctgaaaagc
 61 ggtactgcct ctgtcgtatg cttgctcaac aacttttacc cacgtgaggc taaggtgcag
121 tggaaagtgg ataatgcact tcaatctgga aacagtcaag agtccgtgac agaacaggac
181 agcaaagact caacttattc actctcttcc accctgactc tgtccaaggc agactatgaa
241 aaacacaagg tatacgcctg cgaggttaca caccagggtt tgtctagtcc tgtcaccaag
301 tccttcaata ggggcgaatg t
```

Protein Sequence Defining the Human Kappa Light Chain Constant Region (SEQ ID NO: 180)

```
 1 rtvaapsvfi fppsdeqlks gtasvvclln nfypreakvq wkvdnalqsg nsqesvteqd
61 skdstyslss tltlskadye khkvyacevt hqglsspvtk sfnrgec
```

The following sequences represent the actual or contemplated full length heavy and light chain sequences (i.e., containing both the variable and constant regions sequences) for each antibody described in this Example. Signal sequences for proper secretion of the antibodies are also included at the 5' end of the DNA sequences or the amino terminal end of the protein sequences. It is also contemplated herein that the variable region sequences can be ligated to other constant region sequences to produce active full length IgG heavy and light chains.

Nucleic Acid Sequence Encoding the Full Length Chimeric 24C05 Heavy Chain (Mouse Heavy Chain Variable Region and Human IgG1 Constant Region) (SEQ ID NO: 181)

```
   1 atgaacttcg ggctcagctt gatgttcctt gtccttgtct taaaaggtgt ccagtgtgag
  61 gtgcagctgg tggaatctgg gggaggctta gtgaagcctg gagggtccct gaaactctcc
 121 tgtgcagcct ctggattcac tttcagtgac tatgccatgt cttgggttcg ccagactccg
 181 gaaaagaggc tggagtgggt cgcaaccatt agtgatggtg gtacttacac ctactatcca
 241 gacaatgtaa agggccgatt caccatctcc agagacaatg ccaagaacaa cctgtacctg
 301 caaatgagcc atctgaagtc tgaggacaca gccatgtatt actgtgcaag agaatggggt
 361 gattacgacg gatttgacta ctggggccaa ggcaccactc tcacagtctc ctcggcctca
 421 acaaaaggac caagtgtgtt cccactcgcc cctagcagca gagtacatc cgggggcact
 481 gcagcactcg gctgcctcgt caaggattat tttccagagc cagtaaccgt gagctggaac
 541 agtggagcac tcacttctgg tgtccatact tttcctgctg tcctgcaaag ctctggcctg
 601 tactcactca gctccgtcgt gaccgtgcca tcttcatctc tgggcactca gacctacatc
 661 tgtaatgtaa accacaagcc tagcaatact aaggtcgata gcgggtgga acccaagagc
 721 tgcgacaaga ctcacacttg tcccccatgc cctgcccctg aacttctggg cggtcccagc
 781 gtcttttgt tcccaccaaa gcctaaagat actctgatga taagtagaac acccgaggtg
 841 acatgtgttg ttgtagacgt tccccacgag gacccagagg ttaagttcaa ctggtacgtt
 901 gatggagtcg aagtacataa tgctaagacc aagcctagag aggagcagta taatagtaca
 961 taccgtgtag tcagtgttct cacagtgctg caccaagact ggctcaacgg caaagaatac
1021 aaatgcaaag tgtccaacaa agcactccca gcccctatcg agaagactat tagtaaggca
1081 aagggcagc ctcgtgaacc acaggtgtac actctgccac ccagtagaga ggaaatgaca
1141 aagaaccaag tctcattgac ctgcctggtg aaaggcttct acccagcga catcgccgtt
1201 gagtgggaga gtaacggtca gcctgagaac aattacaaga caccccccc agtgctggat
1261 agtgacgggt ctttctttct gtacagtaag ctgactgtgg acaagtcccg ctggcagcag
```

```
1321 ggtaacgtct tcagctgttc cgtgatgcac gaggcattgc acaaccacta cacccagaag 1381 tcactgagcc tgagcccagg gaag
```

Protein Sequence Defining the Full Length Chimeric 24C05 Heavy Chain (Mouse Heavy Chain Variable Region and Human IgG1 Constant Region) (SEQ ID NO: 182)

```
  1 mnfglslmfl vlvlkgvqce vqlvesgggl vkpggslkls caasgftfsd yamswvrqtp 61 ekrlewvati sdggtytyyp dnvkgrftis rdnaknnlyl qmshlksedt amyycarewg 121 dydgfdywgq gttltvssas tkgpsvfpla psskstsggt aalgclvkdy fpepvtvswn 181 sgaltsgvht fpavlgssgl yslssvvtvp ssslgtqtyi cnvnhkpsnt kvdkrvepks 241 cdkthtcppc papellggps vflfppkpkd tlmisrtpev tcvvvdvshe dpevkfnwyv 301 dgvevhnakt kpreeqynst yrvvsvltvl hqdwlngkey kckvsnkalp apiektiska 361 kgqprepqvy tlppsreemt knqvsltclv kgfypsdiav ewesngqpen nykttppvld 421 sdgsfflysk ltvdksrwqq gnvfscsvmh ealhnhytqk slslspgk
```

Nucleic Acid Sequence Encoding the Full Length Chimeric 24C05 Light Chain (Mouse Kappa Chain Variable Region and Human Kappa Constant Region) (SEQ ID NO: 183)

```
  1 atggacatga gggttcctgc tcacgttttt ggcttcttgt tgctctggtt tccaggtacc 61 agatgtgaca tccagatgac ccagtctcca tcctccttat ctgcctctct gggagaaaga 121 gtcagtctca cttgtcgggc aagtcaggaa attagtggtt acttaagctg gcttcagcag 181 aaaccagatg gaactattaa acgcctgatc tacgccgcat ccactttaga ttctggtgtc 241 ccaaaaaggt tcagtggcag taggtctggg tcagattatt ctctcaccat cggcagcctt 301 gagtctgaag atcttgcaga ctattactgt ctacaatatg atagttatcc gtacacgttc 361 ggagggggga ccaagctgga aataaaacgc acagtcgccg ctccctccgt gttcatcttt 421 ccaccaagtg atgagcaact gaagtctggt actgcttcag tcgtgtgtct gctgaacaat 481 ttctacccct gagaagccaa agtccaatgg aaggtagaca acgcactgca gtccggcaat 541 agccaagaat cagttaccga acaggattca aaggacagta catattccct gagcagcact 601 ctgaccctgt caaaggccga ttacgagaaa cacaaggtct atgcttgcga agtgacacat 661 cagggactgt ccagcccagt gacaaaatct tttaaccgtg gggagtgt
```

Protein Sequence Defining the Full Length Chimeric 24C05 Light Chain (Mouse Kappa Chain Variable Region and Human Kappa Constant Region) (SEQ ID NO: 184)

```
  1 mdmrvpahvf gflllwfpgt rcdiqmtqsp sslsaslger vsltcrasqe isgylswlqq 61 kpdgtikrli yaastldsgv pkrfsgsrsg sdysltigsl esedladyyc lqydsypytf 121 gggtkleikr tvaapsvfif ppsdeqlksg tasvvcllnn fypreakvqw kvdnalqsgn 181 sqesvteqds kdstyslsst ltlskadyek hkvyacevth qglsspvtks fnrgec
```

Nucleic Acid Sequence Encoding the Full Length Humanized sh24C05 Hv3-7 Heavy Chain (Humanized Heavy Chain Variable Region and Human IgG1 Constant Region) (SEQ ID NO: 185)

```
   1 atggacatga gagttcctgc tcagctgctc gggttgctgt tgctttggct ccggggtgct
  61 aggtgcgagg ttcagctggt ggaatctggc ggtgggcttg tacaaccagg aggctccctc
 121 agactgagtt gtgccgcttc agggttcaca ttctccgact atgcgatgtc atgggtcgcc
 181 caagcacccg ggaaaggact ggagtgggtt gccactatca gcgatggcgg aacgtatacc
 241 tattaccctg acaatgtgaa gggtcggttc accatttcca gggataacgc aaagaacagt
 301 ctctacctgc agatgaacag cctgagggct gaggacaccg ccgtctacta ctgcgcccga
 361 gaatggggag attatgatgg gtttgactat tggggccagg gcactttggt gacagtcagt
 421 tctgcctcaa caaaggacc aagtgtgttc ccactcgccc ctagcagcaa gagtacatcc
 481 ggggcactg cagcactcgg ctgcctcgtc aaggattatt tcccagagcc agtaaccgtg
 541 agctggaaca gtggagcact cacttctggt gtccatactt tcctgctgt cctgcaaagc
 601 tctggcctgt actcactcag ctccgtcgtg accgtgccat cttcatctct gggcactcag
 661 acctacatct gtaatgtaaa ccacaagcct agcaatacta aggtcgataa gcgggtggaa
 721 cccaagagct cgcacaagac tcacacttgt cccccatgcc ctgcccctga acttctgggc
 781 ggtcccagcg tcttttttgtt cccaccaaag cctaaagata ctctgatgat aagtagaaca
 841 cccgaggtga catgtgttgt tgtagacgtt tcccacgagg acccagaggt taagttcaac
 901 tggtacgttg atggagtcga agtacataat gctaagacca gcctagaga ggagcagtat
 961 aatagtacat accgtgtagt cagtgttctc acagtgctgc accaagactg gctcaacggc
1021 aaagaataca atgcaaagt gtccaacaaa gcactcccag ccctatcga agagactatt
1081 agtaaggcaa aggggcagcc tcgtgaacca caggtgtaca ctctgccacc cagtagagag
1141 gaaatgacaa agaaccaagt ctcattgacc tgcctggtga aaggcttcta ccccagcgac
1201 atcgccgttg agtgggagag taacggtcag cctgagaaca attacaagac aacccccca
1261 gtgctggata gtgacgggtc tttctttctg tacagtaagc tgactgtgga caagtcccgc
1321 tggcagcagg gtaacgtctt cagctgttcc gtgatgcacg aggcattgca caaccactac
1381 acccagaagt cactgagcct gagcccaggg aag
```

Protein Sequence Defining the Full Length Humanized Sh24C05 Hv3-7 Heavy Chain (Humanized Heavy Chain Variable Region and Human IgG1 Constant Region) (SEQ ID NO: 186)

```
   1 mdmrvpaqll glllwlrga rcevqlvesg gglvqpggsl rlscaasgft fsdyamswvr
  61 qapgkglewv atisdggtyt yypdnvkgrf tisrdnakns lylqmnslra edtavyycar
 121 ewgdydgfdy wgqgtivtvs sastkgpsvf plapssksts ggtaalgclv kdyfpepvtv
 181 swnsgaltsg vhtfpavlqs sglyslssvv tvpsslgtq tyicnvnhkp sntkvdkrve
 241 pkscdkthtc ppcpapellg gpsvflfppk pkdtlmisrt pevtcvvvdv shedpevkfn
 301 wyvdgvevhn aktkpreeqy nstyrvvsvl tvlhqdwlng keykckvsnk alpapiekti
 361 skakgqprep qvytlppsre emtknqvslt clvkgfypsd iavewesngq pennykttpp
 421 vldsdgsffl yskltvdksr wqqgnvfscs vmhealhnhy tqkslslspg k
```

Nucleic Acid Sequence Encoding the Full Length Humanized Sh24C05 Hv3-11 Heavy Chain (Humanized Heavy Chain Variable Region and Human IgG1 Constant Region) (SEQ ID NO: 187)

```
   1 atggacatga gagttcctgc tcagctgctc gggttgctgt tgctttggct ccggggtgct
  61 aggtgccaag ttcagctggt ggaatctggc ggtgggcttg taaagccagg aggctccctc
 121 agactgagtt gtgccgcttc agggttcaca ttctccgact atgcgatgtc atggatcagg
 181 caagcacccg ggaaaggact ggagtgggtt agcactatca gcgatggcgg aacgtatacc
 241 tattaccctg acaatgtgaa gggtcggttc accatttcca gggataacgc aaagaacagt
 301 ctctaccttc agatgaacag cctgagggct gaggacaccg ccgtctacta ctgcgcccga
 361 gaatggggag attatgatgg gtttgactat tggggccagg gcactttggt gacagtcagt
 421 tctgcctcaa caaaaggacc aagtgtgttc ccactcgccc ctagcagcaa gagtacatcc
 481 gggggcactg cagcactcgg ctgcctcgtc aaggattatt ttccagagcc agtaaccgtg
 541 agctggaaca gtggagcact cacttctggt gtccatactt ttcctgctgt cctgcaaagc
 601 tctggcctgt actcactcag ctccgtcgtg accgtgccat cttcatctct gggcactcag
 661 acctacatct gtaatgtaaa ccacaagcct agcaatacta aggtcgataa gcgggtggaa
 721 cccaagagct cgcacaagac tcacacttgt cccccatgcc ctgcccctga acttctgggc
 781 ggtcccagcg tcttttttgtt cccaccaaag cctaaagata ctctgatgat aagtagaaca
 841 cccgaggtga catgtgttgt tgtagacgtt tcccacgagg acccagaggt taagttcaac
 901 tggtacgttg atggagtcga agtacataat gctaagacca gcctagaga ggagcagtat
 961 aatagtacat accgtgtagt cagtgttctc acagtgctgc accaagactg gctcaacggc
1021 aaagaataca atgcaaagt gtccaacaaa gcactcccag cccctatcga aagactatt
1081 agtaaggcaa aggggcagcc tcgtgaacca caggtgtaca ctctgccacc cagtagagag
1141 gaaatgacaa agaaccaagt ctcattgacc tgcctggtga aaggcttcta ccccagcgac
1201 atcgccgttg agtgggagag taacggtcag cctgagaaca attacaagac aaccccccca
1261 gtgctggata gtgacgggtc tttctttctg tacagtaagc tgactgtgga caagtcccgc
1321 tggcagcagg gtaacgtctt cagctgttcc gtgatgcacg aggcattgca caaccactac
1381 acccagaagt cactgagcct gagcccaggg aag
```

Protein Sequence Defining the Full Length Humanized Sh24C05 Hv3-11 Heavy Chain (Humanized Heavy Chain Variable Region and Human IgG1 Constant Region) (SEQ ID NO: 188)

```
   1 mdmrvpaqll glllllwlrga rcqvglvesg gglvkpggsl rlscaasgft fsdyamswir
  61 qapgkglewv stisdggtyt yypdnvkgrf tisrdnakns lylqmnslra edtavyycar
 121 ewgdydgfdy wgqgtlvtvs sastkgpsvf plapssksts ggtaalgclv kdyfpepvtv
 181 swnsgaltsg vhtfpavlqs sglyslssvv tvpsslgtq tyicnvnhkp sntkvdkrve
 241 pkscdkthtc ppcpapellg gpsvflfppk pkdtlmisrt pevtcvvvdv shedpevkfn
 301 wyvdgvevhn aktkpreeqy nstyrvvsvl tvlhqdwlng keykckvsnk alpapiekti
 361 skakgqprep qvytlppsre emtknqvslt clvkgfypsd iavewesngq pennykttpp
 421 vldsdgsffl yskltvdksr wqqgnvfscs vmhealhnhy tqkslslspg k
```

Nucleic Acid Sequence Encoding the Full Length Humanized Sh24C05 Hv3-11 N62S IgG1 Heavy Chain (Humanized Heavy Chain Variable Region and Human IgG1 Constant Region) (SEQ ID NO: 189)

```
   1 atggacatga gagttcctgc tcagctgctc gggttgctgt tgctttggct ccggggtgct
  61 aggtgccaag ttcagctggt ggaatctggc ggtgggcttg taaagccagg aggctccctc
 121 agactgagtt gtgccgcttc agggttcaca ttctccgact atgcgatgtc atggatcagg
 181 caagcacccg ggaaaggact ggagtgggtt agcactatca gcgatggcgg aacgtatacc
 241 tattaccctg actccgtgaa gggtcggttc accatttcca gggataacgc aaagaacagt
 301 ctctaccttc agatgaacag cctgagggct gaggacaccg ccgtctacta ctgcgcccga
 361 gaatggggag attatgatgg gtttgactat tggggccagg gcactttggt gacagtcagt
 421 tctgcctcaa caaaggacc aagtgtgttc ccactcgccc ctagcagcaa gagtacatcc
 481 ggggcactg cagcactcgg ctgcctcgtc aaggattatt ttccagagcc agtaaccgtg
 541 agctggaaca gtggagcact cacttctggt gtccatactt ttcctgctgt cctgcaaagc
 601 tctggcctgt actcactcag ctccgtcgtg accgtgccat cttcatctct gggcactcag
 661 acctacatct gtaatgtaaa ccacaagcct agcaatacta aggtcgataa gcgggtggaa
 721 cccaagagct cgacaagac tcacacttgt cccccatgcc ctgccctga acttctgggc
 781 ggtcccagcg tcttttttgtt cccaccaaag cctaaagata ctctgatgat aagtagaaca
 841 cccgaggtga catgtgttgt tgtagacgtt tcccacgagg acccagaggt taagttcaac
 901 tggtacgttg atggagtcga agtacataat gctaagacca gcctagaga ggagcagtat
 961 aatagtacat accgtgtagt cagtgttctc acagtgctgc accaagactg gctcaacggc
1021 aaagaataca atgcaaagt gtccaacaaa gcactcccag cccctatcga agactatt
1081 agtaaggcaa aggggcagcc tcgtgaacca caggtgtaca ctctgccacc cagtagagag
1141 gaaatgacaa agaaccaagt ctcattgacc tgcctggtga aaggcttcta ccccagcgac
1201 atcgccgttg agtgggagag taacggtcag cctgagaaca attacaagac aaccccccca
1261 gtgctggata gtgacgggtc tttctttctg tacagtaagc tgactgtgga caagtcccgc
1321 tggcagcagg gtaacgtctt cagctgttcc gtgatgcacg aggcattgca caaccactac
1381 acccagaagt cactgagcct gagcccaggg aag
```

Protein Sequence Defining the Full Length Humanized Sh24C05 Hv3-11 N62S IgG1 Heavy Chain (Humanized Heavy Chain Variable Region and Human IgG1 Constant Region) (SEQ ID NO: 190)

```
  1 mdmrvpaqll glllwlrga rcqvqlvesg gglvkpggsl rlscaasgft fsdyamswir
 61 qapgkglewv stisdggtyt yypdsvkgrf tisrdnakns lylqmnslra edtavyycar
121 ewgdydgfdy wgqgtivtvs sastkgpsvf plapssksts ggtaalgclv kdyfpepvtv
181 swnsgaltsg vhtfpavlqs sglyslssvv tvpsslgtq tyicnvnhkp sntkvdkrve
241 pkscdkthtc ppcpapellg gpsvflfppk pkdtlmisrt pevtcvvvdv shedpevkfn
301 wyvdgvevhn aktkpreeqy nstyrvvsvl tvlhqdwlng keykckvsnk alpapiekti
361 skakgqprep qvytlppsre emtknqvslt clvkgfypsd iavewesngq pennykttpp
421 vldsdgsffl ysklltvdksr wqqgnvfscs vmhealhnhy tqkslslspg k
```

Nucleic Acid Sequence Encoding the Full Length Humanized Sh24C05 Hv3-11 N62S IgG2 Heavy Chain (Humanized Heavy Chain Variable Region and Human IgG2 Constant Region) (SEQ ID NO: 191)

```
   1 atggacatga gagttcctgc tcagctgctc gggttgctgt tgctttggct ccggggtgct
  61 aggtgccaag ttcagctggt ggaatctggg ggtgggcttg taaagccagg aggctccctc
 121 agactgagtt gtgccgcttc agggttcaca ttctccgact atgcgatgtc atggatcagg
 181 caagcacccg ggaaaggact ggagtgggtt agcactatca gcgatggcgg aacgtatacc
 241 tattaccctg actccgtgaa gggtcggttc accatttcca gggataacgc aaagaacagt
 301 ctctaccttc agatgaacag cctgagggct gaggacaccg ccgtctacta ctgcgcccga
 361 gaatggggag attatgatgg gtttgactat tggggccagg gcactttggt gacagtcagt
 421 tctgcctcca ccaagggccc atcggtcttc ccctggcgc cctgctccag gagcacctcc
 481 gagagcacag cggccctggg ctgcctggtc aaggactact ccccgaacc ggtgacggtg
 541 tcgtggaact caggcgctct gaccagcggc gtgcacacct tcccagctgt cctacagtcc
 601 tcaggactct actccctcag cagcgtggtg accgtgccct ccagcaactt cggcacccag
 661 acctacacct gcaacgtaga tcacaagccc agcaacacca aggtggacaa gacagttgag
 721 cgcaaatgtt gtgtcgagtg cccaccgtgc ccagcaccac ctgtggcagg accgtcagtc
 781 ttcctcttcc ccccaaaacc caaggacacc ctcatgatct cccggacccc tgaggtcacg
 841 tgcgtggtgg tggacgtgag ccacgaagac cccgaggtcc agttcaactg gtacgtggac
 901 ggcgtggagg tgcataatgc caagacaaag ccacgggagg agcagttcaa cagcacgttc
 961 cgtgtggtca gcgtcctcac cgttgtgcac caggactggc tgaacggcaa ggagtacaag
1021 tgcaaggtct ccaacaaagg cctcccagcc cccatcgaga aaaccatctc caaaaccaaa
1081 gggcagcccc gagaaccaca ggtgtacacc ctgcccccat cccgggagga gatgaccaag
1141 aaccaggtca gcctgacctg cctggtcaaa ggcttctacc ccagcgacat cgccgtggag
1201 tgggagagca atgggcagcc ggagaacaac tacaagacca cacctcccat gctggactcc
1261 gacggctcct tcttcctcta cagcaagctc accgtggaca agagcaggtg gcagcagggg
1321 aacgtcttct catgctccgt gatgcatgag gctctgcaca accactacac gcagaagagc
1381 ctctccctgt ctccgggtaa a
```

Protein Sequence Defining the Full Length Humanized Sh24C05 Hv3-11 N62S IgG2 Heavy Chain (Humanized Heavy Chain Variable Region and Human IgG2 Constant Region) (SEQ ID NO: 192)

```
   1 mdmrvpaqll glllwlrga rcqvqlvesg gglvkpggsl rlscaasgft fsdyamswir
  61 qapgkglewv stisdggtyt yypdsvkgrf tisrdnakns lylqmnslra edtavyycar
 121 ewgdydgfdy wgqgtlvtvs sastkgpsvf plapcsrsts estaalgclv kdyfpepvtv
 181 swnsgaltsg vhtfpavlqs sglyslssvv tvpssnfgtq tytcnvdhkp sntkvdktve
 241 rkccvecppc pappvagpsv flfppkpkdt lmisrtpevt cvvvdvshed pevqfnwyvd
 301 gvevhnaktk preeqfnstf rvvsvltvvh qdwlngkeyk ckvsnkglpa piektisktk
 361 gqprepqvyt lppsreemtk nqvsltclvk gfypsdiave wesngqpenn ykttppmlds
 421 dgsfflyskl tvdksrwqqg nvfscsvmhe alhnhytqks lslspgk
```

Nucleic Acid Sequence Encoding the Full Length Humanized Sh24C05 Hv3-21 Heavy Chain (Humanized Heavy Chain Variable Region and Human IgG1 Constant Region) (SEQ ID NO: 193)

```
   1 atggacatga gagttcctgc tcagctgctc gggttgctgt tgctttggct ccggggtgct
  61 aggtgcgagg ttcagctggt ggaatctggc ggtgggcttg taaagccagg aggctccctc
 121 agactgagtt gtgccgcttc agggttcaca ttctccgact atgcgatgtc atgggtgcgc
 181 caagcacccg ggaaaggact ggagtgggtt agcactatca gcgatggcgg aacgtatacc
 241 tattaccctg acaatgtgaa gggtcggttc accatttcca gggataacgc aaagaacagt
 301 ctctatttgc agatgaacag cctgagggct gaggacaccg ccgtctacta ctgcgcccga
 361 gaatggggag attatgatgg gtttgactat tggggccagg gcactttggt gacagtcagt
 421 tctgcctcaa caaaaggacc aagtgtgttc ccactcgccc tagcagcaa gagtacatcc
 481 gggggcactg cagcactcgg ctgcctcgtc aaggattatt tccagagcc agtaaccgtg
 541 agctggaaca gtggagcact cacttctggt gtccatactt ttcctgctgt cctgcaaagc
 601 tctggcctgt actcactcag ctccgtcgtg accgtgccat cttcatctct gggcactcag
 661 acctacatct gtaatgtaaa ccacaagcct agcaatacta aggtcgataa gcgggtggaa
 721 cccaagagct gcgacaagac tcacacttgt cccccatgcc ctgcccctga acttctgggc
 781 ggtcccagcg tcttttttgtt cccaccaaag cctaaagata ctctgatgat aagtagaaca
 841 cccgaggtga catgtgttgt tgtagacgtt tcccacgagg acccagaggt taagttcaac
 901 tggtacgttg atggagtcga agtacataat gctaagacca gcctagaga ggagcagtat
 961 aatagtacat accgtgtagt cagtgttctc acagtgctgc accaagactg gctcaacggc
1021 aaagaataca atgcaaagt gtccaacaaa gcactcccag cccctatcga aagactatt
1081 agtaaggcaa aggggcagcc tcgtgaacca caggtgtaca ctctgccacc cagtagagag
1141 gaaatgacaa agaaccaagt ctcattgacc tgcctggtga aaggcttcta ccccagcgac
1201 atcgccgttg agtgggagag taacggtcag cctgagaaca attacaagac aaccccccca
1261 gtgctggata gtgacgggtc tttctttctg tacagtaagc tgactgtgga caagtcccgc
1321 tggcagcagg gtaacgtctt cagctgttcc gtgatgcacg aggcattgca caaccactac
1381 acccagaagt cactgagcct gagcccaggg aag
```

Protein Sequence Defining the Full Length Humanized 24C05 Hv3-21 Heavy Chain (Humanized Heavy Chain Variable Region and Human IgG1 Constant Region) (SEQ ID NO: 194)

```
   1 mdmrvpaqll glllllwlrga rcevqlvesg gglvkpggsl rlscaasgft fsdyamswvr
  61 qapgkglewv stisdggtyt yypdnvkgrf tisrdnakns lylqmnslra edtavyycar
 121 ewgdydgfdy wgqgtlvtvs sastkgpsvf plapssksts ggtaalgclv kdyfpepvtv
 181 swnsgaltsg vhtfpavlqs sglyslssvv tvpssslgtq tyicnvnhkp sntkvdkrve
 241 pkscdkthtc ppcpapellg gpsvflfppk pkdtlmisrt pevtcvvvdv shedpevkfn
 301 wyvdgvevhn aktkpreeqy nstyrvvsvl tvlhqdwlng keykckvsnk alpapiekti
 361 skakgqprep qvytlppsre emtknqvslt clvkgfypsd iavewesngq pennykttpp
 421 vldsdgsffl yskltvdksr wqqgnvfscs vmhealhnhy tqkslslspg k
```

Nucleic Acid Sequence Encoding the Full Length Humanized Sh24C05 Hv3-23 Heavy Chain (Humanized Heavy Chain Variable Region and Human IgG1 Constant Region) (SEQ ID NO: 195)

```
   1 atggacatga gagttcctgc tcagctgctc gggttgctgt tgctttggct ccggggtgct
  61 aggtgcgagg ttcagcttct ggaatctggc ggtgggcttg tacagccagg aggctccctc
 121 agactgagtt gtgccgcttc agggttcaca ttctccgact atgcgatgtc atgggtcgc
 181 caagcacccg ggaaaggact ggagtgggtt tcaactatca gcgatggcgg aacgtatacc
 241 tattaccctg acaatgtgaa gggtcggttc accatttcca gggataacag caagaacaca
 301 ctctatctcc agatgaacag cctgagggct gaggacaccg ccgtctacta ctgcgcccga
 361 gaatggggag attatgatgg gttgactat tggggccagg gcactttggt gacagtcagt
 421 tctgcctcaa caaaggacc aagtgtgttc ccactcgccc tagcagcaa gagtacatcc
 481 gggggcactg cagcactcgg ctgcctcgtc aaggattatt ttccagagcc agtaaccgtg
 541 agctggaaca gtggagcact cacttctggt gtccatactt ttcctgctgt cctgcaaagc
 601 tctggcctgt actcactcag ctccgtcgtg accgtgccat cttcatctct gggcactcag
 661 acctacatct gtaatgtaaa ccacaagcct agcaatacta aggtcgataa gcgggtggaa
 721 cccaagagct cgacaagac tcacacttgt cccccatgcc ctgcccctga acttctgggc
 781 ggtcccagcg tcttttgtt cccaccaaag cctaaagata ctctgatgat aagtagaaca
 841 cccgaggtga catgtgttgt tgtagacgtt tcccacgagg acccagaggt taagttcaac
 901 tggtacgttg atggagtcga agtacataat gctaagacca gcctagaga ggagcagtat
 961 aatagtacat accgtgtagt cagtgttctc acagtgctgc accaagactg gctcaacggc
1021 aaagaataca atgcaaagt gtccaacaaa gcactcccag cccctatcga aagactatt
1081 agtaaggcaa aggggcagcc tcgtgaacca caggtgtaca ctctgccacc cagtagagag
1141 gaaatgacaa agaaccaagt ctcattgacc tgcctggtga aaggcttcta ccccagcgac
1201 atcgccgttg agtgggagag taacggtcag cctgagaaca attacaagac aacccccca
1261 gtgctggata gtgacgggtc tttctttctg tacagtaagc tgactgtgga caagtcccgc
1321 tggcagcagg gtaacgtctt cagctgttcc gtgatgcacg aggcattgca caaccactac
1381 acccagaagt cactgagcct gagcccaggg aag
```

Protein Sequence Defining the Full Length Humanized Sh24C05 Hv3-23 Heavy Chain (Humanized Heavy Chain Variable Region and Human IgG1 Constant Region) (SEQ ID NO: 196)

```
   1 mdmrvpaqll glllllwlrga rcevqllesg gglvqpggsl rlscaasgft fsdyamswvr
  61 qapgkglewv stisdggtyt yypdnvkgrf tisrdnsknt lylqmnslra edtavyycar
 121 ewgdydgfdy wgqgtlvtvs sastkgpsvf plapssksts ggtaalgclv kdyfpepvtv
 181 swnsgaltsg vhtfpavlqs sglyslssvv tvpssslgtq tyicnvnhkp sntkvdkrve
 241 pkscdkthtc ppcpapellg gpsvflfppk pkdtlmisrt pevtcvvvdv shedpevkfn
 301 wyvdgvevhn aktkpreeqy nstyrvvsvl tvlhqdwlng keykckvsnk alpapiekti
 361 skakgqprep qvytlppsre emtknqvslt clvkgfypsd iavewesngq pennykttpp
 421 vldsdgsffl yskltvdksr wqqgnvfscs vmhealhnhy tqkslslspg k
```

Nucleic Acid Sequence Encoding the Full Length Humanized Sh24C05 Hv3-30 Heavy Chain (Humanized Heavy Chain Variable Region and Human IgG1 Constant Region) (SEQ ID NO: 197)

```
   1 atggacatga gagttcctgc tcagctgctc gggttgctgt tgctttggct ccggggtgct
  61 aggtgccagg ttcagctggt ggaatctggc ggtggggtag tacaaccagg acggtccctc
 121 agactgagtt gtgccgcttc agggttcaca ttctccgact atgcgatgtc atgggtcgc
 181 caagcacccg ggaaaggact ggagtgggtt gccactatca gcgatggcgg aacgtatacc
 241 tattaccctg acaatgtgaa gggtcggttc accatttcca gggataactc aaagaacacc
 301 ctctatctcc aaatgagtag cctgagggct gaggacaccg ccgtctacta ctgcgcccga
 361 gaatggggag attatgatgg gtttgactat tggggccagg gcactttggt gacagtcagt
 421 tctgcctcaa caaaaggacc aagtgtgttc ccactcgccc tagcagcaa gagtacatcc
 481 gggggcactg cagcactcgg ctgcctcgtc aaggattatt ttccagagcc agtaaccgtg
 541 agctggaaca gtggagcact cacttctggt gtccatactt ttcctgctgt cctgcaaagc
 601 tctggcctgt actcactcag ctccgtcgtg accgtgccat cttcatctct gggcactcag
 661 acctacatct gtaatgtaaa ccacaagcct agcaatacta aggtcgataa gcgggtggaa
 721 cccaagagct cgcacaagac tcacacttgt cccccatgcc ctgcccctga acttctgggc
 781 ggtcccagcg tcttttttgtt cccaccaaag cctaaagata ctctgatgat aagtagaaca
 841 cccgaggtga catgtgttgt tgtagacgtt tcccacgagg acccagaggt taagttcaac
 901 tggtacgttg atggagtcga agtacataat gctaagacca gcctagaga ggagcagtat
 961 aatagtacat accgtgtagt cagtgttctc acagtgctgc accaagactg gctcaacggc
1021 aaagaataca atgcaaagt gtccaacaaa gcactcccag cccctatcga aagactatt
1081 agtaaggcaa aggggcagcc tcgtgaacca caggtgtaca ctctgccacc cagtagagag
1141 gaaatgacaa agaaccaagt ctcattgacc tgcctggtga aaggcttcta ccccagcgac
1201 atcgccgttg agtgggagag taacggtcag cctgagaaca attacaagac aaccccccca
1261 gtgctggata gtgacgggtc tttctttctg tacagtaagc tgactgtgga caagtcccgc
1321 tggcagcagg gtaacgtctt cagctgttcc gtgatgcacg aggcattgca caaccactac
1381 acccagaagt cactgagcct gagcccaggg aag
```

Protein Sequence Defining the Full Length Humanized of Sh24C05 Hv3-30 Heavy Chain (Humanized Heavy Chain Variable Region and Human IgG1 Constant Region) (SEQ ID NO: 198)

```
   1 mdmrvpaqll glllllwlrga rcqvqlvesg ggvvqpgrsl rlscaasgft fsdyamswvr
  61 qapgkglewv atisdggtyt yypdnvkgrf tisrdnsknt lylqmsslra edtavyycar
 121 ewgdydgfdy wgqgtlvtvs sastkgpsvf plapssksts ggtaalgclv kdyfpepvtv
 181 swnsgaltsg vhtfpavlqs sglyslssvv tvpssslgtq tyicnvnhkp sntkvdkrve
 241 pkscdkthtc ppcpapellg gpsvflfppk pkdtlmisrt pevtcvvvdv shedpevkfn
 301 wyvdgvevhn aktkpreeqy nstyrvvsvl tvlhqdwlng keykckvsnk alpapiekti
 361 skakgqprep qvytlppsre emtknqvslt clvkgfypsd iavewesngq penynykttpp
 421 vldsdgsffl yskltvdksr wqqgnvfscs vmhealhnhy tqkslslspg k
```

Nucleic Acid Sequence Encoding the Full Length Humanized Hu24C05 HvA Heavy Chain (Humanized Heavy Chain Variable Region and Human IgG1 Constant Region) (SEQ ID NO: 199)

```
   1 atggacatga gagttcctgc tcagctgctc gggttgctgt tgctttggct ccggggtgct
  61 aggtgcgagg ttcagctggt ggaatctggc ggtgggcttg taaagccagg aggctccctc
 121 agactgagtt gtgccgcttc agggttcaca ttctccgact atgcgatgtc atgggtgcgc
 181 caagcacccg ggaaaggact ggagtgggtt gccactatca gcgatggcgg aacgtatacc
 241 tattaccctg acaatgtgaa gggtcggttc accatttcca gggataacgc aaagaacagt
 301 ctctaccttc agatgaacag cctgagggct gaggacaccg ccgtctacta ctgcgcccga
 361 gaatggggag attatgatgg gtttgactat tggggccagg gcactttggt gacagtcagt
 421 tctgcctcaa caaaggacc aagtgtgttc ccactcgccc ctagcagcaa gagtacatcc
 481 gggggcactg cagcactcgg ctgcctcgtc aaggattatt tccagagcc agtaaccgtg
 541 agctggaaca gtggagcact cacttctggt gtccatactt ttcctgctgt cctgcaaagc
 601 tctggcctgt actcactcag ctccgtcgtg accgtgccat cttcatctct gggcactcag
 661 acctacatct gtaatgtaaa ccacaagcct agcaatacta aggtcgataa gcgggtggaa
 721 cccaagagct gcgacaagac tcacacttgt cccccatgcc ctgcccctga acttctgggc
 781 ggtcccagcg tcttttttgtt cccaccaaag cctaaagata ctctgatgat aagtagaaca
 841 cccgaggtga catgtgttgt tgtagacgtt tcccacgagg acccagaggt taagttcaac
 901 tggtacgttg atggagtcga agtacataat gctaagacca gcctagaga ggagcagtat
 961 aatagtacat accgtgtagt cagtgttctc acagtgctgc accaagactg gctcaacggc
1021 aaagaataca atgcaaagt gtccaacaaa gcactcccag cccctatcga aagactatt
1081 agtaaggcaa aggggcagcc tcgtgaacca caggtgtaca ctctgccacc cagtagagag
1141 gaaatgacaa agaaccaagt ctcattgacc tgcctggtga aaggcttcta ccccagcgac
1201 atcgccgttg agtgggagag taacggtcag cctgagaaca attacaagac aaccccccca
1261 gtgctggata gtgacgggtc tttctttctg tacagtaagc tgactgtgga caagtcccgc
1321 tggcagcagg gtaacgtctt cagctgttcc gtgatgcacg aggcattgca caaccactac
1381 acccagaagt cactgagcct gagcccaggg aag
```

Protein Sequence Defining the Full Length Humanized Hu24C05 HvA Heavy Chain (Humanized Heavy Chain Variable Region and Human IgG1 Constant Region) (SEQ ID NO: 200)

```
   1 mdmrvpaqll glllwlrga rcevqlvesg gglvkpggsl rlscaasgft fsdyamswvr
  61 qapgkglewv atisdggtyt yypdnvkgrf tisrdnakns lylqmnslra edtavyycar
 121 ewgdydgfdy wgqgtlvtvs sastkgpsvf plapssksts ggtaalgclv kdyfpepvtv
 181 swnsgaltsg vhtfpavlqs sglyslssvv tvpssslgtq tyicnvnhkp sntkvdkrve
 241 pkscdkthtc ppcpapellg gpsvflfppk pkdtlmisrt pevtcvvvdv shedpevkfn
 301 wyvdgvevhn aktkpreeqy nstyrvvsvl tvlhqdwlng keykckvsnk alpapiekti
 361 skakgqprep qvytlppsre emtknqvslt clvkgfypsd iavewesngq pennykttpp
 421 vldsdgsffl yskltvdksr wqqgnvfscs vmhealhnhy tqkslslspg k
```

Nucleic Acid Sequence Encoding the Full Length Humanized Sh24C05 Kv1-9 Light Chain (Humanized Kappa Chain Variable Region and Human Constant Region) (SEQ ID NO: 201)

```
  1 atggacatga gggtgcccgc tcaactgctg gggctgctgc tgctgtggct gagaggagct
 61 cgttgcgata ttcagttgac ccaatcacct agcttcctct cagcttccgt gggcgacaga
121 gttaccataa cctgtcgggc aagccaggag atttctgggt acctgtcctg gtaccaacag
181 aagcccggaa aagcccctaa gctgttgatc tatgctgcgt caaccttgga tagcggtgtc
241 ccgagtcgat tctccggttc tggctccgga acagagttca ctctgacaat ttctagcctt
301 cagccagaag atttcgccac gtactattgc ctccagtacg acagctatcc ctatacattt
361 gggcagggca ctaaactgga gatcaaacgc acagttgctg ccccagcgt gttcattttc
421 ccacctagcg atgagcagct gaaaagcggt actgcctctg tcgtatgctt gctcaacaac
481 ttttacccac gtgaggctaa ggtgcagtgg aaagtggata atgcacttca atctggaaac
541 agtcaagagt ccgtgacaga acaggacagc aaagactcaa cttattcact ctcttccacc
601 ctgactctgt ccaaggcaga ctatgaaaaa cacaaggtat acgcctgcga ggttacacac
661 cagggtttgt ctagtcctgt caccaagtcc ttcaataggg gcgaatgt
```

Protein Sequence Defining the Full Length Humanized Sh24C05 Kv1-9 Light Chain (Humanized Kappa Chain Variable Region and Human Constant Region) (SEQ ID NO: 202)

```
  1 mdmrvpaqll gllllwlrga rcdiqltqsp sflsasvgdr vtitcrasqe isgylswyqq
 61 kpgkapklli yaastldsgv psrfsgsgsg teftltissl qpedfatyyc lqydsypytf
121 gqgtkleikr tvaapsvfif ppsdeqlksg tasvvcllnn fypreakvqw kvdnalqsgn
181 sqesvteqds kdstyslsst ltlskadyek hkvyacevth qglsspvtks fnrgec
```

Nucleic Acid Sequence Encoding the Full Length Humanized Sh24C05 Kv1-16 Light Chain (Humanized Kappa Chain Variable Region and Human Constant Region) (SEQ ID NO: 203)

```
  1 atggacatga gggtgcccgc tcaactgctg gggctgctgc tgctgtggct gagaggagct
 61 cgttgcgata ttcagatgac ccaatcacct agcagtctct cagcttccgt gggcgacaga
121 gttaccataa cctgtcgggc aagccaggag atttctgggt acctgtcctg gtttcaacag
181 aagcccggaa aggccccgaa gagcttgatc tatgctgcgt caaccttgga tagcggtgtc
241 ccgagtcgat tctccggttc tggctccgga accgacttta ctctgacaat ttctagcctt
301 cagccagaag atttcgccac gtactattgc ctccagtacg acagctatcc ctatacattt
361 gggcagggca ctaaactgga gatcaaacgc acagttgctg ccccagcgt gttcattttc
421 ccacctagcg atgagcagct gaaaagcggt actgcctctg tcgtatgctt gctcaacaac
481 ttttacccac gtgaggctaa ggtgcagtgg aaagtggata atgcacttca atctggaaac
541 agtcaagagt ccgtgacaga acaggacagc aaagactcaa cttattcact ctcttccacc
601 ctgactctgt ccaaggcaga ctatgaaaaa cacaaggtat acgcctgcga ggttacacac
661 cagggtttgt ctagtcctgt caccaagtcc ttcaataggg gcgaatgt
```

Protein Sequence Defining the Full Length Humanized Sh24C05 Kv1-16 Light Chain (Humanized Kappa Chain Variable Region and Human Constant Region) (SEQ ID NO: 204)

```
  1 mdmrvpaqll glllwlrga rcdiqmtqsp sslsasvgdr vtitcrasqe isgylswfqq
 61 kpgkapksli yaastldsgv psrfsgsgsg tdftltissl qpedfatyyc lqydsypytf
121 gqgtkleikr tvaapsvfif ppsdeqlksg tasvvcllnn fypreakvqw kvdnalqsgn
181 sqesvteqds kdstyslsst ltlskadyek hkvyacevth qglsspvtks fnrgec
```

Nucleic Acid Sequence Encoding the Full Length Humanized Sh24C05 Kv1-17 Light Chain (Humanized Kappa Chain Variable Region and Human Constant Region) (SEQ ID NO: 205)

```
  1 atggacatga gggtgcccgc tcaactgctg gggctgctgc tgctgtggct gagaggagct
 61 cgttgcgata ttcagatgac ccaatcacct agcagtctct cagcttccgt gggcgacaga
121 gttaccataa cctgtcgggc aagccaggag atttctgggt acctgtcctg gtatcaacag
181 aagcccggaa aagcccaaa gaggttgatc tatgctgcgt caaccttgga tagcggtgtc
241 ccgagtcgat tctccggttc tggctccgga accgagttca ctctgacaat ttctagcctt
301 cagccagaag atttcgccac gtactattgc ctccagtacg acagctatcc ctatacattt
361 gggcagggca ctaaactgga gatcaaacgc acagttgctg cccccagcgt gttcattttc
421 ccacctagcg atgagcagct gaaaagcggt actgcctctg tcgtatgctt gctcaacaac
481 ttttacccac gtgaggctaa ggtgcagtgg aaagtggata atgcacttca atctggaaac
541 agtcaagagt ccgtgacaga acaggacagc aaagactcaa cttattcact ctcttccacc
601 ctgactctgt ccaaggcaga ctatgaaaaa cacaaggtat acgcctgcga ggttacacac
661 cagggtttgt ctagtcctgt caccaagtcc ttcaataggg gcgaatgt
```

Protein Sequence Defining the Full Length Humanized Sh24C05 Kv1-17 Light Chain (Humanized Kappa Chain Variable Region and Human Constant Region) (SEQ ID NO: 206)

```
  1 mdmrvpaqll glllwlrga rcdiqmtqsp sslsasvgdr vtitcrasqe isgylswyqq
 61 kpgkapkrli yaastldsgv psrfsgsgsg teftltissl qpedfatyyc lqydsypytf
121 gqgtkleikr tvaapsvfif ppsdeqlksg tasvvcllnn fypreakvqw kvdnalqsgn
181 sqesvteqds kdstyslsst ltlskadyek hkvyacevth qglsspvtks fnrgec
```

Nucleic Acid Sequence Encoding the Full Length Humanized sh24C05 Kv1-33 Light Chain (Humanized Kappa Chain Variable Region and Human Constant Region) (SEQ ID NO: 207)

```
  1 atggacatga gggtgcccgc tcaactgctg gggctgctgc tgctgtggct gagaggagct
 61 cgttgcgata ttcagatgac ccaatcacct agcagtctct cagcttccgt gggcgacaga
121 gttaccataa cctgtcgggc aagccaggag atttctgggt acctgtcctg gtaccaacag
181 aagcccggaa aggcccccaa gctgttgatc tatgctgcgt caaccttgga tagcggtgtc
241 ccgagtcgat tctccggttc tggctccgga acagacttta cttttacaat ttctagcctt
301 cagccagagg acatcgccac gtactattgc ctccagtacg acagctatcc ctatacattt
```

```
361 gggcagggca ctaaactgga gatcaaacgc acagttgctg cccccagcgt gttcattttc
421 ccacctagcg atgagcagct gaaaagcggt actgcctctg tcgtatgctt gctcaacaac
481 ttttacccac gtgaggctaa ggtgcagtgg aaagtggata atgcacttca atctggaaac
541 agtcaagagt ccgtgacaga acaggacagc aaagactcaa cttattcact ctcttccacc
601 ctgactctgt ccaaggcaga ctatgaaaaa cacaaggtat acgcctgcga ggttacacac
661 cagggtttgt ctagtcctgt caccaagtcc ttcaataggg gcgaatgt
```

Protein Sequence Defining the Full Length Humanized Sh24C05 Kv1-33 Light Chain (Humanized Kappa Chain Variable Region and Human Constant Region) (SEQ ID NO: 208)

```
  1 mdmrvpaqll glllwlrga rcdiqmtqsp sslsasvgdr vtitcrasqe isgylswyqq
 61 kpgkapklli yaastldsgv psrfsgsgsg tdftftissl qpediatyyc lqydsypytf
121 gqgtkleikr tvaapsvfif ppsdeqlksg tasvvcllnn fypreakvqw kvdnalqsgn
181 sqesvteqds kdstyslsst ltlskadyek hkvyacevth qglsspvtks fnrgec
```

Nucleic Acid Sequence Encoding the Full Length Humanized Sh24C05 Kv1-39 Light Chain (Humanized Kappa Chain Variable Region and Human Constant Region) (SEQ ID NO: 209)

```
  1 atggacatga gggtgcccgc tcaactgctg gggctgctgc tgctgtggct gagaggagct
 61 cgttgcgata ttcagatgac ccaatcacct agcagtctct cagcttccgt gggcgacaga
121 gttaccataa cctgtcgggc aagccaggag atttctgggt acctgtcctg gtatcaacag
181 aagcccggaa aagcccctaa gctgttgatc tatgctgcgt caaccttgga tagcggtgtc
241 ccgagtcgat tctccggttc tggctccgga actgacttca ctctgacaat ttctagcctt
301 cagccagaag atttcgccac gtactattgc ctccagtacg acagctatcc ctatacattt
361 gggcagggca ctaaactgga gatcaaacgc acagttgctg cccccagcgt gttcattttc
421 ccacctagcg atgagcagct gaaaagcggt actgcctctg tcgtatgctt gctcaacaac
481 ttttacccac gtgaggctaa ggtgcagtgg aaagtggata atgcacttca atctggaaac
541 agtcaagagt ccgtgacaga acaggacagc aaagactcaa cttattcact ctcttccacc
601 ctgactctgt ccaaggcaga ctatgaaaaa cacaaggtat acgcctgcga ggttacacac
661 cagggtttgt ctagtcctgt caccaagtcc ttcaataggg gcgaatgt
```

Protein Sequence Defining the Full Length Humanized Sh24C05 Kv1-39 Light Chain (Humanized Kappa Chain Variable Region and Human Constant Region) (SEQ ID NO: 210)

```
  1 mdmrvpaqll glllwlrga rcdiqmtqsp sslsasvgdr vtitcrasqe isgylswyqq
 61 kpgkapklli yaastldsgv psrfsgsgsg tdftltissl qpedfatyyc lqydsypytf
121 gqgtkleikr tvaapsvfif ppsdeqlksg tasvvcllnn fypreakvqw kvdnalqsgn
181 sqesvteqds kdstyslsst ltlskadyek hkvyacevth qglsspvtks fnrgec
```

Nucleic Acid Sequence Encoding the Full Length Humanized Hu24C05 KvA Light Chain (Humanized Kappa Chain Variable Region and Human Constant Region) (SEQ ID NO: 211)

```
  1 atggacatga gggtgcccgc tcaactgctg gggctgctgc tgctgtggct gagaggagct 61 cgttgcgata ttcagatgac ccaatcacct agcagtctct cagcttccgt gggcgacaga 121 gttaccataa cctgtcgggc aagccaggag atttctgggt acctgtcctg gctgcaacag 181 aagcccggag gcgccatcaa gaggttgatc tatgctgcgt caaccttgga tagcggtgtc 241 ccgagtcgat tctccggttc tggctccgga agtgactaca ctctgacaat ttctagcctt 301 cagccagaag atttcgccac gtactattgc ctccagtacg acagctatcc ctatacattt 361 gggcagggca ctaaactgga gatcaaacgc acagttgctg cccccagcgt gttcattttc 421 ccacctagcg atgagcagct gaaaagcggt actgcctctg tcgtatgctt gctcaacaac 481 ttttacccac gtgaggctaa ggtgcagtgg aaagtggata atgcacttca atctggaaac 541 agtcaagagt ccgtgacaga acaggacagc aaagactcaa cttattcact ctcttccacc 601 ctgactctgt ccaaggcaga ctatgaaaaa cacaaggtat acgcctgcga ggttacacac 661 cagggtttgt ctagtcctgt caccaagtcc ttcaataggg gcgaatgt
```

25

Protein Sequence Defining the Full Length Humanized Hu24C05 KvA Light Chain (Humanized Kappa Chain Variable Region and Human Constant Region) (SEQ ID NO: 212)

```
  1 mdmrvpaqll glllllwlrga rcdiqmtqsp sslsasvgdr vtitcrasqe isgylswlqq 61 kpggaikrli yaastldsgv psrfsgsgsg sdytltissl qpedfatyyc lqydsypytf 121 gqgtkleikr tvaapsvfif ppsdeqlksg tasvvcllnn fypreakvqw kvdnalqsgn 181 sqesvteqds kdstyslsst ltlskadyek hkvyacevth qglsspvtks fnrgec
```

For convenience, Table 13 provides a concordance chart showing the SEQ ID NO. of each sequence discussed in this Example.

TABLE 13

| SEQ ID NO. | Nucleic Acid or Protein |
|---|---|
| 175 | Human IgG1 constant-nucleic acid |
| 176 | Human IgG1 constant-protein |
| 177 | Human IgG2 constant-nucleic acid |
| 178 | Human IgG2 constant-protein |
| 179 | Human Kappa constant-nucleic acid |
| 180 | Human Kappa constant-protein |
| 181 | Chimeric 24C05 Mouse Heavy Chain Variable + Human IgG1 constant-nucleic acid |
| 182 | Chimeric 24C05 Mouse Heavy Chain Variable + Human IgG1 constant-protein |
| 183 | Chimeric 24C05 Mouse Light Chain Variable + Human Kappa constant-nucleic acid |
| 184 | Chimeric 24C05 Mouse Light Chain Variable + Human Kappa constant-protein |
| 185 | Humanized Sh24C05 Hv3-7 Heavy Human Variable + Human IgG1 constant-nucleic acid |
| 186 | Humanized Sh24C05 Hv3-7 Heavy Human Variable + Human IgG1 constant-protein |
| 187 | Humanized Sh24C05 Hv3-11 Heavy Human Variable + Human IgG1 constant-nucleic acid |
| 188 | Humanized Sh24C05 Hv3-11 Heavy Human Variable + Human IgG1 constant-protein |
| 189 | Humanized Sh24C05 Hv3-11 N62S IgG1 Heavy Human Variable + Human IgG1 constant-nucleic acid |
| 190 | Humanized Sh24C05 Hv3-11 N62S IgG1 Heavy Human Variable + Human IgG1 constant-protein |
| 191 | Humanized Sh24C05 Hv3-11 N62S IgG2 Heavy Human Variable + Human IgG2 constant-nucleic acid |

TABLE 13-continued

| SEQ ID NO. | Nucleic Acid or Protein |
|---|---|
| 192 | Humanized Sh24C05 Hv3-11 N62S IgG2 Heavy Human Variable + Human IgG2 constant-protein |
| 193 | Humanized Sh24C05 Hv3-21Heavy Human Variable + Human IgG1 constant-nucleic acid |
| 194 | Humanized Sh24C05 Hv3-21 Heavy Human Variable + Human IgG1 constant-protein |
| 195 | Humanized Sh24C05 Hv3-23 Heavy Human Variable + Human IgG1 constant-nucleic acid |
| 196 | Humanized Sh24C05 Hv3-23 Heavy Human Variable + Human IgG1 constant-protein |
| 197 | Humanized Sh24C05 Hv3-30 Heavy Human Variable + Human IgG1 constant-nucleic acid |
| 198 | Humanized Sh24C05 Hv3-30 Heavy Human Variable + Human IgG1 constant-protein |
| 199 | Humanized Hu24C05 HvA Heavy Human Variable + Human IgG1 constant-nucleic acid |
| 200 | Humanized Hu24C05 HvA Heavy Human Variable + Human IgG1 constant-protein |
| 201 | Humanized Sh24C05 Kv1-9 Human Variable + Human Kappa constant-nucleic acid |
| 202 | Humanized Sh24C05 Kv1-9 Human Variable + Human Kappa constant-protein |
| 203 | Humanized Sh24C05 Kv1-16 Human Variable + Human Kappa constant-nucleic acid |
| 204 | Humanized Sh24C05 Kv1-16 Human Variable + Human Kappa constant-protein |
| 205 | Humanized Sh24C05 Kv1-17 Human Variable + Human Kappa constant-nucleic acid |
| 206 | Humanized Sh24C05 Kv1-17 Human Variable + Human Kappa constant-protein |
| 207 | Humanized Sh24C05 Kv1-33 Human Variable + Human Kappa constant-nucleic acid |
| 208 | Humanized Sh24C05 Kv1-33 Human Variable + Human Kappa constant-protein |
| 209 | Humanized Sh24C05 Kv1-39 Human Variable + Human Kappa constant-nucleic acid |
| 210 | Humanized Sh24C05 Kv1-39 Human Variable + Human Kappa constant-protein |
| 211 | Humanized Hu24C05 KvA Human Variable + Human Kappa constant-nucleic acid |
| 212 | Humanized Hu24C05 KvA Human Variable + Human Kappa constant-protein |

Table 14 below shows antibodies containing chimeric immunoglobulin heavy and light chains and each of the possible combinations of the full-length humanized immunoglobulin heavy and light chains.

TABLE 14

| Antibody Name | Light Chain | Heavy Chain |
|---|---|---|
| Sh24C05-1 | 24C05 Chimeric Kappa (SEQ ID NO: 184) | GP203 24C05 Chimeric Heavy IgG1 (SEQ ID NO: 182) |
| Sh24C05-14 | Hu24C05 KvA Kappa (SEQ ID NO: 212) | Hu24C05 HvA IgG1 (SEQ ID NO: 200) |
| Sh24C05-15 | Hu24C05 KvA Kappa (SEQ ID NO: 212) | Sh24C05 Hv3-21 Heavy IgG1 (SEQ ID NO: 194) |
| Sh24C05-16 | Hu24C05 KvA Kappa (SEQ ID NO: 212) | Sh24C05 Hv3-23 Heavy IgG1 (SEQ ID NO: 196) |
| Sh24C05-17 | Hu24C05 KvA Kappa (SEQ ID NO: 212) | Sh24C05 Hv3-30 Heavy IgG1 (SEQ ID NO: 198) |
| Sh24C05-18 | Hu24C05 KvA Kappa (SEQ ID NO: 212) | Sh24C05 Hv3-7 Heavy IgG1 (SEQ ID NO: 186) |
| Sh24C05-19 | Hu24C05 KvA Kappa (SEQ ID NO: 212) | Sh24C05 Hv3-11 Heavy IgG1 (SEQ ID NO: 188) |
| Sh24C05-19 N62S IgG1 | Hu24C05 KvA Kappa (SEQ ID NO: 212) | Sh24C05 Hv3-11 N62S Heavy IgG1 (SEQ ID NO: 190) |
| Sh24C05-19 N62S IgG2 | Hu24C05 KvA Kappa (SEQ ID NO: 212) | Sh24C05 Hv3-11 N62S Heavy IgG2 (SEQ ID NO: 192) |
| Sh24C05-20 | Sh24C05 Kv1-16 Kappa (SEQ ID NO: 204) | Hu24C05 HvA IgG1 (SEQ ID NO: 200) |
| Sh24C05-21 | Sh24C05 Kv1-16 Kappa (SEQ ID NO: 204) | Sh24C05 Hv3-21 Heavy IgG1 (SEQ ID NO: 194) |
| Sh24C05-22 | Sh24C05 Kv1-16 Kappa (SEQ ID NO: 204) | Sh24C05 Hv3-23 Heavy IgG1 (SEQ ID NO: 196) |
| Sh24C05-23 | Sh24C05 Kv1-16 Kappa (SEQ ID NO: 204) | Sh24C05 Hv3-30 Heavy IgG1 (SEQ ID NO: 198) |
| Sh24C05-24 | Sh24C05 Kv1-16 Kappa (SEQ ID NO: 204) | Sh24C05 Hv3-7 Heavy IgG1 (SEQ ID NO: 186) |
| Sh24C05-25 | Sh24C05 Kv1-16 Kappa (SEQ ID NO: 204) | Sh24C05 Hv3-11 Heavy IgG1 (SEQ ID NO: 188) |
| Sh24C05-25 N62S IgG1 | Sh24C05 Kv1-16 Kappa (SEQ ID NO: 204) | Sh24C05 Hv3-11 N62S Heavy IgG1 (SEQ ID NO: 190) |
| Sh24C05-25 N62S IgG2 | Sh24C05 Kv1-16 Kappa (SEQ ID NO: 204) | Sh24C05 Hv3-11 N62S Heavy IgG2 (SEQ ID NO: 192) |
| Sh24C05-26 | Sh24C05 Kv1-17 Kappa (SEQ ID NO: 206) | Hu24C05 HvA IgG1 (SEQ ID NO: 200) |
| Sh24C05-27 | Sh24C05 Kv1-17 Kappa (SEQ ID NO: 206) | Sh24C05 Hv3-21 Heavy IgG1 (SEQ ID NO: 194) |
| Sh24C05-28 | Sh24C05 Kv1-17 Kappa (SEQ ID NO: 206) | Sh24C05 Hv3-23 Heavy IgG1 (SEQ ID NO: 196) |
| Sh24C05-29 | Sh24C05 Kv1-17 Kappa (SEQ ID NO: 206) | Sh24C05 Hv3-30 Heavy IgG1 (SEQ ID NO: 198) |
| Sh24C05-30 | Sh24C05 Kv1-17 Kappa (SEQ ID NO: 206) | Sh24C05 Hv3-7 Heavy IgG1 (SEQ ID NO: 186) |
| Sh24C05-31 | Sh24C05 Kv1-17 Kappa (SEQ ID NO: 206) | Sh24C05 Hv3-11 Heavy IgG1 (SEQ ID NO: 188) |
| Sh24C05-31 N62S IgG1 | Sh24C05 Kv1-17 Kappa (SEQ ID NO: 206) | Sh24C05 Hv3-11 N62S Heavy IgG1 (SEQ ID NO: 190) |
| Sh24C05-31 N62S IgG2 | Sh24C05 Kv1-17 Kappa (SEQ ID NO: 206) | Sh24C05 Hv3-11 N62S Heavy IgG2 (SEQ ID NO: 192) |
| Sh24C05-32 | Sh24C05 Kv1-33 Kappa (SEQ ID NO: 208) | Hu24C05 HvA IgG1 (SEQ ID NO: 200) |
| Sh24C05-33 | Sh24C05 Kv1-33 Kappa (SEQ ID NO: 208) | Sh24C05 Hv3-21 Heavy IgG1 (SEQ ID NO: 194) |
| Sh24C05-34 | Sh24C05 Kv1-33 Kappa (SEQ ID NO: 208) | Sh24C05 Hv3-23 Heavy IgG1 (SEQ ID NO: 196) |
| Sh24C05-35 | Sh24C05 Kv1-33 Kappa (SEQ ID NO: 208) | Sh24C05 Hv3-30 Heavy IgG1 (SEQ ID NO: 198) |
| Sh24C05-36 | Sh24C05 Kv1-33 Kappa (SEQ ID NO: 208) | Sh24C05 Hv3-7 Heavy IgG1 (SEQ ID NO: 186) |
| Sh24C05-37 | Sh24C05 Kv1-33 Kappa (SEQ ID NO: 208) | Sh24C05 Hv3-11 Heavy IgG1 (SEQ ID NO: 188) |
| Sh24C05-37 N62S IgG1 | Sh24C05 Kv1-33 Kappa (SEQ ID NO: 208) | Sh24C05 Hv3-11 N62S Heavy IgG1 (SEQ ID NO: 190) |

TABLE 14-continued

| Antibody Name | Light Chain | Heavy Chain |
|---|---|---|
| Sh24C05-37 N62S IgG2 | Sh24C05 Kv1-33 Kappa (SEQ ID NO: 208) | Sh24C05 Hv3-11 N62S Heavy IgG2 (SEQ ID NO: 192) |
| Sh24C05-38 | Sh24C05 Kv1-9 Kappa (SEQ ID NO: 202) | Hu24C05 HvA IgG1 (SEQ ID NO: 200) |
| Sh24C05-39 | Sh24C05 Kv1-9 Kappa (SEQ ID NO: 202) | Sh24C05 Hv3-21 Heavy IgG1 (SEQ ID NO: 194) |
| Sh24C05-40 | Sh24C05 Kv1-9 Kappa (SEQ ID NO: 202) | Sh24C05 Hv3-23 Heavy IgG1 (SEQ ID NO: 196) |
| Sh24C05-41 | Sh24C05 Kv1-9 Kappa (SEQ ID NO: 202) | Sh24C05 Hv3-30 Heavy IgG1 (SEQ ID NO: 198) |
| Sh24C05-42 | Sh24C05 Kv1-9 Kappa (SEQ ID NO: 202) | Sh24C05 Hv3-7 Heavy IgG1 (SEQ ID NO: 186) |
| Sh24C05-43 | Sh24C05 Kv1-9 Kappa (SEQ ID NO: 202) | Sh24C05 Hv3-11 Heavy IgG1 (SEQ ID NO: 188) |
| Sh24C05-43 N62S IgG1 | Sh24C05 Kv1-9 Kappa (SEQ ID NO: 202) | Sh24C05 Hv3-11 N62S Heavy IgG1 (SEQ ID NO: 190) |
| Sh24C05-43 N62S IgG2 | Sh24C05 Kv1-9 Kappa (SEQ ID NO: 202) | Sh24C05 Hv3-11 N62SHeavy IgG2 (SEQ ID NO: 192) |
| Sh24C05-44 | Sh24C05 Kv1-39 Kappa (SEQ ID NO: 210) | Hu24C05 HvA IgG1 (SEQ ID NO: 200) |
| Sh24C05-45 | Sh24C05 Kv1-39 Kappa (SEQ ID NO: 210) | Sh24C05 Hv3-21 Heavy IgG1 (SEQ ID NO: 194) |
| Sh24C05-46 | Sh24C05 Kv1-39 Kappa (SEQ ID NO: 210) | Sh24C05 Hv3-23 Heavy IgG1 (SEQ ID NO: 196) |
| Sh24C05-47 | Sh24C05 Kv1-39 Kappa (SEQ ID NO: 210) | Sh24C05 Hv3-30 Heavy IgG1 (SEQ ID NO: 198) |
| Sh24C05-48 | Sh24C05 Kv1-39 Kappa (SEQ ID NO: 210) | Sh24C05 Hv3-7 Heavy IgG1 (SEQ ID NO: 186) |
| Sh24C05-49 | Sh24C05 Kv1-39 Kappa (SEQ ID NO: 210) | Sh24C05 Hv3-11 Heavy IgG1 (SEQ ID NO: 188) |
| Sh24C05-49 N62S IgG1 | Sh24C05 Kv1-39 Kappa (SEQ ID NO: 210) | Sh24C05 Hv3-11 N62S Heavy IgG1 (SEQ ID NO: 190) |
| Sh24C05-49 N62S IgG2 | Sh24C05 Kv1-39 Kappa (SEQ ID NO: 210) | Sh24C05 Hv3-11 N62S Heavy IgG2 (SEQ ID NO: 192) |

The antibody construct containing the full length chimeric heavy and light chains is designated below:

Chimeric 24C05=Full Length Chimeric 24C05 Heavy Chain (Mouse Variable Region and Human IgG1 Constant Region) (SEQ ID NO: 182) plus Full Length Chimeric 24C05 Light Chain (Mouse Variable Region and Human Kappa Constant Region) (SEQ ID NO: 184)

Four of the possible antibody constructs containing the full length immunoglobulin heavy and light chains containing humanized variable regions are designated below:

Sh24C05-25 N62S IgG1=Humanized Sh24C05 Hv3-11 N62S Heavy Chain Variable Region and Human IgG1 Constant Region (SEQ ID NO: 190) plus Sh24C05 Kv1-16 Light Chain Variable Region and Human Kappa Constant Region (SEQ ID NO: 204)

Sh24C05-25 N62S IgG2=Humanized Sh24C05 Hv3-11 N62S Heavy Chain Variable Region and Human IgG2 Constant Region (SEQ ID NO: 192) plus Sh24C05 Kv1-16 Light Chain Variable Region and Human Kappa Constant Region (SEQ ID NO: 204)

Sh24C05-31 N62S IgG1=Humanized Sh24C05 Hv3-11 N62S Heavy Chain Variable Region and Human IgG1 Constant Region (SEQ ID NO: 190) plus Sh24C05 Kv1-17 Light Chain Variable Region and Human Kappa Constant Region (SEQ ID NO: 206)

Sh24C05-31 N62S IgG2=Humanized Sh24C05 Hv3-11 N62S Heavy Chain Variable Region and Human IgG2 Constant Region (SEQ ID NO: 192) plus Sh24C05 Kv1-17 Light Chain Variable Region and Human Kappa Constant Region (SEQ ID NO: 206)

B. Binding Affinities of Humanized and Chimeric Anti-ErbB3 Monoclonal Antibodies The binding affinities and kinetics of interaction of monoclonal antibodies produced in Example 12 against recombinant human ErbB3 monomeric protein (cleaved rhErbB3) were measured by surface plasmon resonance using a BIACORE® T100 (Biacore) instrument. Monomeric ErbB3 was obtained by protease cleavage of rhErbB3-Fc (R&D Systems, Cat. No. 348-RB).

Goat anti-human IgG Fc (Jackson ImmunoResearch, Catalog No. 109-005-098) was immobilized on carboxymethylated dextran CM4 sensor chips (Biacore, Catalog No. BR-1005-34) by amine coupling (Biacore, Catalog No. BR-1000-50) using a standard coupling protocol according to the vendor's instructions. The analyses were performed at 37° C. using PBS (Invitrogen, Catalog No. 14040-133) containing 0.05% surfactant P20 (Biacore, Catalog No. BR-1000-54) as running buffer.

The antibodies were captured in individual flow cells at a flow rate of 60 µl/minute. Injection time was varied for each antibody to yield an $R_{max}$ between 30 and 60 RU. Buffer or cleaved rhErbB3 diluted in running buffer was injected sequentially over a reference surface (no antibody captured) and the active surface (antibody to be tested) for 300 seconds at 60 µl/minute. The dissociation phase was monitored for up to 1200 seconds. The surface was then regenerated with two 60 second injections of Glycine pH 2.25 (made from Glycine pH 2.0 (Biacore, Catalog No. BR-1003-55) and pH 2.5 (Biacore, Catalog No. BR-1003-56)) at 60 µl/minute. For the initial screening, only one or two concentrations of cleaved rhErbB3 were tested, typically 5.0 and 1.25 nM (results are summarized in Table 15).

Kinetic parameters were determined using the kinetic function of the BIAevaluation software (Biacore) with double reference subtraction. Kinetic parameters for each antibody, $k_a$ (association rate constant), $k_d$ (dissociation rate constant) and $K_D$ (equilibrium dissociation constant) were determined. The initial monoclonal antibodies were screened using cell culture media supernatant containing secreted antibody, and kinetic values of the monoclonal antibodies on cleaved rhErbB3 at 37° C. are summarized in Table 15.

TABLE 15

| Antibody | $k_a$ (1/Ms) | $k_d$ (1/s) | $K_D$ (M) | n |
|---|---|---|---|---|
| Sh24C05-1 | 2.52E+06 | 4.48E-04 | 1.78E-10 | 3 |
| Sh24C05-14 | 2.88E+06 | 4.98E-04 | 1.73E-10 | 2 |
| Sh24C05-15 | 2.67E+06 | 4.99E-04 | 1.87E-10 | 2 |
| Sh24C05-16 | 2.75E+06 | 4.04E-04 | 1.47E-10 | 2 |
| Sh24C05-17 | 2.79E+06 | 4.17E-04 | 1.50E-10 | 2 |
| Sh24C05-18 | 2.88E+06 | 4.63E-04 | 1.61E-10 | 2 |
| Sh24C05-19 | 3.00E+06 | 2.55E-04 | 8.55E-11 | 2 |
| Sh24C05-20 | 2.67E+06 | 5.91E-04 | 2.21E-10 | 2 |
| Sh24C05-21 | 3.11E+06 | 6.62E-04 | 2.20E-10 | 2 |
| Sh24C05-22 | 2.79E+06 | 6.01E-04 | 2.16E-10 | 2 |
| Sh24C05-23 | 2.79E+06 | 7.21E-04 | 2.63E-10 | 2 |
| Sh24C05-24 | 2.90E+06 | 6.28E-04 | 2.18E-10 | 2 |
| Sh24C05-25 | 2.63E+06 | 4.59E-04 | 1.75E-10 | 2 |
| Sh24C05-26 | 3.36E+06 | 7.39E-04 | 2.20E-10 | 2 |
| Sh24C05-27 | 3.34E+06 | 7.98E-04 | 2.40E-10 | 2 |
| Sh24C05-28 | 3.26E+06 | 6.14E-04 | 1.89E-10 | 2 |
| Sh24C05-29 | 3.25E+06 | 5.88E-04 | 1.82E-10 | 2 |
| Sh24C05-30 | 4.48E+06 | 7.87E-04 | 1.90E-10 | 2 |
| Sh24C05-31 | 3.47E+06 | 2.92E-04 | 8.65E-11 | 2 |
| Sh24C05-32 | 9.98E+06 | 6.02E-03 | 6.03E-10 | 1 |
| Sh24C05-33 | 4.02E+06 | 4.33E-03 | 1.08E-09 | 1 |
| Sh24C05-34 | 1.09E+07 | 6.00E-03 | 5.52E-10 | 1 |
| Sh24C05-35 | 8.44E+06 | 5.53E-03 | 6.55E-10 | 1 |
| Sh24C05-36 | 5.18E+06 | 4.34E-03 | 8.37E-10 | 1 |
| Sh24C05-37 | 5.94E+06 | 2.00E-03 | 3.74E-10 | 2 |
| Sh24C05-38 | 2.71E+07 | 1.54E-02 | 5.67E-10 | 1 |
| Sh24C05-39 | 1.18E+07 | 9.67E-03 | 8.19E-10 | 1 |

TABLE 15-continued

| Antibody | $k_a$ (1/Ms) | $k_d$ (1/s) | $K_D$ (M) | n |
|---|---|---|---|---|
| Sh24C05-40 | 2.11E+07 | 1.06E-02 | 5.03E-10 | 1 |
| Sh24C05-41 | 1.81E+07 | 1.21E-02 | 6.69E-10 | 1 |
| Sh24C05-42 | 7.35E+06 | 6.82E-03 | 9.27E-10 | 1 |
| Sh24C05-43 | 6.16E+06 | 3.58E-03 | 5.82E-10 | 1 |
| Sh24C05-44 | 7.96E+06 | 5.12E-03 | 6.44E-10 | 1 |
| Sh24C05-45 | 8.57E+06 | 6.06E-03 | 7.07E-10 | 1 |
| Sh24C05-46 | 7.99E+06 | 4.40E-03 | 5.51E-10 | 1 |
| Sh24C05-47 | 7.98E+06 | 4.41E-03 | 5.53E-10 | 1 |
| Sh24C05-48 | 8.72E+06 | 4.90E-03 | 5.62E-10 | 1 |
| Sh24C05-49 | 4.08E+06 | 1.70E-03 | 4.16E-10 | 2 |

The results in Table 15 demonstrate that the chimeric and each of the humanized 24C05 antibodies have fast association rates ($k_a$), very slow disassociation rates ($k_d$) and very high affinities ($K_D$). In particular, the antibodies have affinities ranging from about 87 pM to about 1 nM.

The binding affinities and kinetics of certain purified monoclonal antibodies were also determined. To further characterize certain antibodies, the surface plasmon resonance experiments described above were conducted using concentrations of cleaved rhErbB3 between 0.3125 nM and 5.0 nM (a 2-fold serial dilution).

The kinetic values of certain purified monoclonal antibodies (i.e., Sh24C05-1, Sh24C05-25, Sh24C05-25 N62S IgG1, Sh24C05-25 N62S IgG2, Sh24C05-31, Sh24C05-31 N62S IgG1, and Sh24C05-31 N62S IgG2) on cleaved rhErbB3 at 37° C. are summarized in Table 16.

TABLE 16

| Antibody | $k_a$ (1/Ms) | $k_d$ (1/s) | $K_D$ (M) | n |
|---|---|---|---|---|
| Sh24C05-1 | 3.5E+06 | 4.4E-04 | 1.4E-10 | 3 |
| Sh24C05-25 | 4.0E+06 | 5.0E-04 | 1.3E-10 | 4 |
| Sh24C05-25 N62S IgG1 | 2.9E+06 | 4.5E-04 | 1.6E-10 | 4 |
| Sh24C05-25 N62S IgG2 | 2.7E+06 | 3.4E-04 | 1.2E-10 | 4 |
| Sh24C05-31 | 4.7E+06 | 2.8E-04 | 6.3E-11 | 3 |
| Sh24C05-31 N62S IgG1 | 3.5E+06 | 2.7E-04 | 7.6E-11 | 6 |
| Sh24C05-31 N62S IgG2 | 3.2E+06 | 2.4E-04 | 7.4E-11 | 3 |

The results in Table 16 demonstrate the purified antibodies have a have affinities ranging from about 63 pM to about 160 pM when tested at 37° C.

C. Comparison of Other Anti-ErbB3 Antibodies

Three human antibodies that inhibit the function of human ErbB3 were constructed and expressed using published information. One antibody, referred to as Ab #6, was constructed as a human IgG2/Lambda antibody based the disclosure of Schoeberl et al., US 2009/0291085 (Merrimack Pharmaceuticals, Inc.). Two additional antibodies, referred to as U1-53 and U1-59, were constructed as human IgG1/Kappa antibodies based on the disclosure of Rothe et al., US 2008/0124345 (U3 Pharma AG and Amgen, Inc.).

Figure 17:
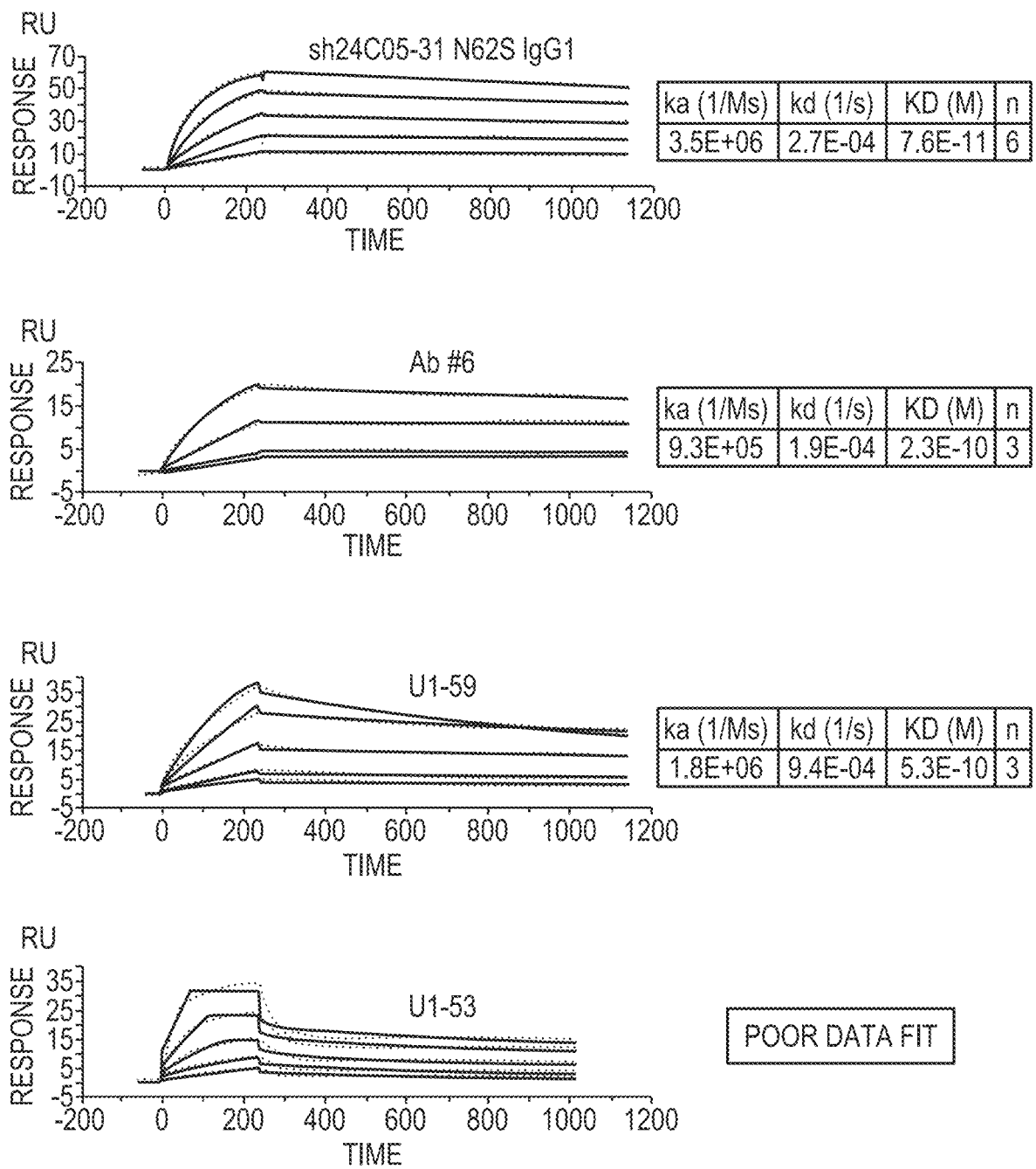
FIG. 17 are Biacore sensorgrams representing results from an experiment to measure the kinetic values of anti-ErbB3 monoclonal antibodies, Sh24C05-31 N62S-IgG1, Ab #6, U1-53, and U1-59.

Kinetic parameters for the Ab #6, U1-53, and U1-59 antibodies were determined by BIACORE® at 37° C. using cleaved rhErbB3 (monomer) as described above (See Section B. Binding Affinities of Humanized and Chimeric Anti-ErbB3 Monoclonal Antibodies). Both BIACORE® sensorgrams (FIG. 17) and kinetic values (Table 17) are displayed for each antibody.

TABLE 17

| Antibody | $k_a$ (1/Ms) | $k_d$ (1/s) | $K_D$ (M) | n |
|---|---|---|---|---|
| Sh24C05-31 N62S IgG1 | 3.5+06 | 2.7E-04 | 7.6E-11 | 6 |
| Ab#6 | 9.3E+05 | 1.9E-04 | 2.3E-10 | 3 |
| U1-59 | 1.8E+06 | 9.4E-04 | 5.3E-10 | 3 |
| U1-53 | — | — | — | — |

The results in Table 17 demonstrate that the overall equilibrium dissociation constant ($K_D$) for the Sh24C05-31 N62S IgG1 (76 pM) was smaller (i.e., higher affinity) than the $K_D$ for the Ab #6 and U1-59 antibodies (230 pM (p<0.01) and 530 pM (p<0.0005), respectively). The equilibrium dissociation constant ($K_D$) for U1-53 could not be determined because of poor curve fits (see FIG. 17, which shows a fast $K_{off}$ rate of U1-53). The $K_D$ of Ab #6, U1-53, and U1-59 antibodies can also be compared with other humanized 24C05 variants by comparing Tables 16 and 17.

Therefore, the affinity for Sh24C05-31 N62S IgG1 is significantly higher than the affinity of Ab #6 and U1-59 as disclosed herein.

Example 13—Neutralization Activity of the Humanized Anti-ErbB3 Antibodies

In this example, the humanized antibodies produced in Example 12 were tested for their ability to inhibit rhErbB3 binding to NRG1-β1 by ECL assay. Multi-array 96-well standard binding plates (Meso Scale Discovery, Cat. No. L15XA-3) were coated with 50 µl of 0.5 µg/mL rhErbB3/Fc (R&D systems, Cat. No. 348-RB) in PBS (Invitrogen, Cat. No. 14040-133) for one hour at room temperature with no agitation. The plates then were washed three times with PBS+0.1% TWEEN™20 (Sigma P5927) and blocked with 200 µl of 100% Horse Serum, heat inactivated (GIBCO, Cat. No. 26050-088) for 1.5 hours at room temperature. After washing the plates three times with PBS+0.1% TWEEN™, 25 µl of the antibody dilutions were added to the plates for another hour at room temperature with agitation. Ligand NRG1-β1 (R&D Systems, Cat. No. 377-HB, 26 kDa) was added to the wells at a final concentration of 0.25 µg/ml. The plates were washed three times with PBS+0.1% TWEEN™ and incubated with 25 µl of 1 µg/mL biotinylated antibody against human NRG1-β1 (R&D systems, Cat. No BAF377) preincubated for one hour with SULTO-TAG Streptavidin (Meso Scale Discovery, Cat. No R32AD-5) for one hour at room temperature with agitation. The plates then were washed three times with PBS+0.1% TWEEN™, and 150 µl of 1× read buffer (Meso Scale Discovery, Cat. No. R92TC-1) was added to each well before the plates were analyzed on a SECTOR® Imager 2400 (Meso Scale Discovery) instrument.

Figure 18A:
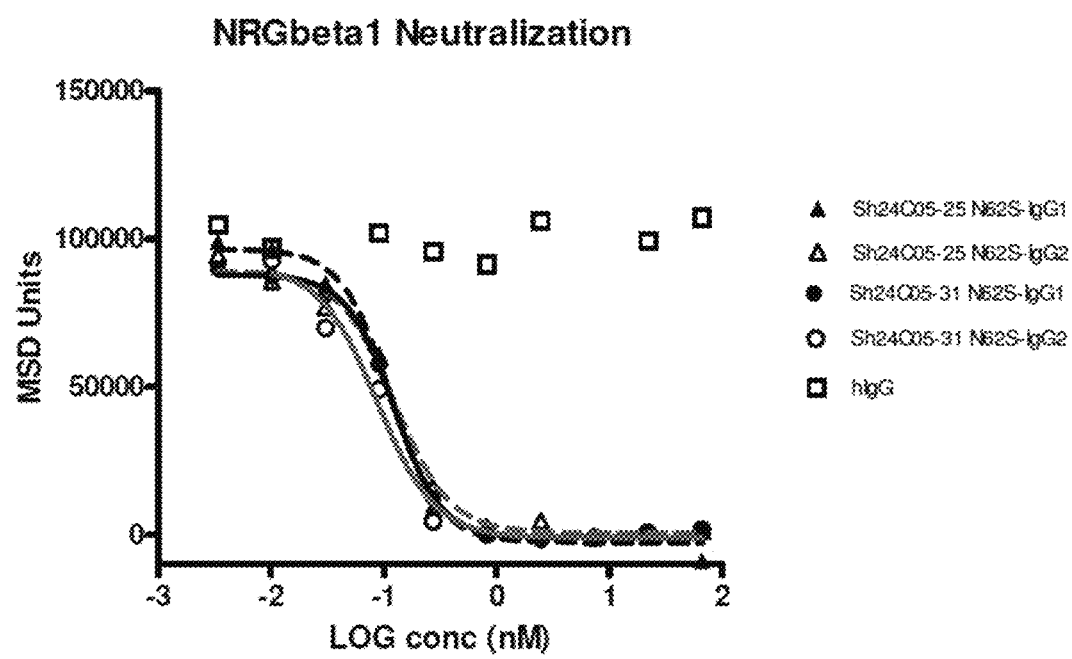
FIG. 18A is a graph summarizing results from an experiment to measure the neutralization activity of negative control (human IgG (□)) and anti-ErbB3 monoclonal antibodies Sh24C05-25 N62S-IgG1 (▲), Sh24C05-25 N62S-IgG2 (Δ), Sh24C05-31 N62S-IgG1(●) and Sh24C05-31 N62S-IgG2 (○).
Figure 18B:
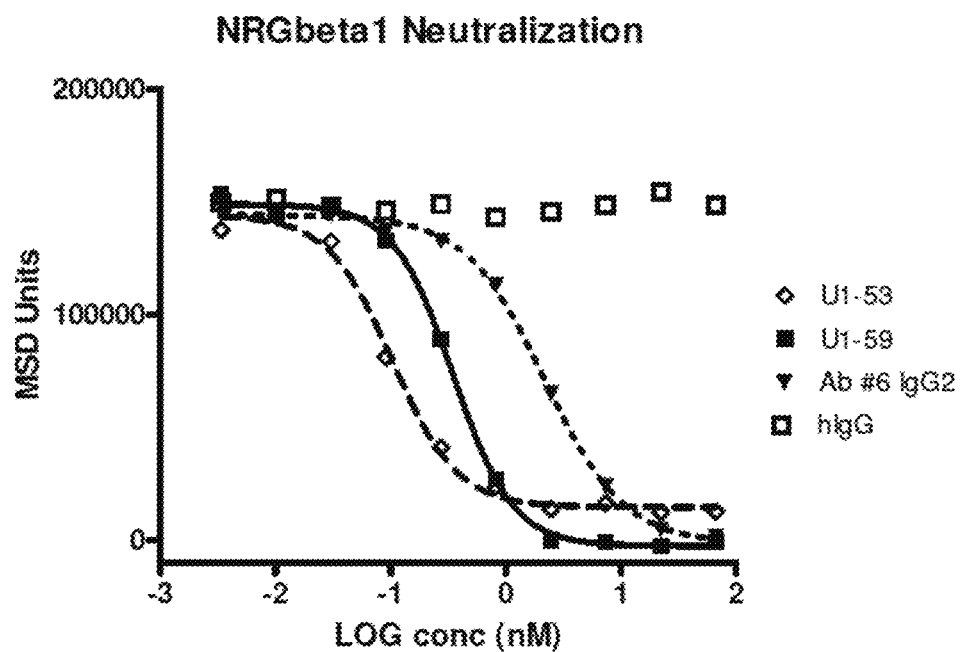
FIG. 18B is a graph summarizing results from an experiment to measure the neutralization activity of human IgG (□) and anti-ErbB3 monoclonal antibodies Ab #6 IgG2 (▼), U1-53 (◇) and U1-59 (■).

The interaction of NRG1-β1 with rhErbB3 was inhibited by antibodies Sh24C05-25 N62S-IgG1, Sh24C05-25 N62S-IgG2, Sh24C05-31 N62S-IgG1, and Sh24C05-31 N62S-IgG2 (FIG. 18A). The Ab #6 IgG2 antibody as described in Schoeberl et al. (supra) and the U1-53 and U1-59 antibodies as described in Rothe et al. (supra) were also tested for their ability to inhibit ErbB3 binding to NRG1-β1. As shown in FIG. 18B, each of the Ab #6 IgG2, U1-53, and U1-59 antibodies inhibited ErbB3 binding to NRG1-β1.

The $IC_{50}$ values for neutralization of NRG1-β1 binding to hErbB3 for the humanized 24C05 antibodies (i.e., Sh24C05-25 N62S-IgG1, Sh24C05-25 N62S-IgG2, Sh24C05-31 N62S-IgG1, and Sh24C05-31 N62S-IgG2) were calculated and are summarized in Table 18. The $IC_{50}$ values for the NRG1-β1 neutralization activity of the anti-ErbB3 human antibodies Ab #6 IgG2, U1-53 and U1-59 are also shown in Table 18.

TABLE 18

| Antibody | IC50 (nM) | | |
| --- | --- | --- | --- |
| | Average | Standard Deviation | n |
| Sh24C05-25 N62S-IgG1 | 0.1219 | 0.0173 | 4 |
| Sh24C05-25 N62S-IgG2 | 0.1117 | 0.0154 | 4 |
| Sh24C05-31 N62S-IgG1 | 0.1242 | 0.0391 | 5 |
| Sh24C05-31 N62S-IgG2 | 0.0860 | 0.0588 | 4 |
| U1-53 | 0.1128 | 0.0615 | 3 |
| U1-59 | 0.3181 | 0.0274 | 3 |
| Ab#6 IgG2 | 1.5161 | 0.5883 | 5 |

The results in Table 18 demonstrate that antibodies Sh24C05-25 N62S-IgG1, Sh24C05-25 N62S-IgG2, Sh24C05-31 N62S-IgG1, and Sh24C05-31 N62S-IgG2 efficiently neutralized NRG1-β1 binding to rhErbB3. While the anti-ErbB3 human antibodies Ab #6 IgG2, U1-53 and U1-59 also showed neutralization activity, the humanized Sh24C05 antibodies (i.e., Sh24C05-25 N62S-IgG1, Sh24C05-25 N62S-IgG2, Sh24C05-31 N62S-IgG1, and Sh24C05-31 N62S-IgG2) had superior neutralization capacity than U1-59 or Ab #6 IgG2.

Example 14—Anti-Proliferative Activity

In this example, the humanized antibodies produced in Example 12 were tested for their ability to inhibit NRG1-β1 dependent proliferation of cells in the BaF/3 cell system engineered to express both human Her2 and ErbB3.

BaF/3 cells expressing Her2 and ErbB3 receptors as described in Example 6 were treated with anti-ErbB3 antibodies in the absence of WEHI conditioned media but in the presence of NRG1-β1 (100 ng/ml). Assays were conducted in a 96-well plate (5,000 cells/well) in the presence of NRG1-β1 (100 ng/ml) and various concentrations of antibodies (0.018-5000 ng/ml in 100 μl of final volume). MTT (3-(4,5-Dimethylthiazol-2-yl)-2,5-diphenyltetrazolium bromide) assays were conducted 3-4 days post NRG1-β1 stimulation.

Figure 19A:
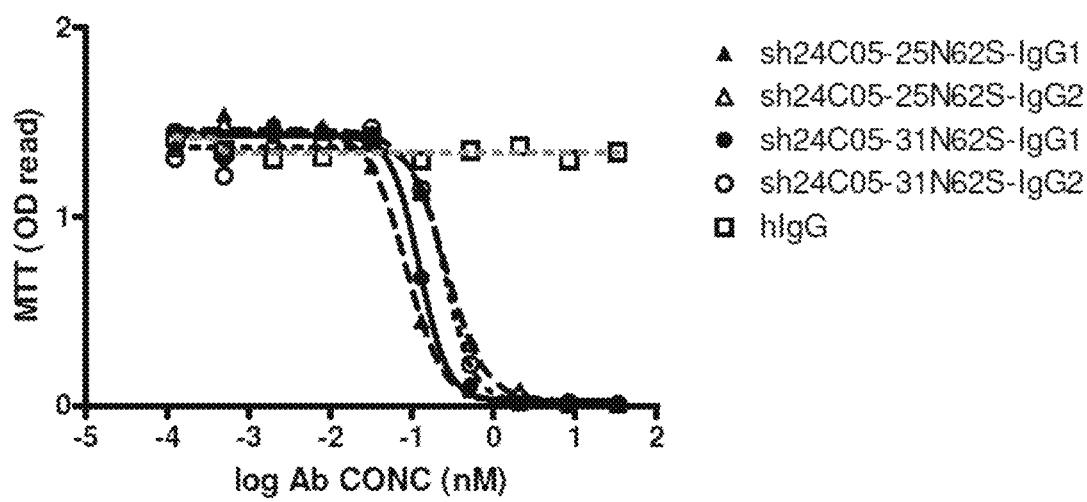
FIG. 19A is a graph summarizing results from an experiment to measure the inhibitory activity of negative control (human IgG (□)) and anti-ErbB3 monoclonal antibodies Sh24C05-25 N62S-IgG1 (▲), Sh24C05-25 N62S-IgG2 (Δ), Sh24C05-31 N62S-IgG1 (●) and Sh24C05-31 N62S-IgG2 (○) in BaF/3 cells expressing Her2 and ErbB3 in the presence of NRG1-β1.

The results demonstrate that Sh24C05-25 N62S-IgG1, Sh24C05-25 N62S-IgG2, Sh24C05-31 N62S-IgG1, and Sh24C05-31 N62S-IgG2 inhibited NRG induced Her2/ErbB3-BaF/3 cell proliferation in a dose dependent manner (FIG. 19A).

The $IC_{50}$ values for the inhibition of NRG1-β1 dependent Her2/ErbB3-BaF/3 cell line proliferation with the humanized 24C05 antibodies (i.e., Sh24C05-25 N62S-IgG1, Sh24C05-25 N62S-IgG2, Sh24C05-31 N62S-IgG1, Sh24C05-31 N62S-IgG2) were calculated and are summarized in Table 19.

TABLE 19

Her2/ErbB3-BaF/3, NRG1-β1 Dependent Proliferation

| Antibody | $IC_{50}$ (nM)-Average | Standard deviation | n |
| --- | --- | --- | --- |
| Sh24C05-25 N62S-IgG1 | 0.0981 | 0.0187 | 2 |
| Sh24C05-25 N62S-IgG2 | 0.2482 | 0.0124 | 2 |
| Sh24C05-31 N62S-IgG1 | 0.1245 | 0.0181 | 5 |
| Sh24C05-31 N62S-IgG2 | 0.2392 | 0.0217 | 2 |
| U1-53 | 0.8128 | 0.0268 | 3 |
| U1-59 | 0.8364 | 0.0434 | 5 |
| Ab#6 IgG2 | 6.3015 | 0.8577 | 2 |

The results in Table 19 demonstrate that antibodies Sh24C05-25 N62S-IgG1, Sh24C05-25 N62S-IgG2, Sh24C05-31 N62S-IgG1, and Sh24C05-31 N62S-IgG2 strongly inhibited NRG1-β1-induced proliferation of BaF/3 cells expressing Her2/ErbB3.

Figure 19B:
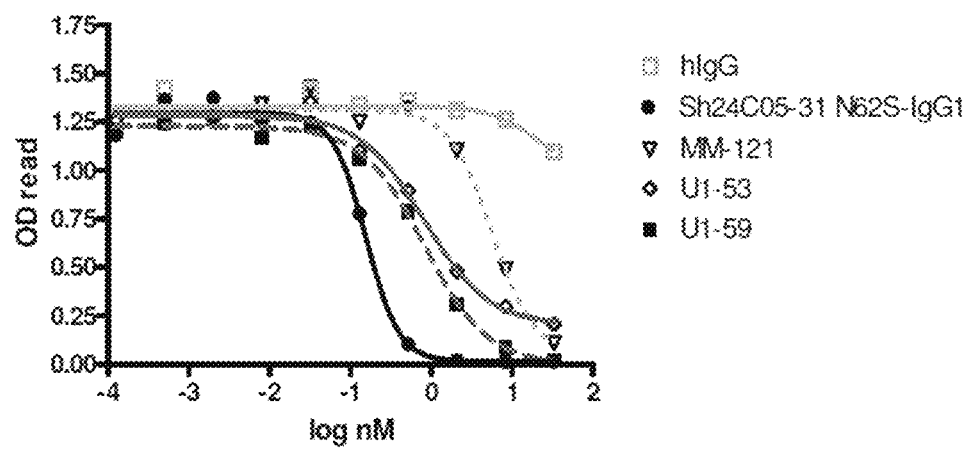
FIG. 19B is a graph summarizing results from an experiment to measure the inhibitory activity of human IgG (□) and anti-ErbB3 monoclonal antibodies Sh24C05-31 N62S-IgG1(●), Ab #6 IgG2 (∇), U1-53 (◇) and U1-59 (■) in BaF/3 cells expressing Her2 and ErbB3 in the presence of NRG1-β1.

The inhibitory activity of anti-ErbB3 Ab #6 IgG2, U1-53 and U1-59 antibodies were also tested in the NRG1-β1 dependent Her2/ErbB3-BaF/3 cells proliferation assay. As shown in FIG. 19B, the results demonstrate that the Ab #6 IgG2, U1-53 and U1-59 antibodies inhibited NRG induced Her2/ErbB3-BaF/3 cell proliferation in a dose dependent manner. Inhibition data of NRG1-β1 dependent Her2/ErbB3-BaF/3 cell proliferation with antibodies Ab #6 IgG2, U1-53 and U1-59 are summarized in Table 19. The results in Table 19 demonstrate that antibodies Ab #6 IgG2, U1-53, and U1-59 inhibited NRG1-β1-induced proliferation of Her2/ErbB3-BaF/3 cells. A comparison of the inhibitory activity of the tested anti-ErbB3 antibodies in the NRG1-β1 dependent Her2/ErbB3-BaF/3 cells proliferation assay indicates that the inhibitory activity of the humanized Sh24C05 antibodies is superior to the inhibitory activity of the Ab #6 IgG2, U1-53 and U1-59 antibodies (e.g., the $IC_{50}$ was 0.1245 nM for Sh24C05-31 N62S-IgG1 compared to 0.8128 nM for U1-53).

Example 15—Inhibition of Downstream Signaling in SKBR-3 Cells

This example describes a characterization of the humanized antibodies produced in Example 12 for their ability to degrade total ErbB3 and inhibit phosphorylation of ErbB3 in exponentially growing SKBR-3 cells.

The breast cancer SKBR-3 cells were maintained as recommended by ATCC. Cells maintained in full serum condition were treated for 1, 2, 4 or 6 hours with 40 μg/ml of anti-ErbB3 antibody (i.e., Sh24C05-25 N62S-IgG1, Sh24C05-25 N62S-IgG2, Sh24C05-31 N62S-IgG1, and Sh24C05-31 N62S-IgG2). Lysates were either analyzed by ELISA with the Total-ErbB3 and the Phospho-ErbB3 kit from R&D Systems (Cat. No DYC234 and Cat. No DYC1769, respectively).

Figure 20:
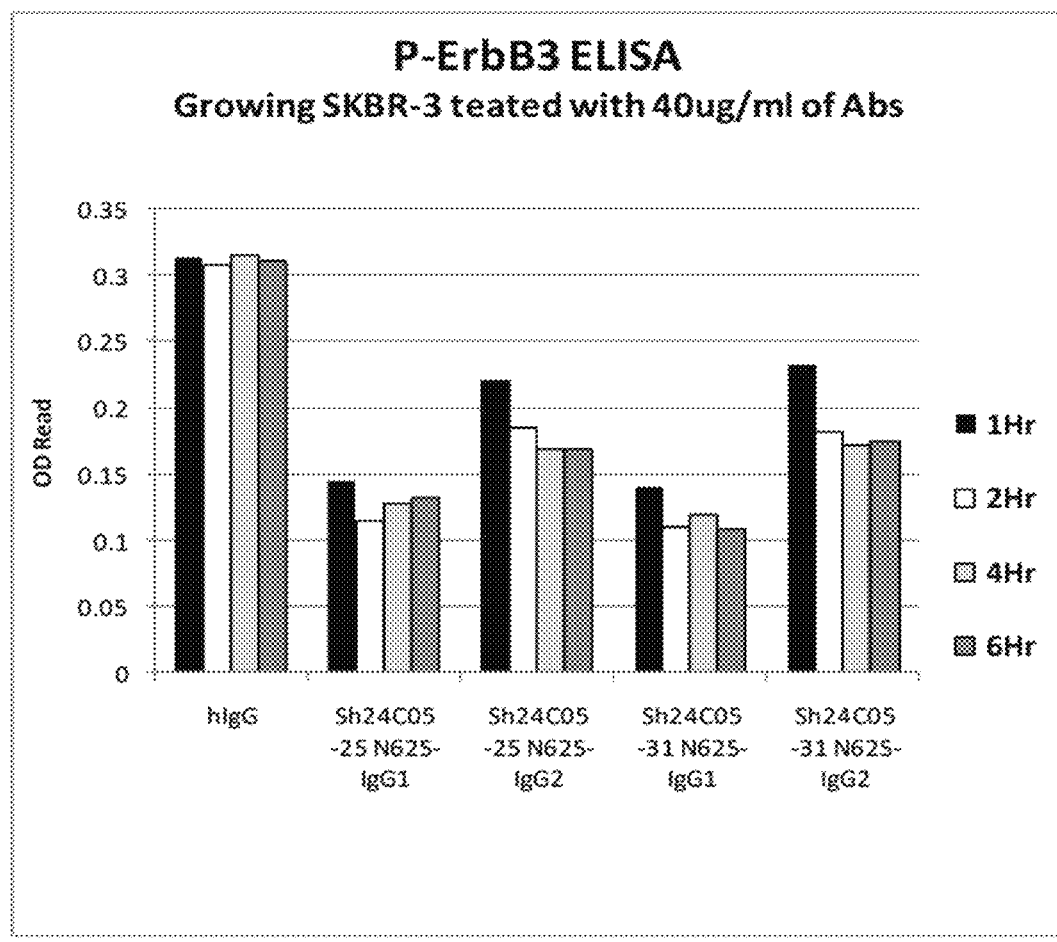
FIG. 20 is a graph summarizing results from an experiment to measure the inhibitory activity of negative control (human IgG) and anti-ErbB3 monoclonal antibodies Sh24C05-25 N62S-IgG1, Sh24C05-25 N62S-IgG2, Sh24C05-31 N62S-IgG1, and Sh24C05-31 N62S-IgG2 on the steady state phosphorylation of ErbB3 in growing SKBR-3 cells.

The results demonstrate that anti-ErbB3 antibodies Sh24C05-25 N62S-IgG1, Sh24C05-25 N62S-IgG2, Sh24C05-31 N62S-IgG1, and Sh24C05-31 N62S-IgG2 inhibit at least 50% of the phosphorylation of ErbB3 in exponentially growing SKBR-3 cells (FIG. 20).

Figure 21:
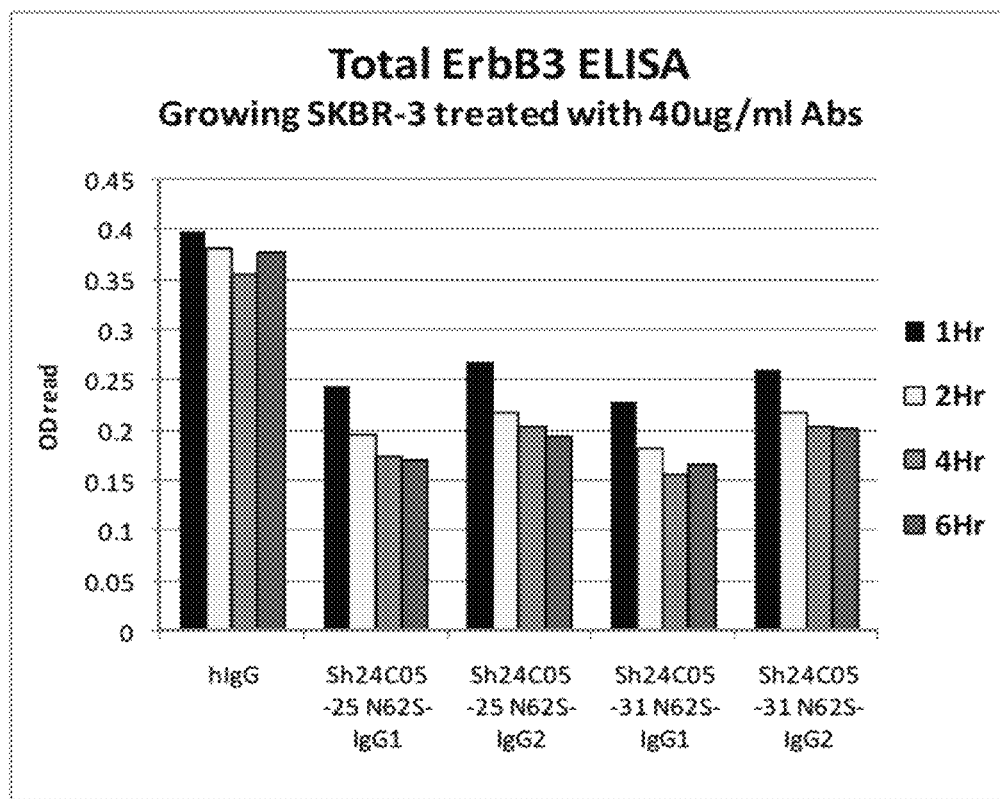
FIG. 21 is a graph summarizing results from an experiment to measure the degradation of ErbB3 receptor by negative control (human IgG) and anti-ErbB3 monoclonal antibodies Sh24C05-25 N62S-IgG1, Sh24C05-25 N62S-IgG2, Sh24C05-31 N62S-IgG1, and Sh24C05-31 N62S-IgG2 in growing SKBR-3 cells.

The results also demonstrate that anti-ErbB3 antibodies Sh24C05-25 N62S-IgG1, Sh24C05-25 N62S-IgG2, Sh24C05-31 N62S-IgG1, and Sh24C05-31 N62S-IgG2 degraded at least 50% of the total ErbB3 receptor present in exponentially growing SKBR-3 cells (FIG. 21).

Example 16—Inhibition of BxPC3 Tumor Xenograft Growth

The ability of the humanized monoclonal antibodies produced in Example 12 to inhibit tumor growth were tested in a BxPC3 pancreatic xenograft model. Human pancreatic BxPC3 cells were grown in culture in 37° C. in an atmosphere containing 5% CO2, using RMPI medium containing 10% fetal bovine serum. BxPC3 cells were inoculated subcutaneously into the flank of 8-week old female CB.17 SCID mice (Taconic Labs) with $10 \times 10^6$ cells per mouse in 50% MATRIGEL® (BD Biosciences, Cat No. 356237). Tumor measurements were taken twice weekly using vernier calipers. Tumor volume was calculated using the formula: width×width×length/2. When tumors reached approximately 200 mm³, the mice were randomized into 8 groups of 10 mice each. One group received PBS, another received huIgG control, and another received muIgG control. Each of the remaining five groups received one of the antibodies (i.e., murine 24C05, Sh24C05-25 N62S-IgG1, Sh24C05-25 N62S-IgG2, Sh24C05-31 N62S-IgG1 or Sh24C05-31 N62S-IgG2). All of the antibodies were dosed at 2 mg/kg body weight, twice per week, by intra-peritoneal injection for 7 weeks. Tumor volumes and mouse body weights were recorded twice per week. Tumor growth inhibition was analyzed using ANOVA and is expressed as percent inhibition compared to the PBS control.

Figure 22:
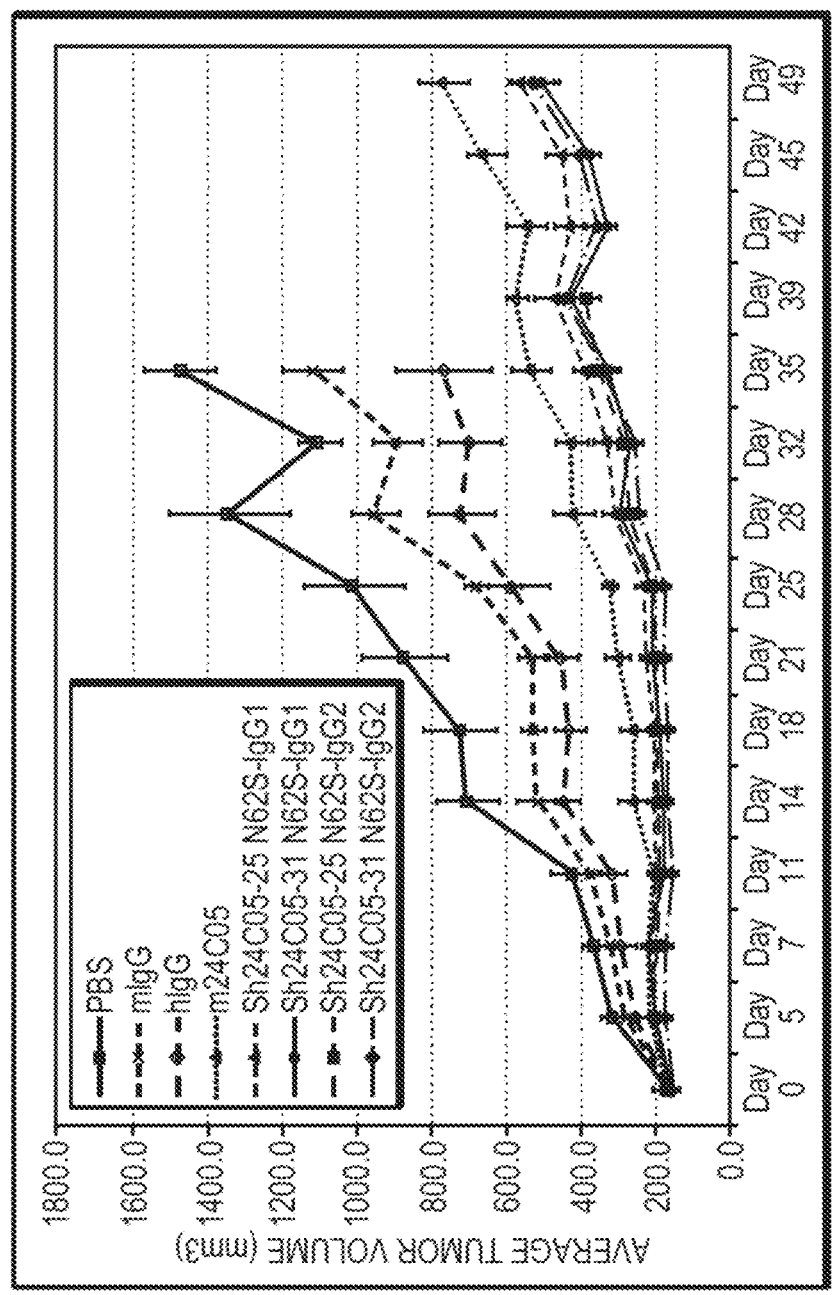
FIG. 22 is a graph summarizing the results from an experiment to measure tumor inhibitory activity of a human IgG, murine IgG, or anti-ErbB3 monoclonal antibodies dosed at 2 mg/kg in a BxPC3 pancreatic tumor xenograft model in CB17 SCID mice (murine 24C05 (Δ), Sh24C05-31 N62S IgG1 (●), Sh24C05-31 N62S IgG2 (♦), Sh24C05-25 N62S IgG1(▲), Sh24C05-25 N62S IgG2 (■), vehicle control (□), murine IgG (x), and human IgG (◇)).
Figure 23A:
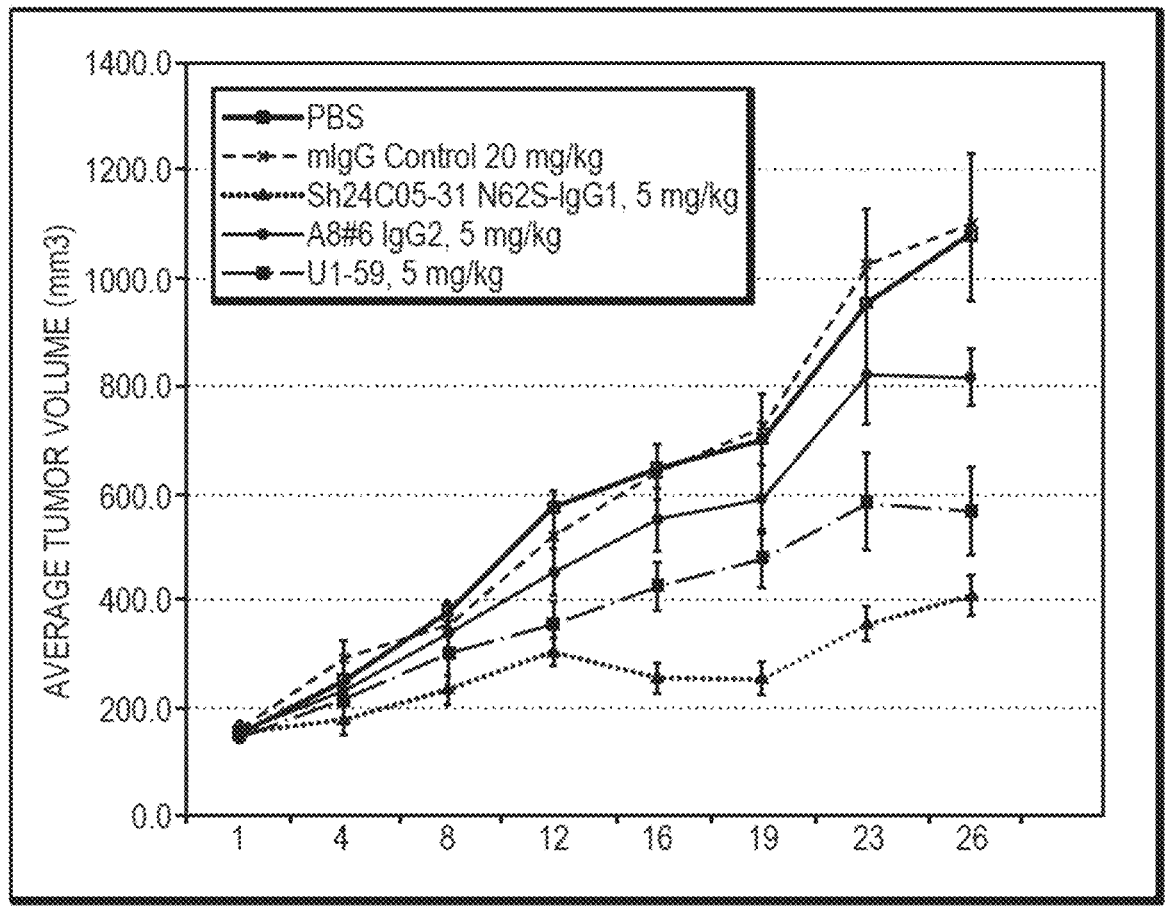
FIG. 23A is a graph summarizing the results from an experiment to measure tumor inhibitory activity of a murine IgG or anti-ErbB3 monoclonal antibodies dosed at 5 mg/kg in a Calu-3 non-small cell lung cancer xenograft model in NCR nude mice (vehicle control (□), murine IgG (x), Sh24C05-31 N62S IgG1 (▲), Ab #6 IgG2 (●), and U1-59 (■)).
Figure 23B:
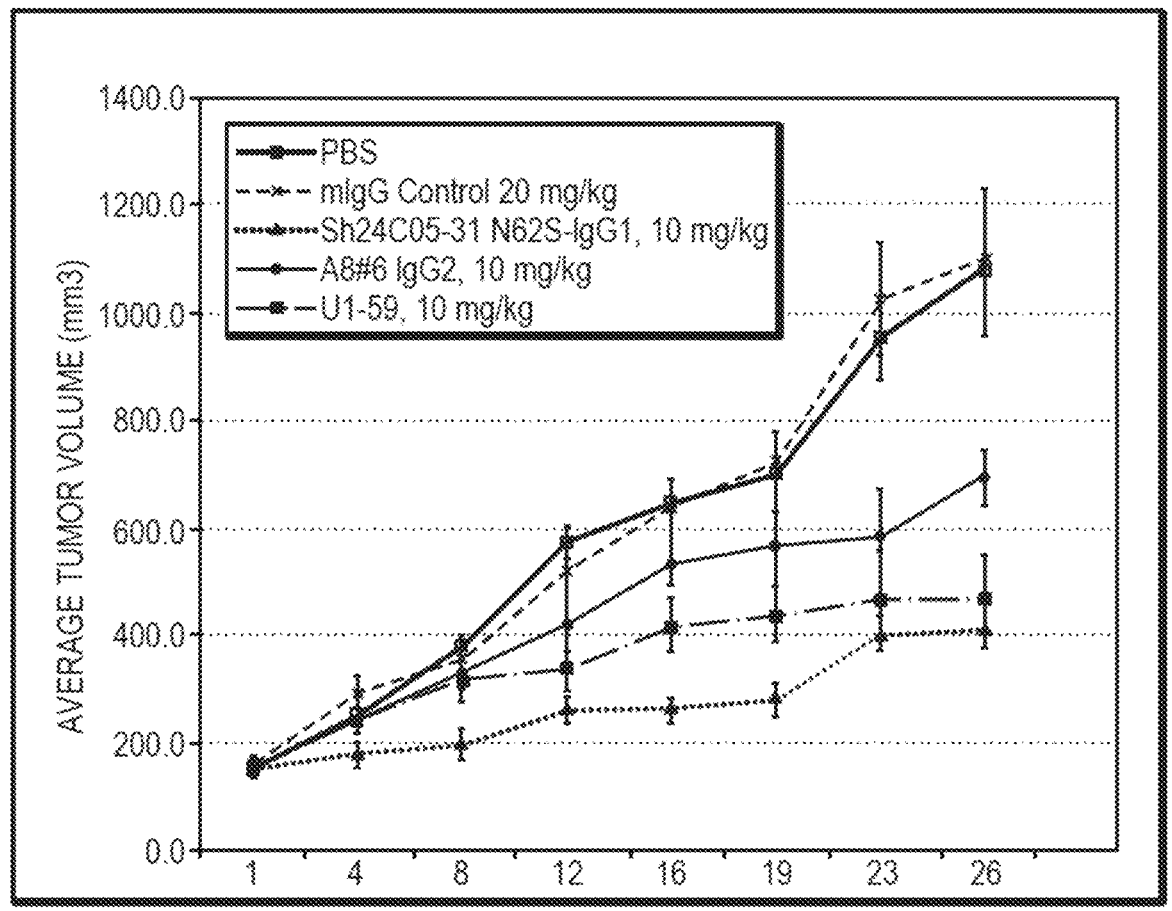
FIG. 23B is a graph summarizing the results from an experiment to measure tumor inhibitory activity of a murine IgG or anti-ErbB3 monoclonal antibodies dosed at 10 mg/kg in a Calu-3 non-small cell lung cancer xenograft model in NCR nude mice (vehicle control (□), murine IgG (x), Sh24C05-31 N62S IgG1 (▲), Ab #6 IgG2 (●), and U1-59 (■)).
Figure 23C:
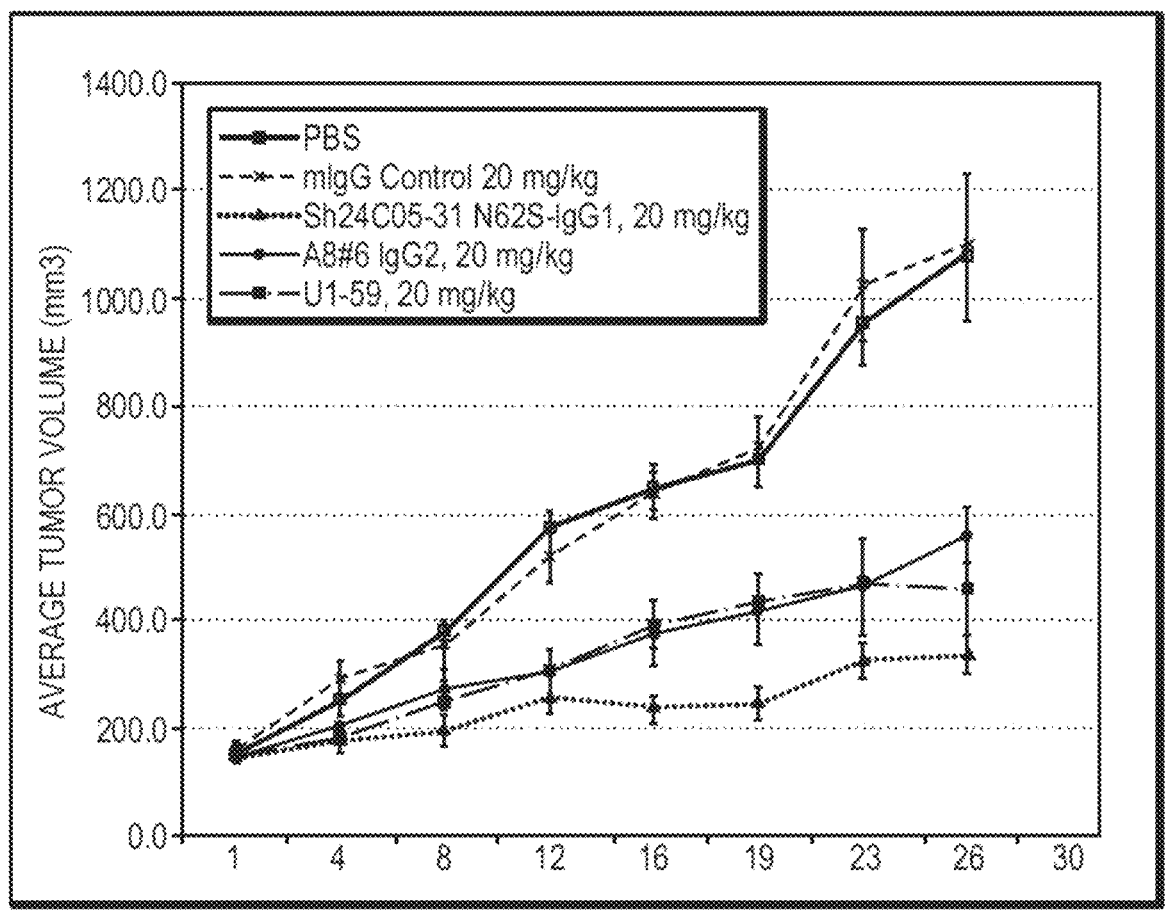
FIG. 23C is a graph summarizing the results from an experiment to measure tumor inhibitory activity of a murine IgG or anti-ErbB3 monoclonal antibodies dosed at 20 mg/kg in a Calu-3 non-small cell lung cancer xenograft model in NCR nude mice (vehicle control (□), murine IgG (x), Sh24C05-31 N62S IgG1 (▲), Ab #6 IgG2 (●), and U1-59 (■)).
Figure 24:
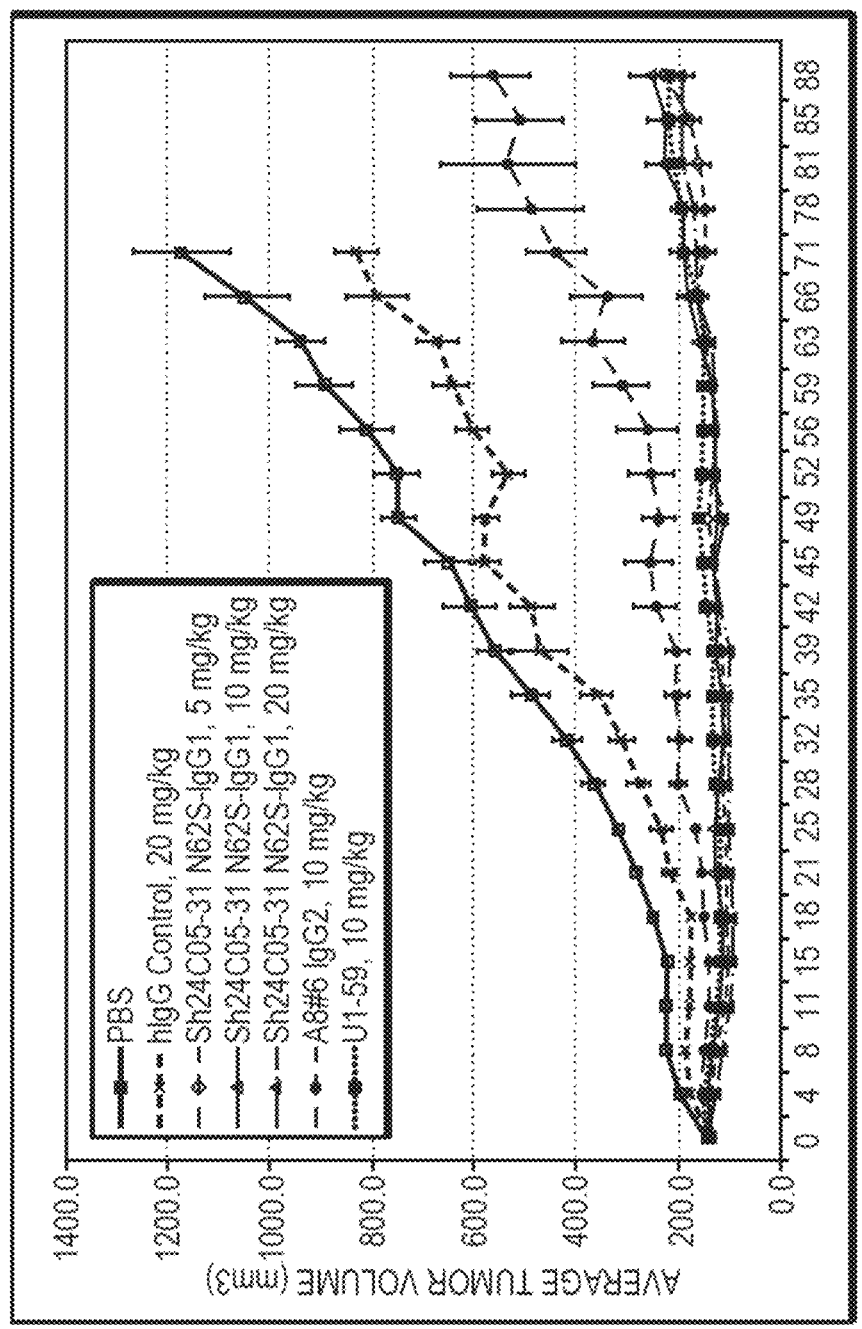
FIG. 24 is a graph summarizing the results from an experiment to measure tumor inhibitory activity of a human IgG, murine or anti-ErbB3 monoclonal antibodies in a MDA-MB-453 breast cancer xenograft model in NOD SCID mice (vehicle control (□), human IgG (x), Sh24C05-31 N62S IgG1 dosed at 5 mg/kg (◇), Sh24C05-31 N62S IgG1 dosed at 10 mg/kg (Δ), Sh24C05-31 N62S IgG1 dosed at 20 mg/kg (▲), Ab #6 IgG2 dosed at 10 mg/kg (●), and U1-59 dosed at 10 mg/kg (■)).

The tested humanized antibodies were active in vivo. All four humanized anti-ErbB3 antibodies had similar efficacy in the BxPC3 model when dosed at 2 mg/kg, ranging from 75-80% tumor growth inhibition ($p<0.001$) (i.e., Sh24C05-25 N62S-IgG1, 75%; Sh24C05-25 N62S-IgG2, 76%; Sh24C05-31 N62S-IgG1, 79%; and Sh24C05-31 N62S-IgG2, 80%) at day 28 of the study (FIG. 22). The murine antibody demonstrated 65% tumor growth inhibition in this study ($p<0.05$). These results suggest similar potency and activity of the four humanized antibodies in this model.

The ability of the humanized monoclonal antibodies U1-53, U1-59, and Ab #6 IgG2 to inhibit tumor growth were also tested in a BxPC3 xenograft model. Using the protocol described above, BxPC3 tumors were generated in CB.17 SCID mice. When tumors reached approximately 200 mm³, the mice were randomized into 11 groups of 10 mice each. One group received PBS and another received huIgG control. Each of the other nine groups received one of the humanized antibodies (i.e., Sh24C05-31 N62S-IgG1, U1-53, U1-59, or Ab #6 IgG2). The antibodies were dosed either at 0.5 mg/kg, 1 mg/kg, or 5 mg/kg body weight, twice per week, by intra-peritoneal injection for 7 weeks. Tumor volumes and mouse body weights were recorded twice per week. Tumor growth inhibition was analyzed using ANOVA and is expressed as percent inhibition compared to the PBS control.

Tumor growth inhibition data determined at day 29 following treatment with one of the humanized antibodies (i.e., Sh24C05-31 N62S-IgG1, U1-59, or Ab #6 IgG2) is shown in Table 20.

TABLE 20

| Gr. | Treatment Agent | mg/kg | Tumor Growth Inhibition (%) | ANOVA Analysis (Compared to PBS) | ANOVA Analysis (Compared to hIgG) |
|---|---|---|---|---|---|
| 1 | PBS | — | NA | NA | NA |
| 2 | hIgG | 5 | 29.2 | NS | NS |
| 3 | Sh24C05-31 N62S-IgG1 | 0.5 | 63.3 | P < 0.001 | P < 0.01 |
| 4 | Sh24C05-31 N62S-IgG1 | 1 | 75.0 | P < 0.001 | P < 0.001 |
| 5 | Sh24C05-31 N62S-IgG1 | 5 | 76.5 | P < 0.001 | P < 0.001 |
| 6 | Ab#6 IgG2 | 0.5 | 31.5 | P < 0.05 | NS |
| 7 | Ab#6 IgG2 | 1 | 2.1 | NS | NS |
| 8 | Ab#6 IgG2 | 5 | 40.6 | P < 0.001 | NS |
| 9 | U1-59 | 0.5 | 32.6 | P < 0.01 | NS |
| 10 | U1-59 | 1 | 52.9 | P < 0.001 | NS |
| 11 | U1-59 | 5 | 60.3 | P < 0.001 | P < 0.05 |

The results demonstrate that Sh24C05-31 N62S-IgG1 showed the greatest tumor growth inhibition by day 29 (76.5%, $p<0.001$) at a dose of 5 mg/kg in the BxPC3 pancreatic xenograft model. The U1-59 and Ab #6 IgG2 antibodies demonstrated approximately 60% and 41% tumor growth inhibition at a dose of 5 mg/kg in the BxPC3 model, respectively ($P<0.001$).

The results also demonstrate that Sh24C05-31 N62S-IgG1 showed the greatest tumor growth inhibition by day 29 at a dose of 0.5 mg/kg (63.3%, $p<0.001$) and at a dose of 1 mg/kg (75.0%, $p<0.001$) in the BxPC3 pancreatic xenograft model. The U1-59 and AB #6 IgG2 antibodies demonstrate approximately 33% ($p<0.01$) and 31% ($p<0.05$) tumor growth inhibition at a dose of 0.5 mg/kg in the BxPC3 model, respectively. The U1-59 and AB #6 IgG2 antibodies demonstrated approximately 53% ($p<0.001$) and 2% (not significant) tumor growth inhibition at a dose of 1.0 mg/kg in the BxPC3 model, respectively.

Example 17—Inhibition of Calu-3 Tumor Xenograft Growth

The ability of the humanized monoclonal antibodies produced in Example 12 to inhibit tumor growth was tested in a Calu-3 non-small cell lung cancer xenograft model. The ability of the humanized monoclonal antibodies U1-59 and Ab #6 IgG2, as described in Example 12, to inhibit tumor growth were also tested in the same model.

Human Non-Small Cell Lung Cancer Calu-3 cells were grown in culture in 37° C. in an atmosphere containing 5% CO2, using EMEM medium containing 10% fetal bovine serum. Calu-3 cells were inoculated subcutaneously into the flank of 8-week old female NCR nude mice (Taconic Labs) with $10\times10^6$ cells per mouse in 50% MATRIGEL® (BD Biosciences, Cat No. 356237). Tumor measurements were taken twice weekly using vernier calipers. Tumor volume was calculated using the formula: width×width×length/2.

When tumors reached approximately 200 mm³, the mice were randomized into 11 groups of 10 mice each. One group received PBS and another received muIgG control. Each of the other nine groups received one of the humanized antibodies (i.e., Sh24C05-31 N62S-IgG1, U1-59, or Ab #6 IgG2) at a dose of either 5 mg/kg, 10 mg/kg or 20 mg/kg body weight, twice per week, by intra-peritoneal injection for 4 weeks. Tumor volumes and mouse body weights were recorded twice per week. Tumor growth inhibition was analyzed using ANOVA and is expressed as percent inhibition compared to the PBS control.

Tumor growth inhibition data determined at day 26 following treatment with one of the humanized antibodies (i.e., Sh24C05-31 N62S-IgG1, U1-59, or Ab #6 IgG2) is shown in Table 21.

TABLE 21

| Gr. | Treatment Agent | mg/kg | Tumor Growth Inhibition (%) | ANOVA Analysis (Compared to PBS) | ANOVA Analysis (Compared to hIgG) |
|---|---|---|---|---|---|
| 1 | PBS | — | NA | NA | NA |
| 2 | muIgG | 20 | -1.2 | NS | NA |
| 3 | Sh24C05-31 N62S-IgG1 | 5 | 62.3 | P < 0.001 | P < 0.001 |
| 4 | Sh24C05-31 N62S-IgG1 | 10 | 62.0 | P < 0.001 | P < 0.001 |
| 5 | Sh24C05-31 N62S-IgG1 | 20 | 69.0 | P < 0.001 | P < 0.001 |
| 6 | Ab# IgG2 | 5 | 24.7 | NS | NS |
| 7 | Ab# IgG2 | 10 | 35.9 | P < 0.01 | P < 0.01 |
| 8 | Ab# IgG2 | 20 | 48.4 | P < 0.001 | P < 0.001 |
| 9 | U1-59 | 5 | 47.8 | P < 0.001 | P < 0.001 |
| 10 | U1-59 | 10 | 56.7 | P < 0.001 | P < 0.001 |
| 11 | U1-59 | 20 | 57.7 | P < 0.001 | P < 0.001 |

The results using the Calu-3 non-small cell lung cancer xenograft model demonstrate that Sh24C05-31 N62S-IgG1 showed the greatest tumor growth inhibition by day 26 at all doses tested (i.e., 5 mg/kg, 10 mg/kg, and 20 mg/kg of body weight).

For example, at the 10 mg/kg dose, Sh24C05-31 N62S-IgG1 showed the greatest tumor growth inhibition by day 26 (62%, P<0.001) when compared to Ab #6 IgG2 (36%, NS) or U1-59 (57%, P<0.001). At the 20 mg/kg dose, Sh24C05-31 N62S-IgG1 also showed the greatest tumor growth inhibition by day 26 (69%, P<0.001) when compared to Ab #6 IgG2 (48%, P<0.001) or U1-59 (58%, P<0.001).

Example 18—Inhibition of MDA-MB-453 Tumor Xenograft Growth

The ability of the humanized monoclonal antibodies produced in Example 12 to inhibit tumor growth were tested in a MDA-MB-453 breast xenograft model (which is a HER2 positive breast model). The ability of the humanized monoclonal antibodies U1-59 and Ab #6 IgG2, as described in Example 12, to inhibit tumor growth were also tested in the same model.

Human Breast MDA-MB-453 cells were grown in culture in 37° C. in an atmosphere containing 0% CO2, using Leibovitz ATCC medium (Cat No. 30-2008) containing 10% fetal bovine serum. MDA-MB-453 cells were inoculated subcutaneously into the flank of 8-week old female NOD SCID mice (Taconic Labs) with $20 \times 10^6$ cells per mouse in 50% MATRIGEL® (BD Biosciences, Cat No. 356237). Tumor measurements were taken twice weekly using vernier calipers. Tumor volume was calculated using the formula: width×width×length/2.

When tumors reached approximately 200 mm³, the mice were randomized into 7 groups of 10 mice each. One group received PBS and another received huIgG control. Each of the other nine groups received one of the humanized antibodies (i.e., Sh24C05-31 N62S-IgG1, U1-59, or Ab #6 IgG2). Sh24C05-31 N62S-IgG1 was dosed either at 5 mg/kg, 10 mg/kg, or 20 mg/kg body weight, twice per week, by intra-peritoneal injection for more than 10 weeks; U1-59, or Ab #6 were dosed at 10 mg/kg with the same frequency. Tumor volumes and mouse body weights were recorded twice per week. Tumor growth inhibition was analyzed using ANOVA and is expressed as percent inhibition compared to the PBS control.

Tumor growth inhibition data determined at day 71 following treatment with one of the humanized antibodies (i.e., Sh24C05-31 N62S-IgG1, U1-59, or Ab #6 IgG2) is shown in Table 22.

TABLE 22

| Gr. | Treatment Agent | mg/kg | Tumor Growth Inhibition (%) | ANOVA Analysis (Compared to PBS) | ANOVA Analysis (Compared to hIgG) |
|---|---|---|---|---|---|
| 1 | PBS | — | NA | NA | NA |
| 2 | hIgG | 20 | 28.87 | p < 0.001 | p < 0.001 |
| 3 | Sh24C05-31 N62S-IgG1 | 5 | 86.57 | p < 0.001 | p < 0.001 |
| 4 | Sh24C05-31 N62S-IgG1 | 10 | 84.09 | p < 0.001 | p < 0.001 |
| 5 | Sh24C05-31 N62S-IgG1 | 20 | 85.26 | p < 0.001 | p < 0.001 |
| 6 | Ab#6 IgG2 | 10 | 62.48 | p < 0.001 | p < 0.001 |
| 7 | U1-59 | 10 | 83.93 | p < 0.001 | p < 0.001 |

The results using the MDA-MB-453 xenograft model demonstrate that Sh24C05-31 N62S-IgG1 showed potent tumor growth inhibition by day 71 at all doses tested (i.e., 5 mg/kg, 10 mg/kg, and 20 mg/kg of body weight).

The results also demonstrate that at the 10 mg/kg dose, Sh24C05-31 N62S-IgG1 showed greater tumor growth inhibition by day 71 (84%, P<0.001) when compared to Ab #6 IgG2 (62%, P<0.001). Sh24C05-31 N62S-IgG1 showed equivalent tumor growth inhibition as U1-59 at the same dose.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated antibody that binds human ErbB3 comprising:
   (i) an immunoglobulin heavy chain variable region comprising a $CDR_{H1}$ comprising the amino acid sequence of SEQ ID NO: 15, a $CDR_{H2}$ comprising the amino acid sequence of SEQ ID NO: 16, and a $CDR_{H3}$ comprising the amino acid sequence of SEQ ID NO: 17; and
   (ii) an immunoglobulin light chain variable region comprising a $CDR_{L1}$ comprising the amino acid sequence of SEQ ID NO: 18, a $CDR_{L2}$ comprising the amino acid sequence of SEQ ID NO: 19, and a $CDR_{L3}$ comprising the amino acid sequence of SEQ ID NO: 20.

2. The antibody of claim 1, wherein the CDR sequences are interposed between human and humanized framework sequences.

3. The antibody of claim 1, wherein the antibody is an antigen-binding fragment.

4. An isolated nucleic acid comprising a nucleotide sequence encoding an immunoglobulin heavy chain variable region of the antibody of claim 1.

5. An isolated nucleic acid comprising a nucleotide sequence encoding an immunoglobulin light chain variable region of the antibody of claim 1.

6. An expression vector comprising the nucleic acid of claim 4.

7. An expression vector comprising the nucleic acid of claim 5.

8. A host cell comprising the expression vector of claim 6.

9. A host cell comprising the expression vector of claim 7.

10. An isolated antibody that binds human ErbB3 comprising an immunoglobulin heavy chain variable region comprising the amino acid sequence of SEQ ID NO: 12, and an immunoglobulin light chain variable region comprising the amino acid sequence of SEQ ID NO: 14.

11. An isolated antibody that binds human ErbB3 comprising an immunoglobulin heavy chain comprising the amino acid sequence of SEQ ID NO: 113, and an immunoglobulin light chain comprising the amino acid sequence of SEQ ID NO: 115.

12. The antibody of claim 10, wherein the antibody is an antigen binding fragment.

13. The antibody of claim 1, wherein the antibody has a $K_D$ of 200 pM or lower as measured by surface plasmon resonance.

14. A method of inhibiting or reducing proliferation of a tumor cell comprising exposing the cell to an effective amount of the antibody of claim 1 to inhibit or reduce proliferation of the tumor cell, wherein said tumor cell expresses human ErbB3.

15. A method of inhibiting or reducing tumor growth in a mammal, the method comprising exposing a mammal having a tumor to an effective amount of the antibody of claim 1 to inhibit or reduce proliferation of the tumor, wherein said tumor expresses human ErbB3.

16. A method of treating cancer in a mammal, the method comprising administering an effective amount of the antibody of claim 1 to a mammal having cancer, wherein said cancer expresses human ErbB3.

* * * * *

SEQUENCE LISTING

```
<160> NUMBER OF SEQ ID NOS: 212

<210> SEQ ID NO 1
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtccaac tgcagcagcc tggggctgaa ctggtgaggc ctgggacttc agtgaagttg      60
tcctgcaagg cttctggcta caccttcacc agccactggt tgcactgggt gaagcagagg     120
```

```
cctggacaag gccttgagtg gatcggagtg cttgatcctt ctgattttta tagtaactac    180
aatcaaaact tcaagggcaa ggccacattg actgtagaca catcctccag cacagcctac    240
atgcagctca gcagcctgac atctgaggac tctgcggtct attactgtgc acgaggccta    300
ctatccgggg actatgctat ggactactgg ggtcaaggaa cctcagtcac cgtctcctca    360
```

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser His
            20                  25                  30

Trp Leu His Trp Val Lys Gln Arg Pro Gly Gln Gly Leu Glu Trp Ile
        35                  40                  45

Gly Val Leu Asp Pro Ser Asp Phe Tyr Ser Asn Tyr Asn Gln Asn Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Leu Leu Ser Gly Asp Tyr Ala Met Asp Tyr Trp Gly Gln
            100                 105                 110

Gly Thr Ser Val Thr Val Ser Ser
        115                 120
```

<210> SEQ ID NO 3
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gatgttttga tgacccaaat tccactctcc ctgcctgtca gtcttggaga tcaagcctcc     60
atctcttgca gatctagtca gagcattgta catagtaatg aaacaccta  tttagaatgg    120 tacctgcaga aaccaggcca gtctccaaag tccctgatct acaaagtttc taaccgattt    180
tctggggtcc cagacaggtt cagtggcagt ggatcaggga cagatttcac actcaagatc    240
agcagagtgg aggctgagga tctgggagtt tattactgct ttcaaggttc atatgttccg    300
tggacgttcg gtggaggcac caagctggaa atcaaa                              336
```

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Asp Val Leu Met Thr Gln Ile Pro Leu Ser Leu Pro Val Ser Leu Gly
```

```
                1               5                  10                  15
Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Ser Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                    85                  90                  95

Ser Tyr Val Pro Trp Thr Phe Gly Gly Gly Thr Lys Leu Glu Ile Lys
                100                 105                 110
```

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Ser His Trp Leu His
1               5
```

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Val Leu Asp Pro Ser Asp Phe Tyr Ser Asn Tyr Asn Gln Asn Phe Lys
1               5                   10                  15

Gly
```

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gly Leu Leu Ser Gly Asp Tyr Ala Met Asp Tyr
1               5                   10
```

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Arg Ser Ser Gln Ser Ile Val His Ser Asn Gly Asn Thr Tyr Leu Glu
1               5                   10                  15
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Lys Val Ser Asn Arg Phe Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Phe Gln Gly Ser Tyr Val Pro Trp Thr
1               5

<210> SEQ ID NO 11
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
caggttactc taaaagagtc tggccctggg atattgcggc cctcccagac cctcagtctg    60
acttgttctt tctctgggtt ttcactgagc acttttggtt tgagtgtagg ctggattcgt   120
cagccttcag ggaagggtct ggagtggctg gcacacattt ggtgggatga tgataagtac   180
tataacccag cccttaagag tcggctcaca atctccaagg atacctccaa aaaccaggta   240
ttcctcaaga tcgccaatgt ggacactgca gatactgcca catactactg tgctcgaata   300
ggggcggacg cccttccttt tgactactgg ggccaaggca ccactctcac agtctcctca   360

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Gln Val Thr Leu Lys Glu Ser Gly Pro Gly Ile Leu Arg Pro Ser Gln
1               5                   10                  15

Thr Leu Ser Leu Thr Cys Ser Phe Ser Gly Phe Ser Leu Ser Thr Phe
            20                  25                  30

Gly Leu Ser Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

```
Cys Ala Arg Ile Gly Ala Asp Ala Leu Pro Phe Asp Tyr Trp Gly Gln
                100                 105                 110

Gly Thr Thr Leu Thr Val Ser Ser
        115                 120

<210> SEQ ID NO 13
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gatattgtgt tgactcagac tgcaccctct gtacctgtca ctcctggaga gtcagtatcc     60
atctcctgca ggtctagtaa gagtctcctg catagtaatg caacactta cttgtattgg    120 ttcctgcaga ggccaggcca gtctcctcag ctcctgatat atcggatgtc aaccttgcc    180 tcaggagtcc cagacaggtt cagtggcagt gggtcaggaa ctgctttcac actgagaatc    240
agtagagtgg aggctgagga tgtgggtgtt tattactgta tgcaacatct agaatatcct    300
ttcacgttcg gctcggggac aaagttggaa ataaaa                              336

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Leu Thr Gln Thr Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Phe Gly Leu Ser Val Gly
1               5

<210> SEQ ID NO 16
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 16

His Ile Trp Trp Asp Asp Asp Lys Tyr Tyr Asn Pro Ala Leu Lys Ser
1               5                   10                  15

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Gly Ala Asp Ala Leu Pro Phe Asp Tyr
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ser Ser Lys Ser Leu Leu His Ser Asn Gly Asn Thr Tyr Leu Tyr
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Met Ser Asn Leu Ala Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Gln His Leu Glu Tyr Pro Phe Thr
1               5

<210> SEQ ID NO 21
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caggttcagc tgcaacagtc tgacgctgag ttggtgaaac ctggagcttc agtgaagata    60
```

```
tcctgcaagg tttctggcta caccttcact gaccatatta ttcactggat gaagcagagg    120
cctgaacagg gcctggaatg gattggatat atttatccta gagatggtta tattaagtac    180
aatgagaagt tcaagggcaa ggccacattg actgcagaca atcctccag cacagcctac     240 atgcaggtca acagcctgac atctgaggac tctgcagtct atttctgtgc aaggggttac    300
tattatgcta tggactactg gggtcaagga acctcagtca ccgtctcctc a             351
```

```
<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22
```

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Ile Ile His Trp Met Lys Gln Arg Pro Glu Gln Gly Leu Glu Trp Ile
        35                  40                  45

Gly Tyr Ile Tyr Pro Arg Asp Gly Tyr Ile Lys Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Val Asn Ser Leu Thr Ser Glu Asp Ser Ala Val Tyr Phe Cys
                85                  90                  95

Ala Arg Gly Tyr Tyr Tyr Ala Met Asp Tyr Trp Gly Gln Gly Thr Ser
            100                 105                 110

Val Thr Val Ser Ser
        115

```
<210> SEQ ID NO 23
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gatgttttga tgacccaaac tccactctcc ctgcctgtca gtcttggaga tcaagcctcc    60
atctcttgca gatctagtca gagcattgta catagtattg gaaacaccta tttagaatgg    120
tacctgcaga aaccaggcca gtctccaaag ctcctgatct acaaagtttc caaccgattt    180
tctggggtcc cagagaggtt cagtggcagt ggatcaggga cagatttcac actcaagatc    240
agcagagtgg aggctgagga tctgggagtt tattactgct ttcaaggttc acatgttcca    300
ttcacgttcg gctcggggac aaagttggaa ataaaa                              336
```

```
<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24
```

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Ile Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Asp His Ile Ile His
1               5
```

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Tyr Ile Tyr Pro Arg Asp Gly Tyr Ile Lys Tyr Asn Glu Lys Phe Lys
1               5                   10                  15

Gly
```

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Gly Tyr Tyr Tyr Ala Met Asp Tyr
1               5
```

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Arg Ser Ser Gln Ser Ile Val His Ser Ile Gly Asn Thr Tyr Leu Glu
1               5                   10                  15
```

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Phe Gln Gly Ser His Val Pro Phe Thr
1               5

<210> SEQ ID NO 30
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30
caggtccaac tgctgcagcc tgggctgag ctggtgaggc ctgggacttc agtgaagttg      60
tcctgcaaga cttctggcta caccttctcc agctactgga tgcactgggt aaagcagagg    120
cctggacaag gccttgagtg gatcggaatg attgatcctt ctgatgttta tactaactac    180
aatccaaagt tcaagggcaa ggccacattg actgttgaca catcctccag cacagcctac    240
atgcagctca gcagcctgac atctgaggac tctgcggtct attactgtgc aagaaactac    300
tctggggact actggggcca aggcaccact ctcacagtct cctca                    345

<210> SEQ ID NO 31
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Gln Val Gln Leu Leu Gln Pro Gly Ala Glu Leu Val Arg Pro Gly Thr
1               5                   10                  15

Ser Val Lys Leu Ser Cys Lys Thr Ser Gly Tyr Thr Phe Ser Ser Tyr
                20                  25                  30

Trp Met His Trp Val Lys Gln Arg Pro Gly Gln Gly Leu Glu Trp Ile
            35                  40                  45

Gly Met Ile Asp Pro Ser Asp Val Tyr Thr Asn Tyr Asn Pro Lys Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Ser Gly Asp Tyr Trp Gly Gln Gly Thr Thr Leu Thr
            100                 105                 110

Val Ser Ser
        115

<210> SEQ ID NO 32
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
gatgttttga tgacccaaat tccactctcc ctgcctgtca gtcttggaga tcaagcctcc    60
atctcttgta gatctagtca gagcattgtc catagtaatg gaaacaccta tttagaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc atatgttccg   300
tggacgttcg gtggaggcac caagctggaa atcaaa                             336
```

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Asp Val Leu Met Thr Gln Ile Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser Tyr Val Pro Trp Thr Phe Gly Gly Gly Thr Lys Leu Glu Ile Lys
            100                 105                 110
```

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

```
Ser Tyr Trp Met His
1               5
```

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

```
Met Ile Asp Pro Ser Asp Val Tyr Thr Asn Tyr Asn Pro Lys Phe Lys
1               5                   10                  15
Gly
```

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Asn Tyr Ser Gly Asp Tyr
1               5

<210> SEQ ID NO 37
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
cagatccagt tggtacagtc tggacctgaa ctgaagaagc ctggagaggc agtcaagatc      60
tcctgcaagt cttctgggta taccttcaca acctatggaa tgagctgggt gaaacaggct     120
ccaggaaggg ctttaaagtg gatgggctgg ataaacacct actctggagt gccaacatat     180
gctgatgact tcaagggacg gtttgccttc tctttggaat cctctgccag cactgcctat     240
ttgcagatca caaacctcaa aaatgaggac acggctacat atttctgtgc aagagggagg     300
gatggttacc aagtggcctg gtttgcttac tggggccaag ggacgctggt cactgtctct     360
gca                                                                   363

<210> SEQ ID NO 38
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Gln Ile Gln Leu Val Gln Ser Gly Pro Glu Leu Lys Lys Pro Gly Glu
1               5                   10                  15

Ala Val Lys Ile Ser Cys Lys Ser Ser Gly Tyr Thr Phe Thr Thr Tyr
            20                  25                  30

Gly Met Ser Trp Val Lys Gln Ala Pro Gly Arg Ala Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Ser Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Arg Asp Gly Tyr Gln Val Ala Trp Phe Ala Tyr Trp Gly
            100                 105                 110

Gln Gly Thr Leu Val Thr Val Ser Ala
        115                 120

<210> SEQ ID NO 39
<211> LENGTH: 321
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 39
gaaacaactg tgacccagtc tccagcatcc ctgtccatgg ctataggaga taaagtcacc    60
atcagatgca taaccagcac tgatattgat gatgatatga actggttcca gcagaagcca   120
ggggaacctc ctaagctcct tatttcagaa ggcaatactc ttcgtcctgg agtcccatcc   180
cgattctccg gcagtggcta tggtacagat tttattttta caattgaaaa catgctctct   240
gaagatgttg cagattacta ctgtttgcaa agtgataact tgccgtacac gttcggaggg   300
gggaccaagc tggaaataaa a                                             321

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Thr Thr Val Thr Gln Ser Pro Ala Ser Leu Ser Met Ala Ile Gly
1               5                   10                  15

Asp Lys Val Thr Ile Arg Cys Ile Thr Ser Thr Asp Ile Asp Asp Asp
            20                  25                  30

Met Asn Trp Phe Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Gly
    50                  55                  60

Ser Gly Tyr Gly Thr Asp Phe Ile Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Tyr Gly Met Ser
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Trp Ile Asn Thr Tyr Ser Gly Val Pro Thr Tyr Ala Asp Asp Phe Lys
1               5                   10                  15

Gly

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Arg Asp Gly Tyr Gln Val Ala Trp Phe Ala Tyr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Thr Ser Thr Asp Ile Asp Asp Asp Met Asn
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Gly Asn Thr Leu Arg Pro
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Gln Ser Asp Asn Leu Pro Tyr Thr
1               5

<210> SEQ ID NO 47
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
caggtccaac tgcagcagcc tggggctgag ctggtgaggc ctgggacttc agtgaagttg     60
tcctgcaagg cttctggcta caccttcacc aactactgga tgcactgggt aaagcagagg    120
cctggacaag gccttgagtg gatcggaatg attgatcctt ctgatagtta tactaactac    180
aatccaaagt tcaagggtaa ggccacattg actgtagaca tcctccag cacagcctac      240 atgcagctca gcagcctgac atctgaggac tctgcggtct attactgtgc aagaaactac    300
tctggggact actggggcca aggcaccact ctcacagtct cctca                    345

<210> SEQ ID NO 48
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Asn Tyr
                20                  25                  30

Trp Met His Trp Val Lys Gln Arg Pro Gly Gln Gly Leu Glu Trp Ile
            35                  40                  45

Gly Met Ile Asp Pro Ser Asp Ser Tyr Thr Asn Tyr Asn Pro Lys Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Ser Gly Asp Tyr Trp Gly Gln Gly Thr Thr Leu Thr
            100                 105                 110

Val Ser Ser
        115

<210> SEQ ID NO 49
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gatgttttga tgacccaaac tccactctcc ctgcctgtca gtcttggaga tcaagcctcc      60
atctcttgca gatctagtca gagcattgta catagtaatg aaacacccta tttagaatgg     120
tacctgcaga accaggccca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattattgct ttcaaggttc atatgttccg     300
tggacgttcg gtggaggcac caagctggaa atcaaa                               336

<210> SEQ ID NO 50
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Tyr Val Pro Trp Thr Phe Gly Gly Gly Thr Lys Leu Glu Ile Lys
            100                 105                 110
```

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 51

```
Asn Tyr Trp Met His
 1               5
```

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 52

```
Met Ile Asp Pro Ser Asp Ser Tyr Thr Asn Tyr Asn Pro Lys Phe Lys
 1               5                  10                  15

Gly
```

<210> SEQ ID NO 53
<211> LENGTH: 357
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 53

```
gaggtgcagc tggtggaatc tgggggaggc ttagtgaagc ctggagggtc cctgaaactc      60
tcctgtgcag cctctggatt cactttcagt gactatgcca tgtcttgggt tcgccagact     120
ccggaaaaga ggctggagtg ggtcgcaacc attagtgatg gtggtactta cacctactat     180
ccagacaatg taagggccg attcaccatc tccagagaca atgccaagaa caacctgtac     240
ctgcaaatga gccatctgaa gtctgaggac acagccatgt attactgtgc aagagaatgg     300
ggtgattacg acggatttga ctactggggc caaggcacca ctctcacagt ctcctcg       357
```

<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 54

```
Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asp Tyr
```

```
                   20                  25                  30
Ala Met Ser Trp Val Arg Gln Thr Pro Glu Lys Arg Leu Glu Trp Val
            35                  40                  45

Ala Thr Ile Ser Asp Gly Gly Thr Tyr Thr Tyr Tyr Pro Asp Asn Val
        50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Glu Trp Gly Asp Tyr Asp Gly Phe Asp Tyr Trp Gly Gln Gly
            100                 105                 110

Thr Thr Leu Thr Val Ser Ser
        115

<210> SEQ ID NO 55
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gacatccaga tgacccagtc tccatcctcc ttatctgcct ctctgggaga aagagtcagt      60
ctcacttgtc gggcaagtca ggaaattagt ggttacttaa gctggcttca gcagaaacca    120
gatggaacta ttaaacgcct gatctacgcc gcatccactt tagattctgg tgtcccaaaa    180
aggttcagtg gcagtaggtc tgggtcagat tattctctca ccatcggcag ccttgagtct    240
gaagatcttg cagactatta ctgtctacaa tatgatagtt atccgtacac gttcggaggg    300
gggaccaagc tggaaataaa a                                              321

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Gly Ser Leu Glu Ser
65                  70                  75                  80

Glu Asp Leu Ala Asp Tyr Tyr Cys Leu Gln Tyr Asp Ser Tyr Pro Tyr
                85                  90                  95

Thr Phe Gly Gly Gly Thr Lys Leu Glu Ile Lys
            100                 105

<210> SEQ ID NO 57
<211> LENGTH: 5
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 57

Asp Tyr Ala Met Ser
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Ile Ser Asp Gly Gly Thr Tyr Thr Tyr Tyr Pro Asp Asn Val Lys
1               5                   10                  15

Gly

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Trp Gly Asp Tyr Asp Gly Phe Asp Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ala Ser Gln Glu Ile Ser Gly Tyr Leu Ser
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ala Ser Thr Leu Asp Ser
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Leu Gln Tyr Asp Ser Tyr Pro Tyr Thr
1               5
```

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Gly Tyr Thr Phe Thr Ser His
1               5
```

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Asp Pro Ser Asp Phe Tyr
1               5
```

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Gly Phe Ser Leu Ser Thr Phe Gly Leu
1               5
```

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Trp Trp Asp Asp Asp
1               5
```

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Gly Tyr Thr Phe Thr Asp His
1               5
```

<210> SEQ ID NO 68
<211> LENGTH: 6
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 68

Tyr Pro Arg Asp Gly Tyr
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Tyr Thr Phe Ser Ser Tyr
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Pro Ser Asp Val Tyr
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Tyr Thr Phe Thr Thr Tyr
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asn Thr Tyr Ser Gly Val
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Tyr Thr Phe Thr Asn Tyr
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Pro Ser Asp Ser Tyr
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Phe Thr Phe Ser Asp Tyr
1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Asp Gly Gly Thr Tyr
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Tyr Thr Phe Thr Ser His Trp
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Asp Pro Ser Asp Phe Tyr Ser
1               5

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Arg Gly Leu Leu Ser Gly Asp Tyr Ala Met Asp Tyr
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Phe Ser Leu Ser Thr Phe Gly Leu Ser
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Trp Trp Asp Asp Asp Lys
1               5

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Arg Ile Gly Ala Asp Ala Leu Pro Phe Asp Tyr
1               5                   10

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Tyr Thr Phe Thr Asp His Ile
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ile Tyr Pro Arg Asp Gly Tyr Ile
1               5

<210> SEQ ID NO 85
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 85

Ala Arg Gly Tyr Tyr Tyr Ala Met Asp Tyr
1               5                   10

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Tyr Thr Phe Ser Ser Tyr Trp
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ile Asp Pro Ser Asp Val Tyr Thr
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Arg Asn Tyr Ser Gly Asp Tyr
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Tyr Thr Phe Thr Thr Tyr Gly
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile Asn Thr Tyr Ser Gly Val Pro
1               5
```

```
<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Gly Arg Asp Gly Tyr Gln Val Ala Trp Phe Ala Tyr
1               5                   10

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Tyr Thr Phe Thr Asn Tyr Trp
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ile Asp Pro Ser Asp Ser Tyr Thr
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Phe Thr Phe Ser Asp Tyr Ala
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ile Ser Asp Gly Gly Thr Tyr Thr
1               5

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 96

Ala Arg Glu Trp Gly Asp Tyr Asp Gly Phe Asp Tyr
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Ser Ile Val His Ser Asn Gly Asn Thr Tyr
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Ser Leu Leu His Ser Asn Gly Asn Thr Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Ser Ile Val His Ser Ile Gly Asn Thr Tyr
1               5                   10

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Asp Ile Asp Asp Asp
1               5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Glu Ile Ser Gly Tyr
1               5

<210> SEQ ID NO 102
<211> LENGTH: 972
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 102

```
gccaaaacga caccccatc tgtctatcca ctggccctg gatctgctgc ccaaactaac      60
tccatggtga ccctgggatg cctggtcaag ggctatttcc ctgagccagt gacagtgacc     120
tggaactctg gatccctgtc cagcggtgtg cacaccttcc cagctgtcct gcagtctgac     180
ctctacactc tgagcagctc agtgactgtc ccctccagca cctggcccag ccagaccgtc     240
acctgcaacg ttgcccaccc ggccagcagc accaaggtgg acaagaaaat tgtgcccagg     300
gattgtggtt gtaagccttg catatgtaca gtcccagaag tatcatctgt cttcatcttc     360
ccccaaagc ccaaggatgt gctcaccatt actctgactc ctaaggtcac gtgtgttgtg     420
gtagacatca gcaaggatga tcccgaggtc cagttcagct ggtttgtaga tgatgtggag    480
gtgcacacag ctcagacgca accccgggag gagcagttca acagcacttt ccgctcagtc    540
agtgaacttc ccatcatgca ccaggactgg ctcaatggca aggagttcaa atgcagggtc    600
aacagtgcag ctttccctgc ccccatcgag aaaaccatct ccaaaaccaa aggcagaccg    660
aaggctccac aggtgtacac cattccacct cccaaggagc agatggccaa ggataaagtc    720
agtctgacct gcatgataac agacttcttc cctgaagaca ttactgtgga gtggcagtgg    780
aatgggcagc cagcggagaa ctacaagaac actcagccca tcatggacac agatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aa                                                        972
```

<210> SEQ ID NO 103
<211> LENGTH: 324
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140
```

Lys Asp Asp Pro Glu Val Gln Phe Ser Trp Phe Val Asp Asp Val Glu
145                 150                 155                 160

Val His Thr Ala Gln Thr Gln Pro Arg Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
        210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys

<210> SEQ ID NO 104
<211> LENGTH: 1008
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
gccaaaacaa cacccccatc agtctatcca ctggcccctg ggtgtggaga tacaactggt      60
tcctctgtga ctctgggatg cctggtcaag ggctacttcc ctgagtcagt gactgtgact     120
tggaactctg gatccctgtc agcagtgtg cacaccttcc cagctctcct gcagtctgga     180
ctctacacta tgagcagctc agtgactgtc ccctccagca cctggccaag tcagaccgtc     240
acctgcagcg ttgctcaccc agccagcagc accacggtgg acaaaaaact tgagcccagc     300
gggcccattt caacaatcaa ccctgtcct ccatgcaagg agtgtcacaa atgcccagct      360
cctaacctcg agggtggacc atccgtcttc atcttccctc caaatatcaa ggatgtactc     420
atgatctccc tgacacccaa ggtcacgtgt gtggtggtgg atgtgagcga ggatgaccca     480
gacgtccaga tcagctggtt tgtgaacaac gtggaagtac acacagctca gacacaaacc     540
catagagagg attacaacag tactatccgg gtggtcagca ccctccccat ccagcaccag     600
gactggatga gtggcaagga gttcaaatgc aaggtcaaca acaaagacct cccatcaccc     660
atcgagagaa ccatctcaaa aattaaaggg ctagtcagag ctccacaagt atacatcttg     720
ccgccaccag cagagcagtt gtccaggaaa gatgtcagtc tcacttgcct ggtcgtgggc     780
ttcaaccctg agacatcag tgtggagtgg accagcaatg gcatacaga ggagaactac       840 aaggacaccg caccagtcct agactctgac ggttcttact tcatatatag caagctcaat     900
atgaaaacaa gcaagtggga gaaaacagat tccttctcat gcaacgtgag acacgagggt     960
ctgaaaaatt actacctgaa gaagaccatc tcccggtctc cgggtaaa              1008

```
<210> SEQ ID NO 105
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335

<210> SEQ ID NO 106
<211> LENGTH: 321
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 106

```
cgggctgatg ctgcaccaac tgtatccatc ttcccaccat ccagtgagca gttaacatct      60
ggaggtgcct cagtcgtgtg cttcttgaac aacttctacc ccagagacat caatgtcaag     120
tggaagattg atggcagtga acgacaaaat ggtgtcctga acgttggac tgatcaggac      180
agcaaagaca gcacctacag catgagcagc accctcacat tgaccaagga cgagtatgaa     240
cgacataaca gctataccctg tgaggccact cacaagacat caacttcacc cattgtcaag    300
agcttcaaca ggaatgagtg t                                                321
```

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Arg Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 108
<211> LENGTH: 1389
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

```
atgggatgga gctgtatcat tgtcctcttg gtatcaacag ctacaggtgt ccactcccag      60
gtccaactgc agcagcctgg ggctgaactg gtgaggcctg ggacttcagt gaagttgtcc     120
tgcaaggctt ctggctacac cttcaccagc cactggttgc actgggtgaa gcagaggcct     180
ggacaaggcc ttgagtggat cggagtgctt gatccttctg attttttatag taactacaat    240
caaaacttca gggcaaggc cacattgact gtagacacat cctccagcac agcctacatg      300
cagctcagca gcctgacatc tgaggactct gcggtctatt actgtgcacg aggcctacta     360
tccggggact atgctatgga ctactggggt caaggaacct cagtcaccgt ctcctcagcc     420
aaaacgacac cccatctgt ctatccactg gcccctggat ctgctgccca aactaactcc      480
atggtgaccc tgggatgcct ggtcaagggc tatttccctg agccagtgac agtgacctgg     540
```

```
aactctggat ccctgtccag cggtgtgcac accttcccag ctgtcctgca gtctgacctc    600
tacactctga gcagctcagt gactgtcccc tccagcacct ggcccagcca gaccgtcacc    660
tgcaacgttg cccacccggc cagcagcacc aaggtggaca gaaaattgt gcccagggat     720 tgtggttgta agccttgcat atgtacagtc ccagaagtat catctgtctt catcttcccc    780
ccaaagccca aggatgtgct caccattact ctgactccta aggtcacgtg tgttgtggta    840
gacatcagca aggatgatcc cgaggtccag ttcagctggt ttgtagatga tgtggaggtg    900
cacacagctc agacgcaacc ccgggaggag cagttcaaca gcactttccg ctcagtcagt    960
gaacttccca tcatgcacca ggactggctc aatggcaagg agttcaaatg cagggtcaac   1020
agtgcagctt tccctgcccc catcgagaaa accatctcca aaaccaaagg cagaccgaag   1080
gctccacagg tgtacaccat tccacctccc aaggagcaga tggccaagga taaagtcagt   1140
ctgacctgca tgataacaga cttcttccct gaagacatta ctgtggagtg cagtggaat    1200 gggcagccag cggagaacta caagaacact cagcccatca tggacacaga tggctcttac   1260
ttcgtctaca gcaagctcaa tgtgcagaag agcaactggg aggcaggaaa tactttcacc   1320
tgctctgtgt tacatgaggg cctgcacaac caccatactg agaagagcct ctcccactct   1380
cctggtaaa                                                          1389
```

<210> SEQ ID NO 109
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Gly Trp Ser Cys Ile Ile Val Leu Leu Val Ser Thr Ala Thr Gly
1               5                   10                  15

Val His Ser Gln Val Gln Leu Gln Gln Pro Gly Ala Glu Leu Val Arg
            20                  25                  30

Pro Gly Thr Ser Val Lys Leu Ser Cys Lys Ala Ser Gly Tyr Thr Phe
        35                  40                  45

Thr Ser His Trp Leu His Trp Val Lys Gln Arg Pro Gly Gln Gly Leu
    50                  55                  60

Glu Trp Ile Gly Val Leu Asp Pro Ser Asp Phe Tyr Ser Asn Tyr Asn
65                  70                  75                  80

Gln Asn Phe Lys Gly Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Leu Leu Ser Gly Asp Tyr Ala Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr

|     |     |     | 195 |     |     |     | 200 |     |     |     | 205 |     |     |
|-----|-----|-----|-----|-----|-----|-----|-----|-----|-----|-----|-----|-----|-----|

Val Pro Ser Ser Thr Trp Pro Ser Gln Thr Val Thr Cys Asn Val Ala
    210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
            260                 265                 270

Pro Lys Val Thr Cys Val Val Val Asp Ile Ser Lys Asp Asp Pro Glu
        275                 280                 285

Val Gln Phe Ser Trp Phe Val Asp Asp Val Glu Val His Thr Ala Gln
    290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
        355                 360                 365

Pro Pro Lys Glu Gln Met Ala Lys Asp Lys Val Ser Leu Thr Cys Met
    370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                405                 410                 415

Asp Gly Ser Tyr Phe Val Tyr Ser Lys Leu Asn Val Gln Lys Ser Asn
            420                 425                 430

Trp Glu Ala Gly Asn Thr Phe Thr Cys Ser Val Leu His Glu Gly Leu
        435                 440                 445

His Asn His His Thr Glu Lys Ser Leu Ser His Ser Pro Gly Lys
    450                 455                 460

<210> SEQ ID NO 110
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
atgaagttgc ctgttaggct gttggtgctg atgttctgga ttcctgcttc cagcagtgat      60
gttttgatga cccaaattcc actctccctg cctgtcagtc ttggagatca agcctccatc     120
tcttgcagat ctagtcagag cattgtacat agtaatggaa acacctattt agaatggtac     180
ctgcagaaac aggccagtc tccaaagtcc ctgatctaca agtttctaa ccgatttct       240 ggggtcccag acaggttcag tggcagtgga tcagggacag atttcacact caagatcagc     300
agagtggagg ctgaggatct gggagtttat tactgctttc aaggttcata tgttccgtgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
aacaacttct accccagaga catcaatgtc aagtggaaga ttgatggcag tgaacgacaa     540

```
aatggtgtcc tgaacagttg gactgatcag gacagcaaag acagcaccta cagcatgagc    600
agcaccctca cattgaccaa ggacgagtat gaacgacata acagctatac ctgtgaggcc    660
actcacaaga catcaacttc acccattgtc aagagcttca acaggaatga gtgt           714
```

<210> SEQ ID NO 111
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Met Lys Leu Pro Val Arg Leu Leu Val Leu Met Phe Trp Ile Pro Ala
1               5                   10                  15

Ser Ser Ser Asp Val Leu Met Thr Gln Ile Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Ser Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 112
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
atgggcaggc ttacttcttc attcctgtta ctgattgtcc ctgcatatgt cctgtcccag    60
gttactctaa aagagtctgg ccctgggata ttgcggccct cccagaccct cagtctgact    120
tgttctttct ctgggttttc actgagcact tttggtttga gtgtaggctg gattcgtcag    180
```

```
ccttcaggga agggtctgga gtggctggca cacatttggt gggatgatga taagtactat      240
aacccagccc ttaagagtcg gctcacaatc tccaaggata cctccaaaaa ccaggtattc      300
ctcaagatcg ccaatgtgga cactgcagat actgccacat actactgtgc tcgaataggg      360
gcggacgccc ttccttttga ctactggggc caaggcacca ctctcacagt tcctcagcc      420 aaaacaacac ccccatcagt ctatccactg gcccctgggt gtggagatac aactggttcc      480
tccgtgacct ctgggtgcct ggtcaagggg tacttccctg agccagtgac tgtgacttgg      540
aactctggat ccctgtccag cagtgtgcac accttcccag ctctcctgca gtctggactc      600
tacactatga gcagctcagt gactgtcccc tccagcacct ggccaagtca gaccgtcacc      660
tgcagcgttg ctcacccagc cagcagcacc acggtggaca aaaaacttga gcccagcggg      720
cccatttcaa caatcaaccc ctgtcctcca tgcaaggagt gtcacaaatg cccagctcct      780
aacctcgagg gtggaccatc cgtcttcatc ttccctccaa atatcaagga tgtactcatg      840
atctccctga cacccaaggt cacgtgtgtg gtggtggatg tgagcgagga tgacccagac      900
gtccagatca gctggtttgt gaacaacgtg gaagtacaca cagctcagac acaaacccat      960
agagaggatt acaacagtac tatccggggtg gtcagcaccc tccccatcca gcaccaggac     1020
tggatgagtg gcaaggagtt caaatgcaag gtgaacaaca agacctccc atcacccatc      1080 gagagaacca tctcaaaaat taagggcta gtcagagctc cacaagtata cactttgccg       1140
ccaccagcag agcagttgtc caggaaagat gtcagtctca cttgcctggt cgtgggcttc      1200
aaccctggag acatcagtgt ggagtggacc agcaatgggc atacagagga aactacaag      1260 gacaccgcac cagttcttga ctctgacggt tcttacttca tatatagcaa gctcaatatg      1320
aaaacaagca agtgggagaa aacagattcc ttctcatgca acgtgagaca cgagggtctg      1380
aaaaattact acctgaagaa gaccatctcc cggtctccgg gtaaa                     1425
```

<210> SEQ ID NO 113
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Gly Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Arg
                20                  25                  30

Pro Ser Gln Thr Leu Ser Leu Thr Cys Ser Phe Ser Gly Phe Ser Leu
            35                  40                  45

Ser Thr Phe Gly Leu Ser Val Gly Trp Ile Arg Gln Pro Ser Gly Lys
        50                  55                  60

Gly Leu Glu Trp Leu Ala His Ile Trp Trp Asp Asp Lys Tyr Tyr
65                  70                  75                  80

Asn Pro Ala Leu Lys Ser Arg Leu Thr Ile Ser Lys Asp Thr Ser Lys
                85                  90                  95

Asn Gln Val Phe Leu Lys Ile Ala Asn Val Asp Thr Ala Asp Thr Ala
            100                 105                 110

Thr Tyr Tyr Cys Ala Arg Ile Gly Ala Asp Ala Leu Pro Phe Asp Tyr
        115                 120                 125

Trp Gly Gln Gly Thr Thr Leu Thr Val Ser Ser Ala Lys Thr Thr Pro
    130                 135                 140

Pro Ser Val Tyr Pro Leu Ala Pro Gly Cys Gly Asp Thr Thr Gly Ser
145                 150                 155                 160

Ser Val Thr Ser Gly Cys Leu Val Lys Gly Tyr Phe Pro Glu Pro Val
            165                 170                 175

Thr Val Thr Trp Asn Ser Gly Ser Leu Ser Ser Val His Thr Phe
        180                 185                 190

Pro Ala Leu Leu Gln Ser Gly Leu Tyr Thr Met Ser Ser Val Thr
            195                 200                 205

Val Pro Ser Ser Thr Trp Pro Ser Gln Thr Val Thr Cys Ser Val Ala
    210                 215                 220

His Pro Ala Ser Ser Thr Thr Val Asp Lys Lys Leu Glu Pro Ser Gly
225                 230                 235                 240

Pro Ile Ser Thr Ile Asn Pro Cys Pro Pro Cys Lys Glu Cys His Lys
                245                 250                 255

Cys Pro Ala Pro Asn Leu Glu Gly Gly Pro Ser Val Phe Ile Phe Pro
            260                 265                 270

Pro Asn Ile Lys Asp Val Leu Met Ile Ser Leu Thr Pro Lys Val Thr
        275                 280                 285

Cys Val Val Val Asp Val Ser Glu Asp Pro Asp Val Gln Ile Ser
    290                 295                 300

Trp Phe Val Asn Asn Val Glu Val His Thr Ala Gln Thr Gln Thr His
305                 310                 315                 320

Arg Glu Asp Tyr Asn Ser Thr Ile Arg Val Val Ser Thr Leu Pro Ile
                325                 330                 335

Gln His Gln Asp Trp Met Ser Gly Lys Glu Phe Lys Cys Lys Val Asn
            340                 345                 350

Asn Lys Asp Leu Pro Ser Pro Ile Glu Arg Thr Ile Ser Lys Ile Lys
        355                 360                 365

Gly Leu Val Arg Ala Pro Gln Val Tyr Thr Leu Pro Pro Pro Ala Glu
    370                 375                 380

Gln Leu Ser Arg Lys Asp Val Ser Leu Thr Cys Leu Val Val Gly Phe
385                 390                 395                 400

Asn Pro Gly Asp Ile Ser Val Glu Trp Thr Ser Asn Gly His Thr Glu
                405                 410                 415

Glu Asn Tyr Lys Asp Thr Ala Pro Val Leu Asp Ser Asp Gly Ser Tyr
            420                 425                 430

Phe Ile Tyr Ser Lys Leu Asn Met Lys Thr Ser Lys Trp Glu Lys Thr
        435                 440                 445

Asp Ser Phe Ser Cys Asn Val Arg His Glu Gly Leu Lys Asn Tyr Tyr
    450                 455                 460

Leu Lys Lys Thr Ile Ser Arg Ser Pro Gly Lys
465                 470                 475

<210> SEQ ID NO 114
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
atgaggtgcc tagctgagtt cctggggctg cttgtgctct ggatccctgg agccattggg      60
gatattgtgt tgactcagac tgcaccctct gtacctgtca ctcctggaga gtcagtatcc     120

```
atctcctgca ggtctagtaa gagtctcctg catagtaatg gcaacactta cttgtattgg   180
ttcctgcaga ggccaggcca gtctcctcag ctcctgatat atcggatgtc caaccttgcc   240
tcaggagtcc cagacaggtt cagtggcagt gggtcaggaa ctgctttcac actgagaatc   300
agtagagtgg aggctgagga tgtgggtgtt tattactgta tgcaacatct agaatatcct   360
ttcacgttcg gctcggggac aaagttggaa ataaaacggg ctgatgctgc accaactgta   420
tccatcttcc caccatccag tgagcagtta acatctggag gtgcctcagt cgtgtgcttc   480
ttgaacaact tctacccag agacatcaat gtcaagtgga gattgatgg cagtgaacga   540 caaaatggtg tcctgaacag ttggactgat caggacagca agacagcac ctacagcatg   600 agcagcaccc tcacattgac caaggacgag tatgaacgac ataacagcta cctgtgag   660 gccactcaca agacatcaac ttcacccatt gtcaagagct tcaacaggaa tgagtgt   717
```

<210> SEQ ID NO 115
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

```
Met Arg Cys Leu Ala Glu Phe Leu Gly Leu Leu Val Leu Trp Ile Pro
1               5                   10                  15

Gly Ala Ile Gly Asp Ile Val Leu Thr Gln Thr Ala Pro Ser Val Pro
                20                  25                  30

Val Thr Pro Gly Glu Ser Val Ser Ile Ser Cys Arg Ser Ser Lys Ser
            35                  40                  45

Leu Leu His Ser Asn Gly Asn Thr Tyr Leu Tyr Trp Phe Leu Gln Arg
        50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Ser Gly Thr Lys
        115                 120                 125

Leu Glu Ile Lys Arg Ala Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Pro Arg Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235
```

<210> SEQ ID NO 116
<211> LENGTH: 1380

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116

```
atggaatgga gctgggtctc tctcttcttc ctgtcagtaa ctacaggtgt ccactcccag      60
gttcagctgc aacagtctga cgctgagttg gtgaaacctg gagcttcagt gaagatatcc    120
tgcaaggttt ctggctacac cttcactgac catattattc actggatgaa gcagaggcct    180
gaacagggcc tggaatggat tggatatatt tatcctagag atggttatat taagtacaat    240
gagaagttca agggcaaggc cacattgact gcagacaaat cctccagcac agcctacatg    300
caggtcaaca gcctgacatc tgaggactct gcagtctatt tctgtgcaag gggttactat    360
tatgctatgg actactgggg tcaaggaacc tcagtcaccg tctcctcagc caaaacgaca    420
cccccatctg tctatccact ggcccctgga tctgctgccc aaactaactc catggtgacc    480
ctgggatgcc tggtcaaggg ctatttccct gagccagtga cagtgacctg gaactctgga    540
tccctgtcca gcggtgtgca caccttccca gctgtcctgc agtctgacct ctacactctg    600
agcagctcag tgactgtccc ctccagcacc tggcccagcc agaccgtcac ctgcaacgtt    660
gcccacccgg ccagcagcac caaggtggac aagaaaattg tgcccaggga ttgtggttgt    720
aagccttgca tatgtacagt cccagaagta catctgtct tcatcttccc cccaaagccc     780
aaggatgtgc tcaccattac tctgactcct aaggtcacgt gtgttgtggt agacatcagc    840
aaggatgatc ccgaggtcca gttcagctgg tttgtagatg atgtggaggt gcacacagct    900
cagacgcaac cccgggagga gcagttcaac agcactttcc gctcagtcag tgaacttccc    960
atcatgcacc aggactggct caatggcaag gagttcaaat gcagggtcaa cagtgcagct   1020
ttccctgccc ccatcgagaa aaccatctcc aaaaccaaag gcagaccgaa ggctccacag   1080
gtgtacacca ttccacctcc caaggagcag atggccaagg ataaagtcag tctgacctgc   1140
atgataacag acttcttccc tgaagacatt actgtggagt ggcagtggaa tgggcagcca   1200
gcggagaact acaagaacac tcagcccatc atggacacag atggctctta cttcgtctac   1260
agcaagctca atgtgcagaa gagcaactgg gaggcaggaa atactttcac ctgctctgtg   1320
ttacatgagg gcctgcacaa ccaccatact gagaagagcc tctcccactc tcctggtaaa   1380
```

<210> SEQ ID NO 117
<211> LENGTH: 460
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Met Glu Trp Ser Trp Val Ser Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Val Ser Gly Tyr Thr Phe
        35                  40                  45

Thr Asp His Ile Ile His Trp Met Lys Gln Arg Pro Glu Gln Gly Leu
    50                  55                  60

Glu Trp Ile Gly Tyr Ile Tyr Pro Arg Asp Gly Tyr Ile Lys Tyr Asn
65                  70                  75                  80
```

Glu Lys Phe Lys Gly Lys Ala Thr Leu Thr Ala Asp Lys Ser Ser Ser
                85                  90                  95

Thr Ala Tyr Met Gln Val Asn Ser Leu Thr Ser Glu Asp Ser Ala Val
            100                 105                 110

Tyr Phe Cys Ala Arg Gly Tyr Tyr Tyr Ala Met Asp Tyr Trp Gly Gln
        115                 120                 125

Gly Thr Ser Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Gln Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460

<210> SEQ ID NO 118
<211> LENGTH: 714
<212> TYPE: DNA
<213> ORGANISM: Artificial Sequence
<220> FEATURE:

<223> OTHER INFORMATION: Description of Artificial Sequence: Synthetic
   polynucleotide

<400> SEQUENCE: 118

```
atgaagttgc ctgttaggct gttggtgctg atgttctgga ttcctgcttc cagaagtgat    60
gttttgatga cccaaactcc actctccctg cctgtcagtc ttggagatca agcctccatc   120
tcttgcagat ctagtcagag cattgtacat agtattggaa acacctattt agaatggtac   180
ctgcagaaac caggccagtc tccaaagctc ctgatctaca agtttccaa ccgatttct    240
ggggtcccag agaggttcag tggcagtgga tcagggacag atttcacact caagatcagc   300
agagtggagg ctgaggatct gggagtttat tactgctttc aaggttcaca tgttccattc   360
acgttcggct cggggacaaa gttggaaata aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc    660
actcacaaga catcaacttc acccattgtc aagagcttca caggaatga gtgt          714
```

<210> SEQ ID NO 119
<211> LENGTH: 238
<212> TYPE: PRT
<213> ORGANISM: Artificial Sequence
<220> FEATURE:
<223> OTHER INFORMATION: Description of Artificial Sequence: Synthetic
   polypeptide

<400> SEQUENCE: 119

| Met | Lys | Leu | Pro | Val | Arg | Leu | Leu | Val | Leu | Met | Phe | Trp | Ile | Pro | Ala |
|---|---|---|---|---|---|---|---|---|---|---|---|---|---|---|---|
| 1 | | | | 5 | | | | | 10 | | | | | 15 | |

| Ser | Arg | Ser | Asp | Val | Leu | Met | Thr | Gln | Thr | Pro | Leu | Ser | Leu | Pro | Val |
|---|---|---|---|---|---|---|---|---|---|---|---|---|---|---|---|
| | | | 20 | | | | | 25 | | | | | 30 | | |

| Ser | Leu | Gly | Asp | Gln | Ala | Ser | Ile | Ser | Cys | Arg | Ser | Ser | Gln | Ser | Ile |
|---|---|---|---|---|---|---|---|---|---|---|---|---|---|---|---|
| | | 35 | | | | | 40 | | | | | 45 | | | |

| Val | His | Ser | Ile | Gly | Asn | Thr | Tyr | Leu | Glu | Trp | Tyr | Leu | Gln | Lys | Pro |
|---|---|---|---|---|---|---|---|---|---|---|---|---|---|---|---|
| | 50 | | | | | 55 | | | | | 60 | | | | |

| Gly | Gln | Ser | Pro | Lys | Leu | Leu | Ile | Tyr | Lys | Val | Ser | Asn | Arg | Phe | Ser |
|---|---|---|---|---|---|---|---|---|---|---|---|---|---|---|---|
| 65 | | | | | 70 | | | | | 75 | | | | | 80 |

| Gly | Val | Pro | Glu | Arg | Phe | Ser | Gly | Ser | Gly | Ser | Gly | Thr | Asp | Phe | Thr |
|---|---|---|---|---|---|---|---|---|---|---|---|---|---|---|---|
| | | | | 85 | | | | | 90 | | | | | 95 | |

| Leu | Lys | Ile | Ser | Arg | Val | Glu | Ala | Glu | Asp | Leu | Gly | Val | Tyr | Tyr | Cys |
|---|---|---|---|---|---|---|---|---|---|---|---|---|---|---|---|
| | | | 100 | | | | | 105 | | | | | 110 | | |

| Phe | Gln | Gly | Ser | His | Val | Pro | Phe | Thr | Phe | Gly | Ser | Gly | Thr | Lys | Leu |
|---|---|---|---|---|---|---|---|---|---|---|---|---|---|---|---|
| | | 115 | | | | | 120 | | | | | 125 | | | |

| Glu | Ile | Lys | Arg | Ala | Asp | Ala | Ala | Pro | Thr | Val | Ser | Ile | Phe | Pro | Pro |
|---|---|---|---|---|---|---|---|---|---|---|---|---|---|---|---|
| | 130 | | | | | 135 | | | | | 140 | | | | |

| Ser | Ser | Glu | Gln | Leu | Thr | Ser | Gly | Gly | Ala | Ser | Val | Val | Cys | Phe | Leu |
|---|---|---|---|---|---|---|---|---|---|---|---|---|---|---|---|
| 145 | | | | | 150 | | | | | 155 | | | | | 160 |

| Asn | Asn | Phe | Tyr | Pro | Lys | Asp | Ile | Asn | Val | Lys | Trp | Lys | Ile | Asp | Gly |
|---|---|---|---|---|---|---|---|---|---|---|---|---|---|---|---|
| | | | | 165 | | | | | 170 | | | | | 175 | |

| Ser | Glu | Arg | Gln | Asn | Gly | Val | Leu | Asn | Ser | Trp | Thr | Asp | Gln | Asp | Ser |
|---|---|---|---|---|---|---|---|---|---|---|---|---|---|---|---|
| | | | 180 | | | | | 185 | | | | | 190 | | |

| Lys | Asp | Ser | Thr | Tyr | Ser | Met | Ser | Ser | Thr | Leu | Thr | Leu | Thr | Lys | Asp |
|---|---|---|---|---|---|---|---|---|---|---|---|---|---|---|---|
| | | 195 | | | | | 200 | | | | | 205 | | | |

```
Glu Tyr Glu Arg His Asn Ser Tyr Thr Cys Glu Ala Thr His Lys Thr
        210                 215                 220

Ser Thr Ser Pro Ile Val Lys Ser Phe Asn Arg Asn Glu Cys
225                 230                 235
```

<210> SEQ ID NO 120
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
atgggatgga gctgtatcat tgtcctcttg gtatcaacag ctacatgtgt ccactcccag      60
gtccaactgc tgcagcctgg ggctgagctg gtgaggcctg ggacttcagt gaagttgtcc    120
tgcaagactt ctggctacac cttctccagc tactggatgc actgggtaaa gcagaggcct    180
ggacaaggcc ttgagtggat cggaatgatt gatccttctg atgtttatac taactacaat    240
ccaaagttca agggcaaggc cacattgact gttgacacat cctccagcac agcctacatg    300
cagctcagca gcctgacatc tgaggactct gcggtctatt actgtgcaag aaactactct    360
ggggactact ggggccaagg caccactctc acagtctcct cagccaaaac gacaccccca    420
tctgtctatc cactggcccc tggatctgct gcccaaacta actccatggt gaccctggga    480
tgcctggtca agggctattt ccctgagcca gtgacagtga cctggaactc tggatccctg    540
tccagcggtg tgcacacctt cccagctgtc ctgcagtctg acctctacac tctgagcagc    600
tcagtgactg tcccctccag cacctggccc agccagacct cacctgcaa cgttgcccac    660
ccggccagca gcaccaaggt ggacaagaaa attgtgccca gggattgtgg ttgtaagcct    720
tgcatatgta cagtcccaga agtatcatct gtcttcatct tccccccaaa gcccaaggat    780
gtgctcacca ttactctgac tcctaaggtc acgtgtgttg tggtagacat cagcaaggat    840
gatcccgagg tccagttcag ctggtttgta gatgatgtgg aggtgcacac agctcagacg    900
caaccccggg aggagcagtt caacagcact ttccgctcag tcagtgaact tcccatcatg    960
caccaggact ggctcaatgg caaggagttc aaatgcaggg tcaacagtgc agctttccct   1020
gcccccatcg agaaaaccat ctccaaaacc aaaggcagac cgaaggctcc acaggtgtac   1080
accattccac ctcccaagga gcagatggcc aaggataaag tcagtctgac ctgcatgata   1140
acagacttct cccctgaaga cattactgtg gagtggcagt ggaatgggca gccagcggag   1200
aactacaaga cactcagcc catcatggac acagatggct cttacttcgt ctacagcaag   1260
ctcaatgtgc agaagagcaa ctgggaggca ggaaatactt tcacctgctc tgtgttacat   1320
gagggcctgc acaaccacca tactgagaag agcctctccc actctcctgg taaa         1374
```

<210> SEQ ID NO 121
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Met Gly Trp Ser Cys Ile Ile Val Leu Leu Val Ser Thr Ala Thr Cys
1               5                   10                  15

Val His Ser Gln Val Gln Leu Leu Gln Pro Gly Ala Glu Leu Val Arg
            20                  25                  30
```

```
Pro Gly Thr Ser Val Lys Leu Ser Cys Lys Thr Ser Gly Tyr Thr Phe
            35                  40                  45

Ser Ser Tyr Trp Met His Trp Val Lys Gln Arg Pro Gly Gln Gly Leu
    50                  55                  60

Glu Trp Ile Gly Met Ile Asp Pro Ser Asp Val Tyr Thr Asn Tyr Asn
65                  70                  75                  80

Pro Lys Phe Lys Gly Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Asn Tyr Ser Gly Asp Tyr Trp Gly Gln Gly Thr
                115                 120                 125

Thr Leu Thr Val Ser Ser Ala Lys Thr Thr Pro Pro Ser Val Tyr Pro
            130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
                180                 185                 190

Ser Asp Leu Tyr Thr Leu Ser Ser Ser Val Thr Val Pro Ser Ser Thr
                195                 200                 205

Trp Pro Ser Gln Thr Val Thr Cys Asn Val Ala His Pro Ala Ser Ser
            210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
                245                 250                 255

Lys Pro Lys Asp Val Leu Thr Ile Thr Leu Thr Pro Lys Val Thr Cys
                260                 265                 270

Val Val Val Asp Ile Ser Lys Asp Asp Pro Glu Val Gln Phe Ser Trp
            275                 280                 285

Phe Val Asp Asp Val Glu Val His Thr Ala Gln Thr Gln Pro Arg Glu
                290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
                325                 330                 335

Ala Ala Phe Pro Ala Pro Ile Glu Lys Thr Ile Ser Lys Thr Lys Gly
                340                 345                 350

Arg Pro Lys Ala Pro Gln Val Tyr Thr Ile Pro Pro Pro Lys Glu Gln
            355                 360                 365

Met Ala Lys Asp Lys Val Ser Leu Thr Cys Met Ile Thr Asp Phe Phe
            370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asp Thr Asp Gly Ser Tyr Phe
                405                 410                 415

Val Tyr Ser Lys Leu Asn Val Gln Lys Ser Asn Trp Glu Ala Gly Asn
                420                 425                 430

Thr Phe Thr Cys Ser Val Leu His Glu Gly Leu His Asn His His Thr
                435                 440                 445
```

```
<210> SEQ ID NO 122
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
atgaagttgc ctgttaggct gttggtgctg atgttctgga ttcctgcttc cagcagtgat     60
gttttgatga cccaaattcc actctccctg cctgtcagtc ttggagatca agcctccatc    120
tcttgtagat ctagtcagag cattgtccat agtaatggaa acacctattt agaatggtac    180
ctgcagaaac caggccagtc tccaaagctc ctgatctaca agtttccaa ccgatttct     240 ggggtcccag acaggttcag tggcagtgga tcaggacag atttcacact caagatcagc    300
agagtggagg ctgaggatct gggagtttat tactgctttc aaggttcata tgttccgtgg    360
acgttcggtg gaggcaccaa gctggaaatc aaacgggctg atgctgcacc aactgtatcc    420
atcttcccac catccagtga gcagttaaca tctggaggtg cctcagtcgt gtgcttcttg    480
aacaacttct accccagaga catcaatgtc aagtggaaga ttgatggcag tgaacgacaa    540
aatggtgtcc tgaacagttg gactgatcag gacagcaaag acagcaccta cagcatgagc    600
agcaccctca cattgaccaa ggacgagtat gaacgacata cagctatac ctgtgaggcc     660 actcacaaga catcaacttc acccattgtc aagagcttca caggaatga gtgt          714

<210> SEQ ID NO 123
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123
```

```
Glu Lys Ser Leu Ser His Ser Pro Gly Lys
    450                 455

Met Lys Leu Pro Val Arg Leu Leu Val Leu Met Phe Trp Ile Pro Ala
1               5                   10                  15

Ser Ser Ser Asp Val Leu Met Thr Gln Ile Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160
```

```
Asn Asn Phe Tyr Pro Arg Asp Ile Asn Val Lys Trp Lys Ile Asp Gly
            165                 170                 175
Ser Glu Arg Gln Asn Gly Val Leu Asn Ser Trp Thr Asp Gln Asp Ser
        180                 185                 190
Lys Asp Ser Thr Tyr Ser Met Ser Ser Thr Leu Thr Leu Thr Lys Asp
    195                 200                 205
Glu Tyr Glu Arg His Asn Ser Tyr Thr Cys Glu Ala Thr His Lys Thr
210                 215                 220
Ser Thr Ser Pro Ile Val Lys Ser Phe Asn Arg Asn Glu Cys
225                 230                 235
```

<210> SEQ ID NO 124
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

```
atgggttggc tgtggaactt gctattcctg atggcagctg cccaaagtgc ccagcacag      60
atccagttgg tacagtctgg acctgaactg aagaagcctg gagaggcagt caagatctcc    120
tgcaagtctt ctgggtatac cttcacaacc tatggaatga ctgggtgaa acaggctcca     180
ggaagggctt taaagtggat gggctggata acacctact ctggagtgcc aacatatgct     240
gatgacttca agggacggtt tgccttctct ttggaatcct ctgccagcac tgcctatttg    300
cagatcaaca acctcaaaaa tgaggacacg gctacatatt tctgtgcaag agggagggat    360
ggttaccaag tggcctggtt tgcttactgg ggccaaggga cgctggtcac tgtctctgca    420
gccaaaacga cacccccatc tgtctatcca ctggcccctg gatctgctgc ccaaactaac    480
tccatggtga ccctgggatg cctggtcaag ggctatttcc ctgagccagt gacagtgacc    540
tggaactctg gatccctgtc cagcggtgtg cacaccttcc cagctgtcct gcagtctgac    600
ctctacactc tgagcagctc agtgactgtc ccctccagca cctggcccag ccagaccgtc    660
acctgcaacg ttgcccaccc ggccagcagc accaaggtgg acaagaaaat tgtgcccagg    720
gattgtggtt gtaagccttg catatgtaca gtcccagaag tatcatctgt cttcatcttc    780
cccccaaagc ccaaggatgt gctcaccatt actctgactc ctaaggtcac gtgtgttgtg    840
gtagacatca gcaaggatga tcccgaggtc cagttcagct ggtttgtaga tgatgtggag    900
gtgcacacag ctcagacgca accccgggag gagcagttca acagcacttt ccgctcagtc    960
agtgaacttc ccatcatgca ccaggactgg ctcaatggca aggagttcaa atgcagggtc   1020
aacagtgcag ctttccctgc ccccatcgag aaaaccatct ccaaaaccaa aggcagaccg   1080
aaggctccac aggtgtacac cattccacct cccaaggagc agatggccaa ggataaagtc   1140
agtctgacct gcatgataac agacttcttc cctgaagaca ttactgtgga gtggcagtgg   1200
aatgggcagc agcggagaa ctacaagaac actcagccca tcatggacac agatggctct   1260
tacttcgtct acagcaagct caatgtgcag aagagcaact gggaggcagg aaatactttc   1320
acctgctctg tgttacatga gggcctgcac aaccaccata ctgagaagag cctctcccac   1380
tctcctggta aatga                                                   1395
```

<210> SEQ ID NO 125
<211> LENGTH: 464
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 125

Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Ala Val Lys Ile Ser Cys Lys Ser Ser Gly Tyr Thr Phe
        35                  40                  45

Thr Thr Tyr Gly Met Ser Trp Val Lys Gln Ala Pro Gly Arg Ala Leu
    50                  55                  60

Lys Trp Met Gly Trp Ile Asn Thr Tyr Ser Gly Val Pro Thr Tyr Ala
65                  70                  75                  80

Asp Asp Phe Lys Gly Arg Phe Ala Phe Ser Leu Glu Ser Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Gly Arg Asp Gly Tyr Gln Val Ala Trp Phe Ala
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Gln Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
```

```
                385                 390                 395                 400
Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
                420                 425                 430

Asn Trp Glu Ala Gly Asn Thr Phe Thr Cys Ser Val Leu His Glu Gly
                435                 440                 445

Leu His Asn His His Thr Glu Lys Ser Leu Ser His Ser Pro Gly Lys
                450                 455                 460

<210> SEQ ID NO 126
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
atgttctcac tagctcttct cctcagtctt cttctcctct gtgtctctga ttctagggca      60
gaaacaactg tgacccagtc tccagcatcc ctgtccatgg ctataggaga taaagtcacc     120
atcagatgca taaccagcac tgatattgat gatgatatga actggttcca gcagaagcca     180
ggggaacctc ctaagctcct tatttcagaa ggcaatactc ttcgtcctgg agtcccatcc     240
cgattctccg gcagtggcta tggtacagat tttatttta caattgaaaa catgctctct     300
gaagatgttg cagattacta ctgtttgcaa agtgataact tgccgtacac gttcggaggg     360
gggaccaagc tggaaataaa acgggctgat gctgcaccaa ctgtatccat cttcccacca     420
tccagtgagc agttaacatc tggaggtgcc tcagtcgtgt gcttcttgaa caacttctac     480
cccagagaca tcaatgtcaa gtggaagatt gatggcagtg aacgacaaaa tggtgtcctg     540
aacagttgga ctgatcagga cagcaaagac agcacctaca gcatgagcag cacccctcaca    600 ttgaccaagg acgagtatga cgacataaca gctatacct gtgaggccac tcacaagaca     660
tcaacttcac ccattgtcaa gagcttcaac aggaatgagt gttag                     705

<210> SEQ ID NO 127
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Phe Ser Leu Ala Leu Leu Leu Ser Leu Leu Leu Leu Cys Val Ser
1               5                   10                  15

Asp Ser Arg Ala Glu Thr Thr Val Thr Gln Ser Pro Ala Ser Leu Ser
                20                  25                  30

Met Ala Ile Gly Asp Lys Val Thr Ile Arg Cys Ile Thr Ser Thr Asp
            35                  40                  45

Ile Asp Asp Asp Met Asn Trp Phe Gln Gln Lys Pro Gly Glu Pro Pro
        50                  55                  60

Lys Leu Leu Ile Ser Glu Gly Asn Thr Leu Arg Pro Gly Val Pro Ser
65                  70                  75                  80

Arg Phe Ser Gly Ser Gly Tyr Gly Thr Asp Phe Ile Phe Thr Ile Glu
                85                  90                  95

Asn Met Leu Ser Glu Asp Val Ala Asp Tyr Tyr Cys Leu Gln Ser Asp
```

```
            100                 105                 110
Asn Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 128
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

```
atgggatgga gctgtatcat tgtcctcttg gtatcaacag ctacaggtgt ccactcccag      60
gtccaactgc agcagcctgg ggctgagctg gtgaggcctg ggacttcagt gaagttgtcc     120
tgcaaggctt ctggctacac cttcaccaac tactggatgc actgggtaaa gcagaggcct     180
ggacaaggcc ttgagtggat cggaatgatt gatccttctg atagttatac taactacaat     240
ccaaagttca gggtaaggc cacattgact gtagacacat cctccagcac agcctacatg      300
cagctcagca gcctgacatc tgaggactct gcggtctatt actgtgcaag aaactactct     360
ggggactact ggggccaagg caccactctc acagtctcct cagccaaaac gacaccccca     420
tctgtctatc cactggcccc tggatctgct gcccaaacta actccatggt gaccctggga     480
tgcctggtca agggctattt ccctgagcca gtgacagtga cctggaactc tggatccctg     540
tccagcggtg tgcacacctt cccagctgtc ctgcagtctg acctctacac tctgagcagc     600
tcagtgactg tcccctccag cacctggccc agccagaccg tcacctgcaa cgttgcccac     660
ccggccagca gcaccaaggt ggacaagaaa attgtgccca gggattgtgg ttgtaagcct     720
tgcatatgta cagtcccaga agtatcatct gtcttcatct tccccccaaa gcccaaggat     780
gtgctcacca ttactctgac tcctaaggtc acgtgtgttg tggtagacat cagcaaggat     840
gatcccgagg tccagttcag ctggtttgta gatgatgtgg aggtgcacac agctcagacg     900
caaccccggg aggagcagtt caacagcact ttccgctcag tcagtgaact tcccatcatg     960
caccaggact ggctcaatgg caaggagttc aaatgcaggg tcaacagtgc agctttccct    1020
gcccccatcg agaaaaccat ctccaaaacc aaaggcagac cgaaggctcc acaggtgtac    1080
accattccac ctcccaagga gcagatggcc aaggataaag tcagtctgac ctgcatgata    1140
acagacttct tccctgaaga cattactgtg gagtggcagt ggaatgggca gccagcggag    1200
aactacaaga cactcagcc catcatggac acagatggct cttacttcgt ctacagcaag    1260
```

```
ctcaatgtgc agaagagcaa ctgggaggca ggaaatactt tcacctgctc tgtgttacat    1320
gagggcctgc acaaccacca tactgagaag agcctctccc actctcctgg taaa          1374
```

<210> SEQ ID NO 129
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Met Gly Trp Ser Cys Ile Ile Val Leu Leu Val Ser Thr Ala Thr Gly
1               5                   10                  15

Val His Ser Gln Val Gln Leu Gln Gln Pro Gly Ala Glu Leu Val Arg
            20                  25                  30

Pro Gly Thr Ser Val Lys Leu Ser Cys Lys Ala Ser Gly Tyr Thr Phe
        35                  40                  45

Thr Asn Tyr Trp Met His Trp Val Lys Gln Arg Pro Gly Gln Gly Leu
    50                  55                  60

Glu Trp Ile Gly Met Ile Asp Pro Ser Asp Ser Tyr Thr Asn Tyr Asn
65                  70                  75                  80

Pro Lys Phe Lys Gly Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Asn Tyr Ser Gly Asp Tyr Trp Gly Gln Gly Thr
        115                 120                 125

Thr Leu Thr Val Ser Ser Ala Lys Thr Thr Pro Pro Ser Val Tyr Pro
    130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Pro Ser Ser Thr
        195                 200                 205

Trp Pro Ser Gln Thr Val Thr Cys Asn Val Ala His Pro Ala Ser Ser
    210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
                245                 250                 255

Lys Pro Lys Asp Val Leu Thr Ile Thr Leu Thr Pro Lys Val Thr Cys
            260                 265                 270

Val Val Val Asp Ile Ser Lys Asp Asp Pro Glu Val Gln Phe Ser Trp
        275                 280                 285

Phe Val Asp Asp Val Glu Val His Thr Ala Gln Thr Gln Pro Arg Glu
    290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
                325                 330                 335

Ala Ala Phe Pro Ala Pro Ile Glu Lys Thr Ile Ser Lys Thr Lys Gly
```

-continued

```
                340             345             350
Arg Pro Lys Ala Pro Gln Val Tyr Thr Ile Pro Pro Lys Glu Gln
            355                 360                 365

Met Ala Lys Asp Lys Val Ser Leu Thr Cys Met Ile Thr Asp Phe Phe
    370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asp Thr Asp Gly Ser Tyr Phe
                405                 410                 415

Val Tyr Ser Lys Leu Asn Val Gln Lys Ser Asn Trp Glu Ala Gly Asn
            420                 425                 430

Thr Phe Thr Cys Ser Val Leu His Glu Gly Leu His Asn His His Thr
        435                 440                 445

Glu Lys Ser Leu Ser His Ser Pro Gly Lys
    450                 455
```

<210> SEQ ID NO 130
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130

```
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca agtttccaa ccgattttct      240
ggggtcccag acaggttcag tggcagtgga tcaggacag atttcacact caagatcagc      300
agagtggagg ctgaggatct gggagtttat tattgctttc aaggttcata tgttccgtgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
aacaacttct accccagaga catcaatgtc aagtggaaga ttgatggcag tgaacgacaa     540
aatggtgtcc tgaacagttg gactgatcag acagcaaag acagcaccta cagcatgagc      600
agcaccctca cattgaccaa ggacgagtat gaacgacata cagctatac ctgtgaggcc      660
actcacaaga catcaacttc acccattgtc aagagcttca caggaatga gtgt            714
```

<210> SEQ ID NO 131
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

```
Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
```

```
                   50                  55                  60
Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
                100                 105                 110

Phe Gln Gly Ser Tyr Val Pro Trp Thr Phe Gly Gly Gly Thr Lys Leu
                115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
                180                 185                 190

Lys Asp Ser Thr Tyr Ser Met Ser Ser Thr Leu Thr Leu Thr Lys Asp
                195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys
225                 230                 235

<210> SEQ ID NO 132
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
atgaacttcg ggctcagctt gatgttcctt gtccttgtct taaaaggtgt ccagtgtgag      60
gtgcagctgg tggaatctgg gggaggctta gtgaagcctg agggtccct gaaactctcc     120 tgtgcagcct ctggattcac tttcagtgac tatgccatgt cttgggttcg ccagactccg     180
gaaaagaggc tggagtgggt cgcaaccatt agtgatggtg gtacttacac ctactatcca     240
gacaatgtaa agggccgatt caccatctcc agagacaatg ccaagaacaa cctgtacctg     300
caaatgagcc atctgaagtc tgaggacaca gccatgtatt actgtgcaag gaatggggt      360 gattacgacg gatttgacta ctggggccaa ggcaccactc tcacagtctc ctcggccaaa     420
acgacacccc catctgtcta tccactggcc cctggatctg ctgcccaaac taactccatg     480
gtgaccctgg gatgcctggt caagggctat ttccctgagc cagtgacagt gacctggaac     540
tctggatccc tgtccagcgg tgtgcacacc ttcccagctg tcctgcagtc tgacctctac     600
actctgagca gctcagtgac tgtcccctcc agcacctggc ccagccagac cgtcacctgc     660
aacgttgccc accggccag cagcaccaag gtggacaaga aaattgtgcc cagggattgt     720
ggttgtaagc cttgcatatg tacagtccca gaagtatcat ctgtcttcat cttcccccca     780
aagcccaagg atgtgctcac cattactctg actcctaagg tcacgtgtgt tgtggtagac     840
atcagcaagg atgatcccga ggtccagttc agctggtttg tagatgatgt ggaggtgcac     900
acagctcaga cgcaacccg ggaggagcag ttcaacagca ctttccgctc agtcagtgaa     960
cttcccatca tgcaccagga ctggctcaat ggcaaggagt tcaaatgcag ggtcaacagt    1020
```

-continued

```
gcagctttcc ctgcccccat cgagaaaacc atctccaaaa ccaaaggcag accgaaggct   1080
ccacaggtgt acaccattcc acctcccaag gagcagatgg ccaaggataa agtcagtctg   1140
acctgcatga taacagactt cttccctgaa gacattactg tggagtggca gtggaatggg   1200
cagccagcgg agaactacaa gaacactcag cccatcatgg acacagatgg ctcttacttc   1260
gtctacagca agctcaatgt gcagaagagc aactgggagg caggaaatac tttcacctgc   1320
tctgtgttac atgagggcct gcacaaccac catactgaga gagcctctc ccactctcct   1380 ggtaaa                                                               1386
```

<210> SEQ ID NO 133
<211> LENGTH: 462
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

```
Met Asn Phe Gly Leu Ser Leu Met Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Ala Met Ser Trp Val Arg Gln Thr Pro Glu Lys Arg Leu
    50                  55                  60

Glu Trp Val Ala Thr Ile Ser Asp Gly Gly Thr Tyr Thr Tyr Tyr Pro
65                  70                  75                  80

Asp Asn Val Lys Gly Arg Phe Thr Ile Ser Arg Asp Asn Ala Lys Asn
                85                  90                  95

Asn Leu Tyr Leu Gln Met Ser His Leu Lys Ser Glu Asp Thr Ala Met
            100                 105                 110

Tyr Tyr Cys Ala Arg Glu Trp Gly Asp Tyr Asp Gly Phe Asp Tyr Trp
        115                 120                 125

Gly Gln Gly Thr Thr Leu Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Val Thr Val
        195                 200                 205

Pro Ser Ser Thr Trp Pro Ser Gln Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
        275                 280                 285
```

-continued

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
    450                 455                 460

<210> SEQ ID NO 134
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
atggacatga gggttcctgc tcacgttttt ggcttcttgt tgctctggtt tccaggtacc      60
agatgtgaca tccagatgac ccagtctcca tcctccttat ctgcctctct gggagaaaga     120
gtcagtctca cttgtcgggc aagtcaggaa attagtggtt acttaagctg gcttcagcag     180
aaaccagatg gaactattaa acgcctgatc tacgccgcat ccactttaga ttctggtgtc     240
ccaaaaaggt tcagtggcag taggtctggg tcagattatt ctctcaccat cggcagcctt     300
gagtctgaag atcttgcaga ctattactgt ctacaatatg atagttatcc gtacacgttc     360 ggaggggggga ccaagctgga aataaaacgg gctgatgctg caccaactgt atccatcttc     420
ccaccatcca gtgagcagtt aacatctgga ggtgcctcag tcgtgtgctt cttgaacaac     480
ttctacccca gagacatcaa tgtcaagtgg aagattgatg gcagtgaacg acaaaatggt     540
gtcctgaaca gttggactga tcaggacagc aaagacagca cctacagcat gagcagcacc     600
ctcacattga ccaaggacga gtatgaacga cataacagct atacctgtga ggccactcac     660
aagacatcaa cttcacccat tgtcaagagc ttcaacagga atgagtgt                  708

<210> SEQ ID NO 135
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Met Asp Met Arg Val Pro Ala His Val Phe Gly Phe Leu Leu Leu Trp
1               5                   10                  15

Phe Pro Gly Thr Arg Cys Asp Ile Gln Met Thr Gln Ser Pro Ser Ser
                20                  25                  30

Leu Ser Ala Ser Leu Gly Glu Arg Val Ser Leu Thr Cys Arg Ala Ser
            35                  40                  45

Gln Glu Ile Ser Gly Tyr Leu Ser Trp Leu Gln Gln Lys Pro Asp Gly
    50                  55                  60

Thr Ile Lys Arg Leu Ile Tyr Ala Ala Ser Thr Leu Asp Ser Gly Val
65                  70                  75                  80

Pro Lys Arg Phe Ser Gly Ser Arg Ser Gly Ser Asp Tyr Ser Leu Thr
                85                  90                  95

Ile Gly Ser Leu Glu Ser Glu Asp Leu Ala Asp Tyr Tyr Cys Leu Gln
            100                 105                 110

Tyr Asp Ser Tyr Pro Tyr Thr Phe Gly Gly Gly Thr Lys Leu Glu Ile
    115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Arg Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
    195                 200                 205

Glu Arg His Asn Ser Tyr Thr Cys Glu Ala Thr His Lys Thr Ser Thr
210                 215                 220

Ser Pro Ile Val Lys Ser Phe Asn Arg Asn Glu Cys
225                 230                 235

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
cgactggagc acgaggacac tga                                          23

<210> SEQ ID NO 137
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ctaatacgac tcactatagg gcaagcagtg gtatcaacgc agagt                  45

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 138
ctaatacgac tcactatagg gc                                              22

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tatgcaaggc ttacaaccac a                                               21

<210> SEQ ID NO 140
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gccagtggat agacagatgg gggtgtcg                                        28

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
aggacagggg ttgattgttg a                                               21

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ggccagtgga tagactgatg ggggtgttgt                                      30

<210> SEQ ID NO 143
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ggaggaacca gttgtatctc cacaccca                                        28

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ctcattcctg ttgaagctct tgacaat                                        27

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
cgactgaggc acctccagat gtt                                            23

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gtaaaacgac ggccagt                                                   17

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
caggaaacag ctatgacc                                                  18

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Ile Ser Asp Gly Gly Thr Tyr Thr Tyr Tyr Pro Asp Ser Val Lys
1               5                   10                  15

Gly

<210> SEQ ID NO 149
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
gaggttcagc tggtggaatc tggcggtggg cttgtacaac aggaggctc cctcagactg      60 agttgtgccg cttcagggtt cacattctcc gactatgcga tgtcatgggt gcgccaagca    120
cccgggaaag gactggagtg ggttgccact atcagcgatg gcggaacgta tacctattac    180
cctgacaatg tgaagggtcg gttcaccatt tccagggata acgcaaagaa cagtctctac    240

```
ctgcagatga acagcctgag ggctgaggac accgccgtct actactgcgc ccgagaatgg    300
ggagattatg atgggtttga ctattggggc cagggcactt tggtgacagt cagttct      357
```

<210> SEQ ID NO 150
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Thr Ile Ser Asp Gly Gly Thr Tyr Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115
```

<210> SEQ ID NO 151
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151

```
caagttcagc tggtggaatc tggcggtggg cttgtaaagc caggaggctc cctcagactg    60
agttgtgccg cttcagggtt cacattctcc gactatgcga tgtcatggat caggcaagca    120
cccgggaaag gactggagtg ggttagcact atcagcgatg gcggaacgta tacctattac    180
cctgacaatg tgaagggtcg gttcaccatt tccaggdata acgcaaagaa cagtctctac    240
cttcagatga acagcctgag ggctgaggac accgccgtct actactgcgc ccgagaatgg    300
ggagattatg atgggtttga ctattggggc cagggcactt tggtgacagt cagttct      357
```

<210> SEQ ID NO 152
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30
```

```
Ala Met Ser Trp Ile Arg Gln Ala Pro Gly Lys Gly Leu Glu Trp Val
            35                  40                  45

Ser Thr Ile Ser Asp Gly Gly Thr Tyr Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
            115
```

<210> SEQ ID NO 153
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153

```
caagttcagc tggtggaatc tggcggtggg cttgtaaagc caggaggctc cctcagactg    60
agttgtgccg cttcgggttt cacattctcc gactatgcga tgtcatggat caggcaagca   120
cccgggaaag gactggagtg ggttagcact atcagcgatg gcggaacgta tacctattac   180
cctgactccg tgaagggtcg gttcaccatt tccaggata acgcaaagaa cagtctctac   240
cttcagatga acagcctgag ggctgaggac accgccgtct actactgcgc ccgagaatgg   300
ggagattatg atgggtttga ctattggggc cagggcactt tggtgacagt cagttct      357
```

<210> SEQ ID NO 154
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
            35                  40                  45

Ser Thr Ile Ser Asp Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
            115
```

<210> SEQ ID NO 155
<211> LENGTH: 357

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155

```
gaggttcagc tggtggaatc tggcggtggg cttgtaaagc caggaggctc cctcagactg    60
agttgtgccg cttcagggtt cacattctcc gactatgcga tgtcatgggt gcgccaagca   120
cccgggaaag gactggagtg ggttagcact atcagcgatg gcggaacgta tacctattac   180
cctgacaatg tgaagggtcg gttcaccatt tccaggata acgcaaagaa cagtctctat   240
ttgcagatga acagcctgag ggctgaggac accgccgtct actactgcgc ccgagaatgg   300
ggagattatg atgggtttga ctattggggc cagggcactt tggtgacagt cagttct     357
```

<210> SEQ ID NO 156
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Ala Met Ser Trp Val Arg Gln Ala Pro Gly Lys Gly Leu Glu Trp Val
        35                  40                  45
Ser Thr Ile Ser Asp Gly Gly Thr Tyr Thr Tyr Tyr Pro Asp Asn Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Trp Gly Asp Tyr Asp Gly Phe Asp Tyr Trp Gly Gln Gly
            100                 105                 110
Thr Leu Val Thr Val Ser Ser
        115

<210> SEQ ID NO 157
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157

```
gaggttcagc ttctggaatc tggcggtggg cttgtacagc caggaggctc cctcagactg    60
agttgtgccg cttcagggtt cacattctcc gactatgcga tgtcatgggt gcgccaagca   120
cccgggaaag gactggagtg ggtttcaact atcagcgatg gcggaacgta tacctattac   180
cctgacaatg tgaagggtcg gttcaccatt tccaggata acagcaagaa cacactctat   240
ctccagatga acagcctgag ggctgaggac accgccgtct actactgcgc ccgagaatgg   300
ggagattatg atgggtttga ctattggggc cagggcactt tggtgacagt cagttct     357
```

<210> SEQ ID NO 158
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ser Asp Gly Gly Thr Tyr Thr Tyr Tyr Pro Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115
```

<210> SEQ ID NO 159
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159

```
caggttcagc tggtggaatc tggcggtggg gtagtacaac aggacggtc cctcagactg      60
agttgtgccg cttcagggtt cacattctcc gactatgcga tgtcatgggt gcgccaagca     120
cccgggaaag gactggagtg ggttgccact atcagcgatg gcggaacgta tacctattac     180
cctgacaatg tgaagggtcg gttcaccatt tccagggata actcaaagaa caccctctat     240
ctccaaatga gtagcctgag ggctgaggac accgccgtct actactgcgc ccgagaatgg     300
ggagattatg atgggtttga ctattggggc cagggcactt tggtgacagt cagttct       357
```

<210> SEQ ID NO 160
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 160

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Thr Ile Ser Asp Gly Gly Thr Tyr Thr Tyr Tyr Pro Asp Asn Val
    50                  55                  60
```

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115

<210> SEQ ID NO 161
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
gaggttcagc tggtggaatc tggcggtggg cttgtaaagc caggaggctc cctcagactg     60
agttgtgccg cttcagggtt cacattctcc gactatgcga tgtcatgggt gcgccaagca    120
cccgggaaag gactggagtg ggttgccact atcagcgatg gcggaacgta tacctattac    180
cctgacaatg tgaagggtcg gttcaccatt tccagggata cgcaaagaa cagtctctac     240 cttcagatga acagcctgag ggctgaggac accgccgtct actactgcgc ccgagaatgg    300
ggagattatg atgggtttga ctattggggc caggggcactt tggtgacagt cagttct     357

<210> SEQ ID NO 162
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Thr Ile Ser Asp Gly Gly Thr Tyr Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115

<210> SEQ ID NO 163
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163

```
gatattcagt tgacccaatc acctagcttc ctctcagctt ccgtgggcga cagagttacc    60
ataacctgtc gggcaagcca ggagatttct gggtacctgt cctggtacca acagaagccc   120
ggaaaagccc ctaagctgtt gatctatgct gcgtcaacct tggatagcgg tgtcccgagt   180
cgattctccg gttctggctc cggaacagag ttcactctga caatttctag ccttcagcca   240
gaagatttcg ccacgtacta ttgcctccag tacgacagct atccctatac atttgggcag   300
ggcactaaac tggagatcaa a                                             321
```

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

```
Asp Ile Gln Leu Thr Gln Ser Pro Ser Phe Leu Ser Ala Ser Val Gly
1               5                   10                  15
Asp Arg Val Thr Ile Thr Cys Arg Ala Ser Gln Glu Ile Ser Gly Tyr
            20                  25                  30
Leu Ser Trp Tyr Gln Gln Lys Pro Gly Lys Ala Pro Lys Leu Leu Ile
        35                  40                  45
Tyr Ala Ala Ser Thr Leu Asp Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln Tyr Asp Ser Tyr Pro Tyr
                85                  90                  95
Thr Phe Gly Gln Gly Thr Lys Leu Glu Ile Lys
            100                 105
```

<210> SEQ ID NO 165
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 165

```
gatattcaga tgacccaatc acctagcagt ctctcagctt ccgtgggcga cagagttacc    60
ataacctgtc gggcaagcca ggagatttct gggtacctgt cctggtttca acagaagccc   120
ggaaaggccc cgaagagctt gatctatgct gcgtcaacct tggatagcgg tgtcccgagt   180
cgattctccg gttctggctc cggaaccgac tttactctga caatttctag ccttcagcca   240
gaagatttcg ccacgtacta ttgcctccag tacgacagct atccctatac atttgggcag   300
ggcactaaac tggagatcaa a                                             321
```

<210> SEQ ID NO 166
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Phe Gln Gln Lys Pro Gly Lys Ala Pro Lys Ser Leu Ile
        35                  40                  45

Tyr Ala Ala Ser Thr Leu Asp Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105

<210> SEQ ID NO 167
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
gatattcaga tgacccaatc acctagcagt ctctcagctt ccgtgggcga cagagttacc      60
ataacctgtc gggcaagcca ggagattttct gggtacctgt cctggtatca acagaagccc    120
ggaaaagccc caaagaggtt gatctatgct gcgtcaacct tggatagcgg tgtcccgagt    180
cgattctccg gttctggctc cggaaccgag ttcactctga caatttctag ccttcagcca    240
gaagatttcg ccacgtacta ttgcctccag tacgacagct atccctatac atttgggcag    300
ggcactaaac tggagatcaa a                                              321

<210> SEQ ID NO 168
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Arg Leu Ile
        35                  40                  45

Tyr Ala Ala Ser Thr Leu Asp Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105

```
<210> SEQ ID NO 169
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
gatattcaga tgacccaatc acctagcagt ctctcagctt ccgtgggcga cagagttacc      60
ataacctgtc gggcaagcca ggagatttct gggtacctgt cctggtacca acagaagccc     120
ggaaaggccc ccaagctgtt gatctatgct gcgtcaacct ggatagcggt gtcccgagt     180 cgattctccg gttctggctc cggaacagac tttacttttta caatttctag ccttcagcca    240
gaggacatcg ccacgtacta ttgcctccag tacgacagct atccctatac atttgggcag     300
ggcactaaac tggagatcaa a                                               321

<210> SEQ ID NO 170
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Leu Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105

<210> SEQ ID NO 171
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171
gatattcaga tgacccaatc acctagcagt ctctcagctt ccgtgggcga cagagttacc      60
ataacctgtc gggcaagcca ggagatttct gggtacctgt cctggtatca acagaagccc     120
ggaaaagccc ctaagctgtt gatctatgct gcgtcaacct ggatagcggt gtcccgagt     180 cgattctccg gttctggctc cggaactgac ttcactctga caatttctag ccttcagcca    240
gaagatttcg ccacgtacta ttgcctccag tacgacagct atccctatac atttgggcag     300
ggcactaaac tggagatcaa a                                               321

<210> SEQ ID NO 172
```

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Leu Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105

<210> SEQ ID NO 173
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
gatattcaga tgacccaatc acctagcagt ctctcagctt ccgtgggcga cagagttacc      60
ataacctgtc gggcaagcca ggagatttct gggtacctgt cctggctgca acagaagccc    120
ggaggcgcca tcaagaggtt gatctatgct gcgtcaacct tggatagcgg tgtcccgagt    180
cgattctccg gttctggctc cggaagtgac tacactctga caatttctag ccttcagcca    240
gaagatttcg ccacgtacta ttgcctccag tacgacagct atccctatac atttgggcag    300
ggcactaaac tggagatcaa a                                              321

<210> SEQ ID NO 174
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Thr Leu Asp Ser Gly Val Pro Ser Arg Phe Ser Gly
    50                  55                  60

Ser Gly Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
            85                  90                  95

Thr Phe Gly Gln Gly Thr Lys Leu Glu Ile Lys
            100                 105

<210> SEQ ID NO 175
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
gcctcaacaa aaggaccaag tgtgttccca ctcgccccta gcagcaagag tacatccggg      60
ggcactgcag cactcggctg cctcgtcaag gattattttc cagagccagt aaccgtgagc     120
tggaacagtg gagcactcac ttctggtgtc catacttttc ctgctgtcct gcaaagctct     180
ggcctgtact cactcagctc cgtcgtgacc gtgccatctt catctctggg cactcagacc     240
tacatctgta atgtaaacca caagcctagc aatactaagg tcgataagcg ggtggaaccc     300
aagagctgcg acaagactca cacttgtccc ccatgccctg cccctgaact tctgggcggt     360
cccagcgtct ttttgttccc accaaagcct aaagatactc tgatgataag tagaacaccc     420
gaggtgacat gtgttgttgt agacgtttcc cacgaggacc cagaggttaa gttcaactgg     480
tacgttgatg gagtcgaagt acataatgct aagaccaagc ctagagagga gcagtataat     540
agtacatacc gtgtagtcag tgttctcaca gtgctgcacc aagactggct caacggcaaa     600
gaatacaaat gcaaagtgtc caacaaagca ctcccagccc ctatcgagaa gactattagt     660
aaggcaaagg ggcagcctcg tgaaccacag gtgtacactc tgccacccag tagagggaa      720 atgacaaaga accaagtctc attgacctgc ctggtgaaag gcttctaccc cagcgacatc     780
gccgttgagt gggagagtaa cggtcagcct gagacaatt acaagacaac ccccccagtg      840
ctggatagtg acgggtcttt ctttctgtac agtaagctga ctgtggacaa gtcccgctgg     900
cagcagggta acgtcttcag ctgttccgtg atgcacgagg cattgcacaa ccactacacc     960
cagaagtcac tgagcctgag cccagggaag                                     990

<210> SEQ ID NO 176
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

```
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 177
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggaccctga ggtcacgtgc      420 gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
```

```
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacac ctcccatgct ggactccgac    840
ggctccttct tcctctacag caagctcacc gtggacaaga gcaggtggca gcaggggaac    900
gtcttctcat gctccgtgat gcatgaggct ctgcacaacc actacacgca gaagagcctc    960
tccctgtctc cgggtaaa                                                  978
```

```
<210> SEQ ID NO 178
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 179
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
cgcacagttg ctgccccag cgtgttcatt ttcccaccta gcgatgagca gctgaaaagc      60
ggtactgcct ctgtcgtatg cttgctcaac aactttttacc cacgtgaggc taaggtgcag    120
tggaaagtgg ataatgcact tcaatctgga aacagtcaag agtccgtgac agaacaggac    180
agcaaagact caacttattc actctcttcc accctgactc tgtccaaggc agactatgaa    240
aaacacaagg tatacgcctg cgaggttaca caccagggtt tgtctagtcc tgtcaccaag    300
tccttcaata ggggcgaatg t                                              321

<210> SEQ ID NO 180
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 181
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
atgaacttcg ggctcagctt gatgttcctt gtccttgtct taaaaggtgt ccagtgtgag    60
gtgcagctgg tggaatctgg gggaggctta gtgaagcctg agggtccct gaaactctcc     120 tgtgcagcct ctggattcac tttcagtgac tatgccatgt cttgggttcg ccagactccg    180

```
gaaaagaggc tggagtgggt cgcaaccatt agtgatggtg gtacttacac ctactatcca    240
gacaatgtaa agggccgatt caccatctcc agagacaatg ccaagaacaa cctgtacctg    300
caaatgagcc atctgaagtc tgaggacaca gccatgtatt actgtgcaag agaatggggt    360
gattacgacg gatttgacta ctggggccaa ggcaccactc tcacagtctc ctcggcctca    420
acaaaaggac caagtgtgtt cccactcgcc cctagcagca gagtacatc cggggcact     480 gcagcactcg gctgcctcgt caaggattat tttccagagc cagtaaccgt gagctggaac    540
agtggagcac tcacttctgg tgtccatact tttcctgctg tcctgcaaag ctctggcctg    600
tactcactca gctccgtcgt gaccgtgcca tcttcatctc tgggcactca gacctacatc    660
tgtaatgtaa accacaagcc tagcaatact aaggtcgata agcgggtgga acccaagagc    720
tgcgacaaga ctcacacttg tccccccatgc cctgcccctg aacttctggg cggtcccagc    780 gtcttttttgt tcccaccaaa gcctaaagat actctgatga agtagaac acccgaggtg    840 acatgtgttg ttgtagacgt ttcccacgag gacccagagg ttaagttcaa ctggtacgtt    900
gatggagtcg aagtacataa tgctaagacc aagcctagag aggagcagta ataatagtaca    960 taccgtgtag tcagtgttct cacagtgctg caccaagact ggctcaacgg caagaatac   1020 aaatgcaaag tgtccaacaa agcactccca gcccctatcg agaagactat tagtaaggca   1080
aaggggcagc ctcgtgaacc acaggtgtac actctgccac ccagtagaga ggaaatgaca   1140
aagaaccaag tctcattgac ctgcctggtg aaaggcttct accccagcga catcgccgtt   1200
gagtgggaga gtaacggtca gcctgagaac aattacaaga caacccccccc agtgctggat   1260 agtgacgggt ctttctttct gtacagtaag ctgactgtgg acaagtcccg ctggcagcag   1320
ggtaacgtct tcagctgttc cgtgatgcac gaggcattgc acaaccacta cacccagaag   1380
tcactgagcc tgagcccagg gaag                                          1404
```

<210> SEQ ID NO 182
<211> LENGTH: 468
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

```
Met Asn Phe Gly Leu Ser Leu Met Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Ala Met Ser Trp Val Arg Gln Thr Pro Glu Lys Arg Leu
    50                  55                  60

Glu Trp Val Ala Thr Ile Ser Asp Gly Gly Thr Tyr Thr Tyr Tyr Pro
65                  70                  75                  80

Asp Asn Val Lys Gly Arg Phe Thr Ile Ser Arg Asp Asn Ala Lys Asn
                85                  90                  95

Asn Leu Tyr Leu Gln Met Ser His Leu Lys Ser Glu Thr Ala Met
            100                 105                 110

Tyr Tyr Cys Ala Arg Glu Trp Gly Asp Tyr Asp Gly Phe Asp Tyr Trp
        115                 120                 125

Gly Gln Gly Thr Thr Leu Thr Val Ser Ser Ala Ser Thr Lys Gly Pro
    130                 135                 140
```

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
        180                 185                 190

Ala Val Leu Gln Ser Ser Gly Leu Tyr Ser Leu Ser Ser Val Val Thr
    195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
            245                 250                 255

Gly Gly Pro Ser Val Phe Leu Phe Pro Pro Lys Pro Lys Asp Thr Leu
        260                 265                 270

Met Ile Ser Arg Thr Pro Glu Val Thr Cys Val Val Val Asp Val Ser
    275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
        340                 345                 350

Ile Glu Lys Thr Ile Ser Lys Ala Lys Gly Gln Pro Arg Glu Pro Gln
    355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
    435                 440                 445

Met His Glu Ala Leu His Asn His Tyr Thr Gln Lys Ser Leu Ser Leu
450                 455                 460

Ser Pro Gly Lys
465

<210> SEQ ID NO 183
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
atggacatga gggttcctgc tcacgttttt ggcttcttgt tgctctggtt tccaggtacc      60
agatgtgaca tccagatgac ccagtctcca tcctccttat ctgcctctct gggagaaaga     120

-continued

```
gtcagtctca cttgtcgggc aagtcaggaa attagtggtt acttaagctg gcttcagcag    180
aaaccagatg gaactattaa acgcctgatc tacgccgcat ccactttaga ttctggtgtc    240
ccaaaaaggt tcagtggcag taggtctggg tcagattatt ctctcaccat cggcagcctt    300
gagtctgaag atcttgcaga ctattactgt ctacaatatg atagttatcc gtacacgttc    360 ggaggggggga ccaagctgga aataaaacgc acagtcgccg ctccctccgt gttcatcttt    420
ccaccaagtg atgagcaact gaagtctggt actgcttcag tcgtgtgtct gctgaacaat    480
ttctaccctc gagaagccaa agtccaatgg aaggtagaca acgcactgca gtccggcaat    540
agccaagaat cagttaccga acaggattca aaggacagta catattccct gagcagcact    600
ctgaccctgt caaaggccga ttcgagaaaa cacaaggtct atgcttgcga agtgacacat    660
cagggactgt ccagcccagt gacaaaatct tttaaccgtg gggagtgt                708
```

<210> SEQ ID NO 184
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 184

```
Met Asp Met Arg Val Pro Ala His Val Phe Gly Phe Leu Leu Leu Trp
1               5                   10                  15

Phe Pro Gly Thr Arg Cys Asp Ile Gln Met Thr Gln Ser Pro Ser Ser
                20                  25                  30

Leu Ser Ala Ser Leu Gly Glu Arg Val Ser Leu Thr Cys Arg Ala Ser
            35                  40                  45

Gln Glu Ile Ser Gly Tyr Leu Ser Trp Leu Gln Gln Lys Pro Asp Gly
        50                  55                  60

Thr Ile Lys Arg Leu Ile Tyr Ala Ala Ser Thr Leu Asp Ser Gly Val
65                  70                  75                  80

Pro Lys Arg Phe Ser Gly Ser Arg Ser Gly Ser Asp Tyr Ser Leu Thr
                85                  90                  95

Ile Gly Ser Leu Glu Ser Glu Asp Leu Ala Asp Tyr Tyr Cys Leu Gln
            100                 105                 110

Tyr Asp Ser Tyr Pro Tyr Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 185
<211> LENGTH: 1413

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185

```
atggacatga gagttcctgc tcagctgctc gggttgctgt tgctttggct ccggggtgct      60
aggtgcgagg ttcagctggt ggaatctggc ggtgggcttg tacaaccagg aggctccctc     120
agactgagtt gtgccgcttc agggttcaca ttctccgact atgcgatgtc atgggtgcgc     180
caagcacccg ggaaaggact ggagtgggtt gccactatca gcgatggcgg aacgtatacc     240
tattaccctg acaatgtgaa gggtcggttc accatttcca gggataacgc aaagaacagt     300
ctctacctgc agatgaacag cctgagggct gaggacaccg ccgtctacta ctgcgcccga     360
gaatggggag attatgatgg gtttgactat tggggccagg gcactttggt gacagtcagt     420
tctgcctcaa caaaggacc aagtgtgttc ccactcgccc ctagcagcaa gagtacatcc     480
ggggggcactg cagcactcgg ctgcctcgtc aaggattatt ttccagagcc agtaaccgtg     540
agctggaaca gtggagcact cacttctggt gtccatactt ttcctgctgt cctgcaaagc     600
tctggcctgt actcactcag ctccgtcgtg accgtgccat cttcatctct gggcactcag     660
acctacatct gtaatgtaaa ccacaagcct agcaatacta aggtcgataa gcgggtggaa     720
cccaagagct gcgacaagac tcacacttgt cccccatgcc ctgcccctga acttctgggc     780
ggtcccagcg tctttttgtt cccaccaaag cctaaagata ctctgatgat aagtagaaca     840
cccgaggtga catgtgttgt tgtagacgtt cccacgagg acccagaggt taagttcaac     900
tggtacgttg atggagtcga agtacataat gctaagacca gcctagaga ggagcagtat     960
aatagtacat accgtgtagt cagtgttctc acagtgctgc accaagactg gctcaacggc    1020
aaagaataca atgcaaagt gtccaacaaa gcactcccag cccctatcga agactatt      1080
agtaaggcaa aggggcagcc tcgtgaacca caggtgtaca ctctgccacc cagtagagag    1140
gaaatgacaa agaaccaagt ctcattgacc tgcctggtga aaggcttcta ccccagcgac    1200
atcgccgttg agtgggagag taacggtcag cctgagaaca attacaagac aaccccccca    1260
gtgctggata gtgacgggtc tttctttctg tacagtaagc tgactgtgga caagtcccgc    1320
tggcagcagg gtaacgtctt cagctgttcc gtgatgcacg aggcattgca caaccactac    1380
acccagaagt cactgagcct gagcccaggg aag                                 1413
```

<210> SEQ ID NO 186
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Asp Tyr Ala Met Ser Trp Val Arg Gln Ala Pro Gly
    50                  55                  60
```

-continued

```
Lys Gly Leu Glu Trp Val Ala Thr Ile Ser Asp Gly Gly Thr Tyr Thr
 65                  70                  75                  80

Tyr Tyr Pro Asp Asn Val Lys Gly Arg Phe Thr Ile Ser Arg Asp Asn
                 85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Glu Trp Gly Asp Tyr Asp Gly Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 187
<211> LENGTH: 1413
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 187

```
atggacatga gagttcctgc tcagctgctc gggttgctgt tgctttggct ccggggtgct    60
aggtgccaag ttcagctggt ggaatctggc ggtgggcttg taaagccagg aggctccctc   120
agactgagtt gtgccgcttc agggttcaca ttctccgact atgcgatgtc atggatcagg   180
caagcacccg ggaaaggact ggagtgggtt agcactatca gcgatggcgg aacgtatacc   240
tattaccctg acaatgtgaa gggtcggttc accatttcca gggataacgc aaagaacagt   300
ctctaccttc agatgaacag cctgagggct gaggacaccg ccgtctacta ctgcgcccga   360
gaatggggag attatgatgg gtttgactat tggggccagg gcactttggt gacagtcagt   420
tctgcctcaa caaaaggacc aagtgtgttc ccactcgccc ctagcagcaa gagtacatcc   480
gggggcactg cagcactcgg ctgcctcgtc aaggattatt ttccagagcc agtaaccgtg   540
agctggaaca gtggagcact cacttctggt gtccatactt tcctgctgt cctgcaaagc   600
tctggcctgt actcactcag ctccgtcgtg accgtgccat cttcatctct gggcactcag   660
acctacatct gtaatgtaaa ccacaagcct agcaatacta aggtcgataa gcgggtggaa   720
cccaagagct gcgacaagac tcacacttgt cccccatgcc ctgcccctga acttctgggc   780
ggtcccagcg tcttttttgtt cccaccaaag cctaaagata ctctgatgat aagtagaaca   840
cccgaggtga catgtgttgt tgtagacgtt tcccacgagg acccagaggt taagttcaac   900
tggtacgttg atggagtcga agtacataat gctaagacca gcctagaga ggagcagtat   960
aatagtacat accgtgtagt cagtgttctc acagtgctgc accaagactg gctcaacggc  1020
aaagaataca atgcaaagt gtccaacaaa gcactcccag cccctatcga aagactatt  1080
agtaaggcaa aggggcagcc tcgtgaacca caggtgtaca ctctgccacc cagtagagag  1140
gaaatgacaa agaaccaagt ctcattgacc tgcctggtga aaggcttcta ccccagcgac  1200
atcgccgttg agtgggagag taacggtcag cctgagaaca attacaagac aaccccccca  1260
gtgctggata gtgacgggtc tttctttctg tacagtaagc tgactgtgga caagtcccgc  1320
tggcagcagg gtaacgtctt cagctgttcc gtgatgcacg aggcattgca caaccactac  1380
acccagaagt cactgagcct gagcccaggg aag                                1413
```

<210> SEQ ID NO 188
<211> LENGTH: 471
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Ala Met Ser Trp Ile Arg Gln Ala Pro Gly
```

-continued

```
            50                  55                  60
Lys Gly Leu Glu Trp Val Ser Thr Ile Ser Asp Gly Thr Tyr Thr
 65                  70                  75                  80

Tyr Tyr Pro Asp Asn Val Lys Gly Arg Phe Thr Ile Ser Arg Asp Asn
                 85                  90                  95

Ala Lys Asn Ser Leu Tyr Leu Gln Met Asn Ser Leu Arg Ala Glu Asp
                100                 105                 110

Thr Ala Val Tyr Tyr Cys Ala Arg Glu Trp Gly Asp Tyr Asp Gly Phe
                115                 120                 125

Asp Tyr Trp Gly Gln Gly Thr Leu Val Thr Val Ser Ser Ala Ser Thr
            130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470
```

<210> SEQ ID NO 189
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189

```
atggacatga gagttcctgc tcagctgctc gggttgctgt tgctttggct ccggggtgct      60
aggtgccaag ttcagctggt ggaatctggc ggtgggcttg taaagccagg aggctccctc     120
agactgagtt gtgccgcttc agggttcaca ttctccgact atgcgatgtc atggatcagg     180
caagcacccg ggaaaggact ggagtgggtt agcactatca gcgatggcgg aacgtatacc     240
tattaccctg actccgtgaa gggtcggttc accatttcca gggataacgc aaagaacagt     300
ctctaccttc agatgaacag cctgagggct gaggacaccg ccgtctacta ctgcgcccga     360
gaatggggag attatgatgg gtttgactat tggggccagg gcactttggt gacagtcagt     420
tctgcctcaa caaaaggacc aagtgtgttc ccactcgccc ctagcagcaa gagtacatcc     480
gggggcactg cagcactcgg ctgcctcgtc aaggattatt tcccagagcc agtaaccgtg     540
agctggaaca gtggagcact cacttctggt gtccatactt tcctgctgt cctgcaaagc     600
tctggcctgt actcactcag ctccgtcgtg accgtgccat cttcatctct gggcactcag     660
acctacatct gtaatgtaaa ccacaagcct agcaatacta aggtcgataa gcgggtggaa     720
cccaagagct cgacaagac tcacacttgt cccccatgcc ctgcccctga acttctgggc     780
ggtcccagcg tcttttgtt cccaccaaag cctaaagata ctctgatgat aagtagaaca     840
cccgaggtga catgtgttgt tgtagacgtt cccacgagg acccagaggt taagttcaac     900
tggtacgttg atggagtcga agtacataat gctaagacca gcctagaga ggagcagtat     960
aatagtacat accgtgtagt cagtgttctc acagtgctgc accaagactg gctcaacggc    1020
aaagaataca atgcaaagt gtccaacaaa gcactcccag cccctatcga aagactatt     1080
agtaaggcaa aggggcagcc tcgtgaacca caggtgtaca ctctgccacc cagtagagag    1140
gaaatgacaa agaaccaagt ctcattgacc tgcctggtga aaggcttcta ccccagcgac    1200
atcgccgttg agtgggagag taacggtcag cctgagaaca attacaagac aaccccccca    1260
gtgctggata tgacgggtc tttctttctg tacagtaagc tgactgtgga caagtcccgc    1320
tggcagcagg gtaacgtctt cagctgttcc gtgatgcacg aggcattgca caaccactac    1380
acccagaagt cactgagcct gagcccaggg aag                                 1413
```

<210> SEQ ID NO 190
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

```
Met Asp Met Arg Val Pro Ala Gln Leu Leu Gly Leu Leu Leu Leu Trp
 1               5                  10                  15

Leu Arg Gly Ala Arg Cys Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45
```

-continued

```
Phe Thr Phe Ser Asp Tyr Ala Met Ser Trp Ile Arg Gln Ala Pro Gly
        50                  55                  60
Lys Gly Leu Glu Trp Val Ser Thr Ile Ser Asp Gly Gly Thr Tyr Thr
 65                  70                  75                  80
Tyr Tyr Pro Asp Ser Val Lys Gly Arg Phe Thr Ile Ser Arg Asp Asn
                85                  90                  95
Ala Lys Asn Ser Leu Tyr Leu Gln Met Asn Ser Leu Arg Ala Glu Asp
            100                 105                 110
Thr Ala Val Tyr Tyr Cys Ala Arg Glu Trp Gly Asp Tyr Asp Gly Phe
        115                 120                 125
Asp Tyr Trp Gly Gln Gly Thr Leu Val Thr Val Ser Ser Ala Ser Thr
    130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Ser Leu Gly Thr Gln Thr Tyr Ile Cys
    210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
```

Leu Ser Leu Ser Pro Gly Lys
465                 470

<210> SEQ ID NO 191
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191

| | |
|---|---|
| atggacatga gagttcctgc tcagctgctc gggttgctgt tgctttggct ccggggtgct | 60 |
| aggtgccaag ttcagctggt ggaatctggc ggtgggcttg taaagccagg aggctccctc | 120 |
| agactgagtt gtgccgcttc agggttcaca ttctccgact atgcgatgtc atggatcagg | 180 |
| caagcacccg ggaaaggact ggagtgggtt agcactatca gcgatggcgg aacgtatacc | 240 |
| tattaccctg actccgtgaa gggtcggttc accatttcca gggataacgc aaagaacagt | 300 |
| ctctaccttc agatgaacag cctgagggct gaggacaccg ccgtctacta ctgcgcccga | 360 |
| gaatggggag attatgatgg gtttgactat tggggccagg gcactttggt gacagtcagt | 420 |
| tctgcctcca ccaagggccc atcggtcttc cccctggcgc cctgctccag gagcacctcc | 480 |
| gagagcacag cggccctggg ctgcctggtc aaggactact ccccgaaccc ggtgacggtg | 540 |
| tcgtggaact caggcgctct gaccagcggc gtgcacacct tcccagctgt cctacagtcc | 600 |
| tcaggactct actccctcag cagcgtggtg accgtgccct ccagcaactt cggcacccag | 660 |
| acctacacct gcaacgtaga tcacaagccc agcaacacca aggtggacaa gacagttgag | 720 |
| cgcaaatgtt gtgtcgagtg cccaccgtgc ccagcaccac ctgtggcagg accgtcagtc | 780 |
| ttcctcttcc ccccaaaacc caaggacacc ctcatgatct cccggacccc tgaggtcacg | 840 |
| tgcgtggtgg tggacgtgag ccacgaagac cccgaggtcc agttcaactg gtacgtggac | 900 |
| ggcgtggagg tgcataatgc caagacaaag ccacgggagg agcagttcaa cagcacgttc | 960 |
| cgtgtggtca gcgtcctcac cgttgtgcac caggactggc tgaacggcaa ggagtacaag | 1020 |
| tgcaaggtct ccaacaaagg cctcccagcc cccatcgaga aaaccatctc caaaaccaaa | 1080 |
| gggcagcccc gagaaccaca ggtgtacacc ctgcccccat cccgggagga gatgaccaag | 1140 |
| aaccaggtca gcctgacctg cctggtcaaa ggcttctacc ccagcgacat cgccgtggag | 1200 |
| tgggagagca atgggcagcc ggagaacaac tacaagacca cacctcccat gctggactcc | 1260 |
| gacggctcct tcttcctcta cagcaagctc accgtggaca agagcaggtg gcagcagggg | 1320 |
| aacgtcttct catgctccgt gatgcatgag gctctgcaca accactacac gcagaagagc | 1380 |
| ctctccctgt ctccgggtaa a | 1401 |

<210> SEQ ID NO 192
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

-continued

```
Leu Val Lys Pro Gly Gly Ser Leu Arg Leu Ser Cys Ala Ser Gly
         35                  40                  45

Phe Thr Phe Ser Asp Tyr Ala Met Ser Trp Ile Arg Gln Ala Pro Gly
 50                  55                  60

Lys Gly Leu Glu Trp Val Ser Thr Ile Ser Asp Gly Gly Thr Tyr Thr
 65                  70                  75                  80

Tyr Tyr Pro Asp Ser Val Lys Gly Arg Phe Thr Ile Ser Arg Asp Asn
                 85                  90                  95

Ala Lys Asn Ser Leu Tyr Leu Gln Met Asn Ser Leu Arg Ala Glu Asp
             100                 105                 110

Thr Ala Val Tyr Tyr Cys Ala Arg Glu Trp Gly Asp Tyr Asp Gly Phe
         115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
             165                 170                 175

Pro Val Thr Val Ser Trp Asn Ser Gly Ala Leu Thr Ser Gly Val His
         180                 185                 190

Thr Phe Pro Ala Val Leu Gln Ser Ser Gly Leu Tyr Ser Leu Ser Ser
     195                 200                 205

Val Val Thr Val Pro Ser Ser Asn Phe Gly Thr Gln Thr Tyr Thr Cys
         210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
             245                 250                 255

Gly Pro Ser Val Phe Leu Phe Pro Pro Lys Pro Lys Asp Thr Leu Met
         260                 265                 270

Ile Ser Arg Thr Pro Glu Val Thr Cys Val Val Val Asp Val Ser His
     275                 280                 285

Glu Asp Pro Glu Val Gln Phe Asn Trp Tyr Val Asp Gly Val Glu Val
         290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
             325                 330                 335

Lys Glu Tyr Lys Cys Lys Val Ser Asn Lys Gly Leu Pro Ala Pro Ile
         340                 345                 350

Glu Lys Thr Ile Ser Lys Thr Lys Gly Gln Pro Arg Glu Pro Gln Val
     355                 360                 365

Tyr Thr Leu Pro Pro Ser Arg Glu Glu Met Thr Lys Asn Gln Val Ser
     370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                 405                 410                 415

Met Leu Asp Ser Asp Gly Ser Phe Phe Leu Tyr Ser Lys Leu Thr Val
             420                 425                 430

Asp Lys Ser Arg Trp Gln Gln Gly Asn Val Phe Ser Cys Ser Val Met
         435                 440                 445

His Glu Ala Leu His Asn His Tyr Thr Gln Lys Ser Leu Ser Leu Ser
```

<210> SEQ ID NO 193
<211> LENGTH: 1413
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 193

```
atggacatga gagttcctgc tcagctgctc gggttgctgt tgctttggct ccggggtgct      60
aggtgcgagg ttcagctggt ggaatctggc ggtgggcttg taaagccagg aggctccctc     120
agactgagtt gtgccgcttc agggttcaca ttctccgact atgcgatgtc atgggtcgc      180
caagcacccg ggaaaggact ggagtgggtt agcactatca gcgatggcgg aacgtatacc     240
tattaccctg acaatgtgaa gggtcggttc accatttcca gggataacgc aaagaacagt     300
ctctatttgc agatgaacag cctgagggct gaggacaccg ccgtctacta ctgcgcccga     360
gaatggggag attatgatgg gtttgactat tggggccagg gcactttggt gacagtcagt     420
tctgcctcaa caaaggacc aagtgtgttc ccactcgccc ctagcagcaa gagtacatcc     480
gggggcactg cagcactcgg ctgcctcgtc aaggattatt tccagagcc agtaaccgtg      540
agctggaaca gtggagcact cacttctggt gtccatactt ttcctgctgt cctgcaaagc     600
tctggcctgt actcactcag ctccgtcgtg accgtgccat cttcatctct gggcactcag     660
acctacatct gtaatgtaaa ccacaagcct agcaatacta aggtcgataa gcgggtggaa     720
cccaagagct cgacaagac tcacacttgt cccccatgcc ctgcccctga acttctgggc     780
ggtcccagcg tcttttttgt tccaccaaag cctaaagata ctctgatgat aagtagaaca     840
cccgaggtga catgtgttgt gtagacgtt tcccacgagg acccagaggt taagttcaac     900
tggtacgttg atggagtcga agtacataat gctaagacca gcctagaga ggagcagtat     960
aatagtacat accgtgtagt cagtgttctc acagtgctgc accaagactg gctcaacggc    1020
aaagaataca atgcaaagt gtccaacaaa gcactcccag cccctatcga aagactatt     1080
agtaaggcaa aggggcagcc tcgtgaacca caggtgtaca ctctgccacc cagtagagag    1140
gaaatgacaa agaaccaagt ctcattgacc tgcctggtga aaggcttcta ccccagcgac    1200
atcgccgttg agtgggagag taacggtcag cctgagaaca attacaagac aacccccca     1260
gtgctggata gtgacgggtc tttctttctg tacagtaagc tgactgtgga caagtcccgc    1320
tggcagcagg gtaacgtctt cagctgttcc gtgatgcacg aggcattgca caaccactac    1380
acccagaagt cactgagcct gagcccaggg aag                                 1413
```

<210> SEQ ID NO 194
<211> LENGTH: 471
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 194

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly

```
                 20                  25                  30
Leu Val Lys Pro Gly Gly Ser Leu Arg Leu Ser Cys Ala Ala Ser Gly
             35                  40                  45
Phe Thr Phe Ser Asp Tyr Ala Met Ser Trp Val Arg Gln Ala Pro Gly
         50                  55                  60
Lys Gly Leu Glu Trp Val Ser Thr Ile Ser Asp Gly Gly Thr Tyr Thr
65                  70                  75                  80
Tyr Tyr Pro Asp Asn Val Lys Gly Arg Phe Thr Ile Ser Arg Asp Asn
                 85                  90                  95
Ala Lys Asn Ser Leu Tyr Leu Gln Met Asn Ser Leu Arg Ala Glu Asp
             100                 105                 110
Thr Ala Val Tyr Tyr Cys Ala Arg Glu Trp Gly Asp Tyr Asp Gly Phe
         115                 120                 125
Asp Tyr Trp Gly Gln Gly Thr Leu Val Thr Val Ser Ser Ala Ser Thr
     130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                 165                 170                 175
Pro Val Thr Val Ser Trp Asn Ser Gly Ala Leu Thr Ser Gly Val His
             180                 185                 190
Thr Phe Pro Ala Val Leu Gln Ser Ser Gly Leu Tyr Ser Leu Ser Ser
         195                 200                 205
Val Val Thr Val Pro Ser Ser Ser Leu Gly Thr Gln Thr Tyr Ile Cys
     210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
                 245                 250                 255
Glu Leu Leu Gly Gly Pro Ser Val Phe Leu Phe Pro Pro Lys Pro Lys
             260                 265                 270
Asp Thr Leu Met Ile Ser Arg Thr Pro Glu Val Thr Cys Val Val Val
         275                 280                 285
Asp Val Ser His Glu Asp Pro Glu Val Lys Phe Asn Trp Tyr Val Asp
     290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                 325                 330                 335
Trp Leu Asn Gly Lys Glu Tyr Lys Cys Lys Val Ser Asn Lys Ala Leu
             340                 345                 350
Pro Ala Pro Ile Glu Lys Thr Ile Ser Lys Ala Lys Gly Gln Pro Arg
         355                 360                 365
Glu Pro Gln Val Tyr Thr Leu Pro Pro Ser Arg Glu Glu Met Thr Lys
     370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                 405                 410                 415
Thr Thr Pro Pro Val Leu Asp Ser Asp Gly Ser Phe Phe Leu Tyr Ser
             420                 425                 430
Lys Leu Thr Val Asp Lys Ser Arg Trp Gln Gln Gly Asn Val Phe Ser
         435                 440                 445
```

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 195
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195

```
atggacatga gagttcctgc tcagctgctc gggttgctgt tgctttggct ccggggtgct      60
aggtgcgagg ttcagcttct ggaatctggc ggtgggcttg tacagccagg aggctccctc     120
agactgagtt gtgccgcttc agggttcaca ttctccgact atgcgatgtc atgggtgcgc     180
caagcacccg ggaaaggact ggagtgggtt caactatca gcgatggcgg aacgtatacc      240
tattaccctg acaatgtgaa gggtcggttc accatttcca gggataacag caagaacaca     300
ctctatctcc agatgaacag cctgagggct gaggacaccg ccgtctacta ctgcgcccga     360
gaatggggag attatgatgg gtttgactat tggggccagg gcactttggt gacagtcagt     420
tctgcctcaa caaaggacc aagtgtgttc ccactcgccc ctagcagcaa gagtacatcc      480
gggggcactg cagcactcgg ctgcctcgtc aaggattatt ttccagagcc agtaaccgtg     540
agctggaaca gtggagcact cacttctggt gtccatactt tcctgctgt cctgcaaagc      600
tctggcctgt actcactcag ctccgtcgtg accgtgccat cttcatctct gggcactcag     660
acctacatct gtaatgtaaa ccacaagcct agcaatacta aggtcgataa gcgggtggaa     720
cccaagagct gcgacaagac tcacacttgt cccccatgcc ctgcccctga acttctgggc     780
ggtcccagcg tcttttttgtt cccaccaaag cctaaagata ctctgatgat aagtagaaca    840
cccgaggtga catgtgttgt tgtagacgtt tcccacgagg acccagaggt taagttcaac     900
tggtacgttg atggagtcga agtacataat gctaagacca agcctagaga ggagcagtat     960
aatagtacat accgtgtagt cagtgttctc acagtgctgc accaagactg gctcaacggc    1020
aaagaataca atgcaaagt gtccaacaaa gcactcccag cccctatcga aagactatt     1080
agtaaggcaa aggggcagcc tcgtgaacca caggtgtaca ctctgccacc cagtagagag    1140
gaaatgacaa agaaccaagt ctcattgacc tgcctggtga aaggcttcta ccccagcgac    1200
atcgccgttg agtgggagag taacggtcag cctgagaaca attacaagac aaccccccca    1260
gtgctggata tgacgggtc tttctttctg tacagtaagc tgactgtgga caagtcccgc    1320
tggcagcagg gtaacgtctt cagctgttcc gtgatgcacg aggcattgca caaccactac    1380
acccagaagt cactgagcct gagcccaggg aag                                 1413
```

<210> SEQ ID NO 196
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Met Asp Met Arg Val Pro Ala Gln Leu Leu Gly Leu Leu Leu Leu Trp
1               5                   10                  15

```
Leu Arg Gly Ala Arg Cys Glu Val Gln Leu Leu Glu Ser Gly Gly
            20                  25                  30

Leu Val Gln Pro Gly Gly Ser Leu Arg Leu Ser Cys Ala Ala Ser Gly
        35                  40                  45

Phe Thr Phe Ser Asp Tyr Ala Met Ser Trp Val Arg Gln Ala Pro Gly
    50                  55                  60

Lys Gly Leu Glu Trp Val Ser Thr Ile Ser Asp Gly Gly Thr Tyr Thr
65                  70                  75                  80

Tyr Tyr Pro Asp Asn Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Glu Trp Gly Asp Tyr Asp Gly Phe
        115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430
```

Lys Leu Thr Val Asp Lys Ser Arg Trp Gln Gln Gly Asn Val Phe Ser
         435                 440                 445

Cys Ser Val Met His Glu Ala Leu His Asn His Tyr Thr Gln Lys Ser
     450                 455                 460

Leu Ser Leu Ser Pro Gly Lys
465                 470

<210> SEQ ID NO 197
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197

| | |
|---|---:|
| atggacatga gagttcctgc tcagctgctc gggttgctgt tgctttggct ccggggtgct | 60 |
| aggtgccagg ttcagctggt ggaatctggc ggtggggtag tacaaccagg acggtccctc | 120 |
| agactgagtt gtgccgcttc agggttcaca ttctccgact atgcgatgtc atgggtgcgc | 180 |
| caagcacccg ggaaaggact ggagtgggtt gccactatca gcgatggcgg aacgtatacc | 240 |
| tattaccctg acaatgtgaa gggtcggttc accatttcca gggataactc aaagaacacc | 300 |
| ctctatctcc aaatgagtag cctgagggct gaggacaccg ccgtctacta ctgcgcccga | 360 |
| gaatggggag attatgatgg gtttgactat tggggccagg gcactttggt gacagtcagt | 420 |
| tctgcctcaa caaaggacc aagtgtgttc ccactcgccc ctagcagcaa gagtacatcc | 480 |
| ggggggcactg cagcactcgg ctgcctcgtc aaggattatt tcccagagcc agtaaccgtg | 540 |
| agctggaaca gtggagcact cacttctggt gtccatactt ttcctgctgt cctgcaaagc | 600 |
| tctggcctgt actcactcag ctccgtcgtg accgtgccat cttcatctct gggcactcag | 660 |
| acctacatct gtaatgtaaa ccacaagcct agcaatacta aggtcgataa gcgggtggaa | 720 |
| cccaagagct cgacaagac tcacacttgt cccccatgcc ctgccctga acttctgggc | 780 |
| ggtcccagcg tcttttttgtt cccaccaaag cctaaagata ctctgatgat aagtagaaca | 840 |
| cccgaggtga catgtgttgt tgtagacgtt tcccacgagg acccagaggt taagttcaac | 900 |
| tggtacgttg atggagtcga agtacataat gctaagacca gcctagaga ggagcagtat | 960 |
| aatagtacat accgtgtagt cagtgttctc acagtgctgc accaagactg gctcaacggc | 1020 |
| aaagaataca atgcaaagt gtccaacaaa gcactcccag cccctatcga gaagactatt | 1080 |
| agtaaggcaa aggggcagcc tcgtgaacca caggtgtaca ctctgccacc cagtagagag | 1140 |
| gaaatgacaa agaaccaagt ctcattgacc tgcctggtga aaggcttcta ccccagcgac | 1200 |
| atcgccgttg agtgggagag taacggtcag cctgagaaca attacaagac aaccccccca | 1260 |
| gtgctggata gtgacgggtc tttctttctg tacagtaagc tgactgtgga caagtcccgc | 1320 |
| tggcagcagg gtaacgtctt cagctgttcc gtgatgcacg aggcattgca caaccactac | 1380 |
| acccagaagt cactgagcct gagcccaggg aag | 1413 |

<210> SEQ ID NO 198
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

```
Met Asp Met Arg Val Pro Ala Gln Leu Leu Gly Leu Leu Leu Trp
1               5                   10                  15

Leu Arg Gly Ala Arg Cys Gln Val Gln Leu Val Glu Ser Gly Gly
            20                  25                  30

Val Val Gln Pro Gly Arg Ser Leu Arg Leu Ser Cys Ala Ala Ser Gly
        35                  40                  45

Phe Thr Phe Ser Asp Tyr Ala Met Ser Trp Val Arg Gln Ala Pro Gly
        50                  55                  60

Lys Gly Leu Glu Trp Val Ala Thr Ile Ser Gly Gly Thr Tyr Thr
65                  70                  75                  80

Tyr Tyr Pro Asp Asn Val Lys Gly Arg Phe Thr Ile Ser Arg Asp Asn
            85                  90                  95

Ser Lys Asn Thr Leu Tyr Leu Gln Met Ser Ser Leu Arg Ala Glu Asp
            100                 105                 110

Thr Ala Val Tyr Tyr Cys Ala Arg Glu Trp Gly Asp Tyr Asp Gly Phe
            115                 120                 125

Asp Tyr Trp Gly Gln Gly Thr Leu Val Thr Val Ser Ser Ala Ser Thr
            130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
```

Lys Leu Thr Val Asp Lys Ser Arg Trp Gln Gln Gly Asn Val Phe Ser
    420                 425                 430
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 199
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199

| | |
|---|---|
| atggacatga gagttcctgc tcagctgctc gggttgctgt tgctttggct ccggggtgct | 60 |
| aggtgcgagg ttcagctggt ggaatctggc ggtgggcttg taaagccagg aggctccctc | 120 |
| agactgagtt gtgccgcttc agggttcaca ttctccgact atgcgatgtc atgggtgcgc | 180 |
| caagcacccg ggaaggact ggagtgggtt gccactatca gcgatggcgg aacgtatacc | 240 |
| tattaccctg acaatgtgaa gggtcggttc accatttcca gggataacgc aaagaacagt | 300 |
| ctctaccttc agatgaacag cctgagggct gaggacaccg ccgtctacta ctgcgcccga | 360 |
| gaatggggag attatgatgg gttgactat ggggccagg gcactttggt gacagtcagt | 420 |
| tctgcctcaa caaaggacc aagtgtgttc ccactcgccc ctagcagcaa gagtacatcc | 480 |
| gggggcactg cagcactcgg ctgcctcgtc aaggattatt ttccagagcc agtaaccgtg | 540 |
| agctggaaca gtggagcact cacttctggt gtccatactt tcctgctgt cctgcaaagc | 600 |
| tctggcctgt actcactcag ctccgtcgtg accgtgccat cttcatctct gggcactcag | 660 |
| acctacatct gtaatgtaaa ccacaagcct agcaatacta aggtcgataa gcgggtggaa | 720 |
| cccaagagct gcgacaagac tcacacttgt cccccatgcc ctgcccctga acttctgggc | 780 |
| ggtcccagcg tcttttttgtt cccaccaaag cctaaagata ctctgatgat aagtagaaca | 840 |
| cccgaggtga catgtgttgt gtagacgtt cccacgagg acccagaggt taagttcaac | 900 |
| tggtacgttg atggagtcga agtacataat gctaagacca gcctagaga ggagcagtat | 960 |
| aatagtacat accgtgtagt cagtgttctc acagtgctgc accaagactg gctcaacggc | 1020 |
| aaagaataca atgcaaagt gtccaacaaa gcactccag cccctatcga aaagactatt | 1080 |
| agtaaggcaa aggggcagcc tcgtgaacca caggtgtaca ctctgccacc cagtagagag | 1140 |
| gaaatgacaa agaaccaagt ctcattgacc tgcctggtga aaggcttcta ccccagcgac | 1200 |
| atcgccgttg agtgggagag taacggtcag cctgagaaca attacaagac aaccccccca | 1260 |
| gtgctggata tgacgggtc tttctttctg tacagtaagc tgactgtgga caagtcccgc | 1320 |
| tggcagcagg gtaacgtctt cagctgttcc gtgatgcacg aggcattgca caaccactac | 1380 |
| acccagaagt cactgagcct gagcccaggg aag | 1413 |

<210> SEQ ID NO 200
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

```
Met Asp Met Arg Val Pro Ala Gln Leu Leu Gly Leu Leu Leu Trp
1               5                   10                  15

Leu Arg Gly Ala Arg Cys Glu Val Gln Leu Val Glu Ser Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Ala Met Ser Trp Val Arg Gln Ala Pro Gly
    50                  55                  60

Lys Gly Leu Glu Trp Val Ala Thr Ile Ser Asp Gly Gly Thr Tyr Thr
65                  70                  75                  80

Tyr Tyr Pro Asp Asn Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Glu Trp Gly Asp Tyr Asp Gly Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 201
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201
atggacatga gggtgcccgc tcaactgctg gggctgctgc tgctgtggct gagaggagct    60
cgttgcgata ttcagttgac ccaatcacct agcttcctct cagcttccgt gggcgacaga   120
gttaccataa cctgtcgggc aagccaggag atttctgggt acctgtcctg gtaccaacag   180
aagcccggaa agcccctaa gctgttgatc tatgctgcgt caaccttgga tagcggtgtc   240
ccgagtcgat tctccggttc tggctccgga acagagttca ctctgacaat ttctagcctt   300
cagccagaag atttcgccac gtactattgc ctccagtacg acagctatcc ctatacattt   360
gggcagggca ctaaactgga gatcaaacgc acagttgctg cccccagcgt gttcattttc   420
ccacctagcg atgagcagct gaaaagcggt actgcctctg tcgtatgctt gctcaacaac   480
ttttacccac gtgaggctaa ggtgcagtgg aaagtggata atgcacttca atctggaaac   540
agtcaagagt ccgtgacaga acaggacagc aaagactcaa cttattcact ctcttccacc   600
ctgactctgt ccaaggcaga ctatgaaaaa cacaaggtat acgcctgcga ggttacacac   660
cagggtttgt ctagtcctgt caccaagtcc ttcaataggg gcgaatgt               708

<210> SEQ ID NO 202
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Met Asp Met Arg Val Pro Ala Gln Leu Leu Gly Leu Leu Leu Leu Trp
1               5                   10                  15

Leu Arg Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Arg Ala Ser
            35                  40                  45

Gln Glu Ile Ser Gly Tyr Leu Ser Trp Tyr Gln Gln Lys Pro Gly Lys
    50                  55                  60

Ala Pro Lys Leu Leu Ile Tyr Ala Ala Ser Thr Leu Asp Ser Gly Val
65                  70                  75                  80

Pro Ser Arg Phe Ser Gly Ser Gly Ser Gly Thr Glu Phe Thr Leu Thr
            85                  90                  95

Ile Ser Ser Leu Gln Pro Glu Asp Phe Ala Thr Tyr Tyr Cys Leu Gln
            100                 105                 110

Tyr Asp Ser Tyr Pro Tyr Thr Phe Gly Gln Gly Thr Lys Leu Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 203
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
atggacatga gggtgcccgc tcaactgctg gggctgctgc tgctgtggct gagaggagct       60
cgttgcgata ttcagatgac ccaatcacct agcagtctct cagcttccgt gggcgacaga     120
gttaccataa cctgtcgggc aagccaggag atttctgggt acctgtcctg gtttcaacag     180
aagcccggaa aggccccgaa gagcttgatc tatgctgcgt caaccttgga tagcggtgtc     240
ccgagtcgat tctccggttc tggctccgga accgacttta ctctgacaat ttctagcctt     300
cagccagaag atttcgccac gtactattgc ctccagtacg acagctatcc ctatacattt     360
gggcagggca ctaaactgga gatcaaacgc acagttgctg cccccagcgt gttcattttc     420
ccacctagcg atgagcagct gaaaagcggt actgcctctg tcgtatgctt gctcaacaac     480
ttttacccac gtgaggctaa ggtgcagtgg aaagtggata atgcacttca atctggaaac     540
agtcaagagt ccgtgacaga acaggacagc aaagactcaa cttattcact ctcttccacc     600
ctgactctgt ccaaggcaga ctatgaaaaa cacaaggtat acgcctgcga ggttacacac     660
cagggtttgt ctagtcctgt caccaagtcc ttcaataggg gcgaatgt               708

<210> SEQ ID NO 204
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Phe Gln Gln Lys Pro Gly Lys
 50                  55                  60

Ala Pro Lys Ser Leu Ile Tyr Ala Ala Ser Thr Leu Asp Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Leu Gln
            100                 105                 110

Tyr Asp Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 205
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
atggacatga gggtgcccgc tcaactgctg gggctgctgc tgctgtggct gagaggagct      60
cgttgcgata ttcagatgac ccaatcacct agcagtctct cagcttccgt gggcgacaga     120
gttaccataa cctgtcgggc aagccaggag atttctgggt acctgtcctg gtatcaacag     180
aagcccggaa aagccccaaa gaggttgatc tatgctgcgt caaccttgga tagcggtgtc     240
ccgagtcgat tctccggttc tggctccgga accgagttca ctctgacaat ttctagcctt     300
cagccagaag atttcgccac gtactattgc ctccagtacg acagctatcc ctatacattt     360
gggcagggca ctaaactgga gatcaaacgc acagttgctg cccccagcgt gttcattttc     420
ccacctagcg atgagcagct gaaaagcggt actgcctctg tcgtatgctt gctcaacaac     480
ttttacccac gtgaggctaa ggtgcagtgg aaagtggata atgcacttca atctggaaac     540
agtcaagagt ccgtgacaga acaggacagc aaagactcaa ctattcact ctcttccacc     600 ctgactctgt ccaaggcaga ctatgaaaaa cacaaggtat acgcctgcga ggttacacac     660
cagggtttgt ctagtcctgt caccaagtcc ttcaataggg gcgaatgt                  708

<210> SEQ ID NO 206
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

| Met | Asp | Met | Arg | Val | Pro | Ala | Gln | Leu | Leu | Gly | Leu | Leu | Leu | Leu | Trp |
|---|---|---|---|---|---|---|---|---|---|---|---|---|---|---|---|
| 1 | | | | 5 | | | | | 10 | | | | | 15 | |

| Leu | Arg | Gly | Ala | Arg | Cys | Asp | Ile | Gln | Met | Thr | Gln | Ser | Pro | Ser | Ser |
|---|---|---|---|---|---|---|---|---|---|---|---|---|---|---|---|
| | | | 20 | | | | | 25 | | | | | 30 | | |

| Leu | Ser | Ala | Ser | Val | Gly | Asp | Arg | Val | Thr | Ile | Thr | Cys | Arg | Ala | Ser |
|---|---|---|---|---|---|---|---|---|---|---|---|---|---|---|---|
| | | 35 | | | | | 40 | | | | | 45 | | | |

| Gln | Glu | Ile | Ser | Gly | Tyr | Leu | Ser | Trp | Tyr | Gln | Lys | Pro | Gly | Lys |
|---|---|---|---|---|---|---|---|---|---|---|---|---|---|---|
| 50 | | | | | 55 | | | | | 60 | | | | |

| Ala | Pro | Lys | Arg | Leu | Ile | Tyr | Ala | Ala | Ser | Thr | Leu | Asp | Ser | Gly | Val |
|---|---|---|---|---|---|---|---|---|---|---|---|---|---|---|---|
| 65 | | | | 70 | | | | | 75 | | | | | 80 | |

| Pro | Ser | Arg | Phe | Ser | Gly | Ser | Gly | Ser | Gly | Thr | Glu | Phe | Thr | Leu | Thr |
|---|---|---|---|---|---|---|---|---|---|---|---|---|---|---|---|
| | | | | 85 | | | | | 90 | | | | | 95 | |

| Ile | Ser | Ser | Leu | Gln | Pro | Glu | Asp | Phe | Ala | Thr | Tyr | Tyr | Cys | Leu | Gln |
|---|---|---|---|---|---|---|---|---|---|---|---|---|---|---|---|
| | | | 100 | | | | | 105 | | | | | 110 | | |

| Tyr | Asp | Ser | Tyr | Pro | Tyr | Thr | Phe | Gly | Gln | Gly | Thr | Lys | Leu | Glu | Ile |
|---|---|---|---|---|---|---|---|---|---|---|---|---|---|---|---|
| | | 115 | | | | | 120 | | | | | 125 | | | |

| Lys | Arg | Thr | Val | Ala | Ala | Pro | Ser | Val | Phe | Ile | Phe | Pro | Pro | Ser | Asp |
|---|---|---|---|---|---|---|---|---|---|---|---|---|---|---|---|
| | 130 | | | | | 135 | | | | | 140 | | | | |

| Glu | Gln | Leu | Lys | Ser | Gly | Thr | Ala | Ser | Val | Val | Cys | Leu | Leu | Asn | Asn |
|---|---|---|---|---|---|---|---|---|---|---|---|---|---|---|---|
| 145 | | | | | 150 | | | | | 155 | | | | | 160 |

| Phe | Tyr | Pro | Arg | Glu | Ala | Lys | Val | Gln | Trp | Lys | Val | Asp | Asn | Ala | Leu |
|---|---|---|---|---|---|---|---|---|---|---|---|---|---|---|---|
| | | | | 165 | | | | | 170 | | | | | 175 | |

| Gln | Ser | Gly | Asn | Ser | Gln | Glu | Ser | Val | Thr | Glu | Gln | Asp | Ser | Lys | Asp |
|---|---|---|---|---|---|---|---|---|---|---|---|---|---|---|---|
| | | | 180 | | | | | 185 | | | | | 190 | | |

| Ser | Thr | Tyr | Ser | Leu | Ser | Ser | Thr | Leu | Thr | Leu | Ser | Lys | Ala | Asp | Tyr |
|---|---|---|---|---|---|---|---|---|---|---|---|---|---|---|---|
| | | 195 | | | | | 200 | | | | | 205 | | | |

| Glu | Lys | His | Lys | Val | Tyr | Ala | Cys | Glu | Val | Thr | His | Gln | Gly | Leu | Ser |
|---|---|---|---|---|---|---|---|---|---|---|---|---|---|---|---|
| | 210 | | | | | 215 | | | | | 220 | | | | |

| Ser | Pro | Val | Thr | Lys | Ser | Phe | Asn | Arg | Gly | Glu | Cys |
|---|---|---|---|---|---|---|---|---|---|---|---|
| 225 | | | | | 230 | | | | | 235 | |

<210> SEQ ID NO 207
<211> LENGTH: 708
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 207

| atggacatga gggtgcccgc tcaactgctg gggctgctgc tgctgtggct gagaggagct | 60 |
| cgttgcgata ttcagatgac ccaatcacct agcagtctct cagcttccgt gggcgacaga | 120 |
| gttaccataa cctgtcgggc aagccaggag atttctgggt acctgtcctg gtaccaacag | 180 |
| aagcccggaa aggcccccaa gctgttgatc tatgctgcgt caaccttgga tagcggtgtc | 240 |
| ccgagtcgat tctccggttc tggctccgga acagacttta cttttacaat ttctagcctt | 300 |
| cagccagagg acatcgccac gtactattgc ctccagtacg acagctatcc ctatacattt | 360 |
| gggcagggca ctaaactgga gatcaaacgc acagttgctg cccccagcgt gttcattttc | 420 |
| ccacctagcg atgagcagct gaaaagcggt actgcctctg tcgtatgctt gctcaacaac | 480 |
| ttttacccac gtgaggctaa ggtgcagtgg aaagtggata tgcacttca atctggaaac | 540 |
| agtcaagagt ccgtgacaga acaggacagc aaagactcaa cttattcact ctcttccacc | 600 |

```
ctgactctgt ccaaggcaga ctatgaaaaa cacaaggtat acgcctgcga ggttacacac      660
cagggtttgt ctagtcctgt caccaagtcc ttcaataggg gcgaatgt                    708
```

<210> SEQ ID NO 208
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Tyr Gln Gln Lys Pro Gly Lys
    50                  55                  60

Ala Pro Lys Leu Leu Ile Tyr Ala Ala Ser Thr Leu Asp Ser Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr Tyr Cys Leu Gln
            100                 105                 110

Tyr Asp Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 209
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

```
atggacatga gggtgcccgc tcaactgctg gggctgctgc tgctgtggct gagaggagct      60
cgttgcgata ttcagatgac ccaatcacct agcagtctct cagcttccgt gggcgacaga     120
gttaccataa cctgtcgggc aagccaggag atttctgggt acctgtcctg gtatcaacag     180
aagcccggaa aagcccctaa gctgttgatc tatgctgcgt caaccttgga tagcggtgtc     240
```

```
ccgagtcgat tctccggttc tggctccgga actgacttca ctctgacaat ttctagcctt      300
cagccagaag atttcgccac gtactattgc ctccagtacg acagctatcc ctatacattt      360
gggcagggca ctaaactgga gatcaaacgc acagttgctg cccccagcgt gttcattttc      420
ccacctagcg atgagcagct gaaaagcggt actgcctctg tcgtatgctt gctcaacaac      480
ttttacccac gtgaggctaa ggtgcagtgg aaagtggata atgcacttca atctggaaac      540
agtcaagagt ccgtgacaga acaggacagc aaagactcaa cttattcact ctcttccacc      600
ctgactctgt ccaaggcaga ctatgaaaaa cacaaggtat acgcctgcga ggttacacac      660
cagggtttgt ctagtcctgt caccaagtcc ttcaataggg gcgaatgt                  708
```

<210> SEQ ID NO 210
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Tyr Gln Gln Lys Pro Gly Lys
    50                  55                  60

Ala Pro Lys Leu Leu Ile Tyr Ala Ala Ser Thr Leu Asp Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Leu Gln
            100                 105                 110

Tyr Asp Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 211
<211> LENGTH: 708
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 211

```
atggacatga gggtgcccgc tcaactgctg gggctgctgc tgctgtggct gagaggagct    60
cgttgcgata ttcagatgac ccaatcacct agcagtctct cagcttccgt gggcgacaga   120
gttaccataa cctgtcgggc aagccaggag atttctgggt acctgtcctg gctgcaacag   180
aagcccggag cgccatcaa gaggttgatc tatgctgcgt caaccttgga tagcggtgtc   240
ccgagtcgat tctccggttc tggctccgga agtgactaca ctctgacaat ttctagcctt   300
cagccagaag atttcgccac gtactattgc ctccagtacg acagctatcc ctatacattt   360
gggcagggca ctaaactgga gatcaaacgc acagttgctg cccccagcgt gttcattttc   420
ccacctagcg atgagcagct gaaaagcggt actgcctctg tcgtatgctt gctcaacaac   480
ttttacccac gtgaggctaa ggtgcagtgg aaagtggata atgcacttca atctggaaac   540
agtcaagagt ccgtgacaga acaggacagc aaagactcaa cttattcact ctcttccacc   600
ctgactctgt ccaaggcaga ctatgaaaaa cacaaggtat acgcctgcga ggttacacac   660
cagggtttgt ctagtcctgt caccaagtcc ttcaataggg gcgaatgt               708
```

<210> SEQ ID NO 212
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

```
Met Asp Met Arg Val Pro Ala Gln Leu Leu Gly Leu Leu Leu Leu Trp
1               5                   10                  15
Leu Arg Gly Ala Arg Cys Asp Ile Gln Met Thr Gln Ser Pro Ser Ser
            20                  25                  30
Leu Ser Ala Ser Val Gly Asp Arg Val Thr Ile Thr Cys Arg Ala Ser
        35                  40                  45
Gln Glu Ile Ser Gly Tyr Leu Ser Trp Leu Gln Gln Lys Pro Gly Gly
    50                  55                  60
Ala Ile Lys Arg Leu Ile Tyr Ala Ala Ser Thr Leu Asp Ser Gly Val
65                  70                  75                  80
Pro Ser Arg Phe Ser Gly Ser Gly Ser Gly Ser Asp Tyr Thr Leu Thr
                85                  90                  95
Ile Ser Ser Leu Gln Pro Glu Asp Phe Ala Thr Tyr Tyr Cys Leu Gln
            100                 105                 110
Tyr Asp Ser Tyr Pro Tyr Thr Phe Gly Gln Gly Thr Lys Leu Glu Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
```

-continued

```
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```